(12) United States Patent
Fasan et al.

(10) Patent No.: US 8,986,953 B2
(45) Date of Patent: Mar. 24, 2015

(54) MACROCYCLIC COMPOUNDS WITH A HYBRID PEPTIDIC/NON-PEPTIDIC BACKBONE AND METHODS FOR THEIR PREPARATION

(75) Inventors: Rudi Fasan, Rochester, NY (US); John R. Frost, Niagara Falls, NY (US); Jessica M. Smith, Hamlin, NY (US); Francesca C. Vitali, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 13/980,083

(22) PCT Filed: Jan. 20, 2012

(86) PCT No.: PCT/US2012/022050
§ 371 (c)(1),
(2), (4) Date: Aug. 29, 2013

(87) PCT Pub. No.: WO2012/100176
PCT Pub. Date: Jul. 26, 2012

(65) Prior Publication Data
US 2013/0330773 A1    Dec. 12, 2013

Related U.S. Application Data

(60) Provisional application No. 61/434,720, filed on Jan. 20, 2011.

(51) Int. Cl.
*C12P 21/06* (2006.01)
*C12P 21/04* (2006.01)
(Continued)

(52) U.S. Cl.
CPC .............. *C07K 14/001* (2013.01); *C07K 1/026* (2013.01); *C12N 9/14* (2013.01); *C12N 15/70* (2013.01);
(Continued)

(58) Field of Classification Search
CPC .............................. C07K 14/001; C07K 14/64
USPC ........................................................ 435/69.7
See application file for complete search history.

(56) References Cited

U.S. PATENT DOCUMENTS

| | | | |
|---|---|---|---|
| 7,354,756 B1 | 4/2008 | Benkovic et al. | |
| 2003/0013148 A1 | 1/2003 | Evans et al. | |
| 2005/0227291 A1 | 10/2005 | Kinsella | |
| 2010/0143972 A1 | 6/2010 | Horswill | |

FOREIGN PATENT DOCUMENTS

WO    WO-2007109620 A2    9/2007

OTHER PUBLICATIONS

Extended European Search Report for EP Application No. 12736111.1 dated Dec. 11, 2013 (6 pages).
Deschuyteneer, Genevieve et al., "Intein-Mediated Cyclization of Randomized Peptides in the Periplasm of *Escherichia coli* and Their Extracellular Secretion," Jun. 2010, ACS Chemical Biology, vol. 5, No. 7 (pp. 691-700).
Korean Intellectual Property Office International Search Report and Written Opinion of the International Searching Authority for International Application No. PCT/US2012/022050 dated Aug. 22, 2012 (10 pages).
Smith, Jessica M. et al., "Modular Assembly of Macrocyclic Organo-Peptide Hybrids Using Synthetic and Genetically Encoded Precursors," 2011 Angew. Chem. Int. Ed. 50 (pp. 5075-5080).

*Primary Examiner* — Alexander Kim
(74) *Attorney, Agent, or Firm* — Harris Beach PLLC

(57) ABSTRACT

Methods and compositions are provided that utilize synthetic molecules and genetically encoded polypeptides to generate macrocyclic peptide-containing molecules with a hybrid peptidic/non-peptidic backbone. Also provided are nucleic acid molecules, polypeptides, and methods for generating libraries of macrocyclic peptide-containing molecules with a hybrid peptidic/non-peptidic backbone. These methods can be used to increase the structural diversity of ligand libraries as well as facilitate the functional screening of these libraries to identify compound(s) with desired activity properties.

25 Claims, 35 Drawing Sheets

(51) Int. Cl.
*C07K 14/00* (2006.01)
*C07K 1/02* (2006.01)
*C12N 9/14* (2006.01)
*C12N 15/70* (2006.01)
*C07D 498/08* (2006.01)
*C12P 17/18* (2006.01)
*C07K 7/64* (2006.01)

(52) U.S. Cl.
CPC ............. *C07D 498/08* (2013.01); *C12P 17/188* (2013.01); *C07K 7/64* (2013.01); *C07K 2319/92* (2013.01)
USPC ........................................ 435/69.1; 435/69.7

MOrPH

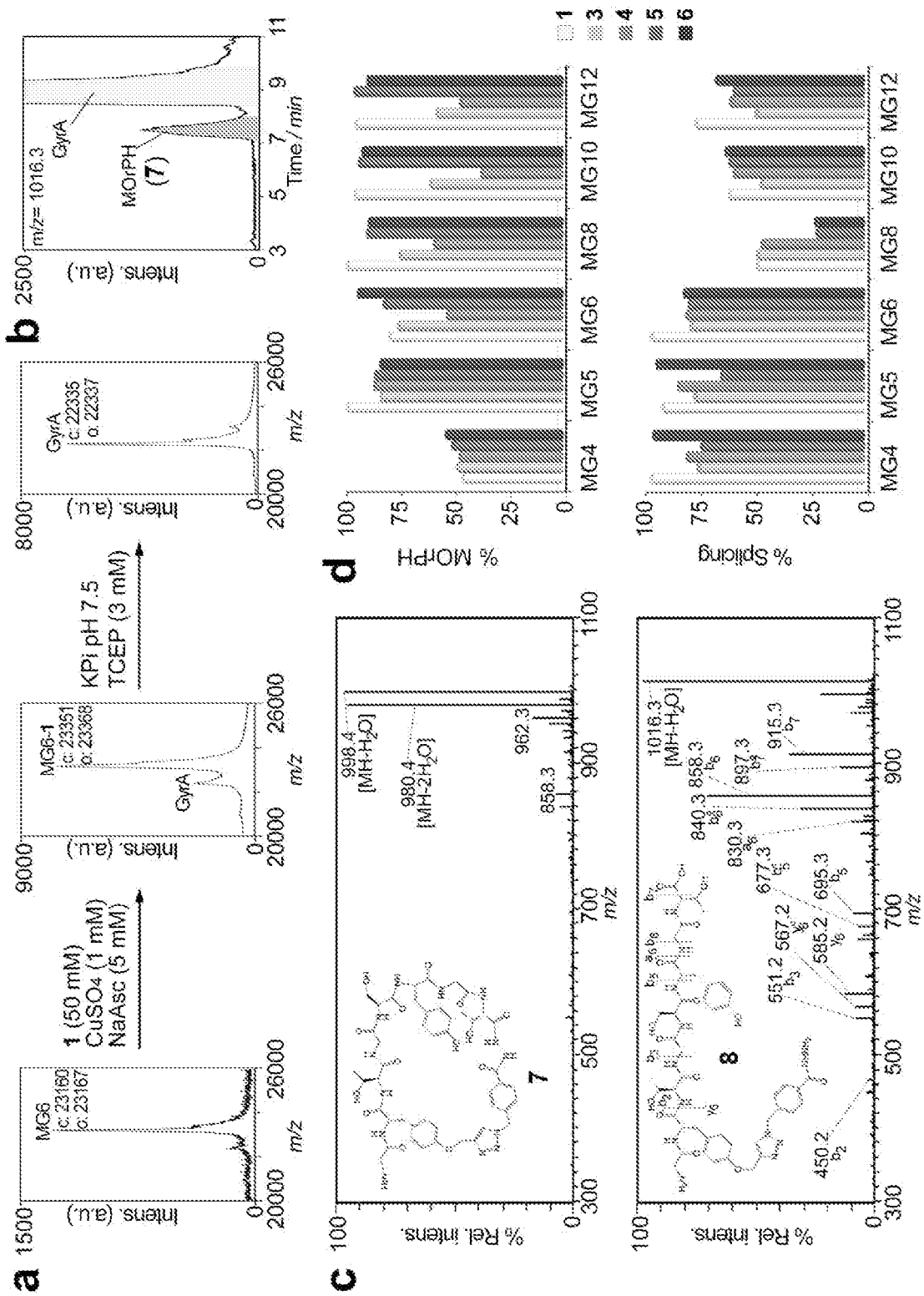
FIGS. 5a-d

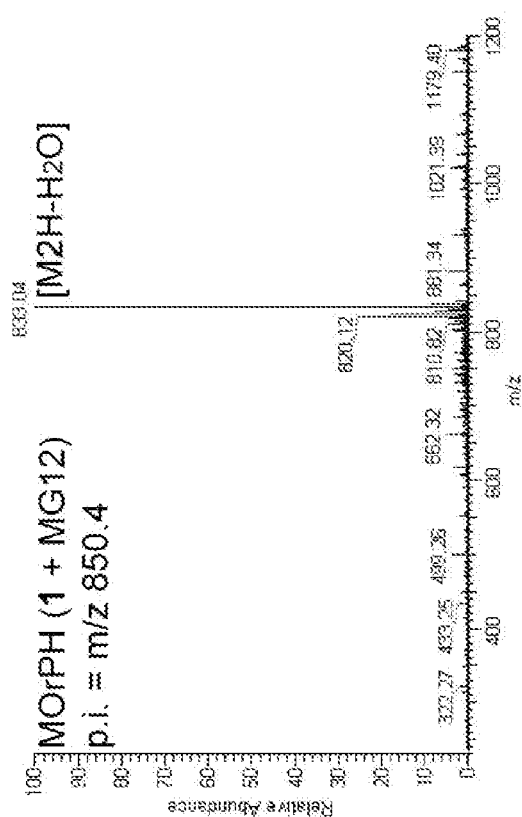
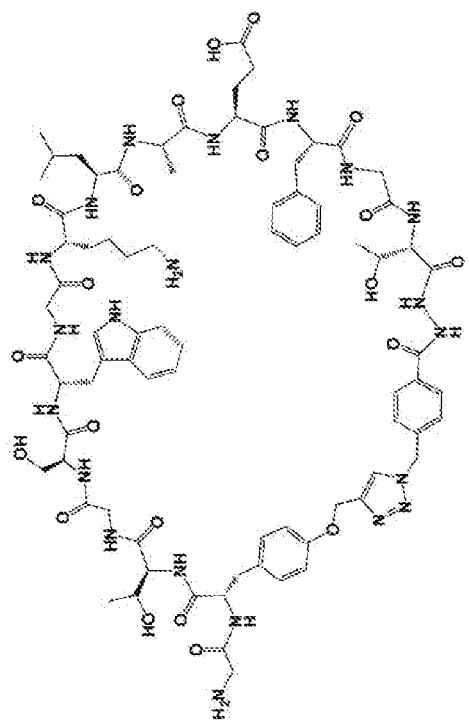
FIG. 6c

FIG. 13a-c

Figure 15:
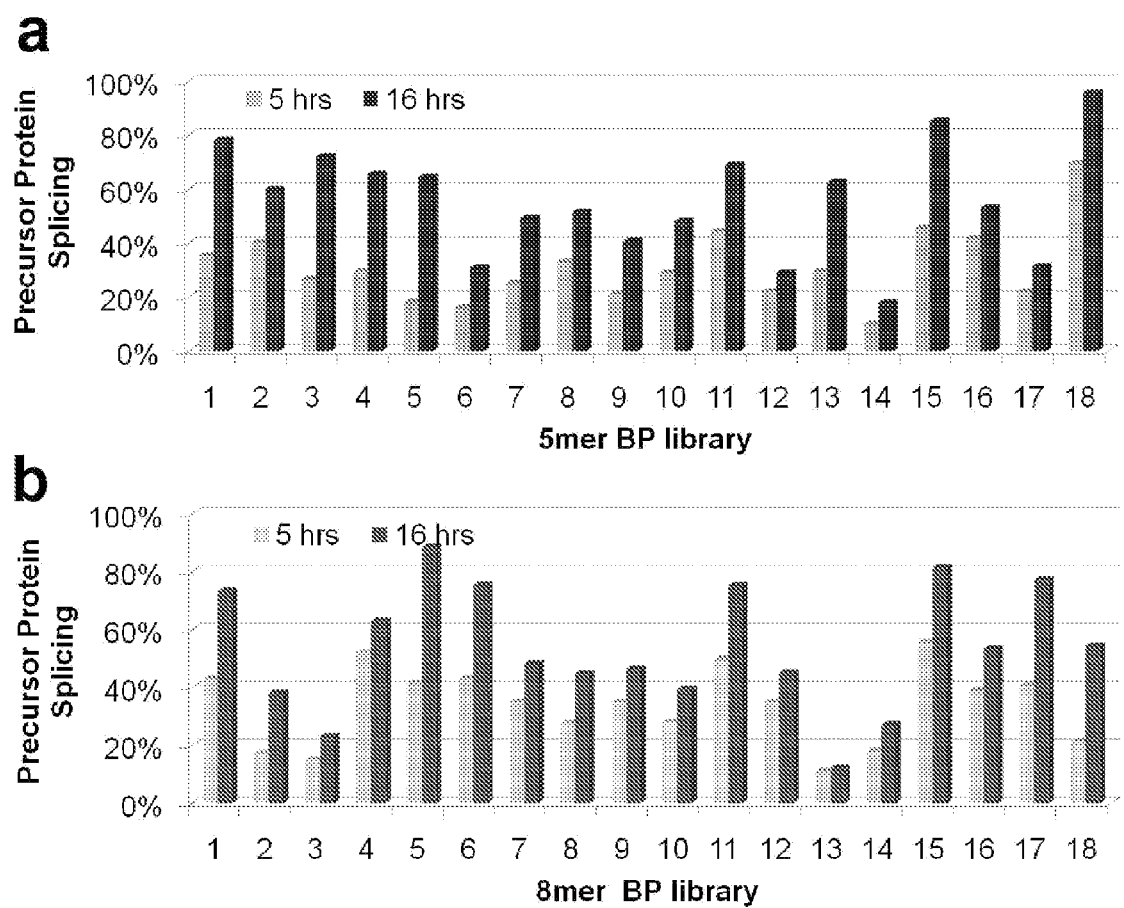

FIGS. 15a-b

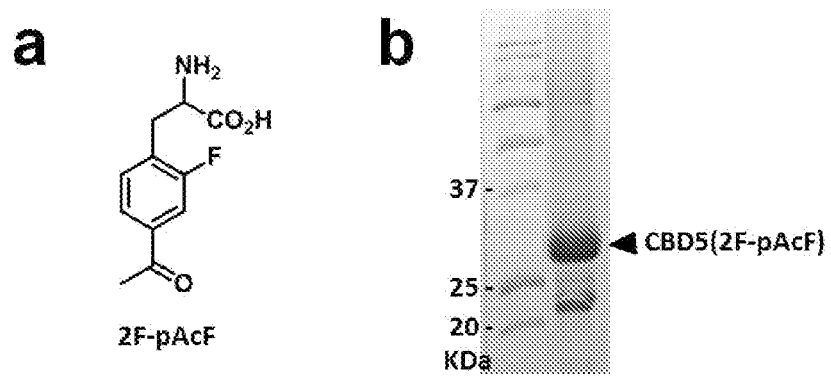
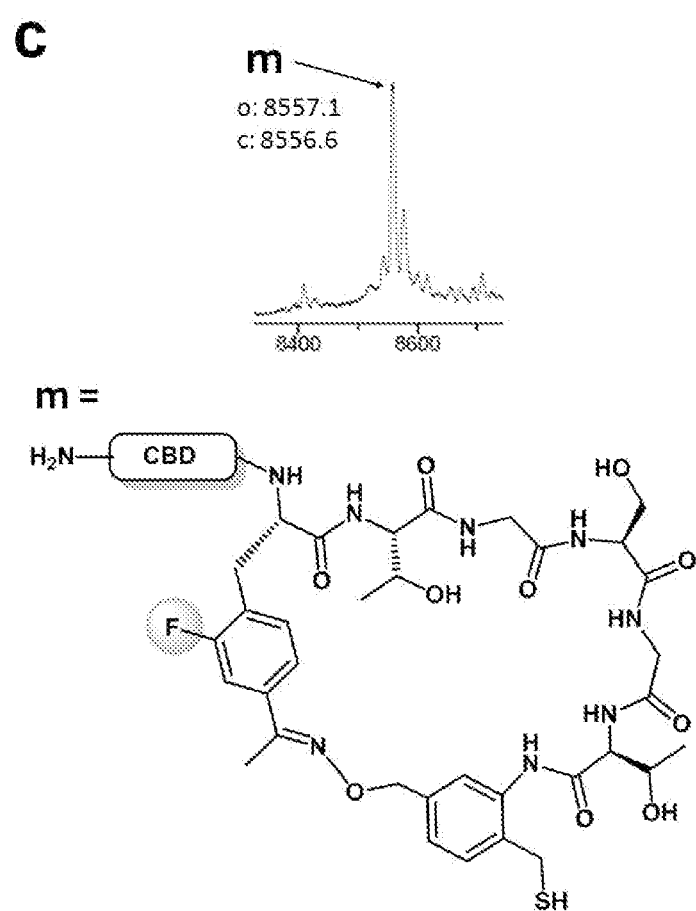
FIGS. 17a-c

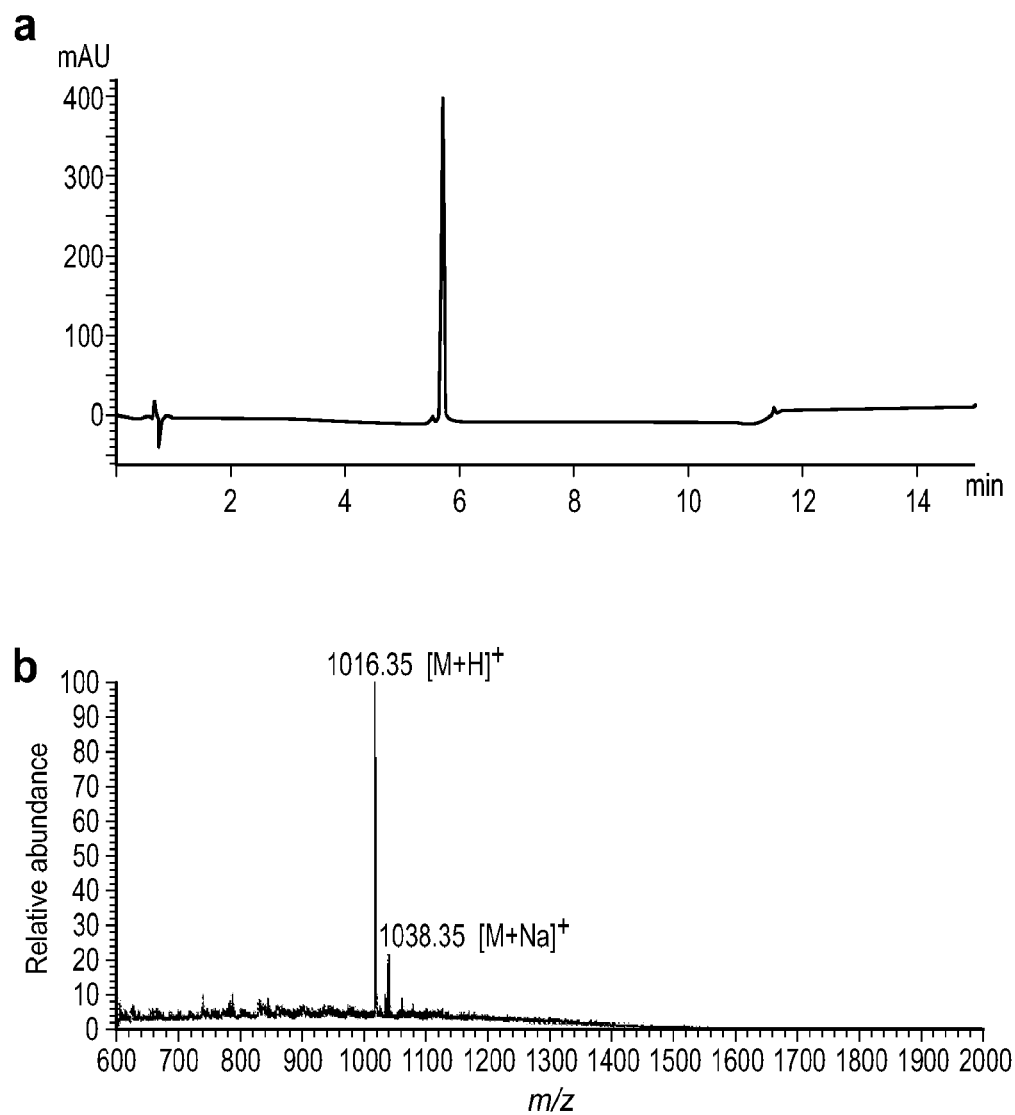
FIGS. 18a-b

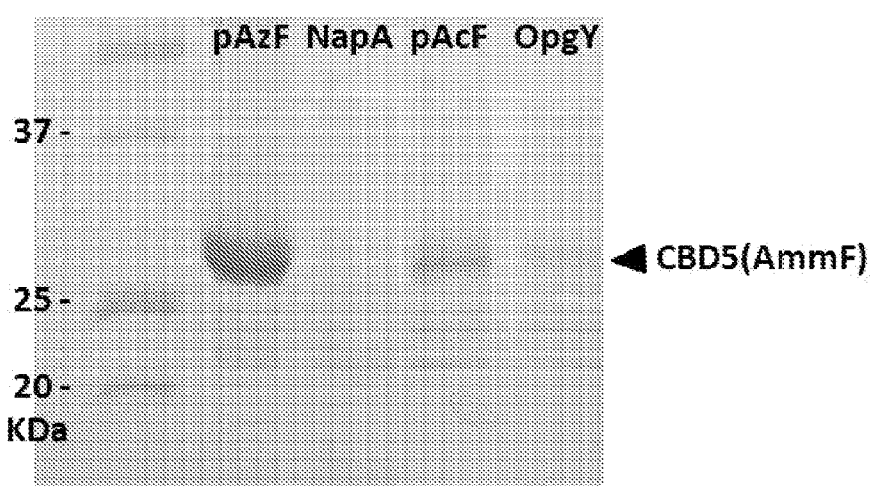
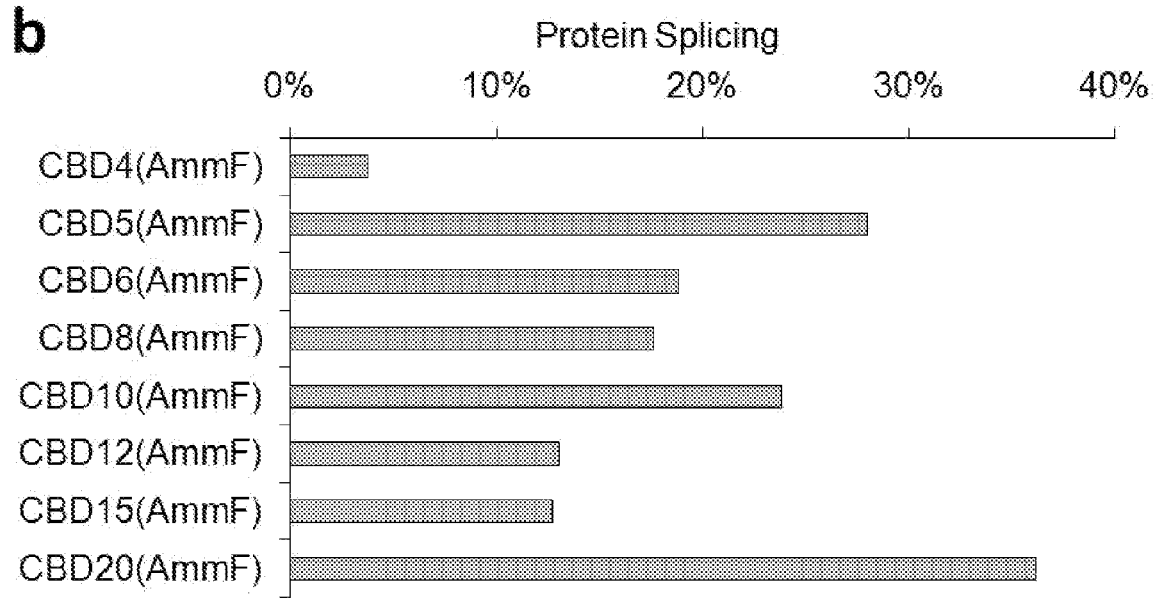
FIGS. 19a-b

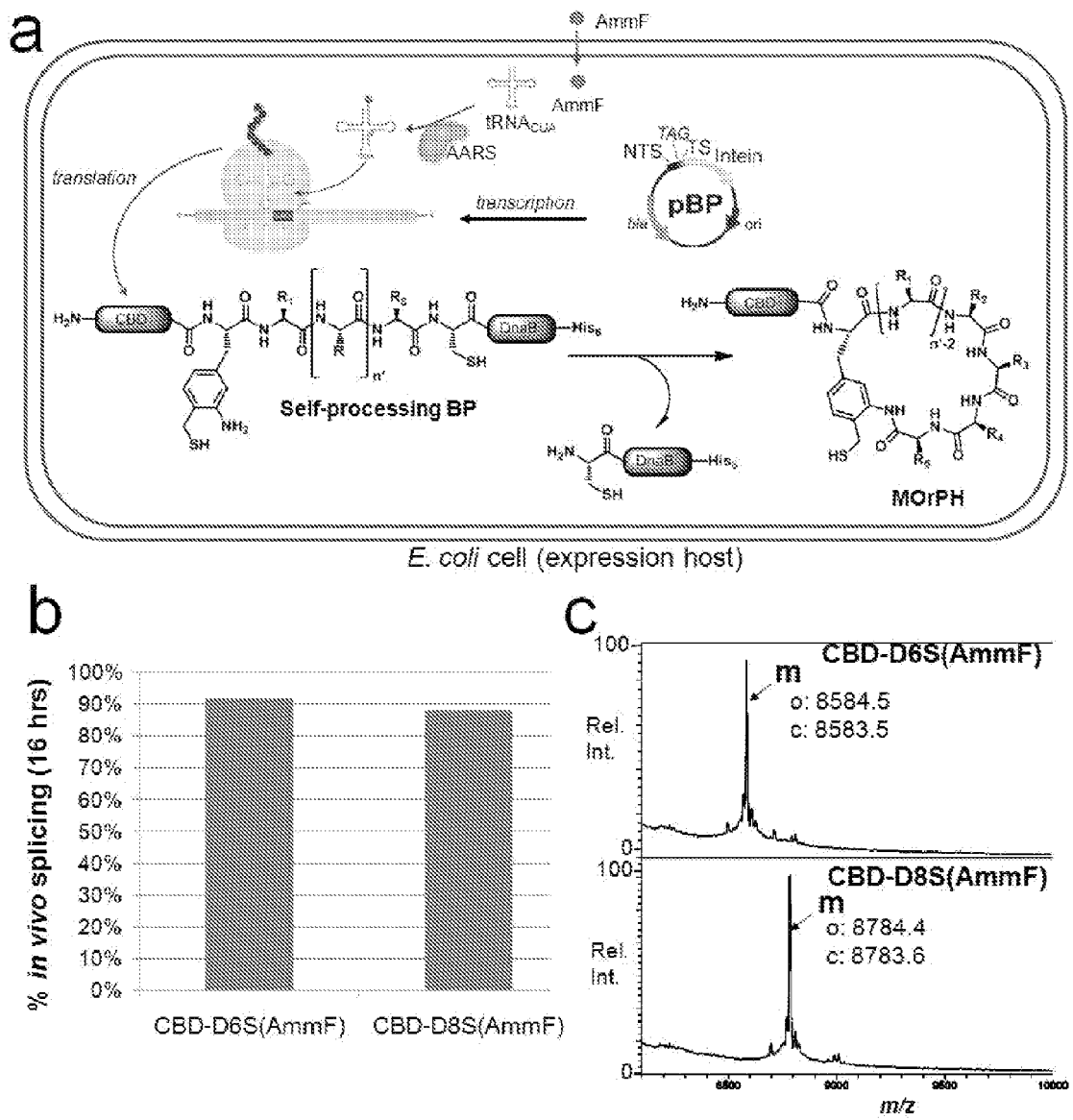
FIGS. 22a-c

Scheme 1. Synthetic route to O-propargyl-tyrosine (OpgY).
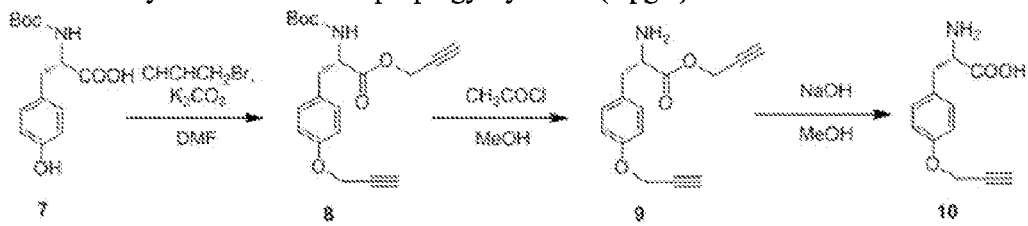
Scheme 2. Synthetic route to synthetic precursor 1.
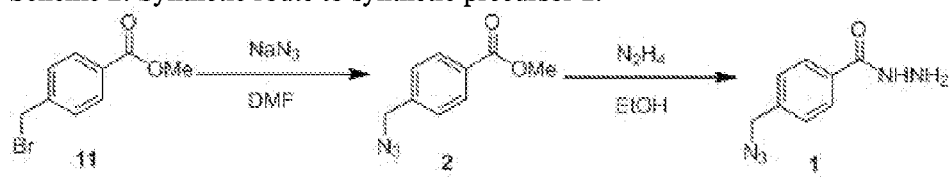
Scheme 3. Synthetic route to synthetic precursor 3.
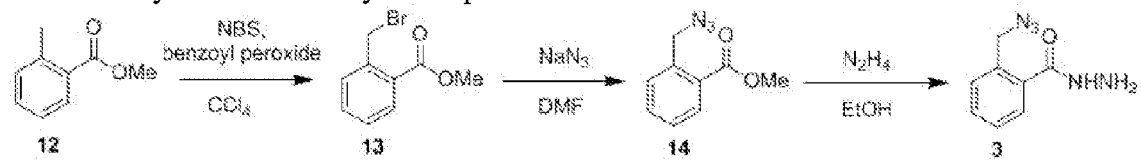
Scheme 4. Synthetic route to synthetic precursor 4.
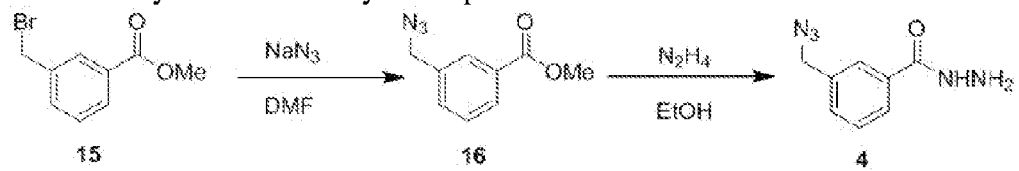
Scheme 5. Synthetic route to synthetic precursor 5.
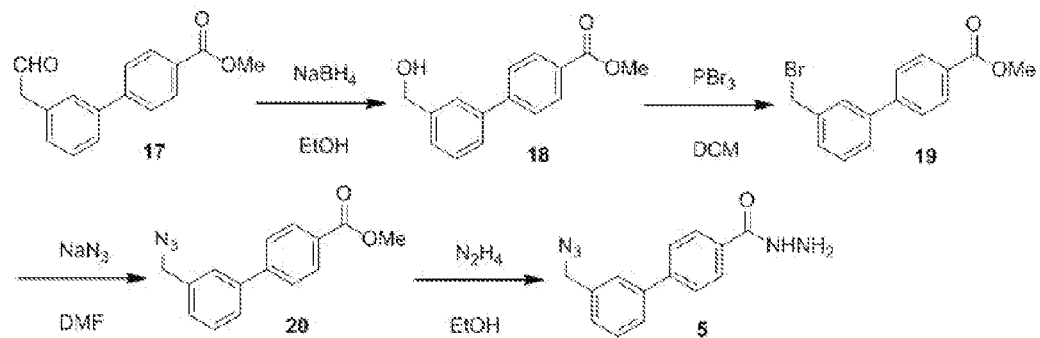
FIG. 23a Scheme 6. Synthetic route to synthetic precursor 6.
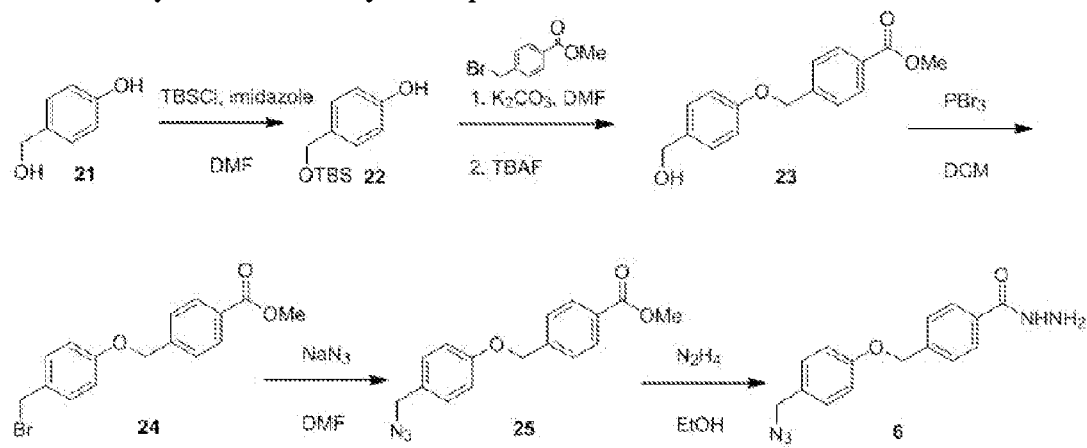
Scheme 7. Synthetic route to *para*-acetylphenylalanine (pAcF).
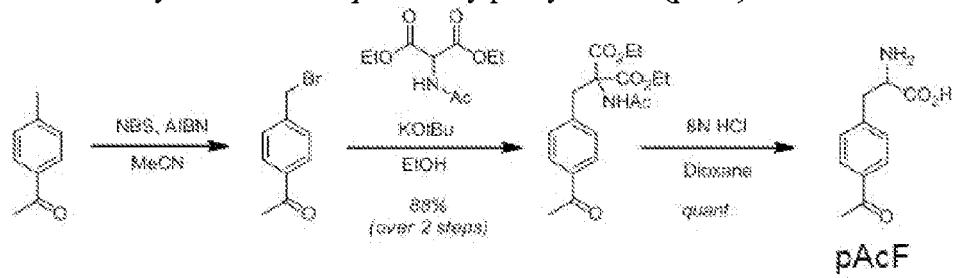
Scheme 8. Synthetic route to synthetic precursor SP3.
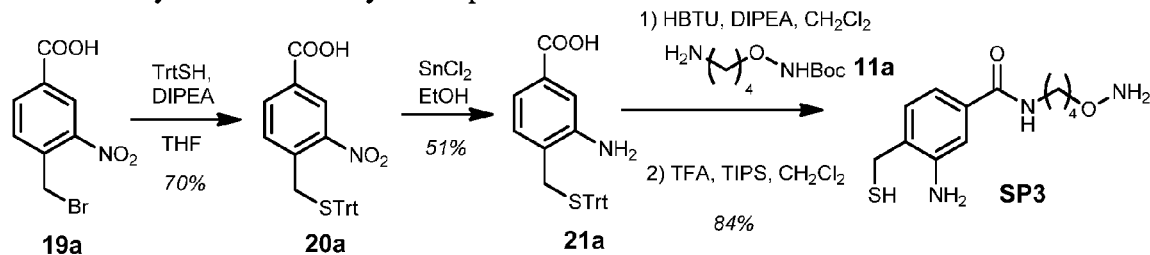
FIG. 23b Scheme 9. Synthetic routes to synthetic precursor SP4, SP5, SP6, SP7, and SP8.

Scheme 10. Synthetic route to synthetic precursor SP10.
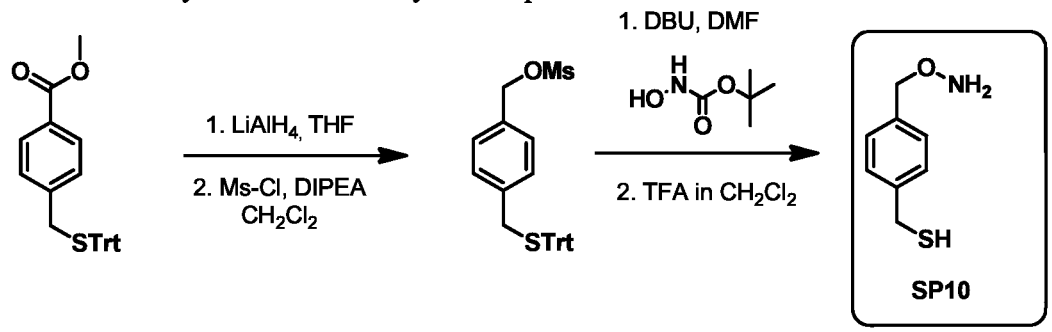
Scheme 11. Synthetic route to synthetic precursor SP9.
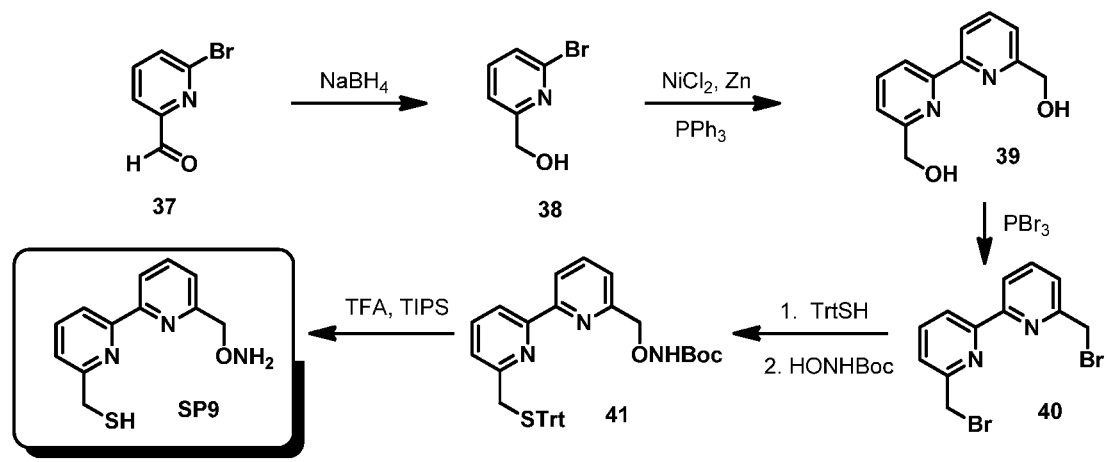
Scheme 12. Synthesis of 3-amino-4-mercaptomethyl-phenylalanine (AmmF)
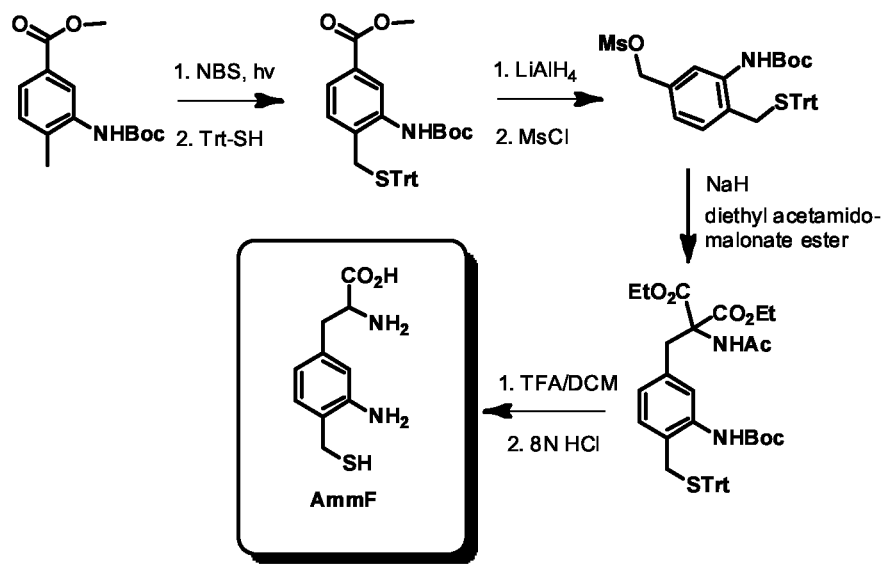
FIG. 23d

SEQUENCE LISTING

<160> NUMBER OF SEQ ID NOS: 124

<210> SEQ ID NO 1
<211> LENGTH: 198
<212> TYPE: PRT
<213> ORGANISM: Mycobacterium xenopi

<400> SEQUENCE: 1

Cys Ile Thr Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
            20                  25                  30

Ile Asp Leu Lys Val Leu Asp Arg His Gly Asn Pro Val Leu Ala Asp
        35                  40                  45

Arg Leu Phe His Ser Gly Glu His Pro Val Tyr Thr Val Arg Thr Val
    50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95

Ile Lys Pro Gly Asp Tyr Ala Val Ile Gln Arg Ser Ala Phe Ser Val
            100                 105                 110

Asp Cys Ala Gly Phe Ala Arg Gly Lys Pro Glu Phe Ala Pro Thr Thr
        115                 120                 125

Tyr Thr Val Gly Val Pro Gly Leu Val Arg Phe Leu Glu Ala His His
    130                 135                 140

Arg Asp Pro Asp Ala Gln Ala Ile Ala Asp Glu Leu Thr Asp Gly Arg
145                 150                 155                 160

Phe Tyr Tyr Ala Lys Val Ala Ser Val Thr Asp Ala Gly Val Gln Pro
                165                 170                 175

Val Tyr Ser Leu Arg Val Asp Thr Ala Asp His Ala Phe Ile Thr Asn
            180                 185                 190

Gly Phe Val Ser His Asn
        195

<210> SEQ ID NO 2
<211> LENGTH: 154
<212> TYPE: PRT
<213> ORGANISM: Artificial Sequence
<220> FEATURE:
<223> OTHER INFORMATION: Synthesized sequence

<400> SEQUENCE: 2

Cys Ile Ser Gly Asp Ser Leu Ile Ser Leu Ala Ser Thr Gly Lys Arg
1               5                   10                  15

Val Ser Ile Lys Asp Leu Leu Asp Glu Lys Asp Phe Glu Ile Trp Ala
            20                  25                  30

Ile Asn Glu Gln Thr Met Lys Leu Glu Ser Ala Lys Val Ser Arg Val
        35                  40                  45

Phe Cys Thr Gly Lys Lys Leu Val Tyr Ile Leu Lys Thr Arg Leu Gly
    50                  55                  60

Arg Thr Ile Lys Ala Thr Ala Asn His Arg Phe Leu Thr Ile Asp Gly
65                  70                  75                  80

Trp Lys Arg Leu Asp Glu Leu Ser Leu Lys Glu His Ile Ala Leu Pro
                85                  90                  95

Arg Lys Leu Glu Ser Ser Ser Leu Gln Leu Ser Pro Glu Ile Glu Lys
            100                 105                 110

Leu Ser Gln Ser Asp Ile Tyr Trp Asp Ser Ile Val Ser Ile Thr Glu
            115                 120                 125

Thr Gly Val Glu Glu Val Phe Asp Leu Thr Val Pro Gly Pro His Asn
        130                 135                 140

Phe Val Ala Asn Asp Ile Ile Val His Asn
145                 150

<210> SEQ ID NO 3
<211> LENGTH: 182
<212> TYPE: PRT
<213> ORGANISM: Halobacterium species NRC1

<400> SEQUENCE: 3

Cys Val Arg Gly Asp Thr Thr Val Ala Leu Ala Asp Gly Ser Glu Arg
1               5                   10                  15

Glu Ile Arg Asp Leu Val Glu Ala Asn Leu Asp Asp Pro Arg Pro Val
            20                  25                  30

Asp Asp Gly Val Trp Asp Gly Val Asp Val Ala Val Pro Ser Leu Ala
        35                  40                  45

Ala Asp Gly Arg Leu Val Gln Arg Arg Ala Thr Lys Val Trp Lys Arg
    50                  55                  60

Glu Ala Pro Glu Thr Met Tyr Arg Val Arg Thr Ala Ala Gly His Arg
65                  70                  75                  80

Leu Thr Val Thr Pro Ser His Pro Leu Phe Val Ala Gly Ser His Gly
                85                  90                  95

Pro Asp Ala Val Arg Thr Glu Asp Leu Glu Val Gly Gln Leu Val Gly
            100                 105                 110

Val Ala Pro Asp Gly Asp Gly Ser Gly Gln Val Ala Pro Asp Gly Gly
        115                 120                 125

Val Ile Arg Asp Ala Gln Pro Ala Pro Val Gly Asp Ala Glu Thr Val
    130                 135                 140

Ala Trp Ser Ala Ile Glu Ser Ile Thr Glu Val Glu Pro Asp Glu Glu
145                 150                 155                 160

Trp Val Tyr Asp Leu Glu Val Glu Gly Thr His Ser Tyr Leu Thr Asp
                165                 170                 175

Gly Val Val Ser His Asn
            180

<210> SEQ ID NO 4
<211> LENGTH: 456
<212> TYPE: PRT
<213> ORGANISM: Chlamydomonas eugametos

<400> SEQUENCE: 4

Cys Leu Thr Ser Asp His Thr Val Leu Thr Thr Arg Gly Trp Ile Pro
1               5                   10                  15

Ile Ala Asp Val Thr Leu Asp Asp Lys Val Ala Val Leu Asp Asn Asn
            20                  25                  30

Thr Gly Glu Met Ser Tyr Gln Asn Pro Gln Lys Val His Lys Tyr Asp
        35                  40                  45

Tyr Glu Gly Pro Met Tyr Glu Val Lys Thr Ala Gly Val Asp Leu Phe
    50                  55                  60

Val Thr Pro Asn His Arg Met Tyr Val Asn Thr Asn Asn Thr Thr
65                  70                  75                  80

Asn Gln Asn Tyr Asn Leu Val Glu Ala Ser Ser Ile Phe Gly Lys Lys
                85                  90                  95

Val Arg Tyr Lys Asn Asp Ala Ile Trp Asn Lys Thr Asp Tyr Gln Phe
                100                 105                 110

Ile Leu Pro Glu Thr Ala Thr Leu Thr Gly His Thr Asn Lys Ile Ser
            115                 120                 125

Ser Thr Pro Ala Ile Gln Pro Glu Met Asn Ala Trp Leu Thr Phe Phe
130                 135                 140

Gly Leu Trp Ile Ala Asn Gly His Thr Thr Lys Ile Ala Glu Lys Thr
145                 150                 155                 160

Ala Glu Asn Asn Gln Gln Lys Gln Arg Tyr Lys Val Ile Leu Thr Gln
                165                 170                 175

Val Lys Glu Asp Val Cys Asp Ile Ile Glu Gln Thr Leu Asn Lys Leu
            180                 185                 190

Gly Phe Asn Phe Ile Arg Ser Gly Lys Asp Tyr Thr Ile Glu Asn Lys
        195                 200                 205

Gln Leu Trp Ser Tyr Leu Asn Pro Phe Asp Asn Gly Ala Leu Asn Lys
    210                 215                 220

Tyr Leu Pro Asp Trp Val Trp Glu Leu Ser Ser Gln Gln Cys Lys Ile
225                 230                 235                 240

Leu Leu Asn Ser Leu Cys Leu Gly Asn Cys Leu Phe Thr Lys Asn Asp
                245                 250                 255

Asp Thr Leu His Tyr Phe Ser Thr Ser Glu Arg Phe Ala Asn Asp Val
            260                 265                 270

Ser Arg Leu Ala Leu His Ala Gly Thr Thr Ser Thr Ile Gln Leu Glu
        275                 280                 285

Ala Ala Pro Ser Asn Leu Tyr Asp Thr Ile Ile Gly Leu Pro Val Glu
    290                 295                 300

Val Asn Thr Thr Leu Trp Arg Val Ile Ile Asn Gln Ser Ser Phe Tyr
305                 310                 315                 320

Ser Tyr Ser Thr Asp Lys Ser Ser Ala Leu Asn Leu Ser Asn Asn Val
                325                 330                 335

Ala Cys Tyr Val Asn Ala Gln Ser Ala Leu Thr Leu Glu Gln Asn Ser
            340                 345                 350

Gln Lys Ile Asn Lys Asn Thr Leu Val Leu Thr Lys Asn Asn Val Lys
        355                 360                 365

Ser Gln Thr Met His Ser Gln Arg Ala Glu Arg Val Asp Thr Ala Leu
    370                 375                 380

Leu Thr Gln Lys Glu Leu Asp Asn Ser Leu Asn His Glu Ile Leu Ile
385                 390                 395                 400

Asn Lys Asn Pro Gly Thr Ser Gln Leu Glu Cys Val Val Asn Pro Glu
                405                 410                 415

Val Asn Thr Ser Thr Asn Asp Arg Phe Val Tyr Tyr Lys Gly Pro
            420                 425                 430

Val Tyr Cys Leu Thr Gly Pro Asn Asn Val Phe Tyr Val Gln Arg Asn
        435                 440                 445

Gly Lys Ala Val Trp Thr Gly Asn
    450                 455

<210> SEQ ID NO 5
<211> LENGTH: 360
<212> TYPE: PRT
<213> ORGANISM: Thermococcus aggregans

<400> SEQUENCE: 5

Cys His Pro Ala Asp Thr Lys Val Ile Val Lys Gly Lys Gly Ile Val

```
              1               5                  10                 15
            Asn Ile Ser Asp Val Lys Glu Gly Asp Tyr Ile Leu Gly Ile Asp Gly
                         20                  25                 30

Trp Gln Arg Val Lys Lys Val Trp Lys Tyr His Tyr Glu Gly Lys Leu
                         35                  40                 45

Ile Asn Ile Asn Gly Leu Lys Cys Thr Pro Asn His Lys Val Pro Val
             50                  55                  60

Val Thr Glu Asn Asp Arg Gln Thr Arg Ile Arg Asp Ser Leu Ala Lys
             65                  70                  75                 80

Ser Phe Leu Ser Gly Lys Val Lys Gly Lys Ile Ile Thr Thr Lys Leu
                             85                  90                 95

Phe Glu Lys Ile Ala Glu Phe Glu Lys Asn Lys Pro Ser Glu Glu Glu
                         100                 105                110

Ile Leu Lys Gly Glu Leu Ser Gly Ile Ile Leu Ala Glu Gly Thr Leu
                         115                 120                125

Leu Arg Lys Asp Ile Glu Tyr Phe Asp Ser Ser Arg Gly Lys Lys Arg
                         130                 135                 140

Ile Ser His Gln Tyr Arg Val Glu Ile Thr Ile Gly Glu Asn Glu Lys
            145                 150                 155                 160

Glu Leu Leu Glu Arg Ile Leu Tyr Ile Phe Asp Lys Leu Phe Gly Ile
                             165                 170                 175

Arg Pro Ser Val Lys Lys Gly Asp Thr Asn Ala Leu Lys Ile Thr
                         180                 185                 190

Thr Ala Lys Lys Ala Val Tyr Leu Gln Ile Glu Glu Leu Leu Lys Asn
                         195                 200                 205

Ile Glu Ser Leu Tyr Ala Pro Ala Val Leu Arg Gly Phe Phe Glu Arg
                210                 215                 220

Asp Ala Thr Val Asn Lys Ile Arg Ser Thr Ile Val Val Thr Gln Gly
            225                 230                 235                 240

Thr Asn Asn Lys Trp Lys Ile Asp Ile Val Ala Lys Leu Leu Asp Ser
                             245                 250                 255

Leu Gly Ile Pro Tyr Ser Arg Tyr Glu Tyr Lys Tyr Ile Glu Asn Gly
                         260                 265                 270

Lys Glu Leu Thr Lys His Ile Leu Glu Ile Thr Gly Arg Asp Gly Leu
                         275                 280                 285

Ile Leu Phe Gln Thr Leu Val Gly Phe Ile Ser Ser Glu Lys Asn Glu
                         290                 295                 300

Ala Leu Glu Lys Ala Ile Glu Val Arg Glu Met Asn Arg Leu Lys Asn
            305                 310                 315                 320

Asn Ser Phe Tyr Asn Leu Ser Thr Phe Glu Val Ser Ser Glu Tyr Tyr
                             325                 330                 335

Lys Gly Glu Val Tyr Asp Leu Thr Leu Glu Gly Asn Pro Tyr Tyr Phe
                         340                 345                 350

Ala Asn Gly Ile Leu Thr His Asn
                         355                 360

<210> SEQ ID NO 6
<211> LENGTH: 360
<212> TYPE: PRT
<213> ORGANISM: Thermococcus fumicolans

<400> SEQUENCE: 6

Cys His Pro Ala Asp Thr Lys Val Ile Val Lys Gly Lys Gly Val Val
            1               5                   10                  15
```

```
Asn Ile Ser Glu Val Arg Glu Gly Asp Tyr Val Leu Gly Ile Asp Gly
             20                  25                  30

Trp Gln Lys Val Gln Arg Val Trp Glu Tyr Asp Tyr Glu Gly Glu Leu
         35                  40                  45

Val Asn Ile Asn Gly Leu Lys Cys Thr Pro Asn His Lys Leu Pro Val
 50                  55                  60

Val Arg Arg Thr Glu Arg Gln Thr Ala Ile Arg Asp Ser Leu Ala Lys
65                  70                  75                  80

Ser Phe Leu Thr Lys Lys Val Lys Gly Lys Leu Ile Thr Thr Pro Leu
                 85                  90                  95

Phe Glu Lys Ile Gly Lys Ile Glu Arg Glu Asp Val Pro Glu Glu Glu
            100                 105                 110

Ile Leu Lys Gly Glu Leu Ala Gly Ile Ile Leu Ala Glu Gly Thr Leu
            115                 120                 125

Leu Arg Lys Asp Val Glu Tyr Phe Asp Ser Ser Arg Gly Lys Lys Arg
    130                 135                 140

Val Ser His Gln Tyr Arg Val Glu Ile Thr Val Gly Ala Gln Glu Glu
145                 150                 155                 160

Asp Phe Gln Arg Arg Ile Val Tyr Ile Phe Glu Arg Leu Phe Gly Val
                165                 170                 175

Thr Pro Ser Val Tyr Arg Lys Lys Asn Thr Asn Ala Ile Thr Phe Lys
            180                 185                 190

Val Ala Lys Lys Glu Val Tyr Leu Arg Val Arg Glu Ile Met Asp Gly
            195                 200                 205

Ile Glu Asn Leu His Ala Pro Ser Val Leu Arg Gly Phe Phe Glu Gly
    210                 215                 220

Asp Gly Ser Val Asn Lys Val Arg Lys Thr Val Val Asn Gln Gly
225                 230                 235                 240

Thr Asn Asn Glu Trp Lys Ile Glu Val Val Ser Lys Leu Leu Asn Lys
                245                 250                 255

Leu Gly Ile Pro His Arg Arg Tyr Thr Tyr Asp Tyr Thr Glu Arg Glu
            260                 265                 270

Lys Thr Met Thr Thr His Ile Leu Glu Ile Ala Gly Arg Asp Gly Leu
            275                 280                 285

Ile Leu Phe Gln Thr Ile Val Gly Phe Ile Ser Thr Glu Lys Asn Met
    290                 295                 300

Ala Leu Glu Glu Ala Ile Arg Asn Arg Glu Val Asn Arg Leu Glu Asn
305                 310                 315                 320

Asn Ala Phe Tyr Thr Leu Ala Asp Phe Thr Ala Lys Thr Glu Tyr Tyr
                325                 330                 335

Lys Gly Lys Val Tyr Asp Leu Thr Leu Glu Gly Thr Pro Tyr Tyr Phe
            340                 345                 350

Ala Asn Gly Ile Leu Thr His Asn
            355                 360

<210> SEQ ID NO 7
<211> LENGTH: 360
<212> TYPE: PRT
<213> ORGANISM: Thermococcus kodakaraensis KOD1

<400> SEQUENCE: 7

Cys His Pro Ala Asp Thr Lys Val Val Lys Gly Lys Gly Ile Ile
1                5                  10                  15

Asn Ile Ser Glu Val Gln Glu Gly Asp Tyr Val Leu Gly Ile Asp Gly
             20                  25                  30
```

Trp Gln Arg Val Arg Lys Val Trp Glu Tyr Asp Tyr Lys Gly Glu Leu
            35                  40                  45

Val Asn Ile Asn Gly Leu Lys Cys Thr Pro Asn His Lys Leu Pro Val
 50                  55                  60

Val Thr Lys Asn Glu Arg Gln Thr Arg Ile Arg Asp Ser Leu Ala Lys
 65                  70                  75                  80

Ser Phe Leu Thr Lys Lys Val Lys Gly Lys Ile Ile Thr Thr Pro Leu
                 85                  90                  95

Phe Tyr Glu Ile Gly Arg Ala Thr Ser Glu Asn Ile Pro Glu Glu Glu
                100                 105                 110

Val Leu Lys Gly Glu Leu Ala Gly Ile Leu Leu Ala Glu Gly Thr Leu
                115                 120                 125

Leu Arg Lys Asp Val Glu Tyr Phe Asp Ser Ser Arg Lys Lys Arg Arg
            130                 135                 140

Ile Ser His Gln Tyr Arg Val Glu Ile Thr Ile Gly Lys Asp Glu Glu
145                 150                 155                 160

Glu Phe Arg Asp Arg Ile Thr Tyr Ile Phe Glu Arg Leu Phe Gly Ile
                165                 170                 175

Thr Pro Ser Ile Ser Glu Lys Lys Gly Thr Asn Ala Val Thr Leu Lys
                180                 185                 190

Val Ala Lys Lys Asn Val Tyr Leu Lys Val Lys Glu Ile Met Asp Asn
            195                 200                 205

Ile Glu Ser Leu His Ala Pro Ser Val Leu Arg Gly Phe Phe Glu Gly
            210                 215                 220

Asp Gly Ser Val Asn Arg Val Arg Arg Ser Ile Val Ala Thr Gln Gly
225                 230                 235                 240

Thr Lys Asn Glu Trp Lys Ile Lys Leu Val Ser Lys Leu Leu Ser Gln
                245                 250                 255

Leu Gly Ile Pro His Gln Thr Tyr Thr Tyr Gln Tyr Gln Glu Asn Gly
                260                 265                 270

Lys Asp Arg Ser Arg Tyr Ile Leu Glu Ile Thr Gly Lys Asp Gly Leu
            275                 280                 285

Ile Leu Phe Gln Thr Leu Ile Gly Phe Ile Ser Glu Arg Lys Asn Ala
            290                 295                 300

Leu Leu Asn Lys Ala Ile Ser Gln Arg Glu Met Asn Asn Leu Glu Asn
305                 310                 315                 320

Asn Gly Phe Tyr Arg Leu Ser Glu Phe Asn Val Ser Thr Glu Tyr Tyr
                325                 330                 335

Glu Gly Lys Val Tyr Asp Leu Thr Leu Gly Thr Pro Tyr Tyr Phe
            340                 345                 350

Ala Asn Gly Ile Leu Thr His Asn
            355                 360

<210> SEQ ID NO 8
<211> LENGTH: 537
<212> TYPE: PRT
<213> ORGANISM: Pyrococcus species GBD

<400> SEQUENCE: 8

Ser Ile Leu Pro Glu Glu Trp Val Pro Leu Ile Lys Asn Gly Lys Val
 1               5                  10                  15

Lys Ile Phe Arg Ile Gly Asp Phe Val Asp Gly Leu Met Lys Ala Asn
             20                  25                  30

Gln Gly Lys Val Lys Lys Thr Gly Asp Thr Glu Val Leu Glu Val Ala

```
                35                  40                  45
Gly Ile His Ala Phe Ser Phe Asp Arg Lys Ser Lys Lys Ala Arg Val
 50                  55                  60

Met Ala Val Lys Ala Val Ile Arg His Arg Tyr Ser Gly Asn Val Tyr
 65                  70                  75                  80

Arg Ile Val Leu Asn Ser Gly Arg Lys Ile Thr Ile Thr Glu Gly His
                 85                  90                  95

Ser Leu Phe Val Tyr Arg Asn Gly Asp Leu Val Glu Ala Thr Gly Glu
                100                 105                 110

Asp Val Lys Ile Gly Asp Leu Leu Ala Val Pro Arg Ser Val Asn Leu
            115                 120                 125

Pro Glu Lys Arg Glu Arg Leu Asn Ile Val Glu Leu Leu Asn Leu
130                 135                 140

Ser Pro Glu Glu Thr Glu Asp Ile Ile Leu Thr Ile Pro Val Lys Gly
145                 150                 155                 160

Arg Lys Asn Phe Phe Lys Gly Met Leu Arg Thr Leu Arg Trp Ile Phe
                165                 170                 175

Gly Glu Glu Lys Arg Val Arg Thr Ala Ser Arg Tyr Leu Arg His Leu
                180                 185                 190

Glu Asn Leu Gly Tyr Ile Arg Leu Arg Lys Ile Gly Tyr Asp Ile Ile
            195                 200                 205

Asp Lys Glu Gly Leu Glu Lys Tyr Arg Thr Leu Tyr Glu Lys Leu Val
210                 215                 220

Asp Val Val Arg Tyr Asn Gly Asn Lys Arg Glu Tyr Leu Val Glu Phe
225                 230                 235                 240

Asn Ala Val Arg Asp Val Ile Ser Leu Met Pro Glu Glu Glu Leu Lys
                245                 250                 255

Glu Trp Arg Ile Gly Thr Arg Asn Gly Phe Arg Met Gly Thr Phe Val
            260                 265                 270

Asp Ile Asp Glu Asp Phe Ala Lys Leu Leu Gly Tyr Tyr Val Ser Glu
            275                 280                 285

Gly Ser Ala Arg Lys Trp Lys Asn Gln Thr Gly Gly Trp Ser Tyr Thr
290                 295                 300

Val Arg Leu Tyr Asn Glu Asn Asp Glu Val Leu Asp Asp Met Glu His
305                 310                 315                 320

Leu Ala Lys Lys Phe Phe Gly Lys Val Lys Arg Gly Lys Asn Tyr Val
                325                 330                 335

Glu Ile Pro Lys Lys Met Ala Tyr Ile Ile Phe Glu Ser Leu Cys Gly
            340                 345                 350

Thr Leu Ala Glu Asn Lys Arg Val Pro Glu Val Ile Phe Thr Ser Ser
            355                 360                 365

Lys Gly Val Arg Trp Ala Phe Leu Glu Gly Tyr Phe Ile Gly Asp Gly
            370                 375                 380

Asp Val His Pro Ser Lys Arg Val Arg Leu Ser Thr Lys Ser Glu Leu
385                 390                 395                 400

Leu Val Asn Gly Leu Val Leu Leu Asn Ser Leu Gly Val Ser Ala
                405                 410                 415

Ile Lys Leu Gly Tyr Asp Ser Gly Val Tyr Arg Val Tyr Val Asn Glu
            420                 425                 430

Glu Leu Lys Phe Thr Glu Tyr Arg Lys Lys Asn Val Tyr His Ser
                435                 440                 445

His Ile Val Pro Lys Asp Ile Leu Lys Glu Thr Phe Gly Lys Val Phe
450                 455                 460
```

```
Gln Lys Asn Ile Ser Tyr Lys Lys Phe Arg Glu Leu Val Glu Asn Gly
465                 470                 475                 480

Lys Leu Asp Arg Glu Lys Ala Lys Arg Ile Glu Trp Leu Leu Asn Gly
                485                 490                 495

Asp Ile Val Leu Asp Arg Val Val Glu Ile Lys Arg Glu Tyr Tyr Asp
            500                 505                 510

Gly Tyr Val Tyr Asp Leu Ser Val Asp Glu Asp Glu Asn Phe Leu Ala
        515                 520                 525

Gly Phe Gly Phe Leu Tyr Ala His Asn
        530                 535

<210> SEQ ID NO 9
<211> LENGTH: 538
<212> TYPE: PRT
<213> ORGANISM: Thermococcus aggregans
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (269)..(269)
<223> OTHER INFORMATION: Xaa can be any naturally occurring amino acid

<400> SEQUENCE: 9

Ser Ile Leu Pro Asn Glu Trp Leu Pro Ile Ile Glu Asn Gly Glu Val
1               5                   10                  15

Lys Phe Val Lys Ile Gly Glu Phe Ile Asp Arg Tyr Met Glu Glu Gln
            20                  25                  30

Lys Asp Lys Val Arg Thr Val Asp Asn Thr Glu Val Leu Glu Val Asp
        35                  40                  45

Asn Ile Phe Ala Phe Ser Leu Asn Lys Glu Ser Lys Ser Glu Ile
    50                  55                  60

Lys Lys Val Lys Ala Leu Ile Arg His Lys Tyr Lys Gly Glu Ala Tyr
65                  70                  75                  80

Glu Val Glu Leu Asn Ser Gly Arg Lys Ile His Ile Thr Arg Gly His
                85                  90                  95

Ser Leu Phe Thr Ile Arg Asn Gly Lys Ile Lys Glu Ile Trp Gly Glu
            100                 105                 110

Glu Val Lys Val Gly Asp Leu Ile Ile Val Pro Lys Lys Val Lys Leu
        115                 120                 125

Asn Glu Lys Glu Ala Val Ile Asn Ile Pro Glu Leu Ile Ser Lys Leu
    130                 135                 140

Pro Asp Glu Asp Thr Ala Asp Val Val Met Thr Thr Pro Val Lys Gly
145                 150                 155                 160

Arg Lys Asn Phe Phe Lys Gly Met Leu Arg Thr Leu Lys Trp Ile Phe
                165                 170                 175

Gly Glu Glu Ser Lys Arg Ile Arg Thr Phe Asn Arg Tyr Leu Phe His
            180                 185                 190

Leu Glu Glu Leu Gly Phe Val Lys Leu Leu Pro Arg Gly Tyr Glu Val
        195                 200                 205

Thr Asp Trp Glu Gly Leu Lys Arg Tyr Arg Gln Leu Tyr Glu Lys Leu
    210                 215                 220

Val Lys Asn Leu Arg Tyr Asn Gly Asn Lys Arg Glu Tyr Leu Val Arg
225                 230                 235                 240

Phe Asn Asp Ile Lys Asp Ser Val Ser Cys Phe Pro Arg Lys Glu Leu
                245                 250                 255
```

-continued

Glu Glu Trp Lys Ile Gly Thr Xaa Lys Gly Phe Arg Xaa Lys Cys Ile
              260                 265                 270

Leu Lys Val Asp Glu Asp Phe Gly Lys Phe Leu Gly Tyr Tyr Val Ser
            275                 280                 285

Glu Gly Tyr Ala Gly Ala Gln Lys Asn Lys Thr Gly Gly Met Ser Tyr
        290                 295                 300

Ser Val Lys Leu Tyr Asn Glu Asn Pro Asn Val Leu Lys Asp Met Lys
305                 310                 315                 320

Asn Ile Ala Glu Lys Phe Phe Gly Lys Val Arg Val Gly Lys Asn Cys
                325                 330                 335

Val Asp Ile Pro Lys Lys Met Ala Tyr Leu Leu Ala Lys Ser Leu Cys
            340                 345                 350

Gly Val Thr Ala Glu Asn Lys Arg Ile Pro Ser Ile Ile Phe Asp Ser
        355                 360                 365

Ser Glu Pro Val Arg Trp Ala Phe Leu Arg Ala Tyr Phe Val Gly Asp
    370                 375                 380

Gly Asp Ile His Pro Ser Lys Arg Leu Arg Leu Ser Thr Lys Ser Glu
385                 390                 395                 400

Leu Leu Ala Asn Gln Leu Val Phe Leu Leu Asn Ser Leu Gly Val Ser
                405                 410                 415

Ser Ile Lys Ile Gly Phe Asp Ser Gly Val Tyr Arg Val Tyr Ile Asn
            420                 425                 430

Glu Asp Leu Pro Phe Leu Gln Thr Ser Arg Gln Lys Asn Thr Tyr Tyr
        435                 440                 445

Pro Asn Leu Ile Pro Lys Glu Val Leu Glu Glu Ile Phe Gly Arg Lys
    450                 455                 460

Phe Gln Lys Asn Ile Thr Phe Glu Lys Phe Lys Glu Leu Ala Asp Ser
465                 470                 475                 480

Gly Lys Leu Asp Lys Arg Lys Val Lys Leu Leu Asp Phe Leu Leu Asn
                485                 490                 495

Gly Asp Ile Val Leu Asp Arg Val Lys Asn Val Glu Lys Arg Glu Tyr
            500                 505                 510

Glu Gly Tyr Val Tyr Asp Leu Ser Val Glu Asp Asn Glu Asn Phe Leu
        515                 520                 525

Val Gly Phe Gly Leu Leu Tyr Ala His Asn
    530                 535

<210> SEQ ID NO 10
<211> LENGTH: 537
<212> TYPE: PRT
<213> ORGANISM: Thermococcus hydrothermalis

<400> SEQUENCE: 10

Ser Leu Leu Pro Glu Glu Trp Ile Pro Leu Val Glu Asn Gly Lys Val
1               5                   10                  15

Arg Leu His Arg Ile Gly Glu Phe Val Asp Lys Leu Met Glu Thr Asp
                20                  25                  30

Ser Glu Leu Val Lys Arg Asn Gly Asp Thr Glu Val Leu Glu Val Arg
            35                  40                  45

Gly Ile Arg Ala Leu Ser Phe Asp Arg Lys Ser Lys Lys Ala Arg Val
        50                  55                  60

Met Pro Val Lys Ala Val Ile Arg His Arg Tyr Ser Gly Asp Val Tyr
65                  70                  75                  80

Glu Ile Val Leu Gly Ser Gly Arg Arg Ile Thr Val Thr Glu Gly His

```
                     85                    90                     95
Ser Leu Phe Ala Tyr Gly Asp Gly Glu Leu Arg Glu Val Thr Gly Gly
                100                   105                   110

Glu Ile Lys Ala Gly Asp Leu Leu Ala Val Pro Arg Arg Val Asn Leu
            115                   120                   125

Pro Glu Lys Lys Glu Arg Leu Asn Leu Val Glu Leu Leu Arg Arg Leu
        130                   135                   140

Pro Glu Glu Glu Thr Gly Asp Ile Ile Leu Thr Ile Pro Val Lys Gly
145                   150                   155                   160

Arg Lys Asn Phe Phe Lys Gly Met Leu Arg Thr Leu Arg Trp Ile Ser
                165                   170                   175

Gly Glu Glu Lys Arg Pro Arg Thr Ala Arg Arg Tyr Leu Glu His Leu
            180                   185                   190

Glu Gly Leu Gly Tyr Val Arg Leu Lys Lys Ile Gly Tyr Glu Val Thr
        195                   200                   205

Asp Arg Glu Gly Leu Glu Arg Tyr Arg Lys Leu Tyr Glu Arg Leu Val
    210                   215                   220

Glu Ala Val Arg Tyr Asn Gly Asn Lys Arg Glu Tyr Leu Val Glu Phe
225                   230                   235                   240

Asn Ala Val Arg Asp Val Ile Ala Leu Met Pro Glu Glu Glu Leu Arg
                245                   250                   255

Asp Trp Leu Val Gly Thr Arg Asn Gly Phe Arg Met Arg Pro Phe Val
            260                   265                   270

Glu Ile Glu Glu Asp Phe Ala Lys Leu Leu Gly Tyr Tyr Val Ser Glu
        275                   280                   285

Gly Asn Ala Arg Lys Trp Arg Asn Gln Lys Asn Gly Trp Ser Tyr Thr
    290                   295                   300

Val Lys Leu Tyr Asn Glu Asn Gln Arg Val Leu Asp Asp Met Glu Ser
305                   310                   315                   320

Leu Ala Glu Arg Phe Phe Gly Arg Val Lys Arg Gly Lys Asn Tyr Ile
                325                   330                   335

Glu Ile Pro Arg Lys Met Ala Tyr Ile Ile Phe Glu Asn Leu Cys Gly
            340                   345                   350

Thr Leu Ala Glu Asn Lys Arg Val Pro Glu Ala Ile Phe Thr Ser Pro
        355                   360                   365

Glu Ser Val Arg Trp Ala Phe Ile Glu Gly Tyr Phe Ile Gly Asp Gly
    370                   375                   380

Asp Val His Pro Ser Lys Arg Val Arg Leu Ser Thr Lys Ser Glu Leu
385                   390                   395                   400

Leu Val Asn Gly Leu Val Leu Leu Asn Ser Leu Gly Val Ser Ala
                405                   410                   415

Ile Lys Ile Arg His Asp Ser Gly Val Tyr Arg Val Tyr Val Asn Glu
            420                   425                   430

Glu Leu Pro Phe Thr Asp Tyr Arg Lys Lys Asn Ala Tyr Tyr Ser
        435                   440                   445

His Val Ile Pro Lys Glu Ile Leu Glu Glu Thr Phe Gly Lys Val Phe
    450                   455                   460

Gln Arg Ser Val Ser Tyr Glu Lys Phe Arg Glu Leu Val Lys Ser Glu
465                   470                   475                   480

Lys Leu Asp Gly Glu Lys Ala Lys Arg Ile Glu Trp Leu Leu Asn Gly
                485                   490                   495

Asp Val Val Leu Asp Lys Val Leu Glu Val Lys Lys Arg Pro Tyr Glu
            500                   505                   510
```

```
Gly Tyr Val Tyr Asp Leu Ser Val Glu Glu Asp Glu Asn Phe Leu Ala
        515                 520                 525

Gly Phe Gly Leu Leu Tyr Ala His Asn
    530                 535

<210> SEQ ID NO 11
<211> LENGTH: 536
<212> TYPE: PRT
<213> ORGANISM: Thermococcus kodakaraensis KOD1

<400> SEQUENCE: 11

Ser Ile Leu Pro Glu Glu Trp Leu Pro Val Leu Glu Glu Gly Glu Val
1               5                   10                  15

His Phe Val Arg Ile Gly Glu Leu Ile Asp Arg Met Met Glu Glu Asn
            20                  25                  30

Ala Gly Lys Val Lys Arg Glu Gly Glu Thr Glu Val Leu Glu Val Ser
        35                  40                  45

Gly Leu Glu Val Pro Ser Phe Asn Arg Arg Thr Asn Lys Ala Glu Leu
    50                  55                  60

Lys Arg Val Lys Ala Leu Ile Arg His Asp Tyr Ser Gly Lys Val Tyr
65                  70                  75                  80

Thr Ile Arg Leu Lys Ser Gly Arg Arg Ile Lys Ile Thr Ser Gly His
                85                  90                  95

Ser Leu Phe Ser Val Arg Asn Gly Glu Leu Val Glu Val Thr Gly Asp
            100                 105                 110

Glu Leu Lys Pro Gly Asp Leu Val Ala Val Pro Arg Arg Leu Glu Leu
        115                 120                 125

Pro Glu Arg Asn His Val Leu Asn Leu Val Glu Leu Leu Leu Gly Thr
    130                 135                 140

Pro Glu Glu Glu Thr Leu Asp Ile Val Met Thr Ile Pro Val Lys Gly
145                 150                 155                 160

Lys Lys Asn Phe Phe Lys Gly Met Leu Arg Thr Leu Arg Trp Ile Phe
                165                 170                 175

Gly Glu Glu Lys Arg Pro Arg Thr Ala Arg Arg Tyr Leu Arg His Leu
            180                 185                 190

Glu Asp Leu Gly Tyr Val Arg Leu Lys Lys Ile Gly Tyr Glu Val Leu
        195                 200                 205

Asp Trp Asp Ser Leu Lys Asn Tyr Arg Arg Leu Tyr Glu Ala Leu Val
    210                 215                 220

Glu Asn Val Arg Tyr Asn Gly Asn Lys Arg Glu Tyr Leu Val Glu Phe
225                 230                 235                 240

Asn Ser Ile Arg Asp Ala Val Gly Ile Met Pro Leu Lys Glu Leu Lys
                245                 250                 255

Glu Trp Lys Ile Gly Thr Leu Asn Gly Phe Arg Met Arg Lys Leu Ile
            260                 265                 270

Glu Val Asp Glu Ser Leu Ala Lys Leu Leu Gly Tyr Tyr Val Ser Glu
        275                 280                 285

Gly Tyr Ala Arg Lys Gln Arg Asn Pro Lys Asn Gly Trp Ser Tyr Ser
    290                 295                 300

Val Lys Leu Tyr Asn Glu Asp Pro Glu Val Leu Asp Asp Met Glu Arg
305                 310                 315                 320

Leu Ala Ser Arg Phe Phe Gly Lys Val Arg Arg Gly Arg Asn Tyr Val
                325                 330                 335

Glu Ile Pro Lys Lys Ile Gly Tyr Leu Leu Phe Glu Asn Met Cys Gly
```

```
                   340                 345                 350
Val Leu Ala Glu Asn Lys Arg Ile Pro Glu Phe Val Phe Thr Ser Pro
            355                 360                 365

Lys Gly Val Arg Leu Ala Phe Leu Glu Gly Tyr Ser Ser Ala Met Ala
        370                 375                 380

Thr Ser Thr Glu Gln Glu Thr Gln Ala Leu Asn Glu Lys Arg Ala Leu
385                 390                 395                 400

Ala Asn Gln Leu Val Leu Leu Asn Ser Val Gly Val Ser Ala Val
            405                 410                 415

Lys Leu Gly His Asp Ser Gly Val Tyr Arg Val Tyr Ile Asn Glu Glu
        420                 425                 430

Leu Pro Phe Val Lys Leu Asp Lys Lys Asn Ala Tyr Tyr Ser His
            435                 440                 445

Val Ile Pro Lys Glu Val Leu Ser Glu Val Phe Gly Lys Val Phe Gln
        450                 455                 460

Lys Asn Val Ser Pro Gln Thr Phe Arg Lys Met Val Glu Asp Gly Arg
465                 470                 475                 480

Leu Asp Pro Glu Lys Ala Gln Arg Leu Ser Trp Leu Ile Glu Gly Asp
            485                 490                 495

Val Val Leu Asp Arg Val Glu Ser Val Asp Val Glu Asp Tyr Asp Gly
        500                 505                 510

Tyr Val Tyr Asp Leu Ser Val Glu Asp Asn Glu Asn Phe Leu Val Gly
            515                 520                 525

Phe Gly Leu Val Tyr Ala His Asn
        530                 535

<210> SEQ ID NO 12
<211> LENGTH: 538
<212> TYPE: PRT
<213> ORGANISM: Thermococcus litoralis

<400> SEQUENCE: 12

Ser Ile Leu Pro Asn Glu Trp Leu Pro Ile Ile Glu Asn Gly Glu Ile
1               5                   10                  15

Lys Phe Val Lys Ile Gly Glu Phe Ile Asn Ser Tyr Met Glu Lys Gln
            20                  25                  30

Lys Glu Asn Val Lys Thr Val Glu Asn Thr Glu Val Leu Glu Val Asn
        35                  40                  45

Asn Leu Phe Ala Phe Ser Phe Asn Lys Lys Ile Lys Glu Ser Glu Val
    50                  55                  60

Lys Lys Val Lys Ala Leu Ile Arg His Lys Tyr Lys Gly Lys Ala Tyr
65                  70                  75                  80

Glu Ile Gln Leu Ser Ser Gly Arg Lys Ile Asn Ile Thr Ala Gly His
                85                  90                  95

Ser Leu Phe Thr Val Arg Asn Gly Glu Ile Lys Glu Val Ser Gly Asp
            100                 105                 110

Gly Ile Lys Glu Gly Asp Leu Ile Val Ala Pro Lys Lys Ile Lys Leu
        115                 120                 125

Asn Glu Lys Gly Val Ser Ile Asn Ile Pro Glu Leu Ile Ser Asp Leu
    130                 135                 140

Ser Glu Glu Glu Thr Ala Asp Ile Val Met Thr Ile Ser Ala Lys Gly
145                 150                 155                 160

Arg Lys Asn Phe Phe Lys Gly Met Leu Arg Thr Leu Arg Trp Met Phe
                165                 170                 175
```

```
Gly Glu Glu Asn Arg Arg Ile Arg Thr Phe Asn Arg Tyr Leu Phe His
            180                 185                 190

Leu Glu Lys Leu Gly Leu Ile Lys Leu Leu Pro Arg Gly Tyr Glu Val
        195                 200                 205

Thr Asp Trp Glu Arg Leu Lys Lys Tyr Lys Gln Leu Tyr Glu Lys Leu
    210                 215                 220

Ala Gly Ser Val Lys Tyr Asn Gly Asn Lys Arg Glu Tyr Leu Val Met
225                 230                 235                 240

Phe Asn Glu Ile Lys Asp Phe Ile Ser Tyr Phe Pro Gln Lys Glu Leu
                245                 250                 255

Glu Glu Trp Lys Ile Gly Thr Leu Asn Gly Phe Arg Thr Asn Cys Ile
            260                 265                 270

Leu Lys Val Asp Glu Asp Phe Gly Lys Leu Gly Tyr Tyr Val Ser
        275                 280                 285

Glu Gly Tyr Ala Gly Ala Gln Lys Asn Lys Thr Gly Gly Ile Ser Tyr
290                 295                 300

Ser Val Lys Leu Tyr Asn Glu Asp Pro Asn Val Leu Glu Ser Met Lys
305                 310                 315                 320

Asn Val Ala Glu Lys Phe Phe Gly Lys Val Arg Val Asp Arg Asn Cys
                325                 330                 335

Val Ser Ile Ser Lys Lys Met Ala Tyr Leu Val Met Lys Cys Leu Cys
            340                 345                 350

Gly Ala Leu Ala Glu Asn Lys Arg Ile Pro Ser Val Ile Leu Thr Ser
        355                 360                 365

Pro Glu Pro Val Arg Trp Ser Phe Leu Glu Ala Tyr Phe Thr Gly Asp
    370                 375                 380

Gly Asp Ile His Pro Ser Lys Arg Phe Arg Leu Ser Thr Lys Ser Glu
385                 390                 395                 400

Leu Leu Ala Asn Gln Leu Val Phe Leu Leu Asn Ser Leu Gly Ile Ser
                405                 410                 415

Ser Val Lys Ile Gly Phe Asp Ser Gly Val Tyr Arg Val Tyr Ile Asn
            420                 425                 430

Glu Asp Leu Gln Phe Pro Gln Thr Ser Arg Glu Lys Asn Thr Tyr Tyr
        435                 440                 445

Ser Asn Leu Ile Pro Lys Glu Ile Leu Arg Asp Val Phe Gly Lys Glu
    450                 455                 460

Phe Gln Lys Asn Met Thr Phe Lys Lys Phe Lys Glu Leu Val Asp Ser
465                 470                 475                 480

Gly Lys Leu Asn Arg Glu Lys Ala Lys Leu Leu Glu Phe Phe Ile Asn
                485                 490                 495

Gly Asp Ile Val Leu Asp Arg Val Lys Ser Val Lys Glu Lys Asp Tyr
            500                 505                 510

Glu Gly Tyr Val Tyr Asp Leu Ser Val Glu Asp Asn Glu Asn Phe Leu
        515                 520                 525

Val Gly Phe Gly Leu Leu Tyr Ala His Asn
    530                 535

<210> SEQ ID NO 13
<211> LENGTH: 537
<212> TYPE: PRT
<213> ORGANISM: Thermococcus marinus

<400> SEQUENCE: 13

Ser Leu Leu Pro Glu Glu Trp Ile Pro Val Val Glu Asn Gly Lys Val
1               5                   10                  15
```

-continued

Lys Leu Val Arg Ile Gly Glu Phe Val Asp Gly Leu Met Lys Asp Glu
            20                  25                  30

Lys Gly Arg Ala Lys Arg Asp Gly Asn Thr Glu Val Leu Glu Val Ser
        35                  40                  45

Gly Ile Arg Ala Val Ser Phe Asp Arg Lys Thr Lys Lys Ala Arg Leu
    50                  55                  60

Met Pro Val Lys Ala Val Ile Arg His Arg Tyr Ser Gly Asp Val Tyr
65                  70                  75                  80

Lys Ile Thr Leu Ser Ser Gly Arg Lys Ile Thr Val Thr Lys Gly His
                85                  90                  95

Ser Leu Phe Ala Tyr Arg Asn Gly Glu Leu Val Glu Val Pro Gly Glu
            100                 105                 110

Glu Ile Lys Ala Gly Asp Leu Leu Ala Val Pro Arg Arg Val His Leu
        115                 120                 125

Pro Glu Arg Tyr Glu Arg Leu Asp Leu Val Glu Leu Leu Lys Leu
130                 135                 140

Pro Glu Glu Glu Thr Glu Asp Ile Ile Leu Thr Ile Pro Ala Lys Gly
145                 150                 155                 160

Arg Lys Asn Phe Phe Lys Gly Met Leu Arg Thr Leu Arg Trp Ile Phe
                165                 170                 175

Gly Glu Glu Lys Arg Pro Arg Thr Ala Arg Arg Tyr Leu Arg His Leu
            180                 185                 190

Glu Gly Leu Gly Tyr Val Lys Leu Arg Lys Ile Gly Tyr Glu Ile Ile
        195                 200                 205

Asp Arg Glu Gly Leu Lys Arg Tyr Arg Lys Leu Tyr Glu Arg Leu Ala
    210                 215                 220

Glu Val Val Arg Tyr Asn Gly Asn Lys Arg Glu Tyr Leu Ile Glu Phe
225                 230                 235                 240

Asn Ala Val Arg Asp Val Ile Ser Leu Met Pro Glu Glu Glu Leu Asn
                245                 250                 255

Glu Trp Gln Val Gly Thr Arg Asn Gly Phe Arg Ile Lys Pro Leu Ile
            260                 265                 270

Glu Val Asp Glu Asp Phe Ala Lys Leu Leu Gly Tyr Tyr Val Ser Glu
        275                 280                 285

Gly Tyr Ala Gly Lys Gln Arg Asn Gln Lys Asn Gly Trp Ser Tyr Thr
    290                 295                 300

Val Lys Leu Tyr Asn Glu Asp Glu Arg Val Leu Asp Asp Met Glu Asn
305                 310                 315                 320

Leu Ala Arg Glu Phe Phe Gly Lys Ala Arg Arg Gly Arg Asn Tyr Val
                325                 330                 335

Glu Ile Pro Arg Lys Met Ala Tyr Ile Phe Glu Ser Leu Cys Gly
            340                 345                 350

Thr Leu Ala Glu Asn Lys Arg Val Pro Glu Val Ile Phe Thr Ser Pro
        355                 360                 365

Glu Asp Val Arg Trp Ala Phe Leu Glu Gly Tyr Phe Ile Gly Asp Gly
    370                 375                 380

Asp Val His Pro Ser Lys Arg Val Arg Leu Ser Thr Lys Ser Glu Leu
385                 390                 395                 400

Leu Ala Asn Gly Leu Val Leu Leu Asn Ser Leu Gly Val Ser Ala
                405                 410                 415

Val Lys Leu Gly His Asp Ser Gly Val Tyr Arg Val Tyr Val Asn Glu
            420                 425                 430

```
Glu Leu Pro Phe Thr Gly Tyr Lys Lys Lys Asn Ala Tyr Tyr Ser
        435                 440                 445

His Val Ile Pro Lys Glu Val Leu Glu Thr Phe Gly Lys Val Phe
    450                 455                 460

Gln Arg Asn Met Ser Tyr Glu Lys Phe Gln Glu Leu Val Ser Glu
465                 470                 475                 480

Lys Leu Glu Gly Glu Lys Ala Lys Arg Ile Glu Trp Leu Ile Ser Gly
            485                 490                 495

Asp Ile Ile Leu Asp Lys Val Val Val Lys Lys Met Asn Tyr Glu
                500                 505                 510

Gly Tyr Val Tyr Asp Leu Ser Val Glu Glu Asp Glu Asn Phe Leu Ala
        515                 520                 525

Gly Phe Gly Phe Leu Tyr Ala His Asn
    530                 535

<210> SEQ ID NO 14
<211> LENGTH: 535
<212> TYPE: PRT
<213> ORGANISM: Thermococcus species GE8

<400> SEQUENCE: 14

Ser Ile Leu Pro Asp Glu Trp Leu Pro Leu Val Asn Gly Arg Leu
1               5                   10                  15

Lys Leu Val Arg Ile Gly Asp Phe Val Asp Asn Thr Met Lys Lys Gly
                20                  25                  30

Gln Pro Leu Glu Asn Asp Gly Thr Glu Val Leu Glu Val Ser Gly Ile
            35                  40                  45

Glu Ala Ile Ser Phe Asn Arg Lys Thr Lys Ile Ala Glu Ile Lys Pro
50                  55                  60

Val Lys Ala Leu Ile Arg His Arg Tyr Arg Gly Lys Val Tyr Asp Ile
65                  70                  75                  80

Lys Leu Ser Ser Gly Arg Asn Ile Lys Val Thr Glu Gly His Ser Leu
                85                  90                  95

Phe Ala Phe Arg Asp Gly Glu Leu Val Glu Val Thr Gly Gly Glu Ile
            100                 105                 110

Lys Pro Gly Asp Phe Ile Ala Val Pro Arg Arg Val Asn Leu Pro Glu
        115                 120                 125

Arg His Glu Arg Ile Asn Leu Ile Glu Ile Leu Leu Gly Leu Pro Pro
    130                 135                 140

Glu Glu Thr Ser Asp Ile Val Leu Thr Ile Pro Val Lys Gly Arg Lys
145                 150                 155                 160

Asn Phe Phe Lys Gly Met Leu Arg Thr Leu Arg Trp Ile Phe Glu Glu
                165                 170                 175

Glu Gln Arg Pro Arg Thr Ala Arg Arg Tyr Leu Glu His Leu Gln Lys
            180                 185                 190

Leu Gly Tyr Val Lys Leu Met Lys Arg Ala Tyr Glu Ile Val Asn Lys
        195                 200                 205

Glu Ala Leu Arg Asn Tyr Arg Lys Leu Tyr Glu Val Leu Ala Glu Arg
    210                 215                 220

Val Lys Tyr Asn Gly Asn Lys Arg Glu Tyr Leu Val His Phe Asn Asp
225                 230                 235                 240

Leu Arg Asn Glu Ile Lys Phe Met Pro Asp Glu Glu Leu Glu Glu Trp
                245                 250                 255

Lys Val Gly Thr Leu Asn Gly Phe Arg Met Glu Pro Phe Ile Glu Val
            260                 265                 270
```

```
Gly Glu Asp Phe Ala Lys Leu Leu Gly Tyr Tyr Val Ser Glu Gly Tyr
            275                 280                 285

Ala Arg Lys Gln Arg Asn Gln Lys Asn Gly Trp Ser Tyr Ser Val Lys
    290                 295                 300

Ile Tyr Asn Asn Asp Gln Arg Val Leu Asp Met Glu Lys Leu Ala
305                 310                 315                 320

Ser Lys Phe Phe Gly Arg Val Arg Arg Gly Lys Asn Tyr Val Glu Ile
                325                 330                 335

Ser Arg Lys Met Ala Tyr Val Leu Phe Glu Ser Leu Cys Gly Thr Leu
            340                 345                 350

Ala Glu Asn Lys Arg Val Pro Glu Val Ile Phe Thr Ser Pro Glu Ser
            355                 360                 365

Val Arg Trp Ala Phe Phe Glu Gly Tyr Phe Ile Gly Asp Gly Asp Leu
    370                 375                 380

His Pro Ser Lys Arg Val Arg Leu Ser Thr Lys Ser Glu Glu Leu Val
385                 390                 395                 400

Asn Gly Leu Val Val Leu Leu Asn Ser Leu Gly Ile Ser Ala Ile Lys
                405                 410                 415

Ile Arg Phe Asp Ser Gly Val Tyr Arg Val Leu Val Asn Glu Glu Leu
            420                 425                 430

Pro Phe Leu Gly Asn Arg Lys Arg Lys Asn Ala Tyr Tyr Ser His Val
    435                 440                 445

Ile Pro Lys Glu Ile Leu Glu Glu Thr Phe Gly Lys Gln Phe Gln Lys
450                 455                 460

Asn Met Ser Pro Ala Lys Leu Asn Glu Lys Val Glu Lys Gly Glu Leu
465                 470                 475                 480

Asp Ala Gly Lys Ala Arg Arg Ile Ala Trp Leu Leu Glu Gly Asp Ile
                485                 490                 495

Val Leu Asp Arg Val Glu Lys Val Thr Val Glu Asp Tyr Glu Gly Tyr
            500                 505                 510

Val Tyr Asp Leu Ser Val Glu Glu Asn Glu Asn Phe Leu Ala Gly Phe
    515                 520                 525

Gly Met Leu Tyr Ala His Asn
    530                 535

<210> SEQ ID NO 15
<211> LENGTH: 536
<212> TYPE: PRT
<213> ORGANISM: Thermococcus thioreducens

<400> SEQUENCE: 15

Ser Leu Leu Pro Glu Glu Trp Val Pro Val Ile Val Gly Asp Glu Val
1               5                   10                  15

Lys Pro Val Arg Ile Gly Glu Phe Val Asp Ala Leu Met Lys Thr Asp
            20                  25                  30

Ser Glu Leu Val Arg Arg Asp Gly Asp Thr Glu Val Leu Glu Val Lys
        35                  40                  45

Glu Ile Arg Ala Leu Ser Phe Asn Arg Lys Ser Lys Lys Ala Arg Thr
    50                  55                  60

Met Pro Val Lys Ala Val Ile Arg His Arg Tyr Ala Gly Asp Val Tyr
65                  70                  75                  80

Glu Ile Val Leu Ser Ser Gly Arg Arg Ile Arg Val Thr Thr Gly His
                85                  90                  95

Ser Leu Phe Ala Tyr Arg Asn Gly Glu Leu Val Glu Ile Thr Gly Gly
```

-continued

```
                100                 105                 110
Glu Val Lys Pro Gly Asp Leu Leu Val Pro Lys Arg Val Ser Leu Pro
        115                 120                 125

Glu Arg Lys Glu Arg Leu Asp Ile Val Glu Leu Leu Lys Leu Pro
        130                 135                 140

Glu Ser Glu Thr Glu Asp Ile Val Met Thr Ile Pro Val Lys Gly Arg
145                 150                 155                 160

Lys Asn Phe Phe Ser Gly Met Leu Arg Thr Leu Arg Trp Ile Phe Gly
                165                 170                 175

Glu Glu Lys Arg Leu Arg Thr Ala Arg Arg Tyr Leu Glu His Leu Glu
        180                 185                 190

Arg Leu Gly Tyr Val Lys Leu Arg Lys Ile Gly Tyr Glu Val Ile Asp
        195                 200                 205

Gly Gly Gly Leu Glu Ser Tyr Arg Lys Leu Tyr Glu Lys Leu Ala Gln
        210                 215                 220

Thr Val Arg Tyr Asn Gly Asn Arg Arg Glu Tyr Leu Val Asp Phe Asn
225                 230                 235                 240

Ala Ile Arg Asp Val Ile Pro Leu Met Pro Val Glu Leu Lys Glu
                245                 250                 255

Trp Leu Ile Gly Thr Arg Asn Gly Phe Arg Met Arg Pro Phe Ile Asp
                260                 265                 270

Val Asn Glu Asp Phe Ala Lys Leu Leu Gly Tyr Tyr Val Ser Glu Gly
                275                 280                 285

Asn Ala Arg Lys Trp Lys Asn His Thr Gly Gly Trp Ser Tyr Ser Val
        290                 295                 300

Lys Leu Tyr Asn Glu Asp Glu Ser Val Leu Asp Asp Met Glu Arg Leu
305                 310                 315                 320

Ala Ser Lys Phe Phe Gly Arg Thr Arg Arg Gly Lys Asn Tyr Val Glu
                325                 330                 335

Ile Pro Arg Lys Met Ala Tyr Ile Ile Phe Glu Gly Leu Cys Gly Val
                340                 345                 350

Leu Ala Glu Asn Lys Arg Val Pro Glu Val Val Phe Thr Ser Pro Glu
        355                 360                 365

Asn Val Arg Trp Ala Phe Leu Gly Gly Tyr Phe Ile Gly Asp Gly Asp
        370                 375                 380

Val His Pro Gly Lys Arg Val Arg Leu Ser Thr Lys Ser Glu Leu Leu
385                 390                 395                 400

Val Asn Gly Leu Val Leu Leu Asn Ser Leu Gly Ile Ser Ala Ile
                405                 410                 415

Lys Ile Arg His Asp Ser Gly Val His Arg Val Tyr Val Asn Glu Glu
                420                 425                 430

Leu Pro Phe Thr Glu Tyr Arg Lys Lys Asn Val Tyr Tyr Ser His
        435                 440                 445

Val Ile Pro Lys Glu Val Leu Glu Glu Thr Phe Arg Lys Val Phe Gln
        450                 455                 460

Lys Asn Met Ser Arg Glu Lys Phe Arg Glu Leu Val Glu Ser Gly Lys
465                 470                 475                 480

Leu Asp Glu Glu Arg Ala Lys Arg Ile Glu Trp Leu Leu Asp Gly Asp
                485                 490                 495

Ile Ala Leu Asp Lys Val Val Glu Val Lys Arg Glu His Tyr Asp Gly
                500                 505                 510

Tyr Val Tyr Asp Leu Ser Val Glu Glu Asp Glu Asn Phe Leu Ala Gly
                515                 520                 525
```

```
Phe Gly Leu Leu Tyr Ala His Asn
    530                 535
```

<210> SEQ ID NO 16
<211> LENGTH: 157
<212> TYPE: PRT
<213> ORGANISM: Thermococcus aggregans

<400> SEQUENCE: 16

```
Ser Val Thr Gly Asp Thr Glu Ile Ile Val Lys Arg Asn Gly Arg Ile
1               5                   10                  15

Glu Phe Val Pro Ile Glu Lys Leu Phe Glu Arg Val Asp Tyr Arg Ile
            20                  25                  30

Gly Glu Lys Glu Tyr Cys Ile Leu Glu Asp Val Glu Ala Leu Thr Leu
        35                  40                  45

Asp Asn Arg Gly Lys Leu Ile Trp Lys Lys Val Pro Tyr Val Met Arg
    50                  55                  60

His Arg Ala Lys Lys Val Tyr Arg Ile Trp Ile Thr Asn Ser Trp
65                  70                  75                  80

Tyr Ile Asp Val Thr Glu Asp His Ser Leu Ile Val Ala Glu Asp Gly
                85                  90                  95

Leu Lys Glu Ala Arg Pro Met Glu Ile Glu Gly Lys Ser Leu Ile Ala
            100                 105                 110

Thr Lys Asp Asp Leu Ser Gly Val Glu Tyr Ile Lys Pro His Ala Ile
        115                 120                 125

Glu Glu Ile Ser Tyr Asn Gly Tyr Val Tyr Asp Ile Glu Val Glu Gly
    130                 135                 140

Thr His Arg Phe Phe Ala Asn Gly Ile Leu Val His Asn
145                 150                 155
```

<210> SEQ ID NO 17
<211> LENGTH: 389
<212> TYPE: PRT
<213> ORGANISM: Thermococcus fumicolans

<400> SEQUENCE: 17

```
Ser Val Thr Gly Asp Thr Glu Val Thr Ile Arg Arg Asn Gly Arg Ile
1               5                   10                  15

Glu Phe Val Pro Ile Glu Lys Leu Phe Glu Arg Val Asp His Arg Val
            20                  25                  30

Gly Glu Lys Glu Tyr Cys Val Leu Gly Gly Val Glu Ala Leu Thr Leu
        35                  40                  45

Asp Asn Arg Gly Arg Leu Val Trp Lys Lys Val Pro Tyr Val Met Arg
    50                  55                  60

His Lys Thr Asp Lys Arg Ile Tyr Arg Val Trp Phe Thr Asn Ser Trp
65                  70                  75                  80

Tyr Leu Asp Val Thr Glu Asp His Ser Leu Ile Gly Tyr Leu Asn Thr
                85                  90                  95

Ser Lys Val Lys Pro Gly Lys Pro Leu Lys Glu Arg Leu Val Glu Val
            100                 105                 110

Lys Pro Glu Glu Leu Gly Gly Lys Val Lys Ser Leu Ile Thr Pro Asn
        115                 120                 125

Arg Pro Ile Ala Arg Thr Ile Lys Ala Asn Pro Ile Ala Val Lys Leu
    130                 135                 140

Trp Glu Leu Ile Gly Leu Leu Val Gly Asp Gly Asn Trp Gly Gly Gln
145                 150                 155                 160
```

```
Ser Asn Trp Ala Lys Tyr Tyr Val Gly Leu Ser Cys Gly Leu Asp Lys
                165                 170                 175

Ala Glu Ile Glu Arg Lys Val Leu Asn Pro Leu Arg Glu Ala Ser Val
            180                 185                 190

Ile Ser Asn Tyr Tyr Asp Lys Ser Lys Lys Gly Asp Val Ser Ile Leu
            195                 200                 205

Ser Lys Trp Leu Ala Gly Phe Met Val Lys Tyr Phe Lys Asp Glu Asn
            210                 215                 220

Gly Asn Lys Ala Ile Pro Ser Phe Met Phe Asn Leu Pro Arg Glu Tyr
225                 230                 235                 240

Ile Glu Ala Phe Leu Arg Gly Leu Phe Ser Ala Asp Gly Thr Val Ser
                245                 250                 255

Leu Arg Arg Gly Ile Pro Glu Ile Arg Leu Thr Ser Val Asn Arg Glu
            260                 265                 270

Leu Ser Asp Ala Val Arg Lys Leu Leu Trp Leu Val Gly Val Ser Asn
            275                 280                 285

Ser Leu Phe Thr Glu Thr Lys Pro Asn Arg Tyr Leu Glu Lys Glu Ser
            290                 295                 300

Gly Thr His Ser Ile His Val Arg Ile Lys Asn Lys His Arg Phe Ala
305                 310                 315                 320

Asp Arg Ile Gly Phe Leu Ile Asp Arg Lys Ser Thr Lys Leu Ser Glu
                325                 330                 335

Asn Leu Gly Gly His Thr Asn Lys Lys Arg Ala Tyr Lys Tyr Asp Phe
            340                 345                 350

Asp Leu Val Tyr Pro Arg Lys Ile Glu Glu Ile Thr Tyr Asp Gly Tyr
            355                 360                 365

Val Tyr Asp Ile Glu Val Glu Gly Thr His Arg Phe Phe Ala Asn Gly
            370                 375                 380

Ile Leu Val His Asn
385

<210> SEQ ID NO 18
<211> LENGTH: 389
<212> TYPE: PRT
<213> ORGANISM: Thermococcus hydrothermalis

<400> SEQUENCE: 18

Ser Val Thr Gly Glu Thr Glu Ile Ile Ile Lys Arg Asn Gly Lys Val
1               5                   10                  15

Glu Phe Val Ala Ile Glu Glu Leu Phe Gln Arg Val Asp Tyr Arg Ile
            20                  25                  30

Gly Glu Lys Glu Tyr Cys Val Leu Glu Gly Val Glu Ala Leu Thr Leu
            35                  40                  45

Asp Asn Arg Gly Arg Leu Val Trp Lys Ser Val Pro Tyr Val Met Arg
50                  55                  60

His Arg Thr Asn Lys Arg Ile Tyr Arg Val Trp Phe Thr Asn Ser Trp
65                  70                  75                  80

Tyr Leu Asp Val Thr Glu Asp His Ser Leu Ile Gly Tyr Met Asn Thr
                85                  90                  95

Ser Lys Val Lys Pro Gly Lys Pro Leu Lys Glu Arg Leu Glu Val
            100                 105                 110

Lys Pro Gly Glu Leu Gly Glu Ser Val Lys Ser Leu Ile Thr Pro Asn
            115                 120                 125

Arg Ala Ile Ala His Gly Ile Arg Val Asn Pro Ile Ala Val Lys Leu
```

```
                130             135             140
Trp Glu Leu Ile Gly Leu Leu Val Gly Asp Gly Asn Trp Gly Gly Gln
145                 150                 155                 160

Ser Asn Trp Ala Lys Tyr Asn Val Gly Leu Ser Leu Gly Leu Asp Lys
                165                 170                 175

Glu Glu Ile Glu Lys Ile Leu Lys Pro Leu Lys Asn Thr Gly Ile
            180                 185                 190

Ile Ser Asn Tyr Tyr Asp Lys Ser Lys Gly Asp Val Ser Ile Leu
        195                 200                 205

Ser Lys Trp Leu Ala Arg Phe Met Val Arg Tyr Phe Lys Asp Glu Ser
210                 215                 220

Gly Ser Lys Arg Ile Pro Glu Phe Met Phe Asn Leu Pro Arg Glu Tyr
225                 230                 235                 240

Ile Glu Ala Phe Leu Arg Gly Leu Phe Ser Ala Asp Gly Thr Val Ser
                245                 250                 255

Leu Arg Lys Gly Val Pro Glu Val Arg Leu Thr Ser Val Asn Pro Glu
            260                 265                 270

Leu Ser Ser Ser Val Arg Lys Leu Leu Trp Leu Val Gly Val Ser Asn
        275                 280                 285

Ser Met Phe Val Glu Thr Asn Pro Asn Arg Tyr Leu Gly Lys Glu Ser
290                 295                 300

Gly Thr His Ser Val His Val Arg Ile Lys Asp Lys His Arg Phe Ala
305                 310                 315                 320

Glu Arg Ile Gly Phe Leu Leu Asp Arg Lys Ala Thr Lys Leu Ser Glu
                325                 330                 335

Asn Leu Gly Gly His Thr Ser Lys Lys Arg Ala Tyr Lys Tyr Asp Phe
            340                 345                 350

Asp Leu Val Tyr Pro Lys Lys Val Glu Ile Ala Tyr Asp Gly Tyr
        355                 360                 365

Val Tyr Asp Ile Glu Val Glu Gly Thr His Arg Phe Phe Ala Asn Gly
370                 375                 380

Ile Leu Val His Asn
385

<210> SEQ ID NO 19
<211> LENGTH: 390
<212> TYPE: PRT
<213> ORGANISM: Thermococcus litoralis

<400> SEQUENCE: 19

Ser Val Ser Gly Glu Ser Glu Ile Ile Arg Gln Asn Gly Lys Ile
1               5                   10                  15

Arg Phe Val Lys Ile Lys Asp Leu Phe Ser Lys Val Asp Tyr Ser Ile
                20                  25                  30

Gly Glu Lys Glu Tyr Cys Ile Leu Glu Gly Val Glu Ala Leu Thr Leu
            35                  40                  45

Asp Asp Asp Gly Lys Leu Val Trp Lys Pro Val Pro Tyr Val Met Arg
        50                  55                  60

His Arg Ala Asn Lys Arg Met Phe Arg Ile Trp Leu Thr Asn Ser Trp
65                  70                  75                  80

Tyr Ile Asp Val Thr Glu Asp His Ser Leu Ile Gly Tyr Leu Asn Thr
                85                  90                  95

Ser Lys Thr Lys Thr Ala Lys Lys Ile Gly Glu Arg Leu Lys Glu Val
            100                 105                 110
```

```
Lys Pro Phe Glu Leu Gly Lys Ala Val Lys Ser Leu Ile Cys Pro Asn
            115                 120                 125

Ala Pro Leu Lys Asp Glu Asn Thr Lys Thr Ser Glu Ile Ala Val Lys
130                 135                 140

Phe Trp Glu Leu Val Gly Leu Ile Val Gly Asp Gly Asn Trp Gly Gly
145                 150                 155                 160

Asp Ser Arg Trp Ala Glu Tyr Tyr Leu Gly Leu Ser Thr Gly Lys Asp
            165                 170                 175

Ala Glu Glu Ile Lys Gln Lys Leu Leu Glu Pro Leu Lys Thr Tyr Gly
            180                 185                 190

Val Ile Ser Asn Tyr Tyr Pro Lys Asn Glu Lys Gly Asp Phe Asn Ile
            195                 200                 205

Leu Ala Lys Ser Leu Val Lys Phe Met Lys Arg His Phe Lys Asp Glu
210                 215                 220

Lys Gly Arg Arg Lys Ile Pro Glu Phe Met Tyr Glu Leu Pro Val Thr
225                 230                 235                 240

Tyr Ile Glu Ala Phe Leu Arg Gly Leu Phe Ser Ala Asp Gly Thr Val
            245                 250                 255

Thr Ile Arg Lys Gly Val Pro Glu Ile Arg Leu Thr Asn Ile Asp Ala
            260                 265                 270

Asp Phe Leu Arg Glu Val Arg Lys Leu Leu Trp Ile Val Gly Ile Ser
            275                 280                 285

Asn Ser Ile Phe Ala Glu Thr Thr Pro Asn Arg Tyr Asn Gly Val Ser
            290                 295                 300

Thr Gly Thr Tyr Ser Lys His Leu Arg Ile Lys Asn Lys Trp Arg Phe
305                 310                 315                 320

Ala Glu Arg Ile Gly Phe Leu Ile Glu Arg Lys Gln Lys Arg Leu Leu
            325                 330                 335

Glu His Leu Lys Ser Ala Arg Val Lys Arg Asn Thr Ile Asp Phe Gly
            340                 345                 350

Phe Asp Leu Val His Val Lys Lys Val Glu Glu Ile Pro Tyr Glu Gly
            355                 360                 365

Tyr Val Tyr Asp Ile Glu Val Glu Glu Thr His Arg Phe Phe Ala Asn
370                 375                 380

Asn Ile Leu Val His Asn
385                 390

<210> SEQ ID NO 20
<211> LENGTH: 389
<212> TYPE: PRT
<213> ORGANISM: Thermococcus species GE8

<400> SEQUENCE: 20

Ser Val Ala Gly Asn Thr Glu Val Ile Ile Arg Arg Asn Gly Lys Val
1               5                   10                  15

Glu Phe Val Pro Ile Glu Lys Leu Phe Gln Arg Val Asp Tyr Arg Ile
            20                  25                  30

Gly Glu Lys Glu Tyr Cys Ala Leu Glu Gly Val Glu Ala Leu Thr Leu
        35                  40                  45

Asp Asn Arg Gly Arg Leu Val Trp Arg Lys Val Pro Tyr Ile Met Arg
50                  55                  60

His Lys Thr Asn Lys Lys Ile Tyr Arg Val Trp Phe Thr Asn Ser Trp
65                  70                  75                  80

Tyr Leu Asp Val Thr Glu Asp His Ser Leu Ile Gly Tyr Leu Asn Thr
            85                  90                  95
```

Ser Lys Val Lys Ser Glu Lys Pro Leu Lys Glu Arg Leu Val Glu Val
            100                 105                 110

Lys Pro Arg Glu Leu Gly Glu Lys Val Lys Ser Leu Ile Thr Leu Asn
            115                 120                 125

Arg Ala Ile Ala Arg Ser Ile Lys Ala Asn Pro Ile Ala Val Arg Leu
            130                 135                 140

Trp Glu Leu Ile Gly Leu Leu Val Gly Asp Gly Asn Trp Gly Gly His
145                 150                 155                 160

Ser Lys Trp Ala Lys Tyr Tyr Val Gly Leu Ser Cys Gly Leu Asp Lys
                165                 170                 175

Ala Glu Ile Glu Glu Lys Val Leu Arg Pro Leu Lys Glu Ala Gly Ile
            180                 185                 190

Ile Ser Asn Tyr Tyr Gly Lys Ser Lys Lys Gly Asp Val Ser Ile Leu
            195                 200                 205

Ser Lys Trp Leu Ala Gly Phe Met Val Lys Tyr Phe Lys Asp Glu Asn
            210                 215                 220

Gly Asn Lys Arg Ile Pro Ser Phe Met Phe Asn Leu Pro Arg Glu Tyr
225                 230                 235                 240

Ile Glu Ala Phe Leu Arg Gly Leu Phe Ser Ala Asp Gly Thr Val Ser
                245                 250                 255

Leu Arg Arg Gly Ile Pro Glu Ile Arg Leu Thr Ser Val Asn Arg Glu
            260                 265                 270

Leu Ser Asn Glu Val Arg Lys Leu Leu Trp Leu Val Gly Val Ser Asn
            275                 280                 285

Ser Met Phe Thr Glu Thr Thr Pro Asn Lys Tyr Leu Gly Asn Glu Ser
            290                 295                 300

Gly Thr Arg Ser Ile His Val Arg Ile Lys Asn Lys His Arg Phe Ala
305                 310                 315                 320

Lys Arg Ile Gly Phe Leu Leu Asp Arg Lys Ala Thr Lys Leu Ser Asp
                325                 330                 335

Asn Leu Arg Glu His Thr Asn Lys Lys Met Ala Tyr Arg Tyr Asp Phe
            340                 345                 350

Asp Leu Val Tyr Pro Lys Lys Ile Glu Glu Ile Asn Tyr Asp Arg Tyr
            355                 360                 365

Val Tyr Asp Ile Glu Val Glu Gly Thr His Arg Phe Phe Ala Asn Gly
            370                 375                 380

Ile Leu Val His Asn
385

<210> SEQ ID NO 21
<211> LENGTH: 184
<212> TYPE: PRT
<213> ORGANISM: Pyrococcus abyssi

<400> SEQUENCE: 21

Cys Phe Pro Gly Asp Thr Arg Ile Leu Val Gln Ile Asp Gly Val Pro
1               5                   10                  15

Gln Lys Ile Thr Leu Arg Glu Leu Tyr Glu Leu Phe Glu Asp Glu Arg
            20                  25                  30

Tyr Glu Asn Met Val Tyr Val Arg Lys Lys Pro Lys Arg Glu Ile Lys
            35                  40                  45

Val Tyr Ser Ile Asp Leu Glu Thr Gly Lys Val Val Leu Thr Asp Ile
            50                  55                  60

Glu Asp Val Ile Lys Ala Pro Ala Thr Asp His Leu Ile Arg Phe Glu

```
                65                  70                  75                  80
Leu Glu Asp Gly Arg Ser Phe Glu Thr Thr Val Asp His Pro Val Leu
                    85                  90                  95

Val Tyr Glu Asn Gly Arg Phe Ile Glu Lys Arg Ala Phe Glu Val Lys
                    100                 105                 110

Glu Gly Asp Lys Val Leu Val Ser Glu Leu Glu Leu Val Glu Gln Ser
                    115                 120                 125

Ser Ser Ser Gln Asp Asn Pro Lys Asn Glu Asn Leu Gly Ser Pro Glu
            130                 135                 140

His Asp Gln Leu Leu Glu Ile Lys Asn Ile Lys Tyr Val Arg Ala Asn
145                 150                 155                 160

Asp Asp Phe Val Phe Ser Leu Asn Ala Lys Lys Tyr His Asn Val Ile
                    165                 170                 175

Ile Asn Glu Asn Ile Val Thr His
                    180

<210> SEQ ID NO 22
<211> LENGTH: 416
<212> TYPE: PRT
<213> ORGANISM: Mycobacterium tuberculosis CDC1551

<400> SEQUENCE: 22

Cys Leu Thr Ala Ser Thr Arg Ile Leu Arg Ala Asp Thr Gly Ala Glu
1               5                   10                  15

Val Ala Phe Gly Glu Leu Met Arg Ser Gly Glu Arg Pro Met Val Trp
                    20                  25                  30

Ser Leu Asp Glu Arg Leu Arg Met Val Ala Arg Pro Met Ile Asn Val
                35                  40                  45

Phe Pro Ser Gly Arg Lys Glu Val Phe Arg Leu Arg Leu Ala Ser Gly
            50                  55                  60

Arg Glu Val Glu Ala Thr Gly Ser His Pro Phe Met Lys Phe Glu Gly
65                  70                  75                  80

Trp Thr Pro Leu Ala Gln Leu Lys Val Gly Asp Arg Ile Ala Ala Pro
                    85                  90                  95

Arg Arg Val Pro Glu Pro Ile Asp Thr Gln Arg Met Pro Glu Ser Glu
                    100                 105                 110

Leu Ile Ser Leu Ala Arg Met Ile Gly Asp Gly Ser Cys Leu Lys Asn
                    115                 120                 125

Gln Pro Ile Arg Tyr Glu Pro Val Asp Glu Ala Asn Leu Ala Ala Val
            130                 135                 140

Thr Val Ser Ala Ala His Ser Asp Gly Ala Ala Ile Arg Asp Asp Tyr
145                 150                 155                 160

Leu Ala Ala Arg Val Pro Ser Leu Arg Pro Ala Arg Gln Arg Leu Pro
                    165                 170                 175

Arg Gly Arg Cys Thr Pro Ile Ala Ala Trp Leu Ala Gly Leu Gly Leu
                    180                 185                 190

Phe Thr Lys Arg Ser His Glu Lys Cys Val Pro Glu Ala Val Phe Arg
                    195                 200                 205

Ala Pro Asn Asp Gln Val Ala Leu Phe Leu Arg His Leu Trp Ser Ala
            210                 215                 220

Gly Gly Ser Val Arg Trp Asp Pro Thr Asn Gly Gln Gly Arg Val Tyr
225                 230                 235                 240

Tyr Gly Ser Thr Ser Arg Arg Leu Ile Asp Asp Val Ala Gln Leu Leu
                    245                 250                 255
```

-continued

```
Leu Arg Val Gly Ile Phe Ser Trp Ile Thr His Ala Pro Lys Leu Gly
            260                 265                 270

Gly His Asp Ser Trp Arg Leu His Ile His Gly Ala Lys Asp Gln Val
        275                 280                 285

Arg Phe Leu Arg His Val Gly Val His Gly Ala Glu Ala Val Ala Ala
    290                 295                 300

Gln Glu Met Leu Arg Gln Leu Lys Gly Pro Val Arg Asn Pro Asn Leu
305                 310                 315                 320

Asp Ser Ala Pro Lys Lys Val Trp Ala Gln Val Arg Asn Arg Leu Ser
                325                 330                 335

Ala Lys Gln Met Met Asp Ile Gln Leu His Glu Pro Thr Met Trp Lys
            340                 345                 350

His Ser Pro Ser Arg Ser Arg Pro His Arg Ala Glu Ala Arg Ile Glu
        355                 360                 365

Asp Arg Ala Ile His Glu Leu Ala Arg Gly Asp Ala Tyr Trp Asp Thr
    370                 375                 380

Val Val Glu Ile Thr Ser Ile Gly Asp Gln His Val Phe Asp Gly Thr
385                 390                 395                 400

Val Ser Gly Thr His Asn Phe Val Ala Asn Gly Ile Ser Leu His Asn
                405                 410                 415

<210> SEQ ID NO 23
<211> LENGTH: 416
<212> TYPE: PRT
<213> ORGANISM: Mycobacterium tuberculosis H37Rv

<400> SEQUENCE: 23

Cys Leu Thr Ala Ser Thr Arg Ile Leu Arg Ala Asp Thr Gly Ala Glu
1               5                   10                  15

Val Ala Phe Gly Glu Leu Met Arg Ser Gly Arg Pro Met Val Trp
            20                  25                  30

Ser Leu Asp Glu Arg Leu Arg Met Val Ala Arg Pro Met Ile Asn Val
        35                  40                  45

Phe Pro Ser Gly Arg Lys Glu Val Phe Arg Leu Arg Leu Ala Ser Gly
    50                  55                  60

Arg Glu Val Glu Ala Thr Gly Ser His Pro Phe Met Lys Phe Glu Gly
65                  70                  75                  80

Trp Thr Pro Leu Ala Gln Leu Lys Val Gly Asp Arg Ile Ala Ala Pro
                85                  90                  95

Arg Arg Val Pro Glu Pro Ile Asp Thr Gln Arg Met Pro Glu Ser Glu
            100                 105                 110

Leu Ile Ser Leu Ala Arg Met Ile Gly Asp Gly Ser Cys Leu Lys Asn
        115                 120                 125

Gln Pro Ile Arg Tyr Glu Pro Val Asp Glu Ala Asn Leu Ala Ala Val
    130                 135                 140

Thr Val Ser Ala Ala His Ser Asp Arg Ala Ala Ile Arg Asp Asp Tyr
145                 150                 155                 160

Leu Ala Ala Arg Val Pro Ser Leu Arg Pro Ala Arg Gln Arg Leu Pro
                165                 170                 175

Arg Gly Arg Cys Thr Pro Ile Ala Ala Trp Leu Ala Gly Leu Gly Leu
            180                 185                 190

Phe Thr Lys Arg Ser His Glu Lys Cys Val Pro Glu Ala Val Phe Arg
        195                 200                 205

Ala Pro Asn Asp Gln Val Ala Leu Phe Leu Arg His Leu Trp Ser Ala
    210                 215                 220
```

```
Gly Gly Ser Val Arg Trp Asp Pro Thr Asn Gly Gln Gly Arg Val Tyr
225                 230                 235                 240

Tyr Gly Ser Thr Ser Arg Arg Leu Ile Asp Asp Val Ala Gln Leu Leu
            245                 250                 255

Leu Arg Val Gly Ile Phe Ser Trp Ile Thr His Ala Pro Lys Leu Gly
            260                 265                 270

Gly His Asp Ser Trp Arg Leu His Ile His Gly Ala Lys Asp Gln Val
            275                 280                 285

Arg Phe Leu Arg His Val Gly Val His Gly Ala Glu Ala Val Ala Ala
            290                 295                 300

Gln Glu Met Leu Arg Gln Leu Lys Gly Pro Val Arg Asn Pro Asn Leu
305                 310                 315                 320

Asp Ser Ala Pro Lys Lys Val Trp Ala Gln Val Arg Asn Arg Leu Ser
            325                 330                 335

Ala Lys Gln Met Met Asp Ile Gln Leu His Glu Pro Thr Met Trp Lys
            340                 345                 350

His Ser Pro Ser Arg Ser Arg Pro His Arg Ala Glu Ala Arg Ile Glu
            355                 360                 365

Asp Arg Ala Ile His Glu Leu Ala Arg Gly Asp Ala Tyr Trp Asp Thr
            370                 375                 380

Val Val Glu Ile Thr Ser Ile Gly Asp Gln His Val Phe Asp Gly Thr
385                 390                 395                 400

Val Ser Gly Thr His Asn Phe Val Ala Asn Gly Ile Ser Leu His Asn
            405                 410                 415

<210> SEQ ID NO 24
<211> LENGTH: 428
<212> TYPE: PRT
<213> ORGANISM: Rhodothermus marinus

<400> SEQUENCE: 24

Cys Leu Ala Gly Asp Thr Leu Ile Thr Leu Ala Asp Gly Arg Arg Val
1               5                   10                  15

Pro Ile Arg Glu Leu Val Ser Gln Gln Asn Phe Ser Val Trp Ala Leu
            20                  25                  30

Asn Pro Gln Thr Tyr Arg Leu Glu Arg Ala Arg Val Ser Arg Ala Phe
        35                  40                  45

Cys Thr Gly Ile Lys Pro Val Tyr Arg Leu Thr Thr Arg Leu Gly Arg
    50                  55                  60

Ser Ile Arg Ala Thr Ala Asn His Arg Phe Leu Thr Pro Gln Gly Trp
65                  70                  75                  80

Lys Arg Val Asp Glu Leu Gln Pro Gly Asp Tyr Leu Ala Leu Pro Arg
                85                  90                  95

Arg Ile Pro Thr Ala Ser Thr Pro Thr Leu Thr Glu Ala Glu Leu Ala
            100                 105                 110

Leu Leu Gly His Leu Ile Gly Asp Gly Cys Thr Leu Pro His His Val
        115                 120                 125

Ile Gln Tyr Thr Ser Arg Asp Ala Asp Leu Ala Thr Leu Val Ala His
    130                 135                 140

Leu Ala Thr Lys Val Phe Gly Ser Lys Val Thr Pro Gln Ile Arg Lys
145                 150                 155                 160

Glu Leu Arg Trp Tyr Gln Val Tyr Leu Arg Ala Ala Arg Pro Leu Ala
                165                 170                 175

Pro Gly Lys Arg Asn Pro Ile Ser Asp Trp Leu Arg Asp Leu Gly Ile
```

```
            180                 185                 190
Phe Gly Leu Arg Ser Tyr Glu Lys Lys Val Pro Ala Leu Leu Phe Cys
                195                 200                 205
Gln Thr Ser Glu Ala Ile Ala Thr Phe Leu Arg His Leu Trp Ala Thr
        210                 215                 220
Asp Gly Cys Ile Gln Met Arg Arg Gly Lys Lys Pro Tyr Pro Ala Val
225                 230                 235                 240
Tyr Tyr Ala Thr Ser Ser Tyr Gln Leu Ala Arg Asp Val Gln Ser Leu
                245                 250                 255
Leu Leu Arg Leu Gly Ile Asn Ala Arg Leu Lys Thr Val Ala Gln Gly
            260                 265                 270
Glu Lys Gly Arg Val Gln Tyr His Val Lys Val Ser Gly Arg Glu Asp
        275                 280                 285
Leu Leu Arg Phe Val Glu Lys Ile Gly Ala Val Gly Ala Arg Gln Arg
    290                 295                 300
Ala Ala Leu Ala Ser Val Tyr Asp Tyr Leu Ser Val Arg Thr Gly Asn
305                 310                 315                 320
Pro Asn Arg Asp Ile Ile Pro Val Ala Leu Trp Tyr Glu Leu Val Arg
                325                 330                 335
Glu Ala Met Tyr Gln Arg Gly Ile Ser His Arg Gln Leu His Ala Asn
            340                 345                 350
Leu Gly Met Ala Tyr Gly Gly Met Thr Leu Phe Arg Gln Asn Leu Ser
        355                 360                 365
Arg Ala Arg Ala Leu Arg Leu Ala Glu Ala Ala Cys Pro Glu Leu
    370                 375                 380
Arg Gln Leu Ala Gln Ser Asp Val Tyr Trp Asp Pro Ile Val Ser Ile
385                 390                 395                 400
Glu Pro Asp Gly Val Glu Glu Val Phe Asp Leu Thr Val Pro Gly Pro
                405                 410                 415
His Asn Phe Val Ala Asn Asp Ile Ile Ala His Asn
            420                 425

<210> SEQ ID NO 25
<211> LENGTH: 1365
<212> TYPE: PRT
<213> ORGANISM: Trichodesmium erythraeum IMS101

<400> SEQUENCE: 25

Cys Leu Pro Lys Gly Thr Leu Ile Asp Gln Pro Asp Gly Ser Arg Glu
1               5                   10                  15
Ala Ile Glu Asn Ile Lys Ser Gly Glu Val Ile Leu Thr Ser Asp Gly
                20                  25                  30
Arg Lys Val Trp Glu Ala Lys Val Ala Lys Gln Trp Arg Ser Gly Val
            35                  40                  45
Arg Glu Ile Leu Lys Ile Thr Leu Ser Ser Gly Thr Val Ile Tyr Ser
        50                  55                  60
Gly Lys Asn His Arg Phe Leu Thr Pro Glu Gly Asp Lys Phe Ala Trp
65                  70                  75                  80
Glu Leu Gln Pro Gln Val Gly Arg Val Lys Asn Ala Leu Ile Tyr Gly
                85                  90                  95
Ser Ala Val Tyr Glu Lys Trp Gln Val Ser Ser Asn Gln Lys Gln Leu
                100                 105                 110
Arg Lys Asn Asp Ala Tyr Leu Leu Gly Leu Leu Val Gly Lys Ser Asn
            115                 120                 125
```

-continued

```
Leu Ile Ser Ser Thr Pro Asn Val Ser Phe Ser Thr Gln Gly Ala Ile
    130                 135                 140

Thr Trp Gly Lys Asn Leu Ile Asp Glu Thr Trp Gly Gly Glu Ala Lys
145                 150                 155                 160

His Tyr Phe Asp Thr Ser Arg Arg Gln Val Tyr Leu Asn Phe Asn Thr
                165                 170                 175

Gln Ser Lys Pro Thr Ala Leu Thr Glu Phe Leu Asp Gly Ile Tyr Gly
            180                 185                 190

Ala Gln Asn Trp Gln Val Glu Val Ala Lys His Leu Pro Glu Asp
        195                 200                 205

Ile Leu Asp Tyr Ser Glu Lys Asp Arg Ile Asp Leu Leu Arg Gly Leu
    210                 215                 220

Trp Asp Ser Gly Gly Phe Asp Gly Lys Lys Leu Leu Tyr Tyr Pro Gly
225                 230                 235                 240

Ser Ser Pro Gln Leu Leu Ser Gln Val Cys Gln Leu Leu Gly Ser Leu
                245                 250                 255

Lys Ile Asp Tyr Tyr Leu Ala Asp Asn Ser Val Arg Ile Ser Asp Arg
            260                 265                 270

Ser Arg Phe Ile Asp Ile Leu Glu Asn Tyr Gln Met Ser Ser Gln Gln
        275                 280                 285

Lys Glu Glu Ile Ser Glu Ser Tyr Leu Pro Ala Ser Ser Trp Phe Leu
    290                 295                 300

Lys Gly Gly Ser Glu Asn Asn Ile Gln Lys Thr Asp Ser Ser Ser Arg
305                 310                 315                 320

Lys Thr Gly Glu Ala Ser Gln Gln Lys Ala Thr Leu Phe Thr Gln Asn
                325                 330                 335

Leu Phe Ser Ala Gln Thr Pro Ala Glu Asn Trp Glu Lys Val Gly Glu
            340                 345                 350

Asn His Leu Leu Ser Ser Trp Phe Leu Thr Asp Ala Ser Glu Asn Asn
        355                 360                 365

Ile Gln Lys Thr Asp Ser Ser Arg Lys Thr Gly Glu Ala Ser Gln
    370                 375                 380

Gln Lys Ala Thr Leu Phe Thr Gln Asn Leu Phe Ser Ala Gln Thr Pro
385                 390                 395                 400

Ala Glu Asn Trp Glu Lys Val Arg Glu Asn His Leu Leu Ser Ser Trp
                405                 410                 415

Phe Leu Thr Asn Ala Ser Glu Ile Tyr Leu Gln Arg Ile Asp Ser Ser
            420                 425                 430

Ser Arg Lys Thr Gly Glu Ala Ser Gln Gln Lys Ala Thr Leu Phe Thr
        435                 440                 445

Gln Asn Leu Phe Ser Val Gln Thr Pro Ala Glu Asn Trp Glu Lys Val
    450                 455                 460

Arg Glu Asn His Leu Leu Ser Ser Trp Phe Leu Thr Asp Ala Ser Glu
465                 470                 475                 480

Asn Asn Ile Gln Lys Thr Asp Ser Ser Arg Lys Thr Gly Glu Ala
                485                 490                 495

Ser Gln Gln Lys Ala Thr Leu Phe Thr Gln Asn Leu Phe Ser Ala Gln
            500                 505                 510

Thr Pro Ala Glu Asn Trp Glu Lys Val Arg Glu Asn His Leu Leu Ser
        515                 520                 525

Ser Trp Phe Leu Thr Asn Ala Ser Glu Asn Asn Ile Gln Lys Thr Asp
    530                 535                 540

Ser Ser Ser Arg Lys Thr Gly Glu Ala Ser Gln Gln Lys Ala Thr Leu
```

-continued

```
545                 550                 555                 560
Phe Thr Gln Asn Leu Phe Ser Ala Gln Thr Pro Ala Glu Asn Trp Lys
                565                 570                 575
Lys Ser Arg Lys Asn His Leu Pro Ser Ser Trp Phe Leu Lys Gly Gly
                580                 585                 590
Ser Glu Asn Asn Ile Gln Lys Thr Asp Ser Ser Arg Lys Thr Gly
                595                 600                 605
Glu Ala Ser Gln Gln Lys Ala Thr Leu Phe Thr Gln Asn Leu Phe Ser
610                 615                 620
Ala Gln Thr Pro Ala Glu Asn Trp Glu Lys Val Arg Glu Asn His Leu
625                 630                 635                 640
Leu Ser Ser Trp Phe Leu Lys Asp Ala Ser Glu Asn Asn Ile Gln Lys
                645                 650                 655
Thr Asp Ser Ser Arg Lys Thr Gly Glu Ala Ser Gln Gln Lys Ala
                660                 665                 670
Thr Leu Phe Thr Gln Asn Leu Phe Ser Ala Gln Thr Pro Ala Glu Asn
                675                 680                 685
Trp Glu Lys Val Arg Glu Asn His Leu Leu Ser Ser Trp Phe Leu Thr
690                 695                 700
Asp Ala Ser Glu Asn Asn Ile Gln Lys Thr Asp Ser Ser Arg Lys
705                 710                 715                 720
Thr Gly Glu Ala Ser Gln Gln Lys Ala Thr Leu Phe Thr Gln Asn Leu
                725                 730                 735
Phe Ser Ala Gln Thr Pro Ala Glu Asn Trp Glu Lys Val Arg Glu Asn
                740                 745                 750
His Leu Leu Ser Ser Trp Phe Leu Thr Asp Ala Ser Glu Asn Asn Ile
                755                 760                 765
Gln Lys Thr Asp Ser Ser Arg Lys Thr Gly Glu Ala Ser Gln Gln
                770                 775                 780
Lys Ala Thr Leu Phe Thr Gln Asn Leu Phe Ser Ala Gln Thr Pro Ala
785                 790                 795                 800
Glu Asn Trp Glu Lys Val Arg Glu Asn His Leu Leu Ser Ser Trp Phe
                805                 810                 815
Leu Thr Asn Ala Ser Glu Asn Asn Ile Gln Lys Thr Asp Ser Ser Ser
                820                 825                 830
Arg Lys Thr Gly Glu Ala Ser Gln Gln Lys Ala Thr Leu Phe Thr Gln
                835                 840                 845
Asn Leu Phe Ser Ala Gln Thr Pro Ala Glu Asn Trp Lys Lys Ala Arg
850                 855                 860
Glu Asn His Leu Leu Ser Ser Trp Phe Leu Thr Asn Ala Ser Glu Ile
865                 870                 875                 880
Tyr Leu Gln Arg Thr Asp Ser Ser Arg Lys Thr Gly Glu Ala Ser
                885                 890                 895
Gln Gln Lys Ala Thr Leu Phe Thr Gln Asn Leu Phe Ser Val Gln Thr
                900                 905                 910
Pro Ala Glu Asn Trp Lys Lys Ala Arg Glu Asn His Leu Leu Ser Ser
                915                 920                 925
Trp Phe Leu Thr Asn Ala Ser Glu Ile Tyr Leu Gln Arg Thr Asp Ser
                930                 935                 940
Ser Ser Arg Lys Thr Gly Gly Ala Ser Gln Gln Lys Ala Thr Leu Phe
945                 950                 955                 960
Asn Gln Asn Leu Phe Ser Val Gln Thr Pro Ala Glu Asn Trp Glu Lys
                965                 970                 975
```

```
Val Arg Glu Asn Tyr Leu Leu Ser Ser Trp Phe Leu Thr Asn Ala Ser
        980                 985                 990

Glu Ile Tyr Leu Gln Arg Thr Asp Ser Ser Ser Arg Lys Thr Gly Glu
        995                 1000                1005

Ala Ser Gln Gln Lys Ala Thr Leu Phe Thr Gln Asn Leu Phe Ser
        1010                1015                1020

Val Gln Thr Pro Ala Glu Asn Trp Lys Lys Ala Arg Glu Asn His
        1025                1030                1035

Leu Leu Ser Ser Trp Phe Leu Thr Asn Ala Ser Glu Ile Tyr Leu
        1040                1045                1050

Gln Arg Thr Asp Ser Ser Arg Lys Thr Gly Gly Ala Ser Gln
        1055                1060                1065

Gln Lys Ala Thr Leu Phe Asn Gln Asn Leu Phe Ser Val Gln Thr
        1070                1075                1080

Pro Ala Glu Asn Trp Lys Lys Ala Arg Glu Asn His Leu Leu Ser
        1085                1090                1095

Ser Trp Phe Leu Thr Asn Ala Ser Glu Ile Tyr Leu Gln Arg Thr
        1100                1105                1110

Asp Ser Ser Arg Lys Thr Val Glu Ala Ser Gln Gln Lys Ala
        1115                1120                1125

Thr Leu Phe Thr Gln Asn Leu Phe Ser Ala Gln Thr Pro Ala Glu
        1130                1135                1140

Asn Trp Glu Lys Val Arg Glu Asn Tyr Leu Leu Ser Ser Trp Phe
        1145                1150                1155

Leu Thr Asn Ala Ser Glu Ile Tyr Leu Gln Arg Ile Asp Ser Ser
        1160                1165                1170

Ser Arg Lys Thr Gly Glu Ala Cys Gln Gln Lys Ala Thr Leu Phe
        1175                1180                1185

Asn Gln Asn Leu Phe Ser Ala Gln Thr Pro Ala Glu Asn Trp Lys
        1190                1195                1200

Lys Val Arg Glu Asn His Leu Leu Ser Ser Trp Phe Leu Thr Asp
        1205                1210                1215

Ala Ser Glu Asn Asn Ile Gln Lys Thr Asp Ser Ser Ser Arg Lys
        1220                1225                1230

Thr Val Glu Ala Ser Gln Gln Lys Ala Thr Leu Phe Thr Gln Asn
        1235                1240                1245

Leu Phe Ser Ala Gln Thr Pro Ala Glu Asn Trp Lys Lys Ser Arg
        1250                1255                1260

Lys Asn His Leu Pro Ser Ser Trp Phe Leu Thr Asp Ala Ser Glu
        1265                1270                1275

Asn Asn Ile Gln Lys Thr Asp Ser Ser Ser Arg Lys Thr Gly Glu
        1280                1285                1290

Ala Ser Gln Gln Lys Ala Thr Leu Phe Thr Gln Asn Leu Phe Ser
        1295                1300                1305

Val Gln Thr Pro Glu Leu Glu Asn Trp Glu Cys Glu Lys Thr Tyr
        1310                1315                1320

Leu Gln Asp Val Arg Val Val His Val Val Ser Val Glu Glu Val
        1325                1330                1335

Gly Glu Ala Glu Cys Phe Asp Leu Glu Met Glu Asp Gln Ser Ser
        1340                1345                1350

Pro Tyr Phe Leu Ala Glu Gly Val Val Val His Asn
        1355                1360                1365
```

```
<210> SEQ ID NO 26
<211> LENGTH: 435
<212> TYPE: PRT
<213> ORGANISM: Synechocystis species PCC6803

<400> SEQUENCE: 26

Cys Phe Ser Gly Asp Thr Leu Val Ala Leu Thr Asp Gly Arg Ser Val
1               5                   10                  15

Ser Phe Glu Gln Leu Val Glu Glu Lys Gln Gly Lys Gln Asn Phe
            20                  25                  30

Cys Tyr Thr Ile Arg His Asp Gly Ser Ile Gly Val Glu Lys Ile Ile
            35                  40                  45

Asn Ala Arg Lys Thr Lys Thr Asn Ala Lys Val Ile Lys Val Thr Leu
        50                  55                  60

Asp Asn Gly Glu Ser Ile Ile Cys Thr Pro Asp His Lys Phe Met Leu
65                  70                  75                  80

Arg Asp Gly Ser Tyr Lys Cys Ala Met Asp Leu Thr Leu Asp Asp Ser
                85                  90                  95

Leu Met Pro Leu His Arg Lys Ile Ser Thr Thr Glu Asp Ser Gly Ile
            100                 105                 110

Thr Ile Asp Gly Tyr Glu Met Val Trp Ser Pro Arg Ser Asp Ser Trp
        115                 120                 125

Leu Phe Thr His Leu Val Ala Asp Trp Tyr Asn Arg Trp Gln Gly Ile
130                 135                 140

Tyr Ile Ala Glu Glu Lys Gln His Cys His His Lys Asp Phe Asn Lys
145                 150                 155                 160

Arg Asn Asn Asn Pro Asp Asn Leu Ile Arg Leu Ser Pro Glu Lys His
                165                 170                 175

Leu Ala Leu His Arg Lys His Ile Ser Lys Thr Leu His Arg Pro Asp
            180                 185                 190

Val Val Glu Lys Cys Arg Arg Ile His Gln Ser Pro Glu Phe Arg Arg
        195                 200                 205

Lys Met Ser Ala Arg Met Gln Ser Pro Glu Thr Arg Ala Ile Leu Ser
210                 215                 220

Lys Gln Ala Gln Ala Gln Trp Gln Asn Glu Thr Tyr Lys Leu Thr Met
225                 230                 235                 240

Met Glu Ser Trp Arg Ser Phe Tyr Asp Ser Asn Glu Asp Tyr Arg Gln
                245                 250                 255

Gln Asn Ala Glu Gln Leu Asn Arg Ala Gln Glu Tyr Trp Ala Gln
            260                 265                 270

Ala Glu Asn Arg Thr Ala Gln Ala Glu Arg Val Arg Gln His Phe Ala
        275                 280                 285

Gln Asn Pro Gly Leu Arg Gln Tyr Ser Glu Asn Ala Val Lys Gln
290                 295                 300

Trp Asn Asn Pro Glu Leu Leu Lys Trp Arg Gln Lys Lys Thr Lys Glu
305                 310                 315                 320

Gln Trp Thr Pro Glu Phe Arg Glu Lys Arg Glu Ala Leu Ala Gln
                325                 330                 335

Thr Tyr Tyr Arg Lys Thr Leu Ala Ala Leu Lys Gln Val Glu Ile Glu
            340                 345                 350

Asn Gly Tyr Leu Asp Ile Ser Ala Tyr Asp Ser Tyr Arg Ile Ser Thr
        355                 360                 365

Lys Asp Lys Ser Leu Leu Arg Phe Asp Arg Phe Cys Glu Arg Tyr Phe
370                 375                 380
```

```
Glu Asn Asp Glu Asn Leu Ala Arg Glu Ala Val Leu Asn Tyr Asn His
385                 390                 395                 400

Arg Ile Val Asn Ile Glu Ala Val Ser Glu Thr Ile Asp Val Tyr Asp
            405                 410                 415

Ile Glu Val Pro His Thr His Asn Phe Ala Leu Ala Ser Gly Val Phe
        420                 425                 430

Val His Asn
        435

<210> SEQ ID NO 27
<211> LENGTH: 421
<212> TYPE: PRT
<213> ORGANISM: Mycobacterium flavescens

<400> SEQUENCE: 27

Cys Val Thr Gly Asp Ala Leu Val Arg Leu Pro Phe Gly Gln Ser Val
1               5                   10                  15

Arg Leu Arg Asp Val Val Ala Gly Ala Arg Ser Ser Asp Asn Ala
            20                  25                  30

Ile Asp Leu Lys Val Leu Asn Arg His Gly Asp Pro Val Val Ala Asp
        35                  40                  45

Lys Leu Phe His Ser Gly Glu His Glu Thr Tyr Thr Val Arg Thr Ala
50                  55                  60

Glu Gly Tyr Glu Val Thr Gly Thr Ala Asn His Pro Leu Leu Cys Leu
65                  70                  75                  80

Val Asp Val Gly Gly Val Pro Thr Leu Leu Trp Lys Leu Thr Glu Glu
                85                  90                  95

Ile Arg Pro Gly Asp His Val Val Leu Gln Arg Thr Pro Pro Thr Glu
            100                 105                 110

Phe Gly Pro Ala Asp Trp Gln Asp Ala Phe Glu Ala Leu His Leu Gly
        115                 120                 125

Ala Phe Ile Ser Glu Gly Phe Val Ser Glu Asn Arg Ala Gly Phe Asn
    130                 135                 140

Asn Leu Asp Arg Glu Phe Phe Asn Ala Val Leu Thr Ala Tyr Asp Thr
145                 150                 155                 160

Ile Val Gly Gly Pro Arg Tyr Val Ser Ser Arg Thr Ile Ala Ser Asp
                165                 170                 175

Ser Leu Leu His Glu Leu Asp Val His Asn Leu Thr Ala Leu Lys Lys
            180                 185                 190

Ser Arg Leu Gly Glu Leu Val Gly Gln Arg Ser Ala Asp Lys Ala Val
        195                 200                 205

Pro Glu Trp Leu Trp Lys Ala Pro Ala Val Val Lys Arg Val Phe Leu
    210                 215                 220

Gln Ala Leu Phe Glu Gly Asp Gly Ser Cys Ser Ala Leu Pro Arg Asn
225                 230                 235                 240

Thr Ile Gln Val Ser Tyr Ser Thr Arg Ser Gly Arg Leu Ala Lys Asp
                245                 250                 255

Ile Gln Gln Met Leu Leu Glu Phe Gly Val Ile Ser Arg Arg Tyr Val
            260                 265                 270

His Ala Thr Gly Glu His Lys Val Val Leu Thr Ser Arg Ala Gln Ala
        275                 280                 285

Glu Leu Phe Ala Ala Gln Ile Gly Phe Gly Gly Ile Lys Gln Ala Lys
    290                 295                 300

Leu Gln Gly Leu Leu Asp Ala Leu Pro Gln Ala Ala Ala Gly Arg Asp
```

```
                305                 310                 315                 320
Gly Asp Tyr Val Pro Gly Leu Ala Gln Phe Val Arg Lys His Ser Gly
                325                 330                 335

Ser Arg Trp Val Asp Lys Asp Trp Leu Asn Arg His Asn Ile Asp Arg
                340                 345                 350

Leu Ser Arg Trp Gln Arg Asp Gly Ala Glu Ile Leu Gly Arg Ile Ala
                355                 360                 365

Asp Pro Asp Val Arg Ala Ile Ala Gln Glu Leu Thr Asp Gly Arg Phe
                370                 375                 380

Tyr Tyr Ala Arg Val Ala Ser Val Thr Asp Ser Gly Val Gln Pro Val
385                 390                 395                 400

Tyr Ser Leu Arg Val Asp Thr Asp His Ser Phe Ile Thr Asn Gly
                405                 410                 415

Phe Val Ser His Asn
                420

<210> SEQ ID NO 28
<211> LENGTH: 420
<212> TYPE: PRT
<213> ORGANISM: Mycobacterium gordonae

<400> SEQUENCE: 28

Cys Leu Thr Gly Asp Ala Leu Val Arg Leu Pro Phe Gly Gln Ser Met
1               5                   10                  15

Arg Ile Gly Asp Val Ala Pro Gly Ala Arg Thr Asn Ser Asp Asn Ala
                20                  25                  30

Gly Glu Leu Lys Val Leu Asp Arg His Gly Asp Pro Val Phe Ala Asp
                35                  40                  45

Arg Leu Phe His Ser Gly Asp His Gln Thr Phe Arg Val Gln Thr Ala
                50                  55                  60

Glu Gly Tyr Glu Val Thr Gly Thr Ser Asn His Pro Val Leu Cys Leu
65                  70                  75                  80

Val Asn Leu Ala Gly Val Pro Thr Leu Leu Trp Met Leu Ile Glu Glu
                85                  90                  95

Ile Arg Pro Asp Asp Tyr Val Val Leu Gln Arg Ala Pro Pro Val Glu
                100                 105                 110

Ser Gly Pro Ala Asn Trp Arg Asp Ala Met Glu Ala Leu Leu Leu Gly
                115                 120                 125

Ala Phe Ile Ser Glu Gly Phe Met Ser Glu Ser Arg Ala Gly Phe Asn
                130                 135                 140

Asn Val Asp Arg Asp Tyr Phe Asn Ala Val Val Ala Ala Tyr Asp Ala
145                 150                 155                 160

Val Val Gly Gly Lys Arg Tyr Val Ala Gln Arg Thr Ile Ala Ser Gly
                165                 170                 175

Ser Val Leu Asn Glu Leu Asp Ile His Asp Val Ser Ala Leu Lys Gly
                180                 185                 190

Thr Arg Leu Gly Val Leu Cys Gly Gln Arg Ser Ala Asp Lys Ser Val
                195                 200                 205

Pro Glu Trp Leu Trp Gln Ser Pro Ala Ala Val Lys Arg Val Phe Leu
                210                 215                 220

Gln Ala Leu Phe Glu Gly Asp Gly Ser Cys Ser Ala Leu Pro Arg Asn
225                 230                 235                 240

Thr Ile Gln Val Ser Tyr Ser Thr Arg Ser Arg Gln Leu Ala Ile Asp
                245                 250                 255
```

Val Gln Gln Met Leu Leu Glu Phe Gly Val Ile Ser Arg Arg Tyr Arg
                260                 265                 270

His Ala Val Gly Glu Tyr Lys Val Val Ile Thr Asn Arg Ala Gln Ala
            275                 280                 285

Glu Leu Phe Ala Thr Gln Ile Gly Phe Gly Gly Ala Lys Gln Ser Lys
        290                 295                 300

Leu Thr Arg Ile Leu Gly Ser Leu Pro Pro Cys Ala Gly Met Asp Thr
305                 310                 315                 320

Asn His Val Pro Gly Leu Ala Ala Phe Ile Arg Ser His Cys Asp Ser
                325                 330                 335

Glu Trp Val Asp Lys Glu Trp Leu Arg Lys His Asn Ile Asp Arg Leu
            340                 345                 350

Ser Arg Trp Arg Arg Asp Gly Ala Glu Ile Leu Ser Arg Ile Ala Asn
        355                 360                 365

Pro Asp Val Arg Ala Ile Ala Thr Asp Leu Thr Asp Gly Arg Phe Tyr
370                 375                 380

Tyr Ala Gln Val Thr Ser Val Thr Glu Ala Gly Val Gln Pro Val Tyr
385                 390                 395                 400

Ser Leu Arg Val Asp Ser Glu Asp His Ala Phe Leu Thr Asn Gly Phe
                405                 410                 415

Val Ser His Asn
            420

<210> SEQ ID NO 29
<211> LENGTH: 420
<212> TYPE: PRT
<213> ORGANISM: Mycobacterium kansasii

<400> SEQUENCE: 29

Cys Val Thr Gly Asp Ala Leu Val Arg Leu Pro Phe Gly Gln Ser Met
1               5                   10                  15

Arg Ile Ala Asp Val Val Pro Gly Ala Arg Pro Asn Ser Asp Asn Ala
            20                  25                  30

Val Glu Leu Lys Val Leu Asp Arg His Gly Asn Pro Val Ala Ala Asp
        35                  40                  45

Arg Leu Phe His Ser Gly Asp His Gln Thr Tyr Met Val Arg Thr Ala
    50                  55                  60

Glu Gly Tyr Glu Val Thr Gly Thr Ala Asn His Pro Leu Leu Cys Leu
65                  70                  75                  80

Val Asp Val Gly Gly Val Pro Thr Leu Leu Trp Lys Leu Ile Glu Glu
                85                  90                  95

Ile His Pro Asp Asp Tyr Val Ala Leu Gln Arg Thr Pro Pro Met Glu
            100                 105                 110

Leu Gly Pro Ala Asp Trp His Asp Thr Met Glu Ala Leu Leu Leu Gly
        115                 120                 125

Ala Phe Ile Ser Glu Gly Cys Val Ser Glu Thr Arg Ala Gly Phe Ala
    130                 135                 140

Asn Leu Asp Arg Asp Tyr Phe Thr Met Val Ala Arg Ala Tyr Asp Ala
145                 150                 155                 160

Val Val Gly Asp Lys Arg Asp Val Tyr Gln Gln Thr Ile Ala Ser Gly
                165                 170                 175

Ser Leu Gln His Thr Leu Tyr Thr Gln Asn Val Thr Ala Leu Lys Gln
            180                 185                 190

Ser Arg Leu Trp Gln Ile Leu Gly Met Arg Ser Ala Asp Thr Tyr Val
        195                 200                 205

```
Pro Glu Trp Met Trp His Ser Pro Ala Ala Val Lys Arg Val Phe Leu
    210                 215                 220

Gln Ala Leu Phe Glu Gly Asp Gly Ser Cys Ser Arg Arg Pro His Asn
225                 230                 235                 240

Thr Ile Gln Ile Ser Tyr Asn Thr Val Ser Lys Gln Leu Ala Met Asp
                245                 250                 255

Val Gln Gln Met Leu Leu Glu Phe Gly Val Ile Ser Arg Arg Tyr Leu
            260                 265                 270

His Ala Ala Gly Glu Tyr Lys Val Val Ile Thr Asp Arg Ala Gln Ala
        275                 280                 285

Glu Leu Phe Pro Lys Gln Ile Gly Phe Gly Ala Lys Gln Thr Glu
    290                 295                 300

Leu Ser Lys Ile Leu Ala Ala Met Pro Pro Cys Ala Gly Arg Asp Ser
305                 310                 315                 320

Asp His Val Pro Gly Leu Ala Arg Phe Ile Arg Arg His Cys Asp Ser
                325                 330                 335

Arg Trp Val Asp Lys Glu Trp Leu His Lys His Asn Ile Asp His Leu
            340                 345                 350

Ser Arg Trp Arg Arg Asp Gly Ala Glu Ile Leu Ser His Ile Ala Asp
        355                 360                 365

Pro Asp Val Arg Thr Ile Ala Thr Asp Leu Thr Asp Gly Arg Phe Tyr
    370                 375                 380

Tyr Ala Arg Val Ala Ser Val Thr Asp Thr Gly Val Gln Pro Val Tyr
385                 390                 395                 400

Ser Leu Arg Val Asp Thr Asp Asp His Ala Phe Leu Thr Asn Gly Phe
                405                 410                 415

Val Ser His Asn
            420

<210> SEQ ID NO 30
<211> LENGTH: 420
<212> TYPE: PRT
<213> ORGANISM: Mycobacterium leprae TN

<400> SEQUENCE: 30

Cys Val Ser Gly Asn Ser Leu Val Arg Leu Leu Phe Gly Lys Ser Ile
1               5                   10                  15

Arg Ile Gly Asp Ile Val Thr Gly Ala Gln Phe Asn Ser Asp Asn Pro
            20                  25                  30

Ile Asp Leu Lys Val Leu Asp Arg His Gly Asn Pro Val Val Ala Asp
        35                  40                  45

Tyr Leu Phe His Ser Gly Glu His Gln Thr Tyr Thr Val Arg Thr Thr
    50                  55                  60

Glu Gly Tyr Glu Ile Thr Gly Thr Ser Asn His Pro Leu Leu Cys Leu
65                  70                  75                  80

Val Asn Val Gly Gly Ile Pro Thr Leu Leu Trp Lys Leu Ile Gly Glu
                85                  90                  95

Ile Arg Ser Gly Asp Tyr Val Val Leu Gln Arg Ile Pro Pro Val Glu
            100                 105                 110

Phe Gly Pro Ala Asp Trp Tyr Ser Thr Met Glu Ala Leu Leu Phe Gly
        115                 120                 125

Ala Phe Ile Ser Gly Gly Phe Val Phe Gln Asp His Ala Gly Phe Asn
    130                 135                 140

Ser Leu Asp Arg Asp Tyr Phe Thr Met Val Val Asn Ala Tyr Asp Thr
```

```
                145                 150                 155                 160
Val Val Gly Gly Leu Arg Cys Ile Ser Ser Arg Ile Thr Val Ser Gly
                165                 170                 175

Ser Thr Leu Leu Glu Leu Asp Val Tyr Asn Leu Ile Glu Phe Lys Lys
                180                 185                 190

Thr Arg Leu Ser Gly Leu Cys Gly Gln Arg Ser Ala Asp Lys Leu Val
                195                 200                 205

Pro Asp Trp Leu Trp His Ser Pro Ser Thr Val Lys Arg Ala Phe Leu
                210                 215                 220

Gln Ala Leu Phe Glu Gly Glu Gly Phe Ser Ser Ile Leu Ser Arg Asn
225                 230                 235                 240

Ile Ile Glu Ile Ser Tyr Ser Thr Leu Ser Glu Arg Leu Ala Ala Asp
                245                 250                 255

Val Gln Gln Met Leu Leu Glu Phe Gly Val Val Ser Glu Arg Tyr Cys
                260                 265                 270

His Thr Val Asn Glu Tyr Lys Val Val Ile Ala Asn Arg Ala Gln Val
                275                 280                 285

Glu Met Phe Phe Thr Gln Val Gly Phe Gly Val Thr Lys Gln Ala Lys
                290                 295                 300

Leu Ile Arg Asp Val Val Ser Met Ser Pro Cys Val Gly Met Asp Ile
305                 310                 315                 320

Asn Cys Val Pro Gly Leu Ala Thr Phe Ile Arg Lys His Cys Asp Asn
                325                 330                 335

Arg Trp Val Glu Glu Asp Ser Phe Asn Gln His Asn Val Asp Cys Val
                340                 345                 350

Gln His Trp His His His Ser Ala Glu Ile Val Gly His Ile Ala Asp
                355                 360                 365

Pro Asp Ile Arg Ala Ile Val Thr Asp Leu Thr Asp Gly Arg Phe Tyr
                370                 375                 380

Tyr Ala Arg Val Ala Ser Val Thr Asp Thr Gly Ile Gln Pro Val Phe
385                 390                 395                 400

Ser Leu His Val Asp Thr Glu Asp His Ser Phe Leu Thr Asn Gly Phe
                405                 410                 415

Ile Ser His Asn
                420

<210> SEQ ID NO 31
<211> LENGTH: 420
<212> TYPE: PRT
<213> ORGANISM: Mycobacterium malmoense

<400> SEQUENCE: 31

Cys Cys Thr Gly Asp Ala Leu Val Arg Leu Pro Phe Gly His Ser Val
1               5                   10                  15

Arg Ile Gly Asn Phe Val Pro Ala Ala Cys Pro Asn Ser Asp Asn Ala
                20                  25                  30

Val Asn Leu Lys Val Leu Asp Arg His Gly Asp Pro Val Ala Asp
                35                  40                  45

Gln Leu Phe His Ser Gly Glu His Gln Thr Tyr Thr Val Arg Thr Ala
                50                  55                  60

Glu Gly Tyr Glu Val Thr Gly Thr Ser Asn His Pro Leu Leu Cys Leu
65                  70                  75                  80

Val Asp Val Gly Gly Val Pro Thr Leu Leu Trp Lys Leu Ile Glu Glu
                85                  90                  95
```

Ile Arg Pro Asp Asp His Val Val Leu Gln Arg Thr Pro Pro Val Glu
                100                 105                 110

Phe Gly Pro Ala Asp Trp His Asp Val Met Glu Ala Leu Leu Leu Gly
            115                 120                 125

Ala Phe Ile Ser Glu Gly Phe Val Ser Glu Val Arg Ala Gly Phe Asn
        130                 135                 140

Asn Cys Asp Arg Asp Tyr Phe Ala Met Val Val Gly Ala Tyr Asp Ala
145                 150                 155                 160

Val Val Gly Gly Arg Arg Tyr Val Ser Ser Arg Arg Ile Ala Ser Gly
                165                 170                 175

Ser Thr Leu His Glu Leu Asp Ile Gln Asn Ile Lys Glu Leu Lys Glu
            180                 185                 190

Ala Arg Leu Gly Asp Leu Cys Gly Gln Arg Pro Ala Asp Lys Ser Val
        195                 200                 205

Pro Asp Trp Leu Trp His Ser Pro Ala Ala Val Lys Arg Val Phe Leu
210                 215                 220

Gln Ala Leu Phe Glu Gly Gly Gly Ser Cys Ser Ala Leu Pro Arg Asn
225                 230                 235                 240

Met Ile Gln Ile Ser Tyr Ser Thr Arg Ser Arg Gln Leu Ala Val Asp
                245                 250                 255

Val Gln Gln Met Leu Leu Glu Phe Gly Ile Ile Thr Arg Arg Tyr Arg
            260                 265                 270

His Ala Val Gly Glu His Lys Val Leu Ile Thr Asn Arg Ala Gln Ala
        275                 280                 285

Glu Leu Phe Ala Thr Arg Val Gly Phe Gly Ala Lys Gln Glu Lys
290                 295                 300

Leu Thr Lys Ile Leu Gly Ser Met Pro Pro Cys Ala Gly Met Asp Ser
305                 310                 315                 320

Asp His Val Pro Gly Leu Ala Arg Phe Ile Arg Lys His Cys Gly Ser
                325                 330                 335

Arg Trp Val Asp Lys Asp Trp Leu Asn Arg His Asn Val Asp Arg Ile
            340                 345                 350

Gln Arg Trp Arg Thr Ser Gly Glu Lys Ile Leu Ser His Ile Ala Asp
        355                 360                 365

Pro Asp Val Arg Ala Ile Ala Thr Asp Leu Thr Asp Gly Arg Phe Tyr
370                 375                 380

Tyr Ala Lys Val Ala Ser Val Thr Glu Ala Gly Val Gln Pro Val Tyr
385                 390                 395                 400

Ser Leu Arg Val Asp Thr Asp Glu His Ala Phe Leu Thr Asn Gly Phe
                405                 410                 415

Val Ser His Asn
            420

<210> SEQ ID NO 32
<211> LENGTH: 430
<212> TYPE: PRT
<213> ORGANISM: Synechocystis species PCC6803

<400> SEQUENCE: 32

Cys Leu Thr Gly Asp Ser Gln Val Leu Thr Arg Asn Gly Leu Met Ser
1               5                   10                  15

Ile Asp Asn Pro Gln Ile Lys Gly Arg Glu Val Leu Ser Tyr Asn Glu
                20                  25                  30

Thr Leu Gln Gln Trp Glu Tyr Lys Lys Val Leu Arg Trp Leu Asp Arg
            35                  40                  45

```
Gly Glu Lys Gln Thr Leu Ser Ile Lys Thr Lys Asn Ser Thr Val Arg
        50                   55                  60

Cys Thr Ala Asn His Leu Ile Arg Thr Glu Gln Gly Trp Thr Arg Ala
 65              70                  75                      80

Glu Asn Ile Thr Pro Gly Met Lys Ile Leu Ser Pro Ala Ser Val Asp
                85                  90                  95

Val Asp Asn Leu Ser Gln Ser Thr Ala Leu Thr Ala Ser Leu Gly Gly
            100                 105                 110

Leu Ser Gly Ala Ile Asn Tyr Glu Ala Ile Asn Thr Asp Lys Lys Asn
            115                 120                 125

Thr Thr Leu Ser Leu Ser Leu Lys Lys Gln Lys Pro Gln Asp Pro Phe
            130                 135                 140

Val Asn Ala Asp Val Ala Lys Asn Leu Ile Phe Gln His Phe Cys Ser
145                 150                 155                 160

Ala Lys Glu Glu Lys Leu Lys Val Ser Asn Pro Ile Gly Glu Asp Ile
                165                 170                 175

Pro Thr Lys Lys Ala Thr Asp Phe Gly Ile Ser Glu Gln Lys Lys Leu
                180                 185                 190

His Gln Gly Gln Asn Arg Trp Glu Gln Lys Phe Ser Val Leu Ser Thr
            195                 200                 205

Glu Pro Cys Leu Gly Met Glu Val Leu Thr Ile Pro Thr His Ile Ala
210                 215                 220

Asp Ser Pro Ala Cys Asp Gly Pro Thr Ala Pro Ser Ser Gln Asn Gly
225                 230                 235                 240

Trp Asn Ile Lys Arg Gln Asp Trp Asp Val Cys His Pro Lys Tyr Asp
                245                 250                 255

Ser Gln Pro Ile Lys Ala Met Gly Lys Val Pro Ser Ala Val Lys Pro
            260                 265                 270

Val Val Pro Gln Thr Leu Leu Met Phe Ser Ala Gln Ser Asn Leu Glu
            275                 280                 285

Val Lys Glu Asn Lys Phe Leu Arg Asn Gly Ser Arg Ile Ser Leu Lys
            290                 295                 300

Lys Glu Trp Leu Gly Gly Thr Trp Thr Val Pro Ser Leu Phe Pro
305                 310                 315                 320

Asn Leu Gly Val His Gln Phe Ser Tyr Thr Gln Arg Ala Phe Ser Arg
                325                 330                 335

Lys Lys Ile Asn Leu Leu Leu Asn Gly Leu Pro Ile Glu Asp Ile Pro
                340                 345                 350

Pro Val Gln Asn Pro Ile Ala Glu Ala Leu Thr Ala Lys Pro Ile Thr
            355                 360                 365

Thr Gln Lys Trp Glu Gln Trp Pro Pro Ala Ser Gly Tyr Arg Thr Trp
            370                 375                 380

Lys Ser Ile Pro Ser Pro Gln Trp His Thr Asn Phe Glu Glu Val Glu
385                 390                 395                 400

Ser Val Thr Lys Gly Gln Val Glu Lys Val Tyr Asp Leu Glu Val Glu
                405                 410                 415

Asp Asn His Asn Phe Val Ala Asn Gly Leu Leu Val His Asn
            420                 425                 430

<210> SEQ ID NO 33
<211> LENGTH: 333
<212> TYPE: PRT
<213> ORGANISM: Pyrococcus abyssi
```

```
<400> SEQUENCE: 33

Cys Phe Ser Gly Glu Glu Thr Val Val Ile Arg Glu Asn Gly Glu Val
1               5                   10                  15

Lys Val Leu Arg Leu Lys Asp Phe Val Glu Lys Ala Leu Glu Lys Pro
            20                  25                  30

Ser Gly Glu Gly Leu Asp Gly Asp Val Lys Val Val Tyr His Asp Phe
        35                  40                  45

Arg Asn Glu Asn Val Glu Val Leu Thr Lys Asp Gly Phe Thr Lys Leu
    50                  55                  60

Leu Tyr Ala Asn Lys Arg Ile Gly Lys Gln Lys Leu Arg Arg Val Val
65                  70                  75                  80

Asn Leu Glu Lys Asp Tyr Trp Phe Ala Leu Thr Pro Asp His Lys Val
                85                  90                  95

Tyr Thr Thr Asp Gly Leu Lys Glu Ala Gly Glu Ile Thr Glu Lys Asp
            100                 105                 110

Glu Leu Ile Ser Val Pro Ile Thr Val Phe Asp Cys Glu Asp Glu Asp
        115                 120                 125

Leu Lys Lys Ile Gly Leu Leu Pro Leu Thr Ser Asp Asp Glu Arg Leu
    130                 135                 140

Arg Lys Ile Ala Thr Leu Met Gly Ile Leu Phe Asn Gly Gly Ser Ile
145                 150                 155                 160

Asp Glu Gly Leu Gly Val Leu Thr Leu Lys Ser Glu Arg Ser Val Ile
                165                 170                 175

Glu Lys Phe Val Ile Thr Leu Lys Glu Leu Phe Gly Lys Phe Glu Tyr
            180                 185                 190

Glu Ile Ile Lys Glu Glu Asn Thr Ile Leu Lys Thr Arg Asp Pro Arg
        195                 200                 205

Ile Ile Lys Phe Leu Val Gly Leu Gly Ala Pro Ile Glu Gly Lys Asp
    210                 215                 220

Leu Lys Met Pro Trp Trp Val Lys Leu Lys Pro Ser Leu Phe Leu Ala
225                 230                 235                 240

Phe Leu Glu Gly Phe Arg Ala His Ile Val Glu Gln Leu Val Asp Asp
                245                 250                 255

Pro Asn Lys Asn Leu Pro Phe Phe Gln Glu Leu Ser Trp Tyr Leu Gly
            260                 265                 270

Leu Phe Gly Ile Lys Ala Asp Ile Lys Val Glu Glu Val Gly Asp Lys
        275                 280                 285

His Lys Ile Ile Phe Asp Ala Gly Arg Leu Asp Val Asp Lys Gln Phe
    290                 295                 300

Ile Glu Thr Trp Glu Asp Val Glu Val Thr Tyr Asn Leu Thr Thr Glu
305                 310                 315                 320

Lys Gly Asn Leu Leu Ala Asn Gly Leu Phe Val Lys Asn
                325                 330

<210> SEQ ID NO 34
<211> LENGTH: 412
<212> TYPE: PRT
<213> ORGANISM: Methanococcus jannaschii

<400> SEQUENCE: 34

Cys Ile Glu Gly Asp Ala Lys Ile Leu Thr Asp Arg Gly Phe Leu Lys
1               5                   10                  15

Met Lys Glu Val Tyr Lys Leu Val Lys Asn Gly Glu Lys Leu Lys Val
            20                  25                  30
```

Leu Gly Leu Asn Ala Glu Thr Leu Lys Thr Glu Trp Lys Glu Ile Ile
             35                  40                  45

Asp Ala Gln Lys Arg Glu Ala Arg Arg Tyr Glu Ile Gly Val Tyr Arg
 50                  55                  60

Lys Asn Lys Asn Thr Lys Asp Thr Ile Lys Ile Thr Pro Asp His Lys
 65                  70                  75                  80

Phe Pro Val Phe Val Asn Gly Glu Leu Ser Lys Val Gln Leu Cys Asp
                 85                  90                  95

Ile Ile Asp Asn Asn Leu Ser Val Leu Ser Ile Asp Tyr Ile Pro Met
            100                 105                 110

Ile Glu Glu Lys Tyr Glu Ser Leu Ala Glu Val Met Tyr Leu Gly Gly
            115                 120                 125

Ala Val Leu Ser Asp Gly His Ile Val Arg Arg Asn Gly Lys Pro Ile
130                 135                 140

Arg Val Arg Phe Thr Gln Lys Asp Thr Glu Glu Lys Lys Asp Phe Ile
145                 150                 155                 160

Glu Lys Val Lys Gly Asp Val Lys Leu Ile Gly Gly Asn Phe Ile Glu
                165                 170                 175

Ile Ser Asn Arg Asn Asn Val Ile Glu Tyr Gln Thr Ser Arg Lys Ile
            180                 185                 190

Pro Ser Glu Ile Leu Gly Phe Ile Glu Val Asn Ile Asn Thr Ile Pro
            195                 200                 205

Leu Tyr Ala Thr Lys Asp Glu Ile Ala Asp Leu Ile Ala Gly Phe Val
        210                 215                 220

Asp Gly Asp Gly Cys Leu Ser Gly Lys Arg Arg Val Glu Ile Tyr Gln
225                 230                 235                 240

Asn Ser Ser His Ile Lys Lys Ile Glu Gly Leu Ile Val Gly Leu Tyr
                245                 250                 255

Arg Leu Gly Ile Ile Pro Arg Leu Arg Tyr Lys Arg Ser Ser Thr Ala
            260                 265                 270

Thr Ile Tyr Phe Asn Asn Asn Leu Glu Thr Ile Leu Gln Arg Thr Arg
        275                 280                 285

Arg Ile Lys Leu Asp Lys Leu Lys Glu Phe Lys Lys Pro Val Glu Asp
290                 295                 300

Lys Lys Leu Ile Asp Ile Ser Gln Ile Leu Pro Glu Leu Lys Glu Phe
305                 310                 315                 320

Asp Tyr Lys Gly Tyr Leu Tyr Lys Thr Tyr Lys Glu Lys Leu Phe Ile
                325                 330                 335

Gly Ile Asn Lys Leu Glu Glu Tyr Leu Ser Lys Ile Asp Lys Asp Gly
            340                 345                 350

Ile Glu Arg Ile Lys Gln Lys Ile Lys Leu Leu Lys Glu Ser Asp Ile
        355                 360                 365

Tyr Ser Ile Arg Ile Lys Lys Val Gly Glu Asp Tyr Gly Glu Val Tyr
370                 375                 380

Asn Ile Thr Val Lys Ala Glu Asn Glu Phe Asn His Asn Tyr Val Val
385                 390                 395                 400

Trp Thr Lys His Tyr Thr Pro Ile Val Val Phe Asn
                405                 410

<210> SEQ ID NO 35
<211> LENGTH: 819
<212> TYPE: PRT
<213> ORGANISM: Aspergillus fumigatus FRR0163

<400> SEQUENCE: 35

```
Cys Leu Ala Lys Gly Thr Arg Leu Leu Arg Tyr Asp Gly Ser Glu Ile
1               5                   10                  15

Glu Val Gln Asp Val Lys Glu Gly Asp Leu Leu Leu Gly Pro Asp Gly
                20                  25                  30

Gly Pro Arg Arg Ala Phe Asn Ile Val Asn Gly Lys Asp Arg Leu Tyr
            35                  40                  45

Arg Ile Lys Ile Gly Gly Ser Lys Glu Asp Leu Val Val Thr Pro Asn
        50                  55                  60

His Ile Leu Val Leu His Arg Glu Lys Arg Ala Arg Asn Val Tyr Thr
65                  70                  75                  80

Gly Pro Ser Val Gln Gly His Ile Gln Arg Ser Glu Asn Gly His Gly
                85                  90                  95

Asn Leu Pro Met Leu Ser Ser Pro Ala Ala His His Pro Asn
                100                 105                 110

Asn Leu Val Lys Asn Arg Gly Asp Phe Trp Ser Ala Leu Lys Ser Ala
            115                 120                 125

Ile Ala Trp Val Leu His Ala Glu Arg Ser Ser Thr Gly Ala Asn Met
        130                 135                 140

Val Arg Asn Val Leu Asn Gly Thr Val Gly Leu Thr Ala His Lys Glu
145                 150                 155                 160

Ser Tyr Thr Val Thr Asn Pro Gln Gln Lys Gly Val Tyr Tyr Thr Tyr
                165                 170                 175

Val Trp Gly Asn Pro Gln Arg Thr Ser Ile Lys Gly His Arg Asp His
            180                 185                 190

Pro Pro Val Phe Leu Pro Thr Lys Glu Asp Ala Phe Ser Ala Ala Ile
        195                 200                 205

Ala Lys Ser Arg Glu Leu Tyr Ser Gln Ser Glu Val Thr Leu Ala Thr
    210                 215                 220

Leu Arg Gln Arg Phe Leu Ala Lys Ser Ala Asp Gly Lys Gly Gly Glu
225                 230                 235                 240

Ile Leu Val Asp Ala Asn Leu Pro Asn Ile Phe Leu Leu Trp Asp Lys
                245                 250                 255

Asn Arg Ser Asn Leu Lys Phe Arg Val Leu Cys Ser Arg Asn Phe Lys
            260                 265                 270

Thr Tyr Gly Arg Val Tyr Thr Phe Glu Ser Met Pro Ser Thr Asn Ala
        275                 280                 285

Glu Glu Pro Gly Tyr Gly Asp Asp Glu Leu Pro Gln Val Ser Ala
    290                 295                 300

Glu Glu Arg Tyr Asp Thr Val Glu Met Thr Ala Ala Glu Phe Ala Ser
305                 310                 315                 320

Leu Ser Thr Glu Glu Arg Ser Arg Tyr Arg Val Phe Arg Cys Pro Gly
                325                 330                 335

Phe Glu Leu Pro Glu Gln Pro Val Pro Val Asn Pro Tyr Phe Leu Gly
            340                 345                 350

Leu Trp Leu Gly Asp Asp Asn His Glu Lys Thr Thr Asn His Asn Ile
        355                 360                 365

His Glu Glu Asn Val Arg Glu Phe Leu Val Asn His Ala Ala Glu Leu
    370                 375                 380

Asp Met Tyr Leu Ala Trp Gln Gly Leu Ile Asp Tyr Ala Thr Val Ala
385                 390                 395                 400

Asn Pro Ala Pro Met Met Val Arg Leu Pro Pro Thr Asn Pro Asp Thr
                405                 410                 415
```

```
Ile Glu His Arg Pro Val Val Cys Gln Ala Arg Gln Ser Ile Arg Lys
                420                 425                 430

Leu Arg Leu Ala Ala Lys Asn Ile Ala Gln Pro Glu Val Val Leu Ser
            435                 440                 445

Thr Ser Pro Arg Pro Glu Ser Gln Met Gln Pro Lys Arg Glu Leu Pro
        450                 455                 460

Ser Asn Thr Glu Thr Ala Leu Arg Ser Glu Ala Glu Ala Ser Ser Ile
465                 470                 475                 480

Ser Ala Ile Leu Asp Ser Lys Ala Gly His Ser Ser Leu Asp Thr Gly
                485                 490                 495

Asp Pro Asn Ser Asp Val Val Pro Glu Ser Ile Pro Asn Asp Val Ala
            500                 505                 510

Asp Phe Gly Leu Asp Gly Val Pro Glu Leu Thr Ser Ser Gly Phe Ser
        515                 520                 525

Glu Leu Thr Ser Asp Ser Glu Leu Met Arg Leu Ile Glu Gln Val Glu
530                 535                 540

Arg Ser Ser Gln Gly Ser Thr Glu Glu Pro Ser Gln Ala Ser Val Val
545                 550                 555                 560

Glu Gln Glu Ala Asp Leu Asn Leu Leu Glu Thr Asp Ser Glu Asp Glu
                565                 570                 575

Glu Ala Asp Ser Ala Asp Asp Glu Phe Gly Asp Pro Glu Ala Ser
            580                 585                 590

Glu Phe Arg Pro Glu Pro Glu Ser Gln Leu Ser Gln Ser His Phe Ser
        595                 600                 605

Asn Arg Arg Arg Asn His Arg Leu Arg Thr Gly Arg Arg Val Tyr Gly
610                 615                 620

Asp Leu Asn Gly Glu Glu Gly Ile Leu Leu Asp Gln Ile Val Glu
625                 630                 635                 640

Gln Ser Glu Gly Ser Arg Val Asn Ser Leu Leu Arg Ala Leu Asp Ala
                645                 650                 655

Leu Gly Ile Ile Ala Gln Lys Gly Thr Gly Pro Glu Thr Asn Arg Lys
            660                 665                 670

His Ile Pro Ser Ile Tyr Met Lys Asn Ser Arg Ser Val Arg Leu Ala
        675                 680                 685

Val Leu Ala Gly Leu Ile Asp Ser Asp Gly Trp Tyr Val Tyr Pro Glu
690                 695                 700

Asn Val Leu Gly Phe Ala Gln Ser Glu Arg Trp His Ser Lys Leu Phe
705                 710                 715                 720

Trp Asp Val Val Ala Leu Ala Arg Ser Leu Gly Leu Ser Val Leu Thr
                725                 730                 735

Lys Arg Arg Met Met Trp Asn Pro Ala Arg Thr Glu Arg Tyr Pro Gln
            740                 745                 750

Leu Phe Ala Gln Ile Ser Gly Asn Val Ala Glu Val Pro Cys Leu Ile
        755                 760                 765

Ala Arg Lys Lys Gly Val Glu Arg Leu Ile Pro Gln Thr His Ser Phe
770                 775                 780

Met Ile Lys Asp Ile Ser Leu Glu Pro Glu Ala Thr Glu Trp Ala Gly
785                 790                 795                 800

Phe Arg Val Asp Lys Asp Gln Leu Tyr Leu Arg His Asp Tyr Leu Val
                805                 810                 815

Leu His Asn

<210> SEQ ID NO 36
```

```
<211> LENGTH: 605
<212> TYPE: PRT
<213> ORGANISM: Aspergillus nidulans FGSC A

<400> SEQUENCE: 36
```

| | | | | | | | | | | | | | | |
|---|---|---|---|---|---|---|---|---|---|---|---|---|---|---|
| Cys | Leu | Ala | Asn | Gly | Thr | Gln | Leu | Leu | Arg | Tyr | Asp | Gly | Thr | Lys | Val |
| 1 | | | | 5 | | | | | 10 | | | | | 15 | |

Asn Val Glu Asp Val Lys Glu Gly Asp Leu Leu Gly Pro Asp Gly
                20                  25                  30

Gly Pro Arg Arg Ala Phe Asn Val Ser Gly Lys Asp Arg Leu Tyr
         35                  40                  45

Arg Ile Lys Ile Asp Gly Asp Lys Glu Asp Leu Val Val Thr Ala Asn
50                  55                  60

His Ile Leu Val Leu His Arg Ala Lys Ala Met Asn Thr Ser Val Cys
65                  70                  75                  80

Phe Asp Arg Ser Lys Glu Gln Gln Gly Gly Ala Gly Glu Gln Leu Asp
                85                  90                  95

Ile Ser Glu Val Ser Ala Ala Glu Arg Tyr Asp Thr Val Glu Met Thr
                100                 105                 110

Ala Ala Glu Phe Ala Ala Leu His Pro Gln Glu Arg Ser Trp Tyr Arg
            115                 120                 125

Ala Ile Arg Cys Pro Gly Phe Glu Leu Pro Glu Gln Asp Val Pro Val
            130                 135                 140

Asn Pro Tyr Phe Leu Gly Leu Trp Leu Gly Asp Glu Ser Arg Asn Gln
145                 150                 155                 160

Ser Ala Ile Tyr Ser Asn His Glu Glu Ala Leu Arg Glu Phe Leu Val
                165                 170                 175

Ser His Ala Ala Glu Leu Asp Met His Leu Val Tyr His Gly Gln Ser
            180                 185                 190

Ala Tyr Ser Thr Val Cys Asn Lys Asp Arg Pro Thr Asn Lys Arg Ile
            195                 200                 205

Gly Pro Ala Asn Gln Thr Gln Thr Val Arg Pro Thr Ile Arg Gln Thr
210                 215                 220

Arg Arg Thr Ile Arg Gln Gln Arg Leu Ala Ala Glu His Ala Ala Ala
225                 230                 235                 240

Glu Tyr Thr Thr Gln Arg Glu Thr Ala Ser Leu Thr Pro Leu Leu Glu
                245                 250                 255

Ser Pro Thr Ser Asp Lys His Gly Leu Leu Ser Ser Val Glu Thr Pro
            260                 265                 270

Gly Arg Leu Ser Asp Ser Val Thr Thr Glu Leu Pro Met Ser Arg Ser
            275                 280                 285

Ala Ser Ala Met Arg Ser Ile Arg Thr Ala Ser Gly Leu Ser Glu Phe
290                 295                 300

Asn Asp Val Thr Asn Val Ser Ala Ser Met Pro Asp Ile Gln Asn Ser
305                 310                 315                 320

Gly Ile Lys Asn Gln Gly Arg Ile Ala Lys Val Thr Arg Gln Gln Asp
                325                 330                 335

Ser Lys Gly Glu Val Asp Phe Arg Gln Gln Tyr Ser Gln Ala Ile Lys
            340                 345                 350

Asp Asp Leu Glu Leu Leu Glu Thr Asp Ile Glu Asp Val Ala Ser
            355                 360                 365

Ser Asp Glu Ile Glu Asp Val Cys Val Val Gly Ser Glu Asn Glu Leu
370                 375                 380

Ile Gly Ser Glu Lys Gln Asp Gln Ser Gly Arg Arg Arg Gln Ile His

```
                385                 390                 395                 400
        Arg Leu Arg Thr Gly His Arg Gly Tyr Gly Asp Leu Ser Asp Glu
                        405                 410                 415

Gln Glu Gln Leu Leu Asp Ser Val Val Glu Arg Tyr Ala Gly Asp Ser
                        420                 425                 430

Arg Leu Asn Thr Leu Gln Gln Glu Leu Ser Lys Met Gly Ile Leu Asn
                        435                 440                 445

Pro Glu Thr Gly Pro Ile Asn Asp Lys Lys Arg Ile Pro Gln Val Phe
                        450                 455                 460

Met Gln Asn Ser Arg Ser Val Arg Leu Ser Val Leu Ala Gly Leu Leu
        465                 470                 475                 480

Asp Ser Asp Gly Trp Tyr Ile Tyr Pro Glu Asn Met Phe Gly Phe Ala
                        485                 490                 495

Gln Ser Glu Leu Cys His Lys Glu Leu Phe Trp Asp Val Val Thr Leu
                        500                 505                 510

Ala Arg Ser Leu Gly Phe Gly Val Trp Thr Lys Lys Arg Met Met Pro
                        515                 520                 525

Asp Pro Thr Gly Lys Arg Met Ser Pro Met Leu Val Ala Gln Ile Ser
                        530                 535                 540

Gly Asp Leu Ala Glu Ile Pro Cys Val Leu Ala Arg Lys Lys Ala Met
        545                 550                 555                 560

Pro Arg Leu Ile Pro Gln Ser His Ser Phe Ala Ile Lys Asp Ile Ser
                        565                 570                 575

Leu Glu Ser Glu Ala Thr Glu Trp Ala Gly Phe Arg Val Asp Lys Asp
                        580                 585                 590

Gln Leu Tyr Leu Arg His Asp Tyr Val Val Leu His Asn
                        595                 600                 605

<210> SEQ ID NO 37
<211> LENGTH: 171
<212> TYPE: PRT
<213> ORGANISM: Cryptococcus neoformans

<400> SEQUENCE: 37

Cys Leu Gln Asn Gly Thr Arg Leu Leu Arg Ala Asp Gly Ser Glu Val
        1               5                   10                  15

Leu Val Glu Asp Val Gln Glu Gly Asp Gln Leu Leu Gly Pro Asp Gly
                        20                  25                  30

Thr Ser Arg Thr Ala Ser Lys Ile Val Arg Gly Glu Arg Leu Tyr
                        35                  40                  45

Arg Ile Lys Thr His Glu Gly Leu Glu Asp Leu Val Cys Thr His Asn
        50                  55                  60

His Ile Leu Ser Met Tyr Lys Glu Arg Phe Gly Arg Glu Gly Ala His
        65                  70                  75                  80

Ser Pro Ser Ala Gly Thr Ser Leu Thr Glu Ser His Glu Arg Val Asp
                        85                  90                  95

Val Thr Val Asp Asp Phe Val Arg Leu Pro Gln Gln Glu Gln Gln Lys
                        100                 105                 110

Tyr Lys Leu Phe Arg Ser Thr Asp Phe Val Arg Arg Glu Gln Pro Ser
                        115                 120                 125

Ala Ser Lys Leu Ala Thr Leu Leu His Ile Asn Ser Ile Glu Leu Glu
                        130                 135                 140

Glu Glu Pro Thr Lys Trp Ser Gly Phe Val Val Asp Lys Asp Ser Leu
        145                 150                 155                 160
```

```
                Tyr Leu Arg Tyr Asp Tyr Leu Val Leu His Asn
                            165                 170

<210> SEQ ID NO 38
<211> LENGTH: 534
<212> TYPE: PRT
<213> ORGANISM: Histoplasma capsulatum

<400> SEQUENCE: 38

Cys Leu Ala Lys Gly Thr Gln Leu Leu Arg Tyr Asp Gly Thr Lys Val
1               5                   10                  15

Gly Val Glu Asn Val Arg Glu Gly Asp Leu Leu Gly Pro Asp Gly
            20                  25                  30

Glu Pro Arg Arg Ala Phe Asn Ile Val Ser Gly Arg Asp Arg Leu Tyr
        35                  40                  45

Arg Ile Ser Ile Asp Ala Asp Lys Glu Asp Leu Val Val Thr Pro Asn
50                  55                  60

His Ile Leu Val Leu His His Glu Lys Glu Asn Gln Lys Arg Gln Ser
65                  70                  75                  80

Glu Leu Ser Ala Ser Ala Thr Glu Arg Tyr Asp Thr Val Glu Met Thr
                85                  90                  95

Ala Ala Asp Phe Ala Ala Leu Asp Pro Glu Arg Arg Trp Tyr Arg
            100                 105                 110

Leu Phe Arg Ser Pro Gly Phe Glu Leu Gly Gln Gln Asn Val Pro Ile
        115                 120                 125

Asp Pro Tyr Phe Val Gly Phe Trp Leu Cys Asp Gly Ile Arg Ala Ser
    130                 135                 140

Thr Thr Ile Tyr Thr Ser Pro Glu Glu Ala Thr Arg Glu Phe Ile Ile
145                 150                 155                 160

Asn His Ala Ala Glu Leu Asp Leu Gln Leu Ala Ser Lys Glu Tyr Met
                165                 170                 175

Gln His Pro Val Arg Arg Val Ala Arg Gln Thr Ile Leu Glu Gln Arg
            180                 185                 190

Leu Ala Val Gln Cys Thr Ala Pro Gln Glu Thr Asp Gly Ser Leu Leu
        195                 200                 205

Ser His Ile Leu Gln Lys Ala Ala Lys Ser Gly Leu Ala Ser Ser Thr
    210                 215                 220

Arg Thr Met Ser Thr Ser Arg Asn Arg Gln Pro Leu Ser Glu Thr Ser
225                 230                 235                 240

Ala Ala Thr Ser Met Asn Ile Leu Pro Gly Phe Ala Ser Asn Ser Thr
                245                 250                 255

Ser Val Val Ser Pro Gly Ile Asp Ser His Glu Ile Leu Ser Leu Arg
            260                 265                 270

Asn Ser Cys Ser Gln Leu Val Gln Ile Ala Glu Lys Ser Gly Leu Arg
        275                 280                 285

Glu Glu Cys Met Ile Asn Pro Pro Ser Ser Arg Glu Asp Leu Val Leu
    290                 295                 300

Asp Leu Phe Asp Thr His Ile Glu Ala Asp Glu Ile Gln Gly Leu Asp
305                 310                 315                 320

Glu Asn Leu Thr Gly Gln Lys His Arg Leu Arg Thr Gly Cys Arg Ala
                325                 330                 335

Tyr Gly Asp Leu Thr Val Asp Glu Glu Gly Gln Ile Leu Asp Asn Ile
            340                 345                 350

Ile Ser Arg Pro Val Gly Thr Pro Asp Ile Gly Thr Leu Leu Arg Ala
        355                 360                 365
```

```
Leu Glu Glu Leu Gly Leu Pro Thr Asn Arg Thr Gly His Gly Val
    370                 375                 380

Glu Asn Lys Arg Ile Pro Leu Met Tyr Met Lys Ser Ser Arg Ser Ile
385                 390                 395                 400

Arg Leu Ala Leu Ala Gly Leu Ile Asp Ser Asp Gly Trp Tyr Cys
                405                 410                 415

Gln Pro Gln Asn Thr Phe Cys Phe Gly Glu Ser Glu Arg Ile Ser Pro
                420                 425                 430

Thr Leu Phe Trp Asp Ile Val Thr Leu Ala Arg Ser Leu Gly Leu Ser
                435                 440                 445

Val Ser Thr Glu Gln His Thr Met Arg Ser Pro Ala Cys Thr Ala Phe
                450                 455                 460

Lys Pro Arg Phe Val Ala Gln Ile Ser Gly Asn Val Ala Glu Val Thr
465                 470                 475                 480

Cys Leu Leu Ala Arg Lys Arg Gly Val Lys Ser Pro Val Ser Gln Ala
                485                 490                 495

His Ser Phe Thr Ile Lys Gly Ile His Leu Glu Ser Glu Met Thr Glu
                500                 505                 510

Trp Ala Gly Phe Arg Val Asp Lys Asp Gln Leu Tyr Leu Arg His Asp
                515                 520                 525

Phe Leu Val Leu His Asn
    530

<210> SEQ ID NO 39
<211> LENGTH: 157
<212> TYPE: PRT
<213> ORGANISM: Penicillium chrysogenum

<400> SEQUENCE: 39

Cys Leu Ala Lys Gly Thr Arg Leu Leu Arg Cys Asp Gly Thr Glu Ile
1               5                   10                  15

Asn Val Glu Asp Val Arg Glu Gly Asp Leu Leu Leu Gly Pro Asp Gly
                20                  25                  30

Glu Pro Arg Arg Ala Phe Asn Ile Val Asn Gly Ile Asp Arg Leu Tyr
            35                  40                  45

Arg Ile Lys Ile Gly Gly Glu Lys Glu Asp Leu Val Val Thr Pro Asn
50                  55                  60

His Ile Leu Val Leu Tyr Arg Glu Asp Gly Ser Lys Asn Val Glu Lys
65                  70                  75                  80

Gln Thr Val Glu Ile Thr Ala Ala Glu Phe Ala Ala Leu Ser Thr Glu
                85                  90                  95

Glu Arg Ser Leu Tyr Ser Ala Phe Thr Ser Pro Arg Ala Glu Lys Gly
            100                 105                 110

Ala Asp Asp Ser Ala Gln Thr His Ser Phe Lys Ile Glu Gln Val Ser
        115                 120                 125

Leu Glu Ser Glu Lys Thr Glu Trp Ala Gly Phe Arg Val Asp Lys Asp
    130                 135                 140

Gln Leu Tyr Leu Arg His Asp Tyr Leu Val Leu His Asn
145                 150                 155

<210> SEQ ID NO 40
<211> LENGTH: 162
<212> TYPE: PRT
<213> ORGANISM: Penicillium expansum

<400> SEQUENCE: 40
```

```
Cys Leu Ala Lys Gly Thr Arg Leu Leu Arg Tyr Asp Gly Thr Glu Ile
1               5                   10                  15

Asn Val Glu Asp Val Arg Glu Gly Asp Gln Leu Leu Gly Pro Asp Gly
            20                  25                  30

Glu Pro Arg Arg Ala Phe Asn Ile Val Asn Gly Ile Asp Arg Leu Tyr
        35                  40                  45

Arg Ile Lys Ile Ala Gly Glu Lys Glu Asp Leu Val Val Thr Pro Asn
50                  55                  60

His Ile Leu Val Leu Tyr Arg Glu Glu Ala Ser Asp Gly Pro Lys
65                  70                  75                  80

Asn Ala Glu Arg Gln Thr Val Glu Ile Thr Ala Ala Glu Phe Ala Ala
                85                  90                  95

Leu Ser Thr Glu Glu Arg Gly Leu His Ser Ala Phe Thr Ser Ser Arg
                100                 105                 110

Val Glu Lys Asp Val Glu Asn Ser Ala Pro Gln Met His Ser Phe Lys
            115                 120                 125

Ile Glu His Ile Asn Leu Glu Tyr Glu Glu Thr Glu Trp Ala Gly Phe
130                 135                 140

Arg Val Asp Lys Asp Gln Leu Tyr Leu Arg His Asp Tyr Leu Val Leu
145                 150                 155                 160

His Asn

<210> SEQ ID NO 41
<211> LENGTH: 161
<212> TYPE: PRT
<213> ORGANISM: Penicillium vulpinum

<400> SEQUENCE: 41

Cys Leu Ala Lys Gly Thr Arg Leu Leu Arg Tyr Asp Gly Thr Glu Ile
1               5                   10                  15

Asn Val Glu Asp Val Arg Glu Gly Asp Gln Leu Leu Gly Pro Asp Gly
            20                  25                  30

Glu Pro Arg Arg Ala Phe Asn Ile Val Ser Gly Ile Asp Arg Leu Tyr
        35                  40                  45

Arg Val Lys Ile Gly Gly Glu Lys Glu Asp Leu Val Val Thr Pro Asn
50                  55                  60

His Ile Leu Val Phe Tyr Arg Glu Gly Pro Ser Asp Gly Pro Glu Asn
65                  70                  75                  80

Ala Glu Arg Gln Thr Val Glu Ile Thr Ala Ala Glu Phe Ala Thr Leu
                85                  90                  95

Ser Thr Glu Glu Arg Ser Leu Tyr Ser Ala Phe Thr Ser Pro Ala Val
                100                 105                 110

Glu Lys Gly Ala Glu Gly Ser Ala Ala Gln Met His Ser Phe Lys Val
            115                 120                 125

Glu Asp Ile Ser Leu Glu Ser Glu Lys Thr Glu Trp Ala Gly Phe Arg
130                 135                 140

Val Asp Lys Asp Gln Leu Tyr Leu Arg His Asp Tyr Leu Val Leu His
145                 150                 155                 160

Asn

<210> SEQ ID NO 42
<211> LENGTH: 440
<212> TYPE: PRT
<213> ORGANISM: Mycobacterium tuberculosis H37Rv
```

```
<400> SEQUENCE: 42

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu His Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gln Pro
                85                  90                  95

Arg Arg Phe Asp Gly Phe Gly Asp Ser Ala Pro Ile Pro Ala Asp His
            100                 105                 110

Ala Arg Leu Leu Gly Tyr Leu Ile Gly Asp Gly Arg Asp Gly Trp Val
        115                 120                 125

Gly Gly Lys Thr Pro Ile Asn Phe Ile Asn Val Gln Arg Ala Leu Ile
130                 135                 140

Asp Asp Val Thr Arg Ile Ala Ala Thr Leu Gly Cys Ala Ala His Pro
145                 150                 155                 160

Gln Gly Arg Ile Ser Leu Ala Ile Ala His Arg Pro Gly Glu Arg Asn
                165                 170                 175

Gly Val Ala Asp Leu Cys Gln Gln Ala Gly Ile Tyr Gly Lys Leu Ala
            180                 185                 190

Trp Glu Lys Thr Ile Pro Asn Trp Phe Phe Glu Pro Asp Ile Ala Ala
        195                 200                 205

Asp Ile Val Gly Asn Leu Leu Phe Gly Leu Phe Glu Ser Asp Gly Trp
210                 215                 220

Val Ser Arg Glu Gln Thr Gly Ala Leu Arg Val Gly Tyr Thr Thr Thr
225                 230                 235                 240

Ser Glu Gln Leu Ala His Gln Ile His Trp Leu Leu Leu Arg Phe Gly
                245                 250                 255

Val Gly Ser Thr Val Arg Asp Tyr Asp Pro Thr Gln Lys Arg Pro Ser
            260                 265                 270

Ile Val Asn Gly Arg Arg Ile Gln Ser Lys Arg Gln Val Phe Glu Val
        275                 280                 285

Arg Ile Ser Gly Met Asp Asn Val Thr Ala Phe Ala Glu Ser Val Pro
290                 295                 300

Met Trp Gly Pro Arg Gly Ala Ala Leu Ile Gln Ala Ile Pro Glu Ala
305                 310                 315                 320

Thr Gln Gly Arg Arg Gly Ser Gln Ala Thr Tyr Leu Ala Ala Glu
                325                 330                 335

Met Thr Asp Ala Val Leu Asn Tyr Leu Asp Glu Arg Gly Val Thr Ala
            340                 345                 350

Gln Glu Ala Ala Ala Met Ile Gly Val Ala Ser Gly Asp Pro Arg Gly
        355                 360                 365

Gly Met Lys Gln Val Leu Gly Ala Ser Arg Leu Arg Arg Asp Arg Val
370                 375                 380

Gln Ala Leu Ala Asp Ala Leu Asp Asp Lys Phe Leu His Asp Met Leu
385                 390                 395                 400

Ala Glu Glu Leu Arg Tyr Ser Val Ile Arg Glu Val Leu Pro Thr Arg
                405                 410                 415
```

```
Arg Ala Arg Thr Phe Asp Leu Glu Val Glu Leu His Thr Leu Val
            420                 425                 430

Ala Glu Gly Val Val His Asn
        435                 440

<210> SEQ ID NO 43
<211> LENGTH: 440
<212> TYPE: PRT
<213> ORGANISM: Mycobacterium tuberculosis So93

<400> SEQUENCE: 43

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu His Ala Arg Pro Val Val Ser Trp
        35                  40                  45

Phe Asp Gln Gly Thr Gln Asp Val Ile Gly Leu Arg Ile Ala Gly Gly
    50                  55                  60

Ala Ile Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gln Pro
                85                  90                  95

Arg Arg Phe Asp Gly Phe Asp Ser Ala Pro Ile Pro Ala Asp His
            100                 105                 110

Ala Arg Leu Leu Gly Tyr Leu Ile Gly Asp Gly Arg Asp Gly Trp Val
        115                 120                 125

Gly Gly Lys Thr Pro Ile Asn Phe Ile Asn Val Gln Arg Ala Leu Ile
    130                 135                 140

Asp Asp Val Thr Arg Ile Ala Ala Thr Leu Gly Cys Ala Ala His Pro
145                 150                 155                 160

Gln Gly Arg Ile Ser Leu Ala Ile Ala His Arg Pro Gly Glu Arg Asn
                165                 170                 175

Gly Val Leu Asp Leu Cys Arg Arg Ala Gly Val His Gly Lys Leu Ala
            180                 185                 190

Trp Glu Lys Thr Ile Pro Asn Trp Phe Phe Glu Pro Asp Ile Ala Ala
        195                 200                 205

Asp Ile Val Gly Asn Leu Leu Phe Gly Leu Phe Glu Ser Asp Gly Trp
    210                 215                 220

Val Ser Arg Glu Gln Thr Gly Ala Leu Arg Val Gly Tyr Thr Thr Thr
225                 230                 235                 240

Ser Glu Gln Leu Ala His Gln Ile His Trp Leu Leu Leu Arg Phe Gly
                245                 250                 255

Val Gly Ser Thr Val Arg Asp Tyr Asp Pro Thr Gln Lys Arg Pro Ser
            260                 265                 270

Ile Val Asn Gly Arg Arg Ile Gln Ser Lys Arg Gln Val Phe Glu Val
        275                 280                 285

Arg Ile Ser Gly Met Asp Asn Val Thr Ala Phe Ala Glu Ser Val Pro
    290                 295                 300

Met Trp Gly Pro Arg Gly Ala Ala Leu Ile Gln Ala Ile Pro Glu Ala
305                 310                 315                 320

Thr Gln Gly Arg Arg Gly Ser Gln Ala Thr Tyr Leu Ala Ala Glu
                325                 330                 335

Met Thr Asp Ala Val Leu Asn Tyr Leu Asp Glu Arg Gly Val Thr Ala
```

```
                    340                 345                 350
Gln Glu Ala Ala Met Ile Gly Val Ala Ser Gly Asp Pro Arg Gly
            355                 360                 365

Gly Met Lys Gln Val Leu Gly Ala Ser Arg Leu Arg Arg Asp Arg Val
        370                 375                 380

Gln Ala Leu Ala Asp Ala Leu Asp Asp Lys Phe Leu His Asp Met Leu
385                 390                 395                 400

Ala Glu Glu Leu Arg Tyr Ser Val Ile Arg Glu Val Leu Pro Thr Arg
                405                 410                 415

Arg Ala Arg Thr Phe Asp Leu Glu Val Glu Glu Leu His Thr Leu Val
            420                 425                 430

Ala Glu Gly Val Val Val His Asn
        435                 440

<210> SEQ ID NO 44
<211> LENGTH: 364
<212> TYPE: PRT
<213> ORGANISM: Mycobacterium flavescens

<400> SEQUENCE: 44

Cys Phe Ala Tyr Gly Thr Arg Gly Ala Leu Ala Asp Gly Thr Thr Glu
1               5                   10                  15

Lys Ile Gly Lys Ile Val Asn Gln Lys Met Asp Val Glu Val Met Ser
            20                  25                  30

Tyr Asp Pro Asp Thr Asp Gln Val Val Pro Arg Lys Val Val Asn Trp
        35                  40                  45

Phe Asn Asn Gly Pro Ala Glu Gln Phe Leu Gln Phe Thr Val Glu Lys
    50                  55                  60

Ser Gly Gly Asn Gly Lys Ser Gln Phe Ala Ala Thr Pro Asn His Leu
65                  70                  75                  80

Ile Arg Thr Pro Ala Gly Trp Thr Glu Ala Gly Asp Leu Val Ala Gly
                85                  90                  95

Asp Arg Val Met Ala Ala Glu Pro His Arg Leu Ser Asp Gln Gln Phe
            100                 105                 110

Gln Val Val Leu Gly Ser Leu Met Gly Asp Gly Asn Leu Ser Pro Asn
        115                 120                 125

Arg Arg Asp Arg Asn Gly Val Arg Phe Arg Met Gly His Gly Ala Lys
    130                 135                 140

Gln Val Asp Tyr Leu Gln Trp Lys Thr Ala Leu Leu Gly Asn Ile Lys
145                 150                 155                 160

His Ser Thr His Val Asn Asp Lys Gly Ala Thr Phe Val Asp Phe Thr
                165                 170                 175

Pro Leu Pro Glu Leu Ala Glu Leu Gln Arg Ala Val Tyr Leu Gly Asp
            180                 185                 190

Gly Lys Lys Phe Leu Ser Glu Glu Asn Phe Lys Ala Leu Thr Pro Leu
        195                 200                 205

Ala Leu Val Phe Trp Tyr Met Asp Asp Gly Pro Phe Thr Val Arg Ser
    210                 215                 220

Lys Gly Leu Gln Glu Arg Thr Ala Gly Gly Ser Gly Arg Ile Glu Ile
225                 230                 235                 240

Cys Val Glu Ala Met Ser Glu Gly Asn Arg Ile Arg Leu Arg Asp Tyr
                245                 250                 255

Leu Arg Asp Thr His Gly Leu Asp Val Arg Leu Arg Leu Ser Gly Ala
            260                 265                 270
```

```
Ala Gly Lys Ser Val Leu Val Phe Ser Thr Ala Ser Ser Ala Lys Phe
            275                 280                 285

Gln Glu Leu Val Ala Pro Tyr Ile Thr Pro Ser Met Glu Tyr Lys Leu
        290                 295                 300

Leu Pro Arg Phe Arg Gly Gln Gly Ala Val Thr Pro Gln Phe Val Glu
305                 310                 315                 320

Pro Thr Gln Arg Leu Val Pro Ala Arg Val Leu Asp Val His Val Lys
                325                 330                 335

Pro His Thr Arg Ser Met Asn Arg Phe Asp Ile Glu Val Glu Gly Asn
                340                 345                 350

His Asn Tyr Phe Val Asp Gly Val Met Val His Asn
            355                 360
```

<210> SEQ ID NO 45
<211> LENGTH: 365
<212> TYPE: PRT
<213> ORGANISM: Mycobacterium leprae TN

<400> SEQUENCE: 45

```
Cys Met Asn Tyr Ser Thr Arg Val Thr Leu Ala Asp Gly Ser Thr Glu
1               5                   10                  15

Lys Ile Gly Lys Ile Val Asn Asn Lys Met Asp Val Arg Val Leu Ser
            20                  25                  30

Tyr Asp Pro Val Thr Asp Arg Ile Val Pro Arg Lys Val Val Asn Trp
        35                  40                  45

Phe Asn Asn Gly Pro Ala Glu Gln Phe Leu Gln Phe Thr Val Glu Lys
    50                  55                  60

Ser Gly Ser Asn Gly Lys Ser Gln Phe Ala Ala Thr Pro Asn His Leu
65                  70                  75                  80

Ile Arg Thr Pro Gly Gly Trp Thr Glu Ala Gly Asn Leu Ile Ala Gly
                85                  90                  95

Asp Arg Val Leu Ala Val Glu Pro His Met Leu Ser Asp Gln Gln Phe
            100                 105                 110

Gln Val Val Leu Gly Ser Leu Met Gly Asp Gly Asn Leu Ser Pro Asn
        115                 120                 125

Leu Cys Asp Arg Asn Gly Val Arg Phe Arg Leu Leu Gly Tyr Gly Cys
    130                 135                 140

Lys Gln Val Glu Tyr Leu Gln Trp Lys Lys Ala Leu Met Gly Asn Ile
145                 150                 155                 160

Arg His Thr Val Arg Glu Asn Ser Met Gly Ala Ser Phe Ile Asp Phe
                165                 170                 175

Thr Pro Leu Pro Glu Leu Val Glu Leu Gln Arg Ala Val Tyr Leu Gly
            180                 185                 190

Asp Gly Lys Lys Phe Leu Ser Glu Tyr Leu Lys Ala Leu Thr Pro
        195                 200                 205

Leu Val Leu Ala Ile Trp Tyr Met Asp Asp Gly Ser Phe Thr Val Gly
    210                 215                 220

Ser Lys Arg Val Gln Glu Arg Thr Ala Gly Ser Gly Arg Ile Glu
225                 230                 235                 240

Ile Cys Val Asp Ala Met Thr Glu Gly Thr Arg Val Arg Leu Arg Asp
                245                 250                 255

Tyr Leu Cys Asp Thr His Gly Leu Asp Val Arg Leu Arg Glu Val Gly
            260                 265                 270

Ser Ala Gly Lys Ala Val Leu Val Phe Ser Thr Ala Ala Thr Ala Lys
        275                 280                 285
```

```
Phe Gln Ser Leu Ile Ala Pro Tyr Val Ala Pro Ser Met Glu Tyr Lys
        290                 295                 300

Leu Leu Pro Gln Phe Arg Gly Arg Gly Ser Val Thr Pro Gln Phe Val
305                 310                 315                 320

Glu Pro Thr Gln Gln Leu Val Pro Ala Arg Val Leu Asp Val His Val
                325                 330                 335

Lys Leu Ser Thr Arg Ser Met Asn Arg Phe Asp Ile Glu Val Glu Gly
            340                 345                 350

Asn His Asn Tyr Phe Val Asp Gly Val Met Val His Asn
        355                 360                 365

<210> SEQ ID NO 46
<211> LENGTH: 394
<212> TYPE: PRT
<213> ORGANISM: Trichodesmium erythraeum IMS101

<400> SEQUENCE: 46

Cys Leu Pro Glu Gly Ala Leu Val His Thr Ala Ser Gly Leu Val Ala
1               5                   10                  15

Ile Glu Lys Ile Arg Ile Gly Asp Arg Val Leu Thr Ser Gln Gly Phe
            20                  25                  30

Tyr Pro Val Thr Asn Phe Phe Asp Gln Gly Ile Gln Ser Leu Cys Arg
        35                  40                  45

Ile Gln Thr Glu Asp Gly Tyr Phe Glu Cys Thr Pro Asp His Lys Val
    50                  55                  60

Ala Val Leu Gln Asp Leu Tyr Gly Asn Tyr Lys Met Ile Lys Ala Lys
65                  70                  75                  80

Asp Leu Gln Glu Gly Asp Arg Leu Ile Phe Val Pro Gln Ala Ile Pro
                85                  90                  95

Gly Thr Pro Thr Glu Leu Pro Glu Leu Lys Ala Val Pro Ser Ser Glu
            100                 105                 110

Ala Lys Leu Ile Thr Ile Pro Ala Leu Gln Ser Glu Val Ala Tyr Phe
        115                 120                 125

Leu Gly Tyr Leu Ser Gly Asn Gly Ser Val Gly Ser Asp Gly Gly Gln
    130                 135                 140

Val Arg Phe Arg Val Ser Gln Asp Ser Pro Glu Ile Leu Glu Arg Leu
145                 150                 155                 160

Ile Asn Val Ala Gln Glu Phe Gly Leu Glu Thr His Arg Leu Arg Thr
                165                 170                 175

Leu Glu Gln Phe Gln Thr Gln Ala Tyr Glu Leu Glu Leu Asn Ser Ser
            180                 185                 190

Thr Leu Asn Lys Tyr Leu Ser Gln Phe Lys Gln Pro Ser Asn Ser Val
        195                 200                 205

Cys Ile Pro Glu Cys Ile Leu Met Gly Thr Thr Glu Ile Arg Gln Ala
    210                 215                 220

Tyr Leu Ala Gly Leu Val Asp Ala Asp Gly Cys His Ser Gln Gly Ile
225                 230                 235                 240

Leu Leu Thr Ser Val Asp Gln Gly Phe Leu Arg Gln Val Gln Ala Leu
                245                 250                 255

Tyr Ala Ser Leu Gly Ile Thr Thr Arg Leu Cys Gly Ser Val Gln Lys
            260                 265                 270

Pro Thr Gly Thr Trp Glu Gly Glu Leu Val Thr Val Ser Glu Gly Gly
        275                 280                 285

Tyr Glu Ala Val Glu Lys Leu Met Met Asn Tyr Ser Thr Gln Phe Pro
```

290                 295                 300
Val Gln Lys Pro Asn His Leu Lys Phe Phe Pro Asp Gln Gly Phe Pro
305                 310                 315                 320

Lys Glu Met Val Arg Pro Leu Val Lys Thr Ser Gln Asp His Leu Gly
                325                 330                 335

Lys Val His Lys Gln Met Ile Phe Pro Ser Val Lys Lys Phe Val Val
            340                 345                 350

Asp Ala Thr Asp Leu Ile Pro Val Lys Val Lys Val Glu Met Asp
            355                 360                 365

Val Arg Glu Ala Ser Thr Tyr Asp Ile Glu Val Ala Ser Ile His Glu
    370                 375                 380

Phe Val Cys Gln Gly Ile Leu Val Ser Asn
385                 390

<210> SEQ ID NO 47
<211> LENGTH: 399
<212> TYPE: PRT
<213> ORGANISM: Pyrococcus abyssi

<400> SEQUENCE: 47

Cys Ile Asp Gly Asn Ala Lys Ile Ile Phe Glu Asn Glu Gly Glu Glu
1               5                   10                  15

His Leu Thr Thr Met Ala Glu Met Tyr Glu Arg Tyr Arg His Leu Gly
            20                  25                  30

Glu Phe Tyr Asp Glu Asn Tyr Asn Arg Trp Gly Ile Asp Val Ser Ser
        35                  40                  45

Val Pro Ile Tyr Val Lys Ser Phe Asp Pro Glu Thr Arg Val Val
    50                  55                  60

Lys Gly Arg Val Arg Ala Ile Trp Lys Tyr Glu Leu Gly Glu Glu Ile
65                  70                  75                  80

Pro Lys Tyr Glu Ile Arg Thr His Lys Gly Thr Lys Ile Leu Thr Ser
                85                  90                  95

Pro Trp His Pro Phe Phe Val Leu Thr Pro Asp Phe Glu Val Ile Glu
            100                 105                 110

Lys Arg Ala Asp Glu Leu Lys Val Gly Asp Ile Leu Ile Gly Gly Met
        115                 120                 125

Pro Asp Gly Glu Asp His Glu Leu Ile Phe Asp Tyr Trp Leu Ala Gly
    130                 135                 140

Phe Ile Ala Gly Asn Gly Asn Leu Asp Asp Ser Glu Arg Glu Tyr Lys
145                 150                 155                 160

Ala Arg Glu Leu Leu Asp Gly Ile Glu Asn Gly Ile Pro Pro Lys Ile
                165                 170                 175

Leu Arg Lys Gly Lys Asn Ala Val Leu Ser Phe Ile Thr Gly Leu Phe
            180                 185                 190

Asp Ala Glu Gly His Val Asn Asp Lys Ser Gly Ile Glu Leu Gly Met
        195                 200                 205

Val Asn Lys Lys Leu Ile Glu Ala Val Thr His Tyr Leu Asn Ser Leu
    210                 215                 220

Gly Ile Lys Ala Arg Met Arg Glu Lys Arg Lys Asn Gly Ile Asp
225                 230                 235                 240

Tyr Ile Met His Val Glu Glu Tyr Ser Ser Leu Leu Arg Phe Tyr Glu
                245                 250                 255

Leu Ile Gly Lys His Leu Gln Asn Asn Glu Lys Lys Glu Lys Leu Glu
            260                 265                 270

```
Ile Leu Leu His Lys His Asn Gly Gly Ala Phe Asp Leu Ser Leu Asn
            275                 280                 285

Phe Asn Ala Phe Lys Glu Trp Ala Ser Arg Tyr Gly Val Glu Phe Lys
    290                 295                 300

Thr Asn Gly Asn Gln Ile Leu Ala Ile Ile Gly Asn Glu Lys Val Ser
305                 310                 315                 320

Leu Gly Gln Trp His Ala Arg Gly His Val Ser Lys Ala Val Leu Val
                325                 330                 335

Lys Met Leu Arg Lys Leu Tyr Glu Val Thr Lys Asn Asp Glu Val Lys
            340                 345                 350

Glu Met Leu His Leu Ile Glu Ser Leu Glu Val Val Lys Glu Ile Thr
        355                 360                 365

Ile Thr Asn Glu Pro Lys Thr Phe Tyr Asp Leu Thr Val Asp Lys Tyr
370                 375                 380

Gln Asn Tyr Leu Ala Gly Glu Asn Gly Met Ile Phe Val His Asn
385                 390                 395

<210> SEQ ID NO 48
<211> LENGTH: 454
<212> TYPE: PRT
<213> ORGANISM: Pyrococcus furiosus

<400> SEQUENCE: 48

Cys Ile Asp Gly Lys Ala Lys Ile Ile Phe Glu Asn Glu Gly Glu
1               5                   10                  15

His Leu Thr Thr Met Glu Glu Met Tyr Glu Arg Tyr Lys His Leu Gly
            20                  25                  30

Glu Phe Tyr Asp Glu Glu Tyr Asn Arg Trp Gly Ile Asp Val Ser Asn
        35                  40                  45

Val Pro Ile Tyr Val Lys Ser Phe Asp Pro Glu Ser Lys Arg Val Val
    50                  55                  60

Lys Gly Lys Val Asn Val Ile Trp Lys Tyr Glu Leu Gly Lys Asp Val
65                  70                  75                  80

Thr Lys Tyr Glu Ile Ile Thr Asn Lys Gly Thr Lys Ile Leu Thr Ser
                85                  90                  95

Pro Trp His Pro Phe Phe Val Leu Thr Pro Asp Phe Lys Ile Val Glu
            100                 105                 110

Lys Arg Ala Asp Glu Leu Lys Glu Gly Asp Ile Leu Ile Gly Gly Met
        115                 120                 125

Pro Asp Gly Glu Asp Tyr Lys Phe Ile Phe Asp Tyr Trp Leu Ala Gly
    130                 135                 140

Phe Ile Ala Gly Asp Gly Cys Phe Asp Lys Tyr His Ser His Val Lys
145                 150                 155                 160

Gly His Glu Tyr Ile Tyr Asp Arg Leu Arg Ile Tyr Asp Tyr Arg Ile
                165                 170                 175

Glu Thr Phe Glu Ile Ile Asn Asp Tyr Leu Glu Lys Thr Phe Gly Arg
            180                 185                 190

Lys Tyr Ser Ile Gln Lys Asp Arg Asn Ile Tyr Tyr Ile Asp Ile Lys
        195                 200                 205

Ala Arg Asn Ile Thr Ser His Tyr Leu Lys Leu Leu Glu Gly Ile Asp
    210                 215                 220

Asn Gly Ile Pro Pro Gln Ile Leu Lys Glu Gly Lys Asn Ala Val Leu
225                 230                 235                 240

Ser Phe Ile Ala Gly Leu Phe Asp Ala Glu Gly His Val Ser Asn Lys
                245                 250                 255
```

```
Pro Gly Ile Glu Leu Gly Met Val Asn Lys Arg Leu Ile Glu Asp Val
            260                 265                 270

Thr His Tyr Leu Asn Ala Leu Gly Ile Lys Ala Arg Ile Arg Glu Lys
            275                 280                 285

Leu Arg Lys Asp Gly Ile Asp Tyr Val Leu His Val Glu Glu Tyr Ser
            290                 295                 300

Ser Leu Leu Arg Phe Tyr Glu Leu Ile Gly Lys Asn Leu Gln Asn Glu
305                 310                 315                 320

Glu Lys Arg Glu Lys Leu Glu Lys Val Leu Ser Asn His Lys Gly Gly
                325                 330                 335

Asn Phe Gly Leu Pro Leu Asn Phe Asn Ala Phe Lys Glu Trp Ala Ser
            340                 345                 350

Glu Tyr Gly Val Glu Phe Lys Thr Asn Gly Ser Gln Thr Ile Ala Ile
            355                 360                 365

Ile Asn Asp Glu Arg Ile Ser Leu Gly Gln Trp His Thr Arg Asn Arg
            370                 375                 380

Val Ser Lys Ala Val Leu Val Lys Met Leu Arg Lys Leu Tyr Glu Ala
385                 390                 395                 400

Thr Lys Asp Glu Glu Val Lys Arg Met Leu His Leu Ile Glu Gly Leu
            405                 410                 415

Glu Val Val Arg His Ile Thr Thr Thr Asn Glu Pro Arg Thr Phe Tyr
            420                 425                 430

Asp Leu Thr Val Glu Asn Tyr Gln Asn Tyr Leu Ala Gly Glu Asn Gly
            435                 440                 445

Met Ile Phe Val His Asn
            450

<210> SEQ ID NO 49
<211> LENGTH: 345
<212> TYPE: PRT
<213> ORGANISM: Carboxydothermus hydrogenoformans

<400> SEQUENCE: 49

Cys Val Thr Gly Asp Thr Leu Val Phe Thr Asp Lys Gly Leu Ile Glu
1               5                   10                  15

Ala Arg Lys Leu Glu Val Gly Met Lys Val Trp Ser Gly Asp Gly Trp
                20                  25                  30

Asn Glu Ile Lys Glu Val Ile Asn Asn Gly Val Lys Pro Val Leu Lys
            35                  40                  45

Leu Lys Leu Lys Thr Gly Leu Glu Ile Lys Val Thr Glu Glu His Lys
        50                  55                  60

Ile Phe Thr Gly Glu Gly Trp Lys Glu Ala Lys Asp Leu Lys Val Gly
65                  70                  75                  80

Asp Lys Leu Tyr Leu Pro Val Ser Tyr Pro Glu Leu Asp Phe Pro Val
                85                  90                  95

Lys Glu Glu Asn Asp Phe Tyr Gly Phe Leu Gly Tyr Phe Leu Gly Asp
            100                 105                 110

Gly Ser Leu Ser Val Ser Asn His Val Ser Leu His Val Gly Asn Asp
        115                 120                 125

Lys Glu Leu Ala Leu Tyr Phe Lys Glu Lys Val Glu Lys Tyr Ala Gly
    130                 135                 140

Ala Ala Tyr Leu Ile Glu Arg Asp Gly Gln Tyr Ile Ile Asp Val His
145                 150                 155                 160

Arg Lys Glu Phe Ala Glu Lys Ile Lys Lys Ile Phe Gly Ile Glu Ile
```

```
                165                 170                 175
Thr Asp Ser Lys Glu Lys Asp Ile Pro Ser Ser Leu Leu Ala Val Asn
            180                 185                 190

Ser Glu Ala Met Lys Ala Leu Leu Arg Gly Leu Phe Ser Ala Asp Gly
        195                 200                 205

Ser Val Tyr Asp Ala Asn Gly Ser Ile Thr Val Ala Leu Ser Ser Thr
    210                 215                 220

Ser Tyr Pro Leu Leu Arg Lys Val Gln Ile Leu Leu Ser Leu Gly
225                 230                 235                 240

Ile Pro Ser Thr Leu Thr Gly Glu Lys Asp Gln Asp Val Lys Ile Ile
            245                 250                 255

Lys Gly Asn Glu Tyr Glu Thr Leu Pro Thr Tyr Arg Leu Ile Ile Ser
        260                 265                 270

Gly Glu Arg Ala Ser Leu Phe Phe Asn Lys Ile Gly Leu Ile Gly Glu
    275                 280                 285

Lys Lys Lys Lys Phe Leu Glu Leu Met Ala Gly Lys Thr Thr Tyr Ser
290                 295                 300

Thr Leu Asn Asn His Leu Tyr Gln Glu Ile Val Ser Ile Glu Pro Ala
305                 310                 315                 320

Gly Glu Glu Glu Val Phe Asp Ile Thr Ala Pro Pro Lys Tyr Thr Trp
                325                 330                 335

Ile Thr Asn Gly Ile Leu Ser Leu Asp
            340                 345

<210> SEQ ID NO 50
<211> LENGTH: 134
<212> TYPE: PRT
<213> ORGANISM: Methanothermobacter thermautotrophicus

<400> SEQUENCE: 50

Cys Val Ser Gly Asp Thr Ile Val Met Thr Ser Gly Gly Pro Arg Thr
1               5                   10                  15

Val Ala Glu Leu Glu Gly Lys Pro Phe Thr Ala Leu Ile Arg Gly Ser
            20                  25                  30

Gly Tyr Pro Cys Pro Ser Gly Phe Phe Arg Thr Cys Glu Arg Asp Val
        35                  40                  45

Tyr Asp Leu Arg Thr Arg Glu Gly His Cys Leu Arg Leu Thr His Asp
    50                  55                  60

His Arg Val Leu Val Met Asp Gly Gly Leu Glu Trp Arg Ala Ala Gly
65                  70                  75                  80

Glu Leu Glu Arg Gly Asp Arg Leu Val Met Asp Asp Ala Ala Gly Glu
            85                  90                  95

Phe Pro Ala Leu Ala Thr Phe Arg Gly Leu Arg Gly Ala Gly Arg Gln
        100                 105                 110

Asp Val Tyr Asp Ala Thr Val Tyr Gly Ala Ser Ala Phe Thr Ala Asn
    115                 120                 125

Gly Phe Ile Val His Asn
        130

<210> SEQ ID NO 51
<211> LENGTH: 382
<212> TYPE: PRT
<213> ORGANISM: Pyrococcus abyssi

<400> SEQUENCE: 51

Cys Val Val Gly Glu Thr Arg Ile Leu Thr Pro Glu Gly Tyr Ile Lys
```

```
1               5                   10                  15
Ala Glu Glu Leu Phe Lys Leu Ala Lys Glu Arg Gly Lys Met Glu Ala
                20                  25                  30

Ile Ala Val Glu Gly Ile Ala Glu Gly Gly Glu Pro Tyr Ala Tyr Ser
                35                  40                  45

Leu Glu Ile Leu Leu Pro Gly Asp Lys Gln Val Lys Tyr Glu Thr Val
                50                  55                  60

His Gly Asn Ala Val Glu Val Ala Asp Pro Val Ser Val Pro Ala Tyr
65                  70                  75                  80

Val Trp Lys Val Gly Met Lys Glu Val Ala Arg Val Arg Thr Lys Glu
                85                  90                  95

Gly Tyr Glu Ile Thr Ala Thr Leu Asp His Lys Leu Met Thr Pro Glu
                100                 105                 110

Gly Trp Lys Glu Ile Lys Asp Leu Lys Pro Gly Asp Lys Ile Leu Leu
                115                 120                 125

Pro Arg Phe Glu Val Glu Glu Asp Phe Gly Ser Glu Ser Ile Gly Glu
130                 135                 140

Asp Leu Ala Phe Val Leu Gly Trp Phe Ile Gly Asp Gly Tyr Leu Asn
145                 150                 155                 160

Val Lys Asp Lys Arg Ala Trp Phe Tyr Phe Asn Ala Glu Lys Glu Glu
                165                 170                 175

Glu Ile Ala Trp Lys Ile Arg Glu Ile Leu Ala Lys Arg Phe Glu Ile
                180                 185                 190

Lys Ala Glu Pro His Arg Tyr Gly Asn Gln Ile Lys Leu Gly Val Arg
                195                 200                 205

Gly Lys Ala Tyr Glu Trp Leu Glu Ser Ile Val Lys Thr Asn Glu Lys
210                 215                 220

Arg Ile Pro Glu Ile Val Tyr Arg Leu Lys Pro Asn Glu Ile Ala Ser
225                 230                 235                 240

Phe Leu Arg Gly Leu Phe Ser Ala Asp Gly Tyr Val Asp Asn Asp Met
                245                 250                 255

Ala Ile Arg Leu Thr Ser Lys Ser Arg Glu Leu Leu Arg Glu Val Gln
                260                 265                 270

Asp Leu Leu Leu Phe Gly Ile Leu Ser Lys Ile Tyr Glu Arg Pro
                275                 280                 285

Tyr Lys Arg Glu Phe Lys Tyr Thr Thr Lys Asp Gly Glu Glu Arg Thr
290                 295                 300

Tyr Thr Thr Glu Gly Tyr Tyr Glu Leu Val Ile Ala Asn Tyr Ser Arg
305                 310                 315                 320

Lys Ile Phe Ala Glu Arg Ile Gly Leu Glu Gly Tyr Lys Met Glu Lys
                325                 330                 335

Leu Ser Leu Glu Lys Ile Lys Val Asp Glu Pro Ile Val Thr Val Glu
                340                 345                 350

Ser Val Glu Ile Leu Gly Lys Lys Leu Val Tyr Asp Phe Thr Val Pro
                355                 360                 365

Glu His His Met Tyr Ile Ser Asn Gly Phe Met Ser His Asn
370                 375                 380
```

<210> SEQ ID NO 52
<211> LENGTH: 382
<212> TYPE: PRT
<213> ORGANISM: Pyrococcus furiosus

<400> SEQUENCE: 52

```
Cys Val Val Gly Asp Thr Arg Ile Leu Thr Pro Glu Gly Tyr Leu Lys
  1               5                  10                  15

Ala Glu Glu Ile Phe Ser Leu Ala Lys Glu Arg Gly Lys Lys Glu Ala
             20                  25                  30

Val Ala Val Glu Gly Ile Ala Glu Gly Glu Pro Tyr Ala Tyr Ser
         35                  40                  45

Val Glu Ile Leu Leu Pro Gly Glu Lys Val Glu Tyr Glu Thr Val
 50                  55                  60

His Gly Lys Val Leu Ala Val Ala Asp Pro Val Ala Val Pro Ala Tyr
 65                  70                  75                  80

Val Trp Lys Val Gly Arg Lys Val Ala Arg Val Lys Thr Lys Glu
                 85                  90                  95

Gly Tyr Glu Ile Thr Ala Thr Leu Asp His Lys Leu Met Thr Pro Glu
                100                 105                 110

Gly Trp Lys Glu Val Gly Lys Leu Lys Glu Gly Asp Lys Ile Leu Leu
                115                 120                 125

Pro Arg Phe Glu Val Glu Glu Phe Gly Ser Glu Ser Ile Gly Glu
130                 135                 140

Asp Leu Ala Phe Val Leu Gly Trp Phe Ile Gly Asp Gly Tyr Leu Asn
145                 150                 155                 160

Val Asn Asp Lys Arg Ala Trp Phe Tyr Phe Asn Ala Glu Lys Glu Glu
                165                 170                 175

Glu Ile Ala Val Arg Ile Arg Asp Ile Leu Val Lys His Phe Gly Ile
                180                 185                 190

Lys Ala Glu Leu His Arg Tyr Gly Asn Gln Ile Lys Leu Gly Val Arg
                195                 200                 205

Gly Glu Ala Tyr Arg Trp Leu Glu Asn Ile Val Lys Asn Asn Glu Lys
210                 215                 220

Arg Ile Pro Glu Ile Val Tyr Arg Leu Lys Pro Arg Glu Ile Ala Ala
225                 230                 235                 240

Phe Leu Arg Gly Leu Phe Ser Ala Asp Gly Tyr Val Asp Lys Asp Met
                245                 250                 255

Ala Ile Arg Leu Thr Ser Lys Ser Arg Glu Leu Leu Arg Glu Val Gln
                260                 265                 270

Asp Leu Leu Leu Phe Gly Ile Leu Ser Lys Ile Tyr Glu Lys Pro
275                 280                 285

Tyr Glu Ser Glu Phe His Tyr Thr Thr Lys Asn Gly Glu Glu Arg Ile
290                 295                 300

Tyr Arg Ser Lys Gly Tyr Tyr Glu Leu Val Ile Thr Asn Tyr Ser Arg
305                 310                 315                 320

Lys Leu Phe Ala Glu Lys Ile Gly Leu Glu Gly Tyr Lys Met Glu Lys
                325                 330                 335

Leu Ser Leu Lys Lys Thr Lys Val Asp Gln Pro Ile Val Thr Val Glu
                340                 345                 350

Ser Val Glu Val Leu Gly Glu Glu Ile Val Tyr Asp Phe Thr Val Pro
                355                 360                 365

Asn Tyr His Met Tyr Ile Ser Asn Gly Phe Met Ser His Asn
                370                 375                 380

<210> SEQ ID NO 53
<211> LENGTH: 373
<212> TYPE: PRT
<213> ORGANISM: Trichodesmium erythraeum IMS101

<400> SEQUENCE: 53
```

Cys His Ser Gly Asp Thr Leu Val Ser Thr Asp Gln Gly Leu Ile Ala
1               5                   10                  15

Ile Gln Asp Leu Val Gly Lys Gln Phe Gln Ala Leu Val Asp Leu Arg
            20                  25                  30

Ser Ile Gly Leu Ser Gly Val Arg Leu Thr Asp Ala Ile Ala Phe Ala
        35                  40                  45

Thr Gly Val Lys Thr Thr Tyr Gln Val Ile Leu Asn Asn Gly Met Gln
50                  55                  60

Met Arg Cys Thr Gly Asp His Gln His Phe Thr Ser Arg Gly Trp Val
65                  70                  75                  80

Ser Thr Arg Asp Leu Thr Asp Asp Asn Ile Tyr Ile Gln Gly Gly
                85                  90                  95

Ala Gly Gln Phe Gly Lys Gly Thr Ile Ser Val Ala Gln Ala Gln Met
                100                 105                 110

Leu Gly Trp Trp Tyr Arg Asp Gly Tyr Asn Val Lys Ile Lys Ala Arg
                115                 120                 125

Ser His Ser His Gly Gly Lys Gln Asp Tyr Phe Ala Thr Gly Phe Val
            130                 135                 140

Phe Asp Gln Asp Tyr Glu Thr Ala Tyr Asn Val Val Glu Lys Ala
145                 150                 155                 160

Val Ala Ser Ile Thr Glu Arg Glu Tyr Val Thr Lys Leu His Lys Gly
                165                 170                 175

Val Tyr Glu Phe Pro Thr Gln Tyr Pro Lys Leu Glu Lys Phe Phe Ala
                180                 185                 190

Asp Leu Gly Ile Val Gly Lys Glu Glu Leu Pro Asn Asn Phe Leu Ser
            195                 200                 205

Gln Ser Gln Glu Val Leu Ile Gly Phe Leu Gly Ile Phe Ser Ala
210                 215                 220

Asp Gly Ile Val Tyr Glu Asp Ser Arg Arg Ile Lys Leu Thr Met Val
225                 230                 235                 240

Ser Glu Lys Leu Leu Gln Gln Ile Gln Leu Ile Leu Ser Asn Leu Gly
                245                 250                 255

Ile Ile Ser Thr Val Gly Leu Val Arg Glu Lys Asp Tyr Ile Gly Val
            260                 265                 270

Pro Tyr Arg Thr Val Asn Val Thr His Glu Val Ser Leu Cys Arg Gly
            275                 280                 285

Ser Tyr Glu Leu Leu Ile Ser Ser Phe Ser Phe Ser Leu Phe Gln Gln
290                 295                 300

Leu Ile Gly Phe Pro Leu Ser Pro Ser Lys Asn Val Lys Ala Glu Lys
305                 310                 315                 320

Leu Leu Val Gln Thr Leu Ala Asn Tyr Ser Glu Ser Thr Ile Asn Ser
                325                 330                 335

Lys Phe Ile Ser Lys Val Lys Lys Val Glu Glu Phe Gly Glu Glu Val
            340                 345                 350

Val Tyr Asp Leu His Val Pro Leu Thr Asn Ser Phe Ile Ala Asn Gly
                355                 360                 365

Cys Leu Thr His Asn
    370

<210> SEQ ID NO 54
<211> LENGTH: 381
<212> TYPE: PRT
<213> ORGANISM: Trichodesmium erythraeum IMS101

<400> SEQUENCE: 54

Cys Leu Asp Lys Thr Ala Leu Arg Ile Phe Asn Gln Gly Leu Leu Tyr
1               5                   10                  15

Ala Asp Glu Val Val Thr Pro Gly Ser Gly Glu Thr Val Gly Leu Gly
            20                  25                  30

Leu Thr Val Arg Asn Gly Ile Gly Ala Ser Thr Ala Ile Ala Asn Gln
        35                  40                  45

Pro Met Glu Leu Val Glu Ile Lys Leu Ala Asn Gly Arg Lys Leu Arg
50                  55                  60

Met Thr Pro Asn His Arg Met Ser Val Lys Gly Lys Trp Ile His Ala
65                  70                  75                  80

Cys Asn Leu Lys Pro Gly Met Leu Leu Asp Tyr Ser Ile Gly Glu Tyr
                85                  90                  95

Gln Lys Arg Glu Asp Thr Leu Leu Ile Pro Leu Gln Leu Glu Asp Tyr
            100                 105                 110

Thr Glu Val Asn Asn Ser Gln Thr Leu Gly His Asn Gly Gly Val Leu
        115                 120                 125

Thr Lys Lys Ile Met Thr Pro Ala Ser Met Thr Ser Asp Leu Ala Tyr
130                 135                 140

Phe Leu Gly Cys Leu Phe Gly Asn Gly Cys Ile Val Gln Asn Lys Tyr
145                 150                 155                 160

Gln Val Cys Phe Tyr His Ser Arg Leu Asp Val Leu Tyr Gly Leu Gln
                165                 170                 175

Glu Lys Gly Lys Lys Leu Phe Gly Ile Lys Gly Ser Leu Asn Asp Phe
            180                 185                 190

Ala Asn Gly Arg Phe Glu Leu Cys Phe Ala Ser Arg Gln Leu Phe Tyr
        195                 200                 205

Trp Leu His Leu Asn Gln Leu Val Lys Thr Gln Lys Ser Glu Asp Leu
210                 215                 220

Glu Arg Ile Pro Leu Ser Leu Arg Arg Ser Ser Arg Val Thr Leu Leu
225                 230                 235                 240

Ser Phe Phe Cys Gly Leu Ile Asp Thr Asn Gly Tyr Val Pro Gln Asp
                245                 250                 255

Gly Lys Leu Ser Ile Ala Ser Ala Ser Ser Asp Phe Ile His Asn Leu
            260                 265                 270

Gln Gln Ile Gly Glu Ser Ile Gly Leu Cys Phe Ser Ile Tyr Gln Asn
        275                 280                 285

Thr Lys Gly Glu Asn Leu Gln Asn Gln His Asn Asn Thr Trp Gly Leu
290                 295                 300

Cys Leu Ser Pro Met Leu Ser Asn Val Asp Ala Leu Asp Tyr Leu Asn
305                 310                 315                 320

His Asn Ser Ile Lys Cys Gln Glu Gly Pro Val Val Ile Ser Lys Cys
                325                 330                 335

Val Leu Asn Tyr Ser Pro Tyr Lys Ile Glu Ser Val Asn Ile Gly Ala
            340                 345                 350

Val Cys Asp Tyr Ser Tyr Asp Phe Ala Ile Glu Gly Ile Asn Asp Asn
        355                 360                 365

Asp Ser Trp Tyr Trp Gln Gly Ala Leu Lys Ser His Asn
370                 375                 380

<210> SEQ ID NO 55
<211> LENGTH: 339
<212> TYPE: PRT
<213> ORGANISM: Chilo iridescent virus

<400> SEQUENCE: 55

Cys Val Ala Pro Glu Thr Met Ile Leu Thr Glu Asp Gly Gln Phe Pro
1               5                   10                  15

Ile Lys Asp Leu Glu Gly Lys Ile Ile Lys Val Trp Asn Gly Asn Glu
            20                  25                  30

Phe Ser Ser Val Thr Val Val Lys Thr Gly Thr Glu Lys Glu Leu Leu
        35                  40                  45

Glu Val Glu Leu Ser Asn Gly Cys Thr Leu Ser Cys Thr Pro Glu His
    50                  55                  60

Lys Phe Ile Ile Val Lys Ser Tyr Thr Glu Ala Lys Lys Gln Lys Thr
65                  70                  75                  80

Asp Asp Asn Ala Ile Ala Asn Ala Glu Arg Val Asp Ala Gln Asp Leu
                85                  90                  95

Lys Pro Arg Met Lys Leu Ile Lys Phe Asp Leu Pro Thr Leu Phe Gly
            100                 105                 110

Asn Ser Glu His Asp Ile Lys Tyr Pro Tyr Thr His Gly Phe Phe Cys
        115                 120                 125

Gly Asp Gly Thr Tyr Thr Lys Tyr Gly Lys Pro Gln Leu Ser Leu Tyr
    130                 135                 140

Gly Asp Lys Lys Glu Leu Leu Thr Tyr Leu Asp Val Arg Thr Met Thr
145                 150                 155                 160

Gly Leu Glu Asp Ala Ser Gly Arg Leu Asn Thr Trp Leu Pro Leu Asp
                165                 170                 175

Leu Ala Pro Lys Phe Asp Val Pro Ile Asn Ser Ser Leu Glu Cys Arg
            180                 185                 190

Met Glu Trp Leu Ala Gly Tyr Leu Asp Ala Asp Gly Cys Val Phe Arg
        195                 200                 205

Asn Gly Thr Asn Glu Ser Ile Gln Val Ser Cys Ile His Leu Asp Phe
    210                 215                 220

Leu Lys Arg Ile Gln Leu Leu Leu Ile Gly Met Gly Val Thr Ser Lys
225                 230                 235                 240

Ile Thr Lys Leu His Asp Glu Lys Ile Thr Thr Met Pro Asp Gly Lys
                245                 250                 255

Gly Gly Gln Lys Pro Tyr Ser Cys Lys Pro Ile Trp Arg Leu Phe Ile
            260                 265                 270

Ser Ser Ser Gly Leu Tyr His Leu Ser Glu Gln Gly Phe Glu Thr Arg
        275                 280                 285

Arg Leu Lys Trp Glu Pro Arg Gln Pro Gln Arg Asn Ala Glu Arg Phe
    290                 295                 300

Val Glu Val Leu Lys Val Asn Lys Thr Gly Arg Val Asp Asp Thr Tyr
305                 310                 315                 320

Cys Phe Thr Glu Pro Ile Asn His Ala Gly Val Phe Asn Gly Ile Leu
                325                 330                 335

Thr Gly Gln

<210> SEQ ID NO 56
<211> LENGTH: 471
<212> TYPE: PRT
<213> ORGANISM: Candida tropicalis

<400> SEQUENCE: 56

Cys Phe Thr Lys Gly Thr Gln Val Met Met Ala Asp Gly Ala Asp Lys
1               5                   10                  15

```
Ser Ile Glu Ser Ile Glu Val Gly Asp Lys Val Met Gly Lys Asp Gly
             20                  25                  30

Met Pro Arg Glu Val Val Gly Leu Pro Arg Gly Tyr Asp Asp Met Tyr
         35                  40                  45

Lys Val Arg Gln Leu Ser Ser Thr Arg Arg Asn Ala Lys Ser Glu Gly
     50                  55                  60

Leu Met Asp Phe Thr Val Ser Ala Asp His Lys Leu Ile Leu Lys Thr
 65                  70                  75                  80

Lys Gln Asp Val Lys Ile Ala Thr Arg Lys Ile Gly Gly Asn Thr Tyr
                 85                  90                  95

Thr Gly Val Thr Phe Tyr Val Leu Glu Lys Thr Lys Thr Gly Ile Glu
            100                 105                 110

Leu Val Lys Ala Lys Thr Lys Val Phe Gly His His Ile His Gly Gln
        115                 120                 125

Asn Gly Ala Glu Glu Lys Ala Ala Thr Phe Ala Ala Gly Ile Asp Ser
130                 135                 140

Lys Glu Tyr Ile Asp Trp Ile Glu Ala Arg Asp Tyr Val Gln Val
145                 150                 155                 160

Asp Glu Ile Val Lys Thr Ser Thr Thr Gln Met Ile Asn Pro Val His
                165                 170                 175

Phe Glu Ser Gly Lys Leu Gly Asn Trp Leu His Glu His Lys Gln Asn
            180                 185                 190

Lys Ser Leu Ala Pro Gln Leu Gly Tyr Leu Leu Gly Thr Trp Ala Gly
        195                 200                 205

Ile Gly Asn Val Lys Ser Ser Ala Phe Thr Met Asn Ser Lys Asp Asp
210                 215                 220

Val Lys Leu Ala Thr Arg Ile Met Asn Tyr Ser Ser Lys Leu Gly Met
225                 230                 235                 240

Thr Cys Ser Ser Thr Glu Ser Gly Glu Leu Asn Val Ala Glu Asn Glu
                245                 250                 255

Glu Glu Phe Phe Asn Asn Leu Gly Ala Glu Lys Asp Glu Ala Gly Asp
            260                 265                 270

Phe Thr Phe Asp Glu Phe Thr Asp Ala Met Asp Glu Leu Thr Ile Asn
        275                 280                 285

Val His Gly Ala Ala Ser Lys Lys Asn Asn Leu Leu Trp Asn Ala
290                 295                 300

Leu Lys Ser Leu Gly Phe Arg Ala Lys Ser Thr Asp Ile Val Lys Ser
305                 310                 315                 320

Ile Pro Gln His Ile Ala Val Asp Asp Ile Val Val Arg Glu Ser Leu
                325                 330                 335

Ile Ala Gly Leu Val Asp Ala Ala Gly Asn Val Glu Thr Lys Ser Asn
            340                 345                 350

Gly Ser Ile Glu Ala Val Val Arg Thr Ser Phe Arg His Val Ala Arg
        355                 360                 365

Gly Leu Val Lys Ile Ala His Ser Leu Gly Ile Glu Ser Ser Ile Asn
        370                 375                 380

Ile Lys Asp Thr His Ile Asp Ala Ala Gly Val Arg Gln Glu Phe Ala
385                 390                 395                 400

Cys Ile Val Asn Leu Thr Gly Ala Pro Leu Ala Gly Val Leu Ser Lys
                405                 410                 415

Cys Ala Leu Ala Arg Asn Gln Thr Pro Val Val Lys Phe Thr Arg Asp
            420                 425                 430

Pro Val Leu Phe Asn Phe Asp Leu Ile Lys Ser Ala Lys Glu Asn Tyr
```

```
                    435                 440                 445
Tyr Gly Ile Thr Leu Ala Glu Glu Thr Asp His Gln Phe Leu Leu Ser
        450                 455                 460

Asn Met Ala Leu Val His Asn
465                 470

<210> SEQ ID NO 57
<211> LENGTH: 454
<212> TYPE: PRT
<213> ORGANISM: Saccharomyces cerevisiae

<400> SEQUENCE: 57

Cys Phe Ala Lys Gly Thr Asn Val Leu Met Ala Asp Gly Ser Ile Glu
1               5                   10                  15

Cys Ile Glu Asn Ile Glu Val Gly Asn Lys Val Met Gly Lys Asp Gly
                20                  25                  30

Arg Pro Arg Glu Val Ile Lys Leu Pro Arg Gly Arg Glu Thr Met Tyr
            35                  40                  45

Ser Val Val Gln Lys Ser Gln His Arg Ala His Lys Ser Asp Ser Ser
        50                  55                  60

Arg Glu Val Pro Glu Leu Leu Lys Phe Thr Cys Asn Ala Thr His Glu
65                  70                  75                  80

Leu Val Val Arg Thr Pro Arg Ser Val Arg Arg Leu Ser Arg Thr Ile
                85                  90                  95

Lys Gly Val Glu Tyr Phe Glu Val Ile Thr Phe Glu Met Gly Gln Lys
            100                 105                 110

Lys Ala Pro Asp Gly Arg Ile Val Glu Leu Val Lys Glu Val Ser Lys
        115                 120                 125

Ser Tyr Pro Ile Ser Glu Gly Pro Glu Arg Ala Asn Glu Leu Val Glu
130                 135                 140

Ser Tyr Arg Lys Ala Ser Asn Lys Ala Tyr Phe Glu Trp Thr Ile Glu
145                 150                 155                 160

Ala Arg Asp Leu Ser Leu Leu Gly Ser His Val Arg Lys Ala Thr Tyr
                165                 170                 175

Gln Thr Tyr Ala Pro Ile Leu Tyr Glu Asn Asp His Phe Phe Asp Tyr
            180                 185                 190

Met Gln Lys Ser Lys Phe His Leu Thr Ile Glu Gly Pro Lys Val Leu
        195                 200                 205

Ala Tyr Leu Leu Gly Leu Trp Ile Gly Asp Gly Leu Ser Asp Arg Ala
210                 215                 220

Thr Phe Ser Val Asp Ser Arg Asp Thr Ser Leu Met Glu Arg Val Thr
225                 230                 235                 240

Glu Tyr Ala Glu Lys Leu Asn Leu Cys Ala Glu Tyr Lys Asp Arg Lys
                245                 250                 255

Glu Pro Gln Val Ala Lys Thr Val Asn Leu Tyr Ser Lys Val Val Arg
            260                 265                 270

Gly Asn Gly Ile Arg Asn Asn Leu Asn Thr Glu Asn Pro Leu Trp Asp
        275                 280                 285

Ala Ile Val Gly Leu Gly Phe Leu Lys Asp Gly Val Lys Asn Ile Pro
290                 295                 300

Ser Phe Leu Ser Thr Asp Asn Ile Gly Thr Arg Glu Thr Phe Leu Ala
305                 310                 315                 320

Gly Leu Ile Asp Ser Asp Gly Tyr Val Thr Asp Glu His Gly Ile Lys
                325                 330                 335
```

```
Ala Thr Ile Lys Thr Ile His Thr Ser Val Arg Asp Gly Leu Val Ser
            340                 345                 350

Leu Ala Arg Ser Leu Gly Leu Val Val Ser Val Asn Ala Glu Pro Ala
        355                 360                 365

Lys Val Asp Met Asn Gly Thr Lys His Lys Ile Ser Tyr Ala Ile Tyr
370                 375                 380

Met Ser Gly Gly Asp Val Leu Leu Asn Val Leu Ser Lys Cys Ala Gly
385                 390                 395                 400

Ser Lys Lys Phe Arg Pro Ala Pro Ala Ala Phe Ala Arg Glu Cys
                405                 410                 415

Arg Gly Phe Tyr Phe Glu Leu Gln Glu Leu Lys Glu Asp Tyr Tyr
            420                 425                 430

Gly Ile Thr Leu Ser Asp Asp Ser Asp His Gln Phe Leu Leu Ala Asn
            435                 440                 445

Gln Val Val Val His Asn
        450

<210> SEQ ID NO 58
<211> LENGTH: 173
<212> TYPE: PRT
<213> ORGANISM: Thermoplasma acidophilum ATCC 25905

<400> SEQUENCE: 58

Cys Val Ser Gly Asp Thr Pro Val Leu Leu Asp Ala Gly Glu Arg Arg
1               5                   10                  15

Ile Gly Asp Leu Phe Met Glu Ala Ile Arg Pro Lys Glu Arg Gly Glu
            20                  25                  30

Ile Gly Gln Asn Glu Glu Ile Val Arg Leu His Asp Ser Trp Arg Ile
        35                  40                  45

Tyr Ser Met Val Gly Ser Glu Ile Val Glu Thr Val Ser His Ala Ile
    50                  55                  60

Tyr His Gly Lys Ser Asn Ala Ile Val Asn Val Arg Thr Glu Asn Gly
65                  70                  75                  80

Arg Glu Val Arg Val Thr Pro Val His Lys Leu Phe Val Lys Ile Gly
                85                  90                  95

Asn Ser Val Ile Glu Arg Pro Ala Ser Glu Val Asn Glu Gly Asp Glu
            100                 105                 110

Ile Ala Trp Pro Ser Val Ser Glu Asn Gly Asp Ser Gln Thr Val Thr
        115                 120                 125

Thr Thr Leu Val Leu Thr Phe Asp Arg Val Val Ser Lys Glu Met His
130                 135                 140

Ser Gly Val Phe Asp Val Tyr Asp Leu Met Val Pro Asp Tyr Gly Tyr
145                 150                 155                 160

Asn Phe Ile Gly Gly Asn Gly Leu Ile Val Leu His Asn
                165                 170

<210> SEQ ID NO 59
<211> LENGTH: 429
<212> TYPE: PRT
<213> ORGANISM: Synechocystis species PCC6803

<400> SEQUENCE: 59

Cys Ile Ser Gly Asp Ser Leu Ile Ser Leu Ala Ser Thr Gly Lys Arg
1               5                   10                  15

Val Ser Ile Lys Asp Leu Leu Asp Glu Lys Asp Phe Glu Ile Trp Ala
            20                  25                  30
```

Ile Asn Glu Gln Thr Met Lys Leu Glu Ser Ala Lys Val Ser Arg Val
 35                  40                  45

Phe Cys Thr Gly Lys Lys Leu Val Tyr Ile Leu Lys Thr Arg Leu Gly
 50                  55                  60

Arg Thr Ile Lys Ala Thr Ala Asn His Arg Phe Leu Thr Ile Asp Gly
 65                  70                  75                  80

Trp Lys Arg Leu Asp Glu Leu Ser Leu Lys Glu His Ile Ala Leu Pro
                 85                  90                  95

Arg Lys Leu Glu Ser Ser Ser Leu Gln Leu Met Ser Asp Glu Glu Leu
            100                 105                 110

Gly Leu Leu Gly His Leu Ile Gly Asp Gly Cys Thr Leu Pro Arg His
        115                 120                 125

Ala Ile Gln Tyr Thr Ser Asn Lys Ile Glu Leu Ala Glu Lys Val Val
    130                 135                 140

Glu Leu Ala Lys Ala Val Phe Gly Asp Gln Ile Asn Pro Arg Ile Ser
145                 150                 155                 160

Gln Glu Arg Gln Trp Tyr Gln Val Tyr Ile Pro Ala Ser Tyr Arg Leu
                165                 170                 175

Thr His Asn Lys Lys Asn Pro Ile Thr Lys Trp Leu Glu Asn Leu Asp
            180                 185                 190

Val Phe Gly Leu Arg Ser Tyr Glu Lys Phe Val Pro Asn Gln Val Phe
        195                 200                 205

Glu Gln Pro Gln Arg Ala Ile Ala Ile Phe Leu Arg His Leu Trp Ser
    210                 215                 220

Thr Asp Gly Cys Val Lys Leu Ile Val Glu Lys Ser Ser Arg Pro Val
225                 230                 235                 240

Ala Tyr Tyr Ala Thr Ser Ser Glu Lys Leu Ala Lys Asp Val Gln Ser
                245                 250                 255

Leu Leu Leu Lys Leu Gly Ile Asn Ala Arg Leu Ser Lys Ile Ser Gln
            260                 265                 270

Asn Gly Lys Gly Arg Asp Asn Tyr His Val Thr Ile Thr Gly Gln Ala
        275                 280                 285

Asp Leu Gln Ile Phe Val Asp Gln Ile Gly Ala Val Asp Lys Asp Lys
    290                 295                 300

Gln Ala Ser Val Glu Glu Ile Lys Thr His Ile Ala Gln His Gln Ala
305                 310                 315                 320

Asn Thr Asn Arg Asp Val Ile Pro Lys Gln Ile Trp Lys Thr Tyr Val
                325                 330                 335

Leu Pro Gln Ile Gln Ile Lys Gly Ile Thr Thr Arg Asp Leu Gln Met
            340                 345                 350

Arg Leu Gly Asn Ala Tyr Cys Gly Thr Ala Leu Tyr Lys His Asn Leu
        355                 360                 365

Ser Arg Glu Arg Ala Ala Lys Ile Ala Thr Ile Thr Gln Ser Pro Glu
    370                 375                 380

Ile Glu Lys Leu Ser Gln Ser Asp Ile Tyr Trp Asp Ser Ile Val Ser
385                 390                 395                 400

Ile Thr Glu Thr Gly Val Glu Glu Val Phe Asp Leu Thr Val Pro Gly
                405                 410                 415

Pro His Asn Phe Val Ala Asn Asp Ile Ile Val His Asn
            420                 425

<210> SEQ ID NO 60
<211> LENGTH: 123
<212> TYPE: PRT

<213> ORGANISM: Synechocystis species PCC6803

<400> SEQUENCE: 60

Cys Leu Ser Phe Gly Thr Glu Ile Leu Thr Val Glu Tyr Gly Pro Leu
1               5                   10                  15

Pro Ile Gly Lys Ile Val Ser Glu Glu Ile Asn Cys Ser Val Tyr Ser
            20                  25                  30

Val Asp Pro Glu Gly Arg Val Tyr Thr Gln Ala Ile Ala Gln Trp His
        35                  40                  45

Asp Arg Gly Glu Gln Glu Val Leu Glu Tyr Glu Leu Glu Asp Gly Ser
    50                  55                  60

Val Ile Arg Ala Thr Ser Asp His Arg Phe Leu Thr Thr Asp Tyr Gln
65                  70                  75                  80

Leu Leu Ala Ile Glu Glu Ile Phe Ala Arg Gln Leu Asp Leu Leu Thr
                85                  90                  95

Leu Glu Asn Ile Lys Gln Thr Glu Glu Ala Leu Asp Asn His Arg Leu
            100                 105                 110

Pro Phe Pro Leu Leu Asp Ala Gly Thr Ile Lys
        115                 120

<210> SEQ ID NO 61
<211> LENGTH: 36
<212> TYPE: PRT
<213> ORGANISM: Synechocystis species PCC6803

<400> SEQUENCE: 61

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Asn
            35

<210> SEQ ID NO 62
<211> LENGTH: 98
<212> TYPE: PRT
<213> ORGANISM: Nanoarchaeum equitans Kin4-M

<400> SEQUENCE: 62

Ser Ile Met Asp Thr Glu Ile Glu Val Ile Glu Asn Gly Ile Lys Lys
1               5                   10                  15

Lys Glu Lys Leu Ser Asp Leu Phe Asn Lys Tyr Tyr Ala Gly Phe Gln
            20                  25                  30

Ile Gly Glu Lys His Tyr Ala Phe Pro Pro Asp Leu Tyr Val Tyr Asp
        35                  40                  45

Gly Glu Arg Trp Val Lys Val Tyr Ser Ile Ile Lys His Glu Thr Glu
    50                  55                  60

Thr Asp Leu Tyr Glu Ile Asn Gly Ile Thr Leu Ser Ala Asn His Leu
65                  70                  75                  80

Val Leu Ser Lys Gly Asn Trp Val Lys Ala Lys Glu Tyr Glu Asn Lys
                85                  90                  95

Asn Asn

<210> SEQ ID NO 63
<211> LENGTH: 30
<212> TYPE: PRT
<213> ORGANISM: Nanoarchaeum equitans Kin4-M

```
<400> SEQUENCE: 63

Met Arg Tyr Leu Gly Lys Lys Arg Val Ile Leu Tyr Asp Leu Ser Thr
1               5                   10                  15

Glu Ser Gly Lys Phe Tyr Val Asn Gly Leu Val Leu His Asn
            20                  25                  30

<210> SEQ ID NO 64
<211> LENGTH: 102
<212> TYPE: PRT
<213> ORGANISM: Anabaena species PCC7120

<400> SEQUENCE: 64

Cys Leu Ser Tyr Asp Thr Glu Val Leu Thr Val Glu Tyr Gly Phe Val
1               5                   10                  15

Pro Ile Gly Glu Ile Val Glu Lys Gly Ile Glu Cys Ser Val Phe Ser
            20                  25                  30

Ile Asn Asn Asn Gly Ile Val Tyr Thr Gln Pro Ile Ala Gln Trp His
        35                  40                  45

His Arg Gly Lys Gln Glu Val Phe Glu Tyr Cys Leu Glu Asp Gly Ser
    50                  55                  60

Ile Ile Lys Ala Thr Lys Asp His Lys Phe Met Thr Gln Asp Gly Lys
65                  70                  75                  80

Met Leu Pro Ile Asp Glu Ile Phe Glu Gln Glu Leu Asp Leu Leu Gln
                85                  90                  95

Val Lys Gly Leu Pro Glu
            100

<210> SEQ ID NO 65
<211> LENGTH: 36
<212> TYPE: PRT
<213> ORGANISM: Anabaena species PCC7120

<400> SEQUENCE: 65

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Asn
        35

<210> SEQ ID NO 66
<211> LENGTH: 102
<212> TYPE: PRT
<213> ORGANISM: Nostoc punctiforme PCC73102

<400> SEQUENCE: 66

Cys Leu Ser Tyr Glu Thr Glu Ile Leu Thr Val Glu Tyr Gly Leu Leu
1               5                   10                  15

Pro Ile Gly Lys Ile Val Glu Lys Arg Ile Glu Cys Thr Val Tyr Ser
            20                  25                  30

Val Asp Asn Asn Gly Asn Ile Tyr Thr Gln Pro Val Ala Gln Trp His
        35                  40                  45

Asp Arg Gly Glu Gln Glu Val Phe Glu Tyr Cys Leu Glu Asp Gly Ser
    50                  55                  60

Leu Ile Arg Ala Thr Lys Asp His Lys Phe Met Thr Val Asp Gly Gln
65                  70                  75                  80

Met Leu Pro Ile Asp Glu Ile Phe Glu Arg Glu Leu Asp Leu Met Arg
                85                  90                  95
```

Val Asp Asn Leu Pro Asn
            100

<210> SEQ ID NO 67
<211> LENGTH: 36
<212> TYPE: PRT
<213> ORGANISM: Nostoc punctiforme PCC73102

<400> SEQUENCE: 67

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Asn
        35

<210> SEQ ID NO 68
<211> LENGTH: 102
<212> TYPE: PRT
<213> ORGANISM: Nostoc species PCC7120

<400> SEQUENCE: 68

Cys Leu Ser Tyr Asp Thr Glu Val Leu Thr Val Glu Tyr Gly Phe Val
1               5                   10                  15

Pro Ile Gly Glu Ile Val Glu Lys Gly Ile Glu Cys Ser Val Phe Ser
            20                  25                  30

Ile Asn Asn Asn Gly Ile Val Tyr Thr Gln Pro Ile Ala Gln Trp His
        35                  40                  45

His Arg Gly Lys Gln Glu Val Phe Glu Tyr Cys Leu Glu Asp Gly Ser
    50                  55                  60

Ile Ile Lys Ala Thr Lys Asp His Lys Phe Met Thr Gln Asp Gly Lys
65                  70                  75                  80

Met Leu Pro Ile Asp Glu Ile Phe Glu Gln Glu Leu Asp Leu Leu Gln
                85                  90                  95

Val Lys Gly Leu Pro Glu
            100

<210> SEQ ID NO 69
<211> LENGTH: 36
<212> TYPE: PRT
<213> ORGANISM: Nostoc species PCC7120

<400> SEQUENCE: 69

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Asn
        35

<210> SEQ ID NO 70
<211> LENGTH: 112
<212> TYPE: PRT
<213> ORGANISM: Oscillatoria limnetica

<400> SEQUENCE: 70

Cys Leu Ser Tyr Asn Thr Glu Val Leu Thr Val Glu Tyr Gly Pro Leu
1               5                   10                  15

Pro Ile Gly Lys Ile Val Asp Glu Gln Ile His Cys Arg Val Tyr Ser

```
            20                  25                  30

Val Asp Glu Asn Gly Phe Val Tyr Thr Gln Ala Ile Ala Gln Trp His
        35                  40                  45

Asp Arg Gly Tyr Gln Glu Ile Phe Ala Tyr Glu Leu Ala Asp Gly Ser
    50                  55                  60

Val Ile Arg Ala Thr Lys Asp His Gln Phe Met Thr Glu Asp Gly Gln
65                  70                  75                  80

Met Phe Pro Ile Asp Glu Ile Trp Glu Lys Gly Leu Asp Leu Lys Lys
                85                  90                  95

Leu Pro Thr Val Gln Asp Leu Pro Ala Ala Val Gly Tyr Thr Val Ser
            100                 105                 110
```

<210> SEQ ID NO 71
<211> LENGTH: 36
<212> TYPE: PRT
<213> ORGANISM: Oscillatoria limnetica

<400> SEQUENCE: 71

```
Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Asn
        35
```

<210> SEQ ID NO 72
<211> LENGTH: 107
<212> TYPE: PRT
<213> ORGANISM: Synechocystis species PCC 7002

<400> SEQUENCE: 72

```
Cys Leu Ala Gly Gly Thr Pro Val Val Thr Val Glu Tyr Gly Val Leu
1               5                   10                  15

Pro Ile Gln Thr Ile Val Glu Gln Glu Leu Leu Cys His Val Tyr Ser
            20                  25                  30

Val Asp Ala Gln Gly Leu Ile Tyr Ala Gln Leu Ile Glu Gln Trp His
        35                  40                  45

Gln Arg Gly Asp Arg Leu Leu Tyr Glu Tyr Glu Leu Glu Asn Gly Gln
    50                  55                  60

Met Ile Arg Ala Thr Pro Asp His Arg Phe Leu Thr Thr Thr Gly Glu
65                  70                  75                  80

Leu Leu Pro Ile Asp Glu Ile Phe Thr Gln Asn Leu Asp Leu Ala Ala
                85                  90                  95

Trp Ala Val Pro Asp Ser Leu Pro Arg Thr Ala
            100                 105
```

<210> SEQ ID NO 73
<211> LENGTH: 36
<212> TYPE: PRT
<213> ORGANISM: Synechocystis species PCC 7002

<400> SEQUENCE: 73

```
Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Asn
        35
```

<210> SEQ ID NO 74
<211> LENGTH: 117
<212> TYPE: PRT
<213> ORGANISM: Thermosynechococcus vulcanus

<400> SEQUENCE: 74

Cys Leu Ser Gly Glu Thr Ala Val Met Thr Val Glu Tyr Gly Ala Ile
1               5                   10                  15

Pro Ile Arg Arg Leu Val Gln Glu Arg Leu Ile Cys Gln Val Tyr Ser
            20                  25                  30

Leu Asp Pro Gln Gly His Leu Tyr Thr Gln Pro Ile Ala Gln Trp His
        35                  40                  45

Phe Gln Gly Phe Arg Pro Val Tyr Ala Tyr Gln Leu Glu Asp Gly Ser
    50                  55                  60

Thr Ile Cys Ala Thr Pro Asp His Arg Phe Met Thr Thr Ser Gly Gln
65                  70                  75                  80

Met Leu Pro Ile Glu Gln Ile Phe Arg Glu Gly Leu Glu Leu Trp Gln
                85                  90                  95

Val Ala Ile Ala Pro Pro Gly Ala Leu Ala Gln Gly Leu Lys Pro Ala
            100                 105                 110

Val Gln Met Ser Cys
        115

<210> SEQ ID NO 75
<211> LENGTH: 35
<212> TYPE: PRT
<213> ORGANISM: Thermosynechococcus vulcanus

<400> SEQUENCE: 75

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Asn
        35

<210> SEQ ID NO 76
<211> LENGTH: 112
<212> TYPE: PRT
<213> ORGANISM: bacteriophage m13

<400> SEQUENCE: 76

Met Pro Val Leu Leu Gly Ile Pro Leu Leu Leu Arg Phe Leu Gly Phe
1               5                   10                  15

Leu Leu Val Thr Leu Phe Gly Tyr Leu Leu Thr Phe Leu Lys Lys Gly
            20                  25                  30

Phe Gly Lys Ile Ala Ile Ala Ile Ser Leu Phe Leu Ala Leu Ile Ile
        35                  40                  45

Gly Leu Asn Ser Ile Leu Val Gly Tyr Leu Ser Asp Ile Ser Ala Gln
    50                  55                  60

Leu Pro Ser Asp Phe Val Gln Gly Val Gln Leu Ile Leu Pro Ser Asn
65                  70                  75                  80

Ala Leu Pro Cys Phe Tyr Val Ile Leu Ser Val Lys Ala Ala Ile Phe
                85                  90                  95

Ile Phe Asp Val Lys Gln Lys Ile Val Ser Tyr Leu Asp Trp Asp Lys
            100                 105                 110

<210> SEQ ID NO 77
<211> LENGTH: 345
<212> TYPE: PRT
<213> ORGANISM: Bacteriophage T7

<400> SEQUENCE: 77

```
Met Ala Ser Met Thr Gly Gly Gln Gln Met Gly Thr Asn Gln Gly Lys
1               5                   10                  15

Gly Val Val Ala Ala Gly Asp Lys Leu Ala Leu Phe Leu Lys Val Phe
            20                  25                  30

Gly Gly Glu Val Leu Thr Ala Phe Ala Arg Thr Ser Val Thr Thr Ser
        35                  40                  45

Arg His Met Val Arg Ser Ile Ser Ser Gly Lys Ser Ala Gln Phe Pro
    50                  55                  60

Val Leu Gly Arg Thr Gln Ala Ala Tyr Leu Ala Pro Gly Glu Asn Leu
65                  70                  75                  80

Asp Asp Lys Arg Lys Asp Ile Lys His Thr Glu Lys Val Ile Thr Ile
                85                  90                  95

Asp Gly Leu Leu Thr Ala Asp Val Leu Ile Tyr Asp Ile Glu Asp Ala
            100                 105                 110

Met Asn His Tyr Asp Val Arg Ser Glu Tyr Thr Ser Gln Leu Gly Glu
        115                 120                 125

Ser Leu Ala Met Ala Ala Asp Gly Ala Val Leu Ala Glu Ile Ala Gly
    130                 135                 140

Leu Cys Asn Val Glu Ser Lys Tyr Asn Glu Asn Ile Glu Gly Leu Gly
145                 150                 155                 160

Thr Ala Thr Val Ile Glu Thr Thr Gln Asn Lys Ala Ala Leu Thr Asp
                165                 170                 175

Gln Val Ala Leu Gly Lys Glu Ile Ile Ala Ala Leu Thr Lys Ala Arg
            180                 185                 190

Ala Ala Leu Thr Lys Asn Tyr Val Pro Ala Ala Asp Arg Val Phe Tyr
        195                 200                 205

Cys Asp Pro Asp Ser Tyr Ser Ala Ile Leu Ala Ala Leu Met Pro Asn
    210                 215                 220

Ala Ala Asn Tyr Ala Ala Leu Ile Asp Pro Glu Lys Gly Ser Ile Arg
225                 230                 235                 240

Asn Val Met Gly Phe Glu Val Val Glu Val Pro His Leu Thr Ala Gly
                245                 250                 255

Gly Ala Gly Thr Ala Arg Glu Gly Thr Thr Gly Gln Lys His Val Phe
            260                 265                 270

Pro Ala Asn Lys Gly Glu Gly Asn Val Lys Val Ala Lys Asp Asn Val
        275                 280                 285

Ile Gly Leu Phe Met His Arg Ser Ala Val Gly Thr Val Lys Leu Arg
    290                 295                 300

Asp Leu Ala Leu Glu Arg Ala Arg Arg Ala Asn Phe Gln Ala Asp Gln
305                 310                 315                 320

Ile Ile Ala Lys Tyr Ala Met Gly His Gly Gly Leu Arg Pro Glu Ala
                325                 330                 335

Ala Gly Ala Val Val Phe Lys Val Glu
            340                 345
```

<210> SEQ ID NO 78
<211> LENGTH: 398
<212> TYPE: PRT
<213> ORGANISM: Bacteriophage T7

<400> SEQUENCE: 78

```
Met Ala Ser Met Thr Gly Gly Gln Gln Met Gly Thr Asn Gln Gly Lys
1               5                   10                  15

Gly Val Val Ala Ala Gly Asp Lys Leu Ala Leu Phe Leu Lys Val Phe
            20                  25                  30

Gly Gly Glu Val Leu Thr Ala Phe Ala Arg Thr Ser Val Thr Thr Ser
        35                  40                  45

Arg His Met Val Arg Ser Ile Ser Ser Gly Lys Ser Ala Gln Phe Pro
    50                  55                  60

Val Leu Gly Arg Thr Gln Ala Ala Tyr Leu Ala Pro Gly Glu Asn Leu
65              70                  75                  80

Asp Asp Lys Arg Lys Asp Ile Lys His Thr Glu Lys Val Ile Thr Ile
            85                  90                  95

Asp Gly Leu Leu Thr Ala Asp Val Leu Ile Tyr Asp Ile Glu Asp Ala
            100                 105                 110

Met Asn His Tyr Asp Val Arg Ser Glu Tyr Thr Ser Gln Leu Gly Glu
        115                 120                 125

Ser Leu Ala Met Ala Ala Asp Gly Ala Val Leu Ala Glu Ile Ala Gly
130                 135                 140

Leu Cys Asn Val Glu Ser Lys Tyr Asn Glu Asn Ile Glu Gly Leu Gly
145                 150                 155                 160

Thr Ala Thr Val Ile Glu Thr Thr Gln Asn Lys Ala Ala Leu Thr Asp
                165                 170                 175

Gln Val Ala Leu Gly Lys Glu Ile Ile Ala Ala Leu Thr Lys Ala Arg
            180                 185                 190

Ala Ala Leu Thr Lys Asn Tyr Val Pro Ala Ala Asp Arg Val Phe Tyr
        195                 200                 205

Cys Asp Pro Asp Ser Tyr Ser Ala Ile Leu Ala Ala Leu Met Pro Asn
    210                 215                 220

Ala Ala Asn Tyr Ala Ala Leu Ile Asp Pro Lys Gly Ser Ile Arg
225                 230                 235                 240

Asn Val Met Gly Phe Glu Val Val Glu Val Pro His Leu Thr Ala Gly
            245                 250                 255

Gly Ala Gly Thr Ala Arg Glu Gly Thr Thr Gly Gln Lys His Val Phe
        260                 265                 270

Pro Ala Asn Lys Gly Glu Gly Asn Val Lys Val Ala Lys Asp Asn Val
    275                 280                 285

Ile Gly Leu Phe Met His Arg Ser Ala Val Gly Thr Val Lys Leu Arg
290                 295                 300

Asp Leu Ala Leu Glu Arg Ala Arg Ala Asn Phe Gln Ala Asp Gln
305                 310                 315                 320

Ile Ile Ala Lys Tyr Ala Met Gly His Gly Gly Leu Arg Pro Glu Ala
            325                 330                 335

Ala Gly Ala Val Val Phe Gln Ser Gly Val Met Leu Gly Val Ala Ser
        340                 345                 350

Thr Val Ala Ala Ser Pro Glu Glu Ala Ser Val Thr Ser Thr Glu Glu
    355                 360                 365

Thr Leu Thr Pro Ala Gln Glu Ala Ala Arg Thr Arg Ala Ala Asn Lys
    370                 375                 380

Ala Arg Lys Glu Ala Glu Leu Ala Ala Ala Thr Ala Glu Gln
385                 390                 395
```

```
<210> SEQ ID NO 79
<211> LENGTH: 29
<212> TYPE: PRT
<213> ORGANISM: Escherichia coli

<400> SEQUENCE: 79

Met Lys Leu Thr Thr His His Leu Arg Thr Gly Ala Ala Leu Leu Leu
1               5                   10                  15

Ala Gly Ile Leu Leu Ala Gly Cys Asp Gln Ser Ser Ser
            20                  25

<210> SEQ ID NO 80
<211> LENGTH: 190
<212> TYPE: PRT
<213> ORGANISM: Escherichia coli

<400> SEQUENCE: 80

Asn Asn Gly Arg Gly Ala Leu Arg Gln Asn Gly Asp Gly Val Gly Gly
1               5                   10                  15

Ser Ile Thr Tyr Asp Tyr Glu Gly Phe Gly Ile Gly Ala Ala Val Ser
            20                  25                  30

Ser Ser Lys Arg Thr Asp Asp Gln Asn Gly Ser Tyr Thr Ser Asn Gly
        35                  40                  45

Val Val Arg Asn Tyr Ile Gly Thr Gly Asp Arg Ala Glu Thr Tyr Thr
    50                  55                  60

Gly Gly Leu Lys Tyr Asp Ala Asn Asn Ile Tyr Leu Ala Ala Gln Tyr
65                  70                  75                  80

Thr Gln Thr Tyr Asn Ala Thr Arg Val Gly Ser Leu Gly Trp Ala Asn
                85                  90                  95

Lys Ala Gln Asn Phe Glu Ala Val Ala Gln Tyr Gln Phe Asp Phe Gly
            100                 105                 110

Leu Arg Pro Ser Leu Ala Tyr Leu Gln Ser Lys Gly Lys Asn Leu Gly
        115                 120                 125

Val Ile Asn Gly Arg Asn Tyr Asp Asp Glu Asp Ile Leu Lys Tyr Val
    130                 135                 140

Asp Val Gly Ala Thr Tyr Tyr Phe Asn Lys Asn Met Ser Thr Tyr Val
145                 150                 155                 160

Asp Tyr Lys Ile Asn Leu Leu Asp Asp Asn Gln Phe Thr Arg Asp Ala
                165                 170                 175

Gly Ile Asn Thr Asp Asn Ile Val Ala Leu Gly Leu Val Tyr
            180                 185                 190

<210> SEQ ID NO 81
<211> LENGTH: 448
<212> TYPE: PRT
<213> ORGANISM: Escherichia coli

<400> SEQUENCE: 81

Met Val Met Ser Gln Lys Thr Leu Phe Thr Lys Ser Ala Leu Ala Val
1               5                   10                  15

Ala Val Ala Leu Ile Ser Thr Gln Ala Trp Ser Ala Gly Phe Gln Leu
            20                  25                  30

Asn Glu Phe Ser Ser Ser Gly Leu Gly Arg Ala Tyr Ser Gly Glu Gly
        35                  40                  45

Ala Ile Ala Asp Asp Ala Gly Asn Val Ser Arg Asn Pro Ala Leu Ile
    50                  55                  60

Thr Met Phe Asp Arg Pro Thr Phe Ser Ala Gly Ala Val Tyr Ile Asp
65                  70                  75                  80
```

```
Pro Asp Val Asn Ile Ser Gly Thr Ser Pro Ser Gly Arg Ser Leu Lys
                 85                  90                  95

Ala Asp Asn Ile Ala Pro Thr Ala Trp Val Pro Asn Met His Phe Val
            100                 105                 110

Ala Pro Ile Asn Asp Gln Phe Gly Trp Gly Ala Ser Ile Thr Ser Asn
            115                 120                 125

Tyr Gly Leu Ala Thr Glu Phe Asn Asp Thr Tyr Ala Gly Gly Ser Val
        130                 135                 140

Gly Gly Thr Thr Asp Leu Glu Thr Met Asn Leu Asn Leu Ser Gly Ala
145                 150                 155                 160

Tyr Arg Leu Asn Asn Ala Trp Ser Phe Gly Leu Gly Phe Asn Ala Val
                165                 170                 175

Tyr Ala Arg Ala Lys Ile Glu Arg Phe Ala Gly Asp Leu Gly Gln Leu
            180                 185                 190

Val Ala Gly Gln Ile Met Gln Ser Pro Ala Gly Lys Thr Pro Gln Gly
        195                 200                 205

Gln Ala Leu Ala Ala Thr Ala Asn Gly Ile Asp Ser Asn Thr Lys Ile
        210                 215                 220

Ala His Leu Asn Gly Asn Gln Trp Gly Phe Gly Trp Asn Ala Gly Ile
225                 230                 235                 240

Leu Tyr Glu Leu Asp Lys Asn Asn Arg Tyr Ala Leu Thr Tyr Arg Ser
                245                 250                 255

Glu Val Lys Ile Asp Phe Lys Gly Asn Tyr Ser Ser Asp Leu Asn Arg
            260                 265                 270

Val Phe Asn Asn Tyr Gly Leu Pro Ile Pro Thr Ala Thr Gly Gly Ala
        275                 280                 285

Thr Gln Ser Gly Tyr Leu Thr Leu Asn Leu Pro Glu Met Trp Glu Val
        290                 295                 300

Ser Gly Tyr Asn Arg Val Asp Pro Gln Trp Ala Ile His Tyr Ser Leu
305                 310                 315                 320

Ala Tyr Thr Ser Trp Ser Gln Phe Gln Gln Leu Lys Ala Thr Ser Thr
                325                 330                 335

Ser Gly Asp Thr Leu Phe Gln Lys His Glu Gly Phe Lys Asp Ala Tyr
            340                 345                 350

Arg Ile Ala Leu Gly Thr Thr Tyr Tyr Tyr Asp Asp Asn Trp Thr Phe
        355                 360                 365

Arg Thr Gly Ile Ala Phe Asp Asp Ser Pro Val Pro Ala Gln Asn Arg
        370                 375                 380

Ser Ile Ser Ile Pro Asp Gln Asp Arg Phe Trp Leu Ser Ala Gly Thr
385                 390                 395                 400

Thr Tyr Ala Phe Asn Lys Asp Ala Ser Val Asp Val Gly Val Ser Tyr
                405                 410                 415

Met His Gly Gln Ser Val Lys Ile Asn Glu Gly Pro Tyr Gln Phe Glu
            420                 425                 430

Ser Glu Gly Lys Ala Trp Leu Phe Gly Thr Asn Phe Asn Tyr Ala Phe
        435                 440                 445

<210> SEQ ID NO 82
<211> LENGTH: 122
<212> TYPE: PRT
<213> ORGANISM: Escherichia coli

<400> SEQUENCE: 82

Cys Ser Ser Asn Ala Lys Ile Asp Gln Pro Tyr Val Gly Phe Glu Met
```

```
                1               5                   10                  15
            Gly Tyr Asp Trp Leu Gly Arg Met Pro Tyr Lys Gly Ser Val Glu Asn
                            20                  25                  30

Gly Ala Tyr Lys Ala Gln Gly Val Gln Leu Thr Ala Lys Leu Gly Tyr
                            35                  40                  45

Pro Ile Thr Asp Asp Leu Asp Ile Tyr Thr Arg Leu Gly Gly Met Val
                            50                  55                  60

Trp Arg Ala Asp Thr Lys Ser Asn Val Tyr Gly Lys Asn His Asp Thr
            65                  70                  75                  80

Gly Val Ser Pro Val Phe Ala Gly Gly Val Glu Tyr Ala Ile Thr Pro
                                85                  90                  95

Glu Ile Ala Thr Arg Leu Glu Tyr Gln Trp Thr Asn Asn Ile Gly Asp
                            100                 105                 110

Ala His Thr Ile Gly Thr Arg Pro Asp Asn
                            115                 120

<210> SEQ ID NO 83
<211> LENGTH: 182
<212> TYPE: PRT
<213> ORGANISM: Escherichia coli

<400> SEQUENCE: 83

Met Gln Phe Asn Ile Pro Thr Leu Leu Thr Leu Phe Arg Val Ile Leu
            1               5                   10                  15

Ile Pro Phe Phe Val Leu Val Phe Tyr Leu Pro Val Thr Trp Ser Pro
                            20                  25                  30

Phe Ala Ala Ala Leu Ile Phe Cys Val Ala Ala Val Thr Asp Trp Phe
                            35                  40                  45

Asp Gly Phe Leu Ala Arg Arg Trp Asn Gln Ser Thr Arg Phe Gly Ala
                            50                  55                  60

Phe Leu Asp Pro Val Ala Asp Lys Val Leu Val Ala Ile Ala Met Val
            65                  70                  75                  80

Leu Val Thr Glu His Tyr His Ser Trp Trp Val Thr Leu Pro Ala Ala
                                85                  90                  95

Thr Met Ile Ala Arg Glu Ile Ile Ser Ala Leu Arg Glu Trp Met
                            100                 105                 110

Ala Glu Leu Gly Lys Arg Ser Ser Val Ala Val Ser Trp Ile Gly Lys
                            115                 120                 125

Val Lys Thr Thr Ala Gln Met Val Ala Leu Ala Trp Leu Leu Trp Arg
            130                 135                 140

Pro Asn Ile Trp Val Glu Tyr Ala Gly Ile Ala Leu Phe Phe Val Ala
            145                 150                 155                 160

Ala Val Leu Thr Leu Trp Ser Met Leu Gln Tyr Leu Ser Ala Ala Arg
                            165                 170                 175

Ala Asp Leu Leu Asp Gln
                            180

<210> SEQ ID NO 84
<211> LENGTH: 948
<212> TYPE: PRT
<213> ORGANISM: Escherichia coli

<400> SEQUENCE: 84

Met Ile Thr His Gly Phe Tyr Ala Arg Thr Arg His Lys His Lys Leu
            1               5                   10                  15

Lys Lys Thr Phe Ile Met Leu Ser Ala Gly Leu Gly Leu Phe Phe Tyr
```

-continued

```
                20                  25                  30
Val Asn Gln Asn Ser Phe Ala Asn Gly Glu Asn Tyr Phe Lys Leu Gly
            35                  40                  45

Ser Asp Ser Lys Leu Leu Thr His Asp Ser Tyr Gln Asn Arg Leu Phe
 50                  55                  60

Tyr Thr Leu Lys Thr Gly Glu Thr Val Ala Asp Leu Ser Lys Ser Gln
 65                  70                  75                  80

Asp Ile Asn Leu Ser Thr Ile Trp Ser Leu Asn Lys His Leu Tyr Ser
                85                  90                  95

Ser Glu Ser Glu Met Met Lys Ala Ala Pro Gly Gln Gln Ile Ile Leu
            100                 105                 110

Pro Leu Lys Lys Leu Pro Phe Glu Tyr Ser Ala Leu Pro Leu Leu Gly
            115                 120                 125

Ser Ala Pro Leu Val Ala Ala Gly Gly Val Ala Gly His Thr Asn Lys
            130                 135                 140

Leu Thr Lys Met Ser Pro Asp Val Thr Lys Ser Asn Met Thr Asp Asp
145                 150                 155                 160

Lys Ala Leu Asn Tyr Ala Ala Gln Gln Ala Ala Ser Leu Gly Ser Gln
                165                 170                 175

Leu Gln Ser Arg Ser Leu Asn Gly Asp Tyr Ala Lys Asp Thr Ala Leu
            180                 185                 190

Gly Ile Ala Gly Asn Gln Ala Ser Ser Gln Leu Gln Ala Trp Leu Gln
            195                 200                 205

His Tyr Gly Thr Ala Glu Val Asn Leu Gln Ser Gly Asn Asn Phe Asp
            210                 215                 220

Gly Ser Ser Leu Asp Phe Leu Leu Pro Phe Tyr Asp Ser Glu Lys Met
225                 230                 235                 240

Leu Ala Phe Gly Gln Val Gly Ala Arg Tyr Ile Asp Ser Arg Phe Thr
                245                 250                 255

Ala Asn Leu Gly Ala Gly Gln Arg Phe Phe Leu Pro Glu Asn Met Leu
            260                 265                 270

Gly Tyr Asn Val Phe Ile Asp Gln Asp Phe Ser Gly Asp Asn Thr Arg
            275                 280                 285

Leu Gly Ile Gly Gly Glu Tyr Trp Arg Asp Tyr Phe Lys Ser Ser Val
            290                 295                 300

Asn Gly Tyr Phe Arg Met Ser Gly Trp His Glu Ser Tyr Asn Lys Lys
305                 310                 315                 320

Asp Tyr Asp Glu Arg Pro Ala Asn Gly Phe Asp Ile Arg Phe Asn Gly
                325                 330                 335

Tyr Leu Pro Ser Tyr Pro Ala Leu Gly Ala Arg Leu Met Tyr Glu Gln
            340                 345                 350

Tyr Tyr Gly Asp Asn Val Ala Leu Phe Asn Ser Asp Lys Leu Gln Ser
            355                 360                 365

Asn Pro Gly Ala Ala Thr Val Gly Val Asn Tyr Thr Pro Ile Pro Leu
            370                 375                 380

Val Thr Met Gly Ile Asp Tyr Arg His Gly Thr Gly Asn Glu Asn Asp
385                 390                 395                 400

Leu Leu Tyr Ser Met Gln Phe Arg Tyr Gln Phe Asp Lys Pro Trp Ser
                405                 410                 415

Gln Gln Ile Glu Pro Gln Tyr Val Asn Glu Leu Arg Thr Leu Ser Gly
            420                 425                 430

Ser Arg Tyr Asp Leu Val Gln Arg Asn Asn Asn Ile Ile Leu Glu Tyr
            435                 440                 445
```

```
Lys Lys Gln Asp Ile Leu Ser Leu Asn Ile Pro His Asp Ile Asn Gly
    450                 455                 460
Thr Glu Arg Ser Thr Gln Lys Ile Gln Leu Ile Val Lys Ser Lys Tyr
465                 470                 475                 480
Gly Leu Asp Arg Ile Val Trp Asp Asp Ser Ser Leu Arg Ser Gln Gly
                485                 490                 495
Gly Gln Ile Gln His Ser Gly Ser Gln Ser Ala Gln Asp Tyr Gln Ala
            500                 505                 510
Ile Leu Pro Ala Tyr Val Gln Gly Gly Ser Asn Val Tyr Lys Val Thr
        515                 520                 525
Ala Arg Ala Tyr Asp Arg Asn Gly Asn Ser Ser Asn Val Gln Leu
    530                 535                 540
Thr Ile Thr Val Leu Ser Asn Gly Gln Val Val Asp Gln Val Gly Val
545                 550                 555                 560
Thr Asp Phe Thr Ala Asp Lys Thr Ser Ala Lys Ala Asp Asn Thr Asp
                565                 570                 575
Thr Ile Thr Tyr Thr Ala Met Val Lys Lys Asn Gly Val Thr Gln Ala
            580                 585                 590
Asn Val Pro Val Ser Phe Asn Ile Val Ser Gly Thr Ala Thr Leu Gly
        595                 600                 605
Ala Asn Ser Ala Lys Thr Asp Ala Asn Gly Lys Ala Thr Val Thr Leu
    610                 615                 620
Lys Ser Ser Thr Pro Gly Gln Val Val Ser Ala Lys Thr Ala Glu
625                 630                 635                 640
Met Thr Ser Ala Leu Asn Ala Ser Ala Val Ile Phe Val Asp Gln Thr
                645                 650                 655
Lys Ala Ser Ile Thr Glu Ile Lys Ala Asp Lys Thr Thr Ala Lys Ala
            660                 665                 670
Asn Gly Ser Asp Ala Ile Thr Tyr Thr Val Lys Val Met Lys Asn Asn
        675                 680                 685
Gln Pro Glu Val Asn His Ser Val Thr Phe Ser Thr Asn Phe Gly Asn
    690                 695                 700
Leu Gly Gly Asn Ser Gln Thr Gln Ile Val Gln Thr Asp Lys Asp Gly
705                 710                 715                 720
Lys Ala Thr Val Lys Leu Thr Ser Gly Ser Glu Gly Ser Ala Val Val
                725                 730                 735
Ser Ala Lys Val Ser Glu Val Asn Thr Glu Val Lys Ala Ser Glu Val
            740                 745                 750
Lys Phe Phe Ser Val Leu Ser Ile Gly Asn Asn Val Asn Ile Ile Gly
        755                 760                 765
Thr Ser Ala Asp Gly Ala Leu Pro Asn Ile Trp Leu Gln Tyr Gly Gln
    770                 775                 780
Phe Lys Leu Thr Ala Lys Gly Gly Asp Gly Lys Tyr Lys Trp His Ser
785                 790                 795                 800
Lys Asp Thr Ser Val Ala Ser Val Asp Ala Ser Thr Gly Gln Val Thr
                805                 810                 815
Leu Leu Lys Lys Gly Thr Thr Thr Ile Glu Val Val Ser Gly Asp Asn
            820                 825                 830
Gln Thr Ala Thr Tyr Thr Ile Asn Gln Pro Glu Asn Ile Ile Thr Val
        835                 840                 845
Glu Thr Gln Asp Lys Val Leu Tyr Asn Val Ala Lys Thr Lys Cys Glu
    850                 855                 860
```

Met Asn Ser Gly Arg Leu Pro Ser Ser Thr Ser Glu Leu Lys Asp Val
865                 870                 875                 880

Tyr Asn Gln Trp Gly Pro Ala Asn Ser Tyr Asp Gly Tyr Lys Gly Lys
            885                 890                 895

Asn Thr Ile Thr Ala Trp Thr Gln Gln Thr Ala Asp Asp Ile Pro Lys
        900                 905                 910

Gly Trp Thr Ser Thr Phe Asp Ile Val Thr Lys Asn Glu Ile Pro Asn
    915                 920                 925

Asn Gly Ile Lys Val Lys Val Asn Val Asp Ala Ala Asn Ala Phe Ala
930                 935                 940

Val Cys Val Lys
945

<210> SEQ ID NO 85
<211> LENGTH: 87
<212> TYPE: PRT
<213> ORGANISM: Saccharomyces cerevisiae

<400> SEQUENCE: 85

Met Gln Leu Leu Arg Cys Phe Ser Ile Phe Ser Val Ile Ala Ser Val
1               5                   10                  15

Leu Ala Gln Glu Leu Thr Thr Ile Cys Glu Gln Ile Pro Ser Pro Thr
            20                  25                  30

Leu Glu Ser Thr Pro Tyr Ser Leu Ser Thr Thr Thr Ile Leu Ala Asn
        35                  40                  45

Gly Lys Ala Met Gln Gly Val Phe Glu Tyr Tyr Lys Ser Val Thr Phe
    50                  55                  60

Val Ser Asn Cys Gly Ser His Pro Ser Thr Thr Ser Lys Gly Ser Pro
65                  70                  75                  80

Ile Asn Thr Gln Tyr Val Phe
                85

<210> SEQ ID NO 86
<211> LENGTH: 335
<212> TYPE: PRT
<213> ORGANISM: Homo sapiens

<400> SEQUENCE: 86

Met Ala Asp Gly Pro Tyr Leu Gln Ile Leu Glu Gln Pro Lys Gln Arg
1               5                   10                  15

Gly Phe Arg Phe Arg Tyr Val Cys Glu Gly Pro Ser His Gly Gly Leu
            20                  25                  30

Pro Gly Ala Ser Ser Glu Lys Asn Lys Lys Ser Tyr Pro Gln Val Lys
        35                  40                  45

Ile Cys Asn Tyr Val Gly Pro Ala Lys Val Ile Val Gln Leu Val Thr
    50                  55                  60

Asn Gly Lys Asn Ile His Leu His Ala His Ser Leu Val Gly Lys His
65                  70                  75                  80

Cys Glu Asp Gly Ile Cys Thr Val Thr Ala Gly Pro Lys Asp Met Val
            85                  90                  95

Val Gly Phe Ala Asn Leu Gly Ile Leu His Val Thr Lys Lys Lys Val
            100                 105                 110

Phe Glu Thr Leu Glu Ala Arg Met Thr Glu Ala Cys Ile Arg Gly Tyr
        115                 120                 125

Asn Pro Gly Leu Leu Val His Pro Asp Leu Ala Tyr Leu Gln Ala Glu
    130                 135                 140

```
Gly Gly Gly Asp Arg Gln Leu Gly Asp Arg Glu Lys Glu Leu Ile Arg
145                 150                 155                 160

Gln Ala Ala Leu Gln Gln Thr Lys Glu Met Asp Leu Ser Val Val Arg
                165                 170                 175

Leu Met Phe Thr Ala Phe Leu Pro Asp Ser Thr Gly Ser Phe Thr Arg
            180                 185                 190

Arg Leu Glu Pro Val Val Ser Asp Ala Ile Tyr Asp Ser Lys Ala Pro
        195                 200                 205

Asn Ala Ser Asn Leu Lys Ile Val Arg Met Asp Arg Thr Ala Gly Cys
    210                 215                 220

Val Thr Gly Gly Glu Glu Ile Tyr Leu Leu Cys Asp Lys Val Gln Lys
225                 230                 235                 240

Asp Asp Ile Gln Ile Arg Phe Tyr Glu Glu Glu Asn Gly Gly Val
                245                 250                 255

Trp Glu Gly Phe Gly Asp Phe Ser Pro Thr Asp Val His Arg Gln Phe
                260                 265                 270

Ala Ile Val Phe Lys Thr Pro Lys Tyr Lys Asp Ile Asn Ile Thr Lys
                275                 280                 285

Pro Ala Ser Val Phe Val Gln Leu Arg Arg Lys Ser Asp Leu Glu Thr
290                 295                 300

Ser Glu Pro Lys Pro Phe Leu Tyr Tyr Pro Glu Ile Lys Asp Lys Glu
305                 310                 315                 320

Glu Val Gln Arg Lys Arg Gln Lys Val Gln Arg Lys Gln Lys
                325                 330                 335
```

<210> SEQ ID NO 87
<211> LENGTH: 5
<212> TYPE: PRT
<213> ORGANISM: Artificial Sequence
<220> FEATURE:
<223> OTHER INFORMATION: Synthetic sequence

<400> SEQUENCE: 87

```
Arg Arg Arg Arg Arg
1               5
```

<210> SEQ ID NO 88
<211> LENGTH: 6
<212> TYPE: PRT
<213> ORGANISM: Artificial Sequence
<220> FEATURE:
<223> OTHER INFORMATION: Synthetic sequence

<400> SEQUENCE: 88

```
His His His His His His
1               5
```

<210> SEQ ID NO 89
<211> LENGTH: 19
<212> TYPE: PRT
<213> ORGANISM: Artificial Sequence
<220> FEATURE:
<223> OTHER INFORMATION: Synthetic sequence

<400> SEQUENCE: 89

```
Ser Gly Leu Asn Asp Ile Phe Glu Ala Gln Lys Ile Glu Trp His Glu
1               5                   10                  15

Leu Glu Leu
```

<210> SEQ ID NO 90

```
<211> LENGTH: 8
<212> TYPE: PRT
<213> ORGANISM: Artificial Sequence
<220> FEATURE:
<223> OTHER INFORMATION: Synthetic sequence

<400> SEQUENCE: 90

Asp Tyr Lys Asp Asp Asp Asp Lys
1               5

<210> SEQ ID NO 91
<211> LENGTH: 8
<212> TYPE: PRT
<213> ORGANISM: Artificial Sequence
<220> FEATURE:
<223> OTHER INFORMATION: Synthetic sequence

<400> SEQUENCE: 91

Trp Ser His Pro Gln Phe Glu Lys
1               5

<210> SEQ ID NO 92
<211> LENGTH: 10
<212> TYPE: PRT
<213> ORGANISM: Artificial Sequence
<220> FEATURE:
<223> OTHER INFORMATION: Synthetic sequence

<400> SEQUENCE: 92

Glu Gln Lys Leu Ile Ser Glu Glu Asp Leu
1               5                   10

<210> SEQ ID NO 93
<211> LENGTH: 15
<212> TYPE: PRT
<213> ORGANISM: Artificial Sequence
<220> FEATURE:
<223> OTHER INFORMATION: Synthetic sequence

<400> SEQUENCE: 93

Lys Glu Thr Ala Ala Ala Lys Phe Glu Arg Gln His Met Asp Ser
1               5                   10                  15

<210> SEQ ID NO 94
<211> LENGTH: 26
<212> TYPE: PRT
<213> ORGANISM: Artificial Sequence
<220> FEATURE:
<223> OTHER INFORMATION: Synthetic sequence

<400> SEQUENCE: 94

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 95
<211> LENGTH: 38
<212> TYPE: PRT
<213> ORGANISM: Artificial Sequence
<220> FEATURE:
<223> OTHER INFORMATION: Synthetic sequence

<400> SEQUENCE: 95

Met Asp Glu Lys Thr Thr Gly Trp Arg Gly Gly His Val Val Glu Gly
1               5                   10                  15
```

Leu Ala Gly Glu Leu Glu Gln Leu Arg Ala Arg Leu Glu His His Pro
            20                  25                  30

Gln Gly Gln Arg Glu Pro
        35

<210> SEQ ID NO 96
<211> LENGTH: 4
<212> TYPE: PRT
<213> ORGANISM: Artificial Sequence
<220> FEATURE:
<223> OTHER INFORMATION: Synthetic sequence

<400> SEQUENCE: 96

Thr Gly Ser Thr
1

<210> SEQ ID NO 97
<211> LENGTH: 5
<212> TYPE: PRT
<213> ORGANISM: Artificial Sequence
<220> FEATURE:
<223> OTHER INFORMATION: Synthetic sequence

<400> SEQUENCE: 97

Thr Gly Ser Gly Thr
1               5

<210> SEQ ID NO 98
<211> LENGTH: 6
<212> TYPE: PRT
<213> ORGANISM: Artificial Sequence
<220> FEATURE:
<223> OTHER INFORMATION: Synthetic sequence

<400> SEQUENCE: 98

Thr Gly Ser Tyr Gly Thr
1               5

<210> SEQ ID NO 99
<211> LENGTH: 7
<212> TYPE: PRT
<213> ORGANISM: Artificial Sequence
<220> FEATURE:
<223> OTHER INFORMATION: Synthetic sequence

<400> SEQUENCE: 99

Thr Gly Ser Glu Tyr Gly Thr
1               5

<210> SEQ ID NO 100
<211> LENGTH: 8
<212> TYPE: PRT
<213> ORGANISM: Artificial Sequence
<220> FEATURE:
<223> OTHER INFORMATION: Synthetic sequence

<400> SEQUENCE: 100

Thr Gly Ser Ala Glu Tyr Gly Thr
1               5

<210> SEQ ID NO 101
<211> LENGTH: 10
<212> TYPE: PRT
<213> ORGANISM: Artificial Sequence
<220> FEATURE:
<223> OTHER INFORMATION: Synthetic sequence

```
<400> SEQUENCE: 101

Thr Gly Ser Lys Leu Ala Glu Tyr Gly Thr
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Synthetic sequence

<400> SEQUENCE: 102

Thr Gly Ser Trp Gly Lys Leu Ala Glu Tyr Gly Thr
1               5                   10

<210> SEQ ID NO 103
<211> LENGTH: 7
<212> TYPE: PRT
<213> ORGANISM: Artificial Sequence
<220> FEATURE:
<223> OTHER INFORMATION: Synthetic sequence

<400> SEQUENCE: 103

Thr Lys Ser Ile Pro Pro Ile
1               5

<210> SEQ ID NO 104
<211> LENGTH: 9
<212> TYPE: PRT
<213> ORGANISM: Artificial Sequence
<220> FEATURE:
<223> OTHER INFORMATION: Synthetic sequence

<400> SEQUENCE: 104

Arg Ser Thr Lys Ser Ile Pro Pro Ile
1               5

<210> SEQ ID NO 105
<211> LENGTH: 5
<212> TYPE: PRT
<213> ORGANISM: Artificial Sequence
<220> FEATURE:
<223> OTHER INFORMATION: Synthetic sequence

<400> SEQUENCE: 105

Ala Asp Trp Gly Thr
1               5

<210> SEQ ID NO 106
<211> LENGTH: 6
<212> TYPE: PRT
<213> ORGANISM: Artificial Sequence
<220> FEATURE:
<223> OTHER INFORMATION: Synthetic sequence

<400> SEQUENCE: 106

Val Arg Pro Ile Ala Thr
1               5

<210> SEQ ID NO 107
<211> LENGTH: 5
<212> TYPE: PRT
<213> ORGANISM: Artificial Sequence
<220> FEATURE:
<223> OTHER INFORMATION: Synthetic sequence

<400> SEQUENCE: 107
```

```
Thr Gly Ser Gly Trp
1               5

<210> SEQ ID NO 108
<211> LENGTH: 8
<212> TYPE: PRT
<213> ORGANISM: Artificial Sequence
<220> FEATURE:
<223> OTHER INFORMATION: Synthetic sequence

<400> SEQUENCE: 108

Thr Gly Ser Ala Glu Tyr Gly Trp
1               5

<210> SEQ ID NO 109
<211> LENGTH: 8
<212> TYPE: PRT
<213> ORGANISM: Artificial Sequence
<220> FEATURE:
<223> OTHER INFORMATION: Synthetic sequence

<400> SEQUENCE: 109

Thr Gly Ser Ala Glu Tyr Gly Lys
1               5

<210> SEQ ID NO 110
<211> LENGTH: 71
<212> TYPE: PRT
<213> ORGANISM: Artificial Sequence
<220> FEATURE:
<223> OTHER INFORMATION: Synthetic sequence

<400> SEQUENCE: 110

Met Lys Ile Glu Glu Gly Lys Leu Thr Asn Pro Gly Val Ser Ala Trp
1               5                   10                  15

Gln Val Asn Thr Ala Tyr Thr Ala Gly Gln Leu Val Thr Tyr Asn Gly
                20                  25                  30

Lys Thr Tyr Lys Cys Leu Gln Pro His Thr Ser Leu Ala Gly Trp Glu
            35                  40                  45

Pro Ser Asn Val Pro Ala Leu Trp Gln Leu Gln Asn Asn Gly Asn Asn
        50                  55                  60

Gly Leu Glu Leu Arg His Gly
65                  70

<210> SEQ ID NO 111
<211> LENGTH: 10
<212> TYPE: PRT
<213> ORGANISM: Artificial Sequence
<220> FEATURE:
<223> OTHER INFORMATION: Synthetic sequence

<400> SEQUENCE: 111

Thr Leu Asp Asp Met Glu Glu Met Asp Gly
1               5                   10

<210> SEQ ID NO 112
<211> LENGTH: 17
<212> TYPE: PRT
<213> ORGANISM: Artificial Sequence
<220> FEATURE:
<223> OTHER INFORMATION: Synthetic sequence

<400> SEQUENCE: 112

Gly Met Ile Thr Leu Asp Asp Met Glu Glu Met Asp Gly Leu Ser Asp
```

```
1               5                   10                  15
Phe

<210> SEQ ID NO 113
<211> LENGTH: 15
<212> TYPE: PRT
<213> ORGANISM: Artificial Sequence
<220> FEATURE:
<223> OTHER INFORMATION: Synthetic sequence

<400> SEQUENCE: 113

Thr Gly Ser His Asn Arg Trp Gly Lys Leu Ala Glu Tyr Gly Thr
1               5                   10                  15

<210> SEQ ID NO 114
<211> LENGTH: 20
<212> TYPE: PRT
<213> ORGANISM: Artificial Sequence
<220> FEATURE:
<223> OTHER INFORMATION: Synthetic sequence

<400> SEQUENCE: 114

Thr Gly Ser Tyr Thr Gly Asp Gln His Asn Arg Trp Gly Lys Leu Ala
1               5                   10                  15

Glu Tyr Gly Thr
            20

<210> SEQ ID NO 115
<211> LENGTH: 5
<212> TYPE: PRT
<213> ORGANISM: Artificial Sequence
<220> FEATURE:
<223> OTHER INFORMATION: Synthetic sequence

<400> SEQUENCE: 115

Thr Gly Ser Gly Tyr
1               5

<210> SEQ ID NO 116
<211> LENGTH: 5
<212> TYPE: PRT
<213> ORGANISM: Artificial Sequence
<220> FEATURE:
<223> OTHER INFORMATION: Synthetic sequence

<400> SEQUENCE: 116

Thr Gly Ser Gly Phe
1               5

<210> SEQ ID NO 117
<211> LENGTH: 239
<212> TYPE: PRT
<213> ORGANISM: Artificial Sequence
<220> FEATURE:
<223> OTHER INFORMATION: Synthetic sequence

<400> SEQUENCE: 117

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
```

```
              50                  55                  60
Leu Thr Trp Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 118
<211> LENGTH: 6
<212> TYPE: PRT
<213> ORGANISM: Artificial Sequence
<220> FEATURE:
<223> OTHER INFORMATION: Synthetic sequence

<400> SEQUENCE: 118

Thr Gly Ser Tyr Gly Ser
1               5

<210> SEQ ID NO 119
<211> LENGTH: 8
<212> TYPE: PRT
<213> ORGANISM: Artificial Sequence
<220> FEATURE:
<223> OTHER INFORMATION: Synthetic sequence

<400> SEQUENCE: 119

Thr Gly Ser Ala Glu Tyr Gly Ser
1               5

<210> SEQ ID NO 120
<211> LENGTH: 407
<212> TYPE: PRT
<213> ORGANISM: Nostoc species PCC7120

<400> SEQUENCE: 120

Cys Leu Pro Glu Asp Ala Leu Val His Thr Ala Lys Gly Leu Val Pro
1               5                  10                  15

Ile Arg Asp Val Gln Val Gly Asp Leu Val Gln Thr Pro Leu Gly Phe
            20                  25                  30

Arg Arg Val Val Asp Lys Phe Asp Gln Gly Phe Gln Asp Val Tyr Glu
        35                  40                  45

Ile Glu Thr Asn Ala Thr Tyr Pro Arg Ala Thr Leu Asn His Arg Gln
```

```
           50                  55                  60
Ala Val Leu Glu Asp Ala Lys Gly Gly Ile Val Trp Lys His Ile Ala
 65                  70                  75                  80

Ser Leu Glu Ala Gly Asp Arg Leu Leu His Asn Lys Gln Val Leu Pro
                 85                  90                  95

Gly Thr Val Thr His Leu Pro Ala Asp Phe Thr Glu Ser Arg Pro Ser
                100                 105                 110

His Ser Arg Thr Ala Lys Ser Phe Val Val Pro Glu Leu Thr Ala Glu
            115                 120                 125

Val Ala Trp Leu Ile Gly Phe Thr His Gly Asp Gly Tyr Val Ala Leu
        130                 135                 140

Gly Arg Asn Lys Tyr Asp Lys Pro Tyr Gly Arg Val Glu Trp Ser Met
145                 150                 155                 160

Asn Ser Leu Asp Ala Glu Val Thr Ser Arg Ile Gln Ala Lys Ile Asp
                165                 170                 175

Ala Ala Leu Ala Leu Phe Gly Leu Ser Ala Val His Ser Ile Thr Lys
            180                 185                 190

Gly Glu Asn Thr Ala Lys Ser Ile Cys Ser Ser Ile Arg Leu Ala Glu
        195                 200                 205

Tyr Phe His Arg His Ile Lys Gln Pro Asn Ile Pro Leu Thr Val Pro
210                 215                 220

Ser Phe Ile Leu Gln Gly Ser Val Asp Ile Arg Ala Ala Tyr Leu Ala
225                 230                 235                 240

Gly Leu Met Asp Ser Asp Gly Ala Val Asn Asn Arg Pro Pro His Leu
                245                 250                 255

Ile Thr Ser Val Tyr Arg Ser Phe Ile Arg Gln Val Ser Val Val Leu
            260                 265                 270

Ser Ser Leu Gly Ile Ala Gly Arg Leu Thr Thr Thr Tyr Pro Gln Asn
        275                 280                 285

Ser Asn Trp Gln Val Lys Tyr Asn Leu Thr Ile Pro Ala Leu Lys Glu
290                 295                 300

Arg Tyr Asn Ala Leu Ile Ser Pro His Ser Ala Lys Gly Glu Leu Arg
305                 310                 315                 320

Gln Gly Leu Lys Met Tyr Gly Phe Thr Val Pro Gly Ala Val Met Arg
                325                 330                 335

Glu Thr Tyr Thr Tyr Ser Glu Met Arg Glu Met Gly Phe Gln Gly Ser
            340                 345                 350

Arg Thr Val Asp Ala Asn Tyr Glu Arg Tyr Val Ala Glu Ala Asp Ile
        355                 360                 365

Ser Leu Asp Ile Pro Val Thr Val Lys Gly Leu Gly Ser Tyr Asp His
370                 375                 380

Val Gln Thr Tyr Asp Ile Glu Val Asp Glu Ala His Cys Phe Tyr Cys
385                 390                 395                 400

Asp Gly Tyr Leu Thr His Asn
                405

<210> SEQ ID NO 121
<211> LENGTH: 1537
<212> TYPE: PRT
<213> ORGANISM: Saccharomyces cerevisiae

<400> SEQUENCE: 121

Met Thr Met Pro His Arg Tyr Met Phe Leu Ala Val Phe Thr Leu Leu
 1               5                  10                  15
```

```
Ala Leu Thr Ser Val Ala Ser Gly Ala Thr Glu Ala Cys Leu Pro Ala
             20                  25                  30

Gly Gln Arg Lys Ser Gly Met Asn Ile Asn Phe Tyr Gln Tyr Ser Leu
         35                  40                  45

Lys Asp Ser Ser Thr Tyr Ser Asn Ala Ala Tyr Met Ala Tyr Gly Tyr
 50                  55                  60

Ala Ser Lys Thr Lys Leu Gly Ser Val Gly Gly Gln Thr Asp Ile Ser
 65                  70                  75                  80

Ile Asp Tyr Asn Ile Pro Cys Val Ser Ser Gly Thr Phe Pro Cys
                 85                  90                  95

Pro Gln Glu Asp Ser Tyr Gly Asn Trp Gly Cys Lys Gly Met Gly Ala
             100                 105                 110

Cys Ser Asn Ser Gln Gly Ile Ala Tyr Trp Ser Thr Asp Leu Phe Gly
         115                 120                 125

Phe Tyr Thr Thr Pro Thr Asn Val Thr Leu Glu Met Thr Gly Tyr Phe
 130                 135                 140

Leu Pro Pro Gln Thr Gly Ser Tyr Thr Phe Lys Phe Ala Thr Val Asp
145                 150                 155                 160

Asp Ser Ala Ile Leu Ser Val Gly Gly Ala Thr Ala Phe Asn Cys Cys
             165                 170                 175

Ala Gln Gln Gln Pro Ile Thr Ser Thr Asn Phe Thr Ile Asp Gly
         180                 185                 190

Ile Lys Pro Trp Gly Gly Ser Leu Pro Pro Asn Ile Glu Gly Thr Val
 195                 200                 205

Tyr Met Tyr Ala Gly Tyr Tyr Tyr Pro Met Lys Val Val Tyr Ser Asn
 210                 215                 220

Ala Val Ser Trp Gly Thr Leu Pro Ile Ser Val Thr Leu Pro Asp Gly
225                 230                 235                 240

Thr Thr Val Ser Asp Asp Phe Glu Gly Tyr Val Tyr Ser Phe Asp Asp
             245                 250                 255

Asp Leu Ser Gln Ser Asn Cys Thr Val Pro Asp Pro Ser Asn Tyr Ala
         260                 265                 270

Val Ser Thr Thr Thr Thr Thr Glu Pro Trp Thr Gly Thr Phe Thr
 275                 280                 285

Ser Thr Ser Thr Glu Met Thr Thr Val Thr Gly Thr Asn Gly Val Pro
 290                 295                 300

Thr Asp Glu Thr Val Ile Val Ile Arg Thr Pro Thr Thr Ala Ser Thr
305                 310                 315                 320

Ile Ile Thr Thr Thr Glu Pro Trp Asn Ser Thr Phe Thr Ser Thr Ser
             325                 330                 335

Thr Glu Leu Thr Thr Val Thr Gly Thr Asn Gly Val Arg Thr Asp Glu
         340                 345                 350

Thr Ile Ile Val Ile Arg Thr Pro Thr Thr Ala Thr Ala Ile Thr
 355                 360                 365

Thr Thr Glu Pro Trp Asn Ser Thr Phe Thr Ser Thr Ser Thr Glu Leu
 370                 375                 380

Thr Thr Val Thr Gly Thr Asn Gly Leu Pro Thr Asp Glu Thr Ile Ile
385                 390                 395                 400

Val Ile Arg Thr Pro Thr Thr Ala Thr Thr Ala Met Thr Thr Thr Gln
             405                 410                 415

Pro Trp Asn Asp Thr Phe Thr Ser Thr Ser Thr Glu Leu Thr Thr Val
         420                 425                 430

Thr Gly Thr Asn Gly Leu Pro Thr Asp Glu Thr Ile Ile Val Ile Arg
```

```
                435                 440                 445
Thr Pro Thr Thr Ala Thr Thr Ala Met Thr Thr Thr Gln Pro Trp Asn
450                 455                 460

Asp Thr Phe Thr Ser Thr Ser Thr Glu Leu Thr Thr Val Thr Gly Thr
465                 470                 475                 480

Asn Gly Leu Pro Thr Asp Glu Thr Ile Ile Val Ile Arg Thr Pro Thr
                485                 490                 495

Thr Ala Thr Thr Ala Met Thr Thr Thr Gln Pro Trp Asn Asp Thr Phe
                500                 505                 510

Thr Ser Thr Ser Thr Glu Ile Thr Thr Val Thr Gly Thr Asn Gly Leu
                515                 520                 525

Pro Thr Asp Glu Thr Ile Ile Val Ile Arg Thr Pro Thr Thr Ala Thr
530                 535                 540

Thr Ala Met Thr Thr Pro Gln Pro Trp Asn Asp Thr Phe Thr Ser Thr
545                 550                 555                 560

Ser Thr Glu Met Thr Thr Val Thr Gly Thr Asn Gly Leu Pro Thr Asp
                565                 570                 575

Glu Thr Ile Ile Val Ile Arg Thr Pro Thr Thr Ala Thr Thr Ala Ile
                580                 585                 590

Thr Thr Thr Glu Pro Trp Asn Ser Thr Phe Thr Ser Thr Ser Thr Glu
                595                 600                 605

Met Thr Thr Val Thr Gly Thr Asn Gly Leu Pro Thr Asp Glu Thr Ile
                610                 615                 620

Ile Val Ile Arg Thr Pro Thr Thr Ala Thr Thr Ala Ile Thr Thr Thr
625                 630                 635                 640

Gln Pro Trp Asn Asp Thr Phe Thr Ser Thr Ser Thr Glu Met Thr Thr
                645                 650                 655

Val Thr Gly Thr Asn Gly Leu Pro Thr Asp Glu Thr Ile Ile Val Ile
                660                 665                 670

Arg Thr Pro Thr Thr Ala Thr Thr Ala Met Thr Thr Thr Gln Pro Trp
                675                 680                 685

Asn Asp Thr Phe Thr Ser Thr Ser Thr Glu Ile Thr Thr Val Thr Gly
                690                 695                 700

Thr Thr Gly Leu Pro Thr Asp Glu Thr Ile Ile Val Ile Arg Thr Pro
705                 710                 715                 720

Thr Thr Ala Thr Thr Ala Met Thr Thr Thr Gln Pro Trp Asn Asp Thr
                725                 730                 735

Phe Thr Ser Thr Ser Thr Glu Met Thr Thr Val Thr Gly Thr Asn Gly
                740                 745                 750

Val Pro Thr Asp Glu Thr Val Ile Val Ile Arg Thr Pro Thr Ser Glu
                755                 760                 765

Gly Leu Ile Ser Thr Thr Thr Glu Pro Trp Thr Gly Thr Phe Thr Ser
                770                 775                 780

Thr Ser Thr Glu Met Thr Thr Val Thr Gly Thr Asn Gly Gln Pro Thr
785                 790                 795                 800

Asp Glu Thr Val Ile Val Ile Arg Thr Pro Thr Ser Glu Gly Leu Val
                805                 810                 815

Thr Thr Thr Thr Glu Pro Trp Thr Gly Thr Phe Thr Ser Thr Ser Thr
                820                 825                 830

Glu Met Thr Thr Ile Thr Gly Thr Asn Gly Val Pro Thr Asp Glu Thr
                835                 840                 845

Val Ile Val Ile Arg Thr Pro Thr Ser Glu Gly Leu Ile Ser Thr Thr
850                 855                 860
```

-continued

```
Thr Glu Pro Trp Thr Gly Thr Phe Thr Ser Thr Ser Thr Glu Met Thr
865                 870                 875                 880

Thr Ile Thr Gly Thr Asn Gly Gln Pro Thr Asp Glu Thr Val Ile Val
            885                 890                 895

Ile Arg Thr Pro Thr Ser Glu Gly Leu Ile Ser Thr Thr Thr Glu Pro
        900                 905                 910

Trp Thr Gly Thr Phe Thr Ser Thr Glu Met Thr His Val Thr
    915                 920                 925

Gly Thr Asn Gly Val Pro Thr Asp Glu Thr Val Ile Val Ile Arg Thr
930                 935                 940

Pro Thr Ser Glu Gly Leu Ile Ser Thr Thr Glu Pro Trp Thr Gly
945                 950                 955                 960

Thr Phe Thr Ser Thr Ser Thr Glu Val Thr Thr Ile Thr Gly Thr Asn
                965                 970                 975

Gly Gln Pro Thr Asp Glu Thr Val Ile Val Ile Arg Thr Pro Thr Ser
                980                 985                 990

Glu Gly Leu Ile Ser Thr Thr Thr  Glu Pro Trp Thr Gly  Thr Phe Thr
                995                 1000                1005

Ser Thr Ser Thr Glu Met Thr  Thr Val Thr Gly Thr  Asn Gly Gln
    1010                1015                1020

Pro Thr Asp Glu Thr Val Ile  Val Ile Arg Thr Pro  Thr Ser Glu
    1025                1030                1035

Gly Leu Val Thr Thr Thr Thr  Glu Pro Trp Thr Gly  Thr Phe Thr
    1040                1045                1050

Ser Thr Ser Thr Glu Met Ser  Thr Val Thr Gly Thr  Asn Gly Leu
    1055                1060                1065

Pro Thr Asp Glu Thr Val Ile  Val Val Lys Thr Pro  Thr Thr Ala
    1070                1075                1080

Ile Ser Ser Ser Leu Ser Ser  Ser Ser Ser Gly Gln  Ile Thr Ser
    1085                1090                1095

Ser Ile Thr Ser Ser Arg Pro  Ile Ile Thr Pro Phe  Tyr Pro Ser
    1100                1105                1110

Asn Gly Thr Ser Val Ile Ser  Ser Ser Val Ile Ser  Ser Ser Val
    1115                1120                1125

Thr Ser Ser Leu Phe Thr Ser  Ser Pro Val Ile Ser  Ser Ser Val
    1130                1135                1140

Ile Ser Ser Ser Thr Thr Thr  Ser Thr Ser Ile Phe  Ser Glu Ser
    1145                1150                1155

Ser Lys Ser Ser Val Ile Pro  Thr Ser Ser Ser Thr  Ser Gly Ser
    1160                1165                1170

Ser Glu Ser Glu Thr Ser Ser  Ala Gly Ser Val Ser  Ser Ser Ser
    1175                1180                1185

Phe Ile Ser Ser Glu Ser Ser  Lys Ser Pro Thr Tyr  Ser Ser Ser
    1190                1195                1200

Ser Leu Pro Leu Val Thr Ser  Ala Thr Thr Ser Gln  Glu Thr Ala
    1205                1210                1215

Ser Ser Leu Pro Pro Ala Thr  Thr Thr Lys Thr Ser  Glu Gln Thr
    1220                1225                1230

Thr Leu Val Thr Val Thr Ser  Cys Glu Ser His Val  Cys Thr Glu
    1235                1240                1245

Ser Ile Ser Pro Ala Ile Val  Ser Thr Ala Thr Val  Thr Val Ser
    1250                1255                1260
```

-continued

Gly Val Thr Thr Glu Tyr Thr Thr Trp Cys Pro Ile Ser Thr Thr
    1265                1270                1275

Glu Thr Thr Lys Gln Thr Lys Gly Thr Thr Glu Gln Thr Thr Glu
    1280                1285                1290

Thr Thr Lys Gln Thr Thr Val Val Thr Ile Ser Ser Cys Glu Ser
    1295                1300                1305

Asp Val Cys Ser Lys Thr Ala Ser Pro Ala Ile Val Ser Thr Ser
    1310                1315                1320

Thr Ala Thr Ile Asn Gly Val Thr Thr Glu Tyr Thr Thr Trp Cys
    1325                1330                1335

Pro Ile Ser Thr Thr Glu Ser Arg Gln Gln Thr Thr Leu Val Thr
    1340                1345                1350

Val Thr Ser Cys Glu Ser Gly Val Cys Ser Glu Thr Ala Ser Pro
    1355                1360                1365

Ala Ile Val Ser Thr Ala Thr Ala Thr Val Asn Asp Val Val Thr
    1370                1375                1380

Val Tyr Pro Thr Trp Arg Pro Gln Thr Ala Asn Glu Glu Ser Val
    1385                1390                1395

Ser Ser Lys Met Asn Ser Ala Thr Gly Glu Thr Thr Asn Thr
    1400                1405                1410

Leu Ala Ala Glu Thr Thr Thr Asn Thr Val Ala Ala Glu Thr Ile
    1415                1420                1425

Thr Asn Thr Gly Ala Ala Glu Thr Lys Thr Val Val Thr Ser Ser
    1430                1435                1440

Leu Ser Arg Ser Asn His Ala Glu Thr Gln Thr Ala Ser Ala Thr
    1445                1450                1455

Asp Val Ile Gly His Ser Ser Val Val Ser Val Ser Glu Thr
    1460                1465                1470

Gly Asn Thr Lys Ser Leu Thr Ser Ser Gly Leu Ser Thr Met Ser
    1475                1480                1485

Gln Gln Pro Arg Ser Thr Pro Ala Ser Ser Met Val Gly Tyr Ser
    1490                1495                1500

Thr Ala Ser Leu Glu Ile Ser Thr Tyr Ala Gly Ser Ala Asn Ser
    1505                1510                1515

Leu Leu Ala Gly Ser Gly Leu Ser Val Phe Ile Ala Ser Leu Leu
    1520                1525                1530

Leu Ala Ile Ile
    1535

<210> SEQ ID NO 122
<211> LENGTH: 8
<212> TYPE: PRT
<213> ORGANISM: Artificial Sequence
<220> FEATURE:
<223> OTHER INFORMATION: Synthetic sequence

<400> SEQUENCE: 122

Leu Glu His His His His His His
1               5

<210> SEQ ID NO 123
<211> LENGTH: 5
<212> TYPE: PRT
<213> ORGANISM: Artificial Sequence
<220> FEATURE:
<223> OTHER INFORMATION: Synthetic sequence

<400> SEQUENCE: 123

```
Met Gly Tyr Thr Ala
1               5

<210> SEQ ID NO 124
<211> LENGTH: 8
<212> TYPE: PRT
<213> ORGANISM: Artificial Sequence
<220> FEATURE:
<223> OTHER INFORMATION: Synthetic sequence

<400> SEQUENCE: 124

Met Gly Thr Ser Gly Tyr Ser Thr
1               5
```

MACROCYCLIC COMPOUNDS WITH A HYBRID PEPTIDIC/NON-PEPTIDIC BACKBONE AND METHODS FOR THEIR PREPARATION

CROSS-REFERENCE TO RELATED APPLICATIONS

This application is a national stage application under 35 U.S.C. §371 of PCT Application No. PCT/US2012/022050, filed Jan. 20, 2012, which claims priority to and the benefit of U.S. provisional patent application Ser. No. 61/434,720, filed Jan. 20, 2011, which is incorporated herein by reference in its entirety.

1. TECHNICAL FIELD

The present invention relates to methods and compositions for generating macrocyclic peptide-containing molecules with a hybrid peptidic/non-peptidic backbone. The invention also relates to nucleic acid molecules, polypeptides, and methods for generating libraries of macrocyclic peptide-containing molecules.

2. BACKGROUND OF THE INVENTION

Peptides and peptide-containing molecules represent valuable tools for investigating biological systems, studying the binding and activity properties of biomolecules (e.g., enzymes, cell receptors, antibodies, kinases), exploring the etiopathological causes of diseases, and for validating pharmacological targets. Peptides and peptide-containing molecules are also attractive ligands for targeting protein-protein interactions and modulating the function of biological molecules such as enzymes and nucleic acids. The synthesis of combinatorial libraries of small peptides and peptide-containing molecules followed by screening of these chemical libraries in biological assays can enable the identification of compounds that exhibit a variety of biological and pharmacological properties. Bioactive peptides and peptide-containing molecules identified in this manner can constitute valuable lead compounds or facilitate the development of lead compounds towards the discovery of new drugs.

Both biosynthetic and synthetic methods are available in the art for preparing chemical libraries of peptides and peptide-containing molecules. Biological peptide libraries have been prepared, for example, by expressing a target polypeptide sequence fused to, or embedded within, a viral particle (e.g., phage display), a membrane receptor, or another protein scaffold in a host organism such as *Escherichia coli* or yeast, and randomizing the oligonucleotide sequence encoding for the target polypeptide sequence by random cassette mutagenesis or similar methods. These genetically-encoded peptide libraries can be used to identify peptide ligands with the desired property (e.g., high binding affinity toward a target protein) by displaying the peptide library on the surface of bacteriophage, bacteria or yeast and isolating the members of the library that bind to the target molecule by phage-panning, affinity separation, fluorescence-activated cell sorting or similar methods known in the art.

An advantage of these biosynthetic approaches is that very large collections of peptide ligands ($10^8$-$10^{10}$ members or higher) can be generated within a short time and at low costs. After the screening step, the composition of the peptide ligands that exhibit the desired property can be rapidly determined by sequencing of the genetic elements that encodes for them. A potential limitation of these genetically encoded libraries, however, is that they rely on the combinatorial assembly of a relatively small pool of building blocks, i.e., naturally occurring amino acids, which limits the structural and functional diversity that these libraries can provide. Achieving a high degree of structural and functional diversity in a chemical library is crucial for increasing the likelihood of identifying a member within the library that exhibits the desired property or biological activity (e.g., high inhibitory activity toward a target enzyme or a protein-protein interaction).

Libraries of small peptides and peptide-containing molecules have been prepared synthetically by using solution- or solid-phase peptide synthesis in combination with combinatorial chemistry techniques. Split-and-mix methods and solid-phase peptide synthesis have been applied, for example, to prepare libraries of linear peptides where each members of the library is covalently bound to a resin bead (e.g., one-bead-one-compound library). Alternatively, arrays of peptides or peptide-containing molecules have been synthesized on glass slides, paper sheets, pins or other solid supports. These synthetic libraries can be screened for members displaying the desired activity by cleaving the peptide or peptide-containing molecule from the solid support and testing each member of the libraries in a biological assay. In some cases, the activity of the library members can be tested while they are still tethered to the solid support.

An advantage of these synthetic approaches is that a huge variety of diverse chemical structures can be used as building blocks in addition to the twenty natural amino acids. These alternative building blocks can include, but are not limited to, unnatural amino acids, peptoids, β- and γ-peptides, peptidomimetics, or amino acid-unrelated structures. These alternative scaffolds can be useful in conferring novel or improved conformational, binding or chemical/enzymatic stability properties to the peptide-based ligands not provided by naturally occurring amino acid structures. Compared to biological peptide libraries, a higher degree of structural and functional diversity is potentially accessible in libraries of synthetic peptide-based compounds and, in turn, this can facilitate the identification of compounds with the desired activity. However, sample handling and the need to spatially resolve each member of the library limits the number of molecules that can be prepared and screened in a productive and time-effective manner in the context of synthetic peptide libraries. In addition, unambiguous identification of the positive hits isolated during the screening step can be a laborious process faced with several pitfalls. This process has proven to be very challenging during the screening of large synthetic peptide libraries (>$10^5$).

While many peptides exhibit interesting biological activity, linear peptides do not generally represent suitable pharmacological agents as they are generally only poorly adsorbed, do not cross biological membranes readily, and are prone to proteolytic degradation. In addition, linear peptides fail to bind proteins that recognize discontinuous epitopes. The use of molecular constraints to restrict the conformational freedom of the molecule backbone can be used to overcome these limitations. In many cases, conformationally constrained peptides and peptide-containing molecules exhibit enhanced enzymatic stability, favorable membrane-crossing properties, and accessibility to structural analysis. Constraints that lock-in the active conformation of a peptide can also result in increased affinity due to the reduced conformational entropy loss upon binding to the receptor. Most therapeutically relevant peptides isolated from natural sources occur in cyclized form or contain intramolecular bridges that reduce the conformational flexibility of these molecules (e.g., immunosuppressant cyclosporin A, antitumor dolastatin 3 and diazonamide A, anti-HIV luzopeptin E2, and the antimicrobial vancomycin).

Various methods have been developed for preparing synthetic peptides and peptide-containing molecules in conformationally constrained configurations. Head-to-tail cyclic peptides can be prepared synthetically by cyclizing protected peptides in solution, by coupling the cyclization step with the removal of the cyclic chain from the solid support, or via 'on-resin' cyclization. Alternative cyclization strategies involve the use of native chemical ligation, photolabile auxiliary groups, or enzymes. Other strategies to restrict the conformational flexibility of linear peptides involve the formation of intramolecular bridges through the amino acid side chains, such as disulfide, lactam, oxime or alkenyl bridges.

While synthetic libraries of cyclic peptides can be prepared using these methods, the deconvolution of these libraries is faced with significant challenges. For example, Edman microsequencing of the active compounds isolated from the screening step cannot be carried out for cyclic peptides that lack free N-termini. Alternative methods (e.g., bead encoding/decoding with binary tags or MS/MS spectrometry) have been implemented to deconvolute libraries of cyclic peptides, but these procedures are complex, low-throughput, or they may not warrant unambiguous identification of the isolated compounds. Efficient and clean macrocyclization of peptide-based compounds can also be problematic. Altogether, these problems pose important constraints to the size of libraries of synthetic cyclic peptides that can be feasibly prepared and screened.

Methods for producing biological libraries of conformationally constrained peptides are also known in the art. For example, libraries of disulfide-constrained cyclic peptides have been prepared using phage display and fusing randomized polypeptide sequences flanked by two cysteines to a phage particle as described, e.g., in U.S. Pat. No. 7,235,626. Disulfide bridges are however potentially reactive and this chemical linkage is unstable under reducing conditions or in a reductive environment (e.g., inside a cell). Ribosomally produced peptides have also been constrained through the use of cysteine- or amine-reactive cross-linking agents. However, these methods rely on non-bioorthogonal reactions (e.g., cysteine-mediated alkylation or terminal/side-chain amine acylation) and thus bear the inherent risk of producing multiple undesired products via reaction of the cross-linking agents with multiple sites within the randomized peptide sequence or the carrier protein in a display system. Methods have also been described that allow for the preparation of head-to-tail cyclized peptides by using natural or engineered split inteins, as described in U.S. Pat. No. 7,354,756, U.S. Pat. No. 7,252,952, and U.S. Pat. No. 7,105,341. Similar to the biological libraries of linear peptides, however, the ribosomal nature of these compounds pose limitations to the chemical diversity of the ligand libraries generated through these methods. In addition, only head-to-tail cyclic ligand architectures can be obtained through these methods, which inherently limits the extent of structural diversity of the ligand libraries generated through these methods. Head-to-tail cyclic architectures also complicate the immobilization and isolation of these compounds for screening and identification purposes.

Citation or identification of any reference in Section 2, or in any other section of this application, shall not be considered an admission that such reference is available as prior art to the present invention.

3. SUMMARY OF THE INVENTION

Methods are provided for macrocyclic peptide-containing molecules with a hybrid peptidic/non-peptidic backbone (also referred to herein as macrocyclic peptide-containing molecules or macrocyclic organo-peptide hybrids or MOrPHs) that utilize synthetic molecules and genetically encoded polypeptides. These methods are based on the ability of a polypeptide which is fused via its C-terminus to the N-terminus of an intein and which incorporates a non-canonical amino acid residue carrying a bioorthogonal functional group (referred to as $FG_1$) to react with an appropriately functionalized synthetic molecule to produce a loop structure where the synthetic moiety is connected to a peptidic moiety through covalent bonds.

Methods are also provided for making macrocyclic peptide-containing molecules with a hybrid peptidic/non-peptidic backbone that utilize genetically encoded polypeptides. These methods are based on the ability of a polypeptide which is fused via its C-terminus to the N-terminus of an intein and which incorporates a non-canonical amino acid residue carrying a nucleophilic functional group (referred to as $FG_3$) to produce a loop structure where the side-chain of the non-canonical amino acid residue is connected to a C-terminus of the polypeptide through a covalent bond.

The methods disclosed herein can be used to produce macrocyclic molecules whose structure and composition can be varied by altering the genetically encoded amino acid sequence in the biosynthetic precursor or self-processing biosynthetic precursor (i.e., N-terminal sequence and target peptide sequence), the structure of the non-canonical amino acid in the biosynthetic precursor or self-processing biosynthetic precursor, and the structure of the synthetic precursor. These molecules can be screened to identify compounds that can modulate, inhibit or promote interactions between biomolecules, such as enzymes, proteins, and nucleic acids.

A method is provided for making a macrocyclic peptide-containing molecule, the method comprising the steps of:

a. providing a nucleic acid molecule encoding for a polypeptide of structure:

$$(AA)_m\text{-}Z\text{-}(AA)_n\text{-}INT \qquad (I)$$

or $$(AA)_m\text{-}Z\text{-}(AA)_n\text{-}INT\text{-}(AA)_p \qquad (II)$$

wherein:

i. $(AA)_m$ is a N-terminal amino acid or peptide sequence, ii. Z is an amino acid carrying a side-chain functional group $FG_1$, said $FG_1$ being a functional group selected from the group consisting of alkynyl (—C≡CR'), azido (—$N_3$), alkoxyamino (—$ONR'_2$), hydrazino (—$NR'NR'_2$), hydrazido (—$CONR'NR'_2$), carbonyl (—CO—R'), alkenyl (—CR'=$CR'_2$), phosphine (—$PR'_2$), thiol (—SR'), selenyl (—SeR'), tetrazole, tetrazine, aziridine, 2H-azirine, norbornadiene, boronaryl (Ar—$B(OH)_2$), and bromoaryl (Ar—Br), iodoaryl (Ar—I) groups, where R' is a hydrogen, alkyl or aryl group and Ar is an aryl group, iii. $(AA)_n$ is a target peptide sequence, iv. INT is an intein, and v. $(AA)_p$ is a peptide sequence fused to the C-terminus of the intein;

b. introducing the nucleic acid molecule into an expression system and expressing the nucleic acid molecule, thereby producing the polypeptide; and c. providing a chemical species of formula $$cFG_1\text{-}cFG_2 \quad (III)$$

or $$cFG_1\text{-}L\text{-}cFG_2 \quad (IV)$$

or a salt thereof, wherein:

i. $cFG_1$ is a functional group selected from the group consisting of alkynyl (—C≡CR'), azido (—N$_3$), alkoxyamino (—ONR'$_2$), hydrazino (—NR'NR'$_2$), hydrazido (—CONR'NR'$_2$), carbonyl (—CO—R'), alkenyl (—CR'=CR'$_2$), phosphine (—PR'$_2$), thiol (—SR'), selenyl (—SeR'), tetrazole, tetrazine, aziridine, dihydroazirine, norbornadiene, boronaryl (Ar—B(OH)$_2$), bromoaryl (Ar—Br), and iodoaryl (Ar—I) groups, where R' is a hydrogen, alkyl or aryl group and Ar is an aryl group, ii. $cFG_2$ is a functional group selected from the group consisting of alkoxyamino (—ONR'$_2$), hydrazino (—NR'NR'$_2$), hydrazido (—CONR'NR'$_2$), thiol (—SR'), selenyl (—SeR'), phenyl-methanethiol, phenyl-methaneselenol, aryl-methanethiol, aryl-methaneselenol, 2-amino-benzene-thiol, 2-amino-benzene-selenol, 2-amino-aryl-thiol, 2-amino-aryl-selenol, (2-aminophenyl)-methanethiol, (2-aminophenyl)-methaneselenol, (2-aminoaryl)-methanethiol, (2-aminoaryl)-methaneselenol, N-alkyl-(2-aminophenyl)-methanethiol, N-alkyl-(2-aminophenyl)-methaneselenol, N-alkyl-(2-aminoaryl)-methanethiol, N-alkyl-(2-aminoaryl)-methaneselenol, where R' is a hydrogen, alkyl or aryl group, and iii. L is linker group selected from the group consisting of aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, aryloxy groups; and d. contacting the polypeptide with the chemical species for a time and under conditions to allow a covalent bond-forming reaction between $FG_1$ and $cFG_1$ and a covalent bond-forming reaction between $FG_2$ and $cFG_2$ to occur, thereby producing the macrocyclic peptide-containing molecule.

In one embodiment, Z is an amino acid of structure:

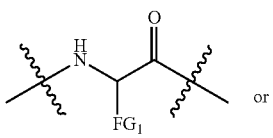

(V)

or

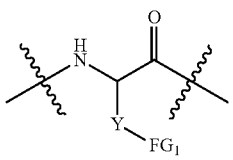

(VI)

wherein $FG_1$ is a functional group selected from the group consisting of alkynyl (—C≡CR'), azido (—N$_3$), alkoxyamino (—ONR'$_2$), hydrazino (—NR'NR'$_2$), hydrazido (—CONR'NR'$_2$), carbonyl (—CO—R'), alkenyl (—CR'=CR'$_2$), phosphine (—PR'$_2$), thiol (—SR'), selenyl (—SeR'), tetrazole, tetrazine, aziridine, 2H-azirine, norbornadiene, boronaryl (Ar—B(OH)$_2$), bromoaryl (Ar—Br), iodoaryl (Ar—I) groups, where R' is a hydrogen, alkyl or aryl group and Ar is an aryl group, and wherein Y is a linker group selected from the group consisting of aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, aryloxy groups.

In another embodiment, L is a linker group selected from the group consisting of $C_1$-$C_{24}$ alkyl, $C_1$-$C_{24}$ substituted alkyl, $C_1$-$C_{24}$ substituted heteroatom-containing alkyl, $C_1$-$C_{24}$ substituted heteroatom-containing alkyl, $C_2$-$C_{24}$ alkenyl, $C_2$-$C_{24}$ substituted alkenyl, $C_2$-$C_{24}$ substituted heteroatom-containing alkenyl, $C_2$-$C_{24}$ substituted heteroatom-containing alkenyl, $C_5$-$C_{24}$ aryl, $C_5$-$C_{24}$ substituted aryl, $C_5$-$C_{24}$ substituted heteroatom-containing aryl, $C_5$-$C_{24}$ substituted heteroatom-containing aryl, $C_1$-$C_{24}$ alkoxy, $C_5$-$C_{24}$ aryloxy groups.

In another embodiment, Y is a linker group selected from the group consisting of $C_1$-$C_{24}$ alkyl, $C_1$-$C_{24}$ substituted alkyl, $C_1$-$C_{24}$ substituted heteroatom-containing alkyl, $C_1$-$C_{24}$ substituted heteroatom-containing alkyl, $C_2$-$C_{24}$ alkenyl, $C_2$-$C_{24}$ substituted alkenyl, $C_2$-$C_{24}$ substituted heteroatom-containing alkenyl, $C_2$-$C_{24}$ substituted heteroatom-containing alkenyl, $C_5$-$C_{24}$ aryl, $C_5$-$C_{24}$ substituted aryl, $C_5$-$C_{24}$ substituted heteroatom-containing aryl, $C_5$-$C_{24}$ substituted heteroatom-containing aryl, $C_1$-$C_{24}$ alkoxy, and $C_5$-$C_{24}$ aryloxy groups.

In another embodiment, amino acid Z is selected from the group consisting of para-acetyl-phenylalanine, O-propargyl-tyrosine, 3-fluoro-4-acetyl-phenylalanine, meta-acetyl-phenylalanine, para-butyl-1,3-dione-phenylalanine, O-allyl-tyrosine, para-azido-phenylalanine, para-borono-phenylalanine, para-bromo-phenylalanine, para-iodo-phenylalanine, 3-iodo-tyrosine, para-benzoyl-phenylalanine, para-benzoyl-phenylalanine, ε-N-allyloxycarbonyl-lysine, ε-N-propargyloxycarbonyl-lysine, ε-N-azidoethyloxycarbonyl-lysine, and ε-N-(o-azido-benzyl)-oxycarbonyl-lysine.

In another embodiment, the codon encoding for Z is an amber stop codon TAG, an ochre stop codon TAA, an opal stop codon TGA, or a four base codon.

In another embodiment, the intein is selected from the group consisting of a naturally occurring intein, an engineered variant of a naturally occurring intein, a fusion of the N-terminal and C-terminal fragments of a naturally occurring split intein and a fusion of the N-terminal and C-terminal fragments of an artificial split intein.

In another embodiment, the intein is selected from the group consisting of GyrA, DnaB, RecA, RIR1, Vma, DnaE inteins.

In another embodiment, the intein is selected from the group consisting of Mxe GyrA (SEQ ID NO:1), Ssp eDnaB (SEQ ID NO:2), Hsp-NRC1 CDC21 (SEQ ID NO:3), Ceu ClpP (SEQ ID NO:4), Tag Pol-1 (SEQ ID NO:5), Tfu Pol-1 (SEQ ID NO:6), Tko Pol-1 (SEQ ID NO:7), Psp-GBD Pol (SEQ ID NO:8), Tag Pol-2 (SEQ ID NO:9), Thy Pol-1 (SEQ ID NO:10), Tko Pol-2 (SEQ ID NO:11), Tli Pol-1 (SEQ ID NO:12), Tma Pol (SEQ ID NO:13), Tsp-GE8 Pol-1 (SEQ ID NO:14), Tthi Pol (SEQ ID NO:15), Tag Pol-3 (SEQ ID NO:16), Tfu Pol-2 (SEQ ID NO:17), Thy Pol-2 (SEQ ID NO:18), Tli Pol-2 (SEQ ID NO:19), Tsp-GE8 Pol-2 (SEQ ID NO:20), Pab Pol-II (SEQ ID NO:21), Mtu-CDC1551 DnaB (SEQ ID NO:22), Mtu-H37Rv DnaB (SEQ ID NO:23), Rma DnaB (SEQ ID NO:24), Ter DnaE-1 (SEQ ID NO:25), Ssp GyrB (SEQ ID NO:26), Mfl GyrA (SEQ ID NO:27), Mgo GyrA (SEQ ID NO:28), Mkas GyrA (SEQ ID NO:29), Mle-TN GyrA (SEQ ID NO:30), Mma GyrA (SEQ ID NO:31), Ssp DnaX (SEQ ID NO:32), Pab Lon (SEQ ID NO:33), Mja PEP (SEQ ID NO:34), Afu-FRR0163 PRP8 (SEQ ID NO:35), Ani-FGSCA4 PRP8 (SEQ ID NO:36), Cne-A PRP8 (SEQ ID NO:37), Hca PRP8 (SEQ ID NO:38), Pch PRP8 (SEQ ID NO:39), Pex PRP8 (SEQ ID NO:40), Pvu PRP8

(SEQ ID NO:41), Mtu-H37Rv RecA (SEQ ID NO:42), Mtu-So93 RecA (SEQ ID NO:43), Mfl RecA (SEQ ID NO:44), Mle-TN RecA (SEQ ID NO:45), Nsp-PCC7120 RIR1 (SEQ ID NO:120), Ter RIR1-1 (SEQ ID NO:46), Pab RIR1-1 (SEQ ID NO:47), Pfu RIR1-1 (SEQ ID NO:48), Chy RIR1 (SEQ ID NO:49), Mth RIR1 (SEQ ID NO:50), Pab RIR1-3 (SEQ ID NO:51), Pfu RIR1-2 (SEQ ID NO:52), Ter RIR1-2 (SEQ ID NO:53), Ter RIR1-4 (SEQ ID NO:54), CIV RIR1 (SEQ ID NO:55), Ctr VMA (SEQ ID NO:56), Sce VMA (SEQ ID NO:57), Tac-ATCC25905 VMA (SEQ ID NO:58), Ssp DnaB (SEQ ID NO:59), and variants thereof.

In another embodiment, the intein is a fusion product of a split intein selected from the group consisting of Ssp DnaE (SEQ ID NO:60-SEQ ID NO:61), Neq Pol (SEQ ID NO:62-SEQ ID NO:63), Asp DnaE (SEQ ID NO:64-SEQ ID NO:65), Npu-PCC73102 DnaE (SEQ ID NO:66-SEQ ID NO:67), Nsp-PCC7120 DnaE (SEQ ID NO:68-SEQ ID NO:69), Oli DnaE (SEQ ID NO:70-SEQ ID NO:71), Ssp-PCC7002 DnaE (SEQ ID NO:72-SEQ ID NO:73), Tvu DnaE (SEQ ID NO:74-SEQ ID NO:75), and variants thereof.

In another embodiment, the polypeptide $(AA)_m$ comprises an affinity tag, a DNA-binding protein, a protein-binding protein, or a fluorescent protein.

In another embodiment, the affinity tag is selected from the group consisting of polyarginine tag, polyhistidine tag, Avi-Tag (SEQ ID NO:89), FLAG tag (SEQ ID NO:90), Strep-tag II (SEQ ID NO:91), c-myc tag (SEQ ID NO:92), S tag (SEQ ID NO:93), calmodulin-binding peptide (SEQ ID NO:94), streptavidin-binding peptide (SEQ ID NO:95), chitin-binding domain (SEQ ID NO:110), glutathione S-transferase, and maltose-binding protein (MBP).

In another embodiment, the polypeptide $(AA)_m$ comprises a protein selected from the group consisting of M13 phage protein pVI (SEQ ID NO:76), T7 phage protein 10A (SEQ ID NO:77), T7 phage protein 10B (SEQ ID NO:78), *E. coli* NlpA signal peptide sequence (SEQ ID NO:79), *E. coli* OmpC (SEQ ID NO:80), *E. coli* FadL (SEQ ID NO:81), *E. coli* Lpp-OmpA (SEQ ID NO:82), *E. coli* PgsA (SEQ ID NO:83), *E. coli* EaeA (SEQ ID NO:84), *S. cerevisiae* protein Aga2p (SEQ ID NO:85), *S. cerevisiae* Flo1p (SEQ ID NO:121), human NF-κB p50 protein (SEQ ID NO:86), green fluorescent protein, and variants thereof.

In another embodiment, the polypeptide $(AA)_n$ has a sequence of 3 to 20 amino acids.

In another embodiment, the polypeptide $(AA)_p$ comprises an affinity tag.

In another embodiment, $FG_1$ is a terminal alkyne (—C≡CH), $cFG_1$ is an azido group (—N$_3$), and $cFG_2$ is a hydrazido group (—CONHNH$_2$).

In another embodiment, $FG_1$ is a carbonyl (—CO—), $cFG_1$ is an oxyamine (—ONH$_2$), and $cFG_2$ is selected from the group consisting of aryl-methanethiol group, (2-amino-aryl)-methanethiol group, and N-substituted (2-amino-aryl)-methanethiol group.

In another embodiment, the expression system is selected from the group consisting of a prokaryotic cell, a eukaryotic cell, and a cell-free expression system.

In another embodiment, the prokaryotic cell is *Escherichia coli*.

In another embodiment, the eukaryotic cell is a mammalian, insect or plant cell.

In another embodiment, the polypeptide $(AA)_n$ or a portion thereof is genetically randomized so that a plurality of macrocyclic peptide-containing molecules is obtained upon reaction with a chemical species of formula (III) or (IV).

In another embodiment, the polypeptide $(AA)_m$ or a portion thereof is genetically randomized so that a plurality of macrocyclic peptide-containing molecules is obtained upon reaction with a chemical species of formula (III) or (IV).

A method is also provided for making a macrocyclic peptide-containing molecule, the method comprising the steps of:

a. providing a nucleic acid molecule encoding for a polypeptide of structure:

$$(AA)_m\text{-J-}(AA)_n\text{-INT} \tag{VII}$$

or $$(AA)_m\text{-J-}(AA)_n\text{-INT-}(AA)_p \tag{VIII}$$

wherein:
i. $(AA)_m$ is a N-terminal amino acid or peptide sequence,
ii. J is an amino acid carrying a side-chain functional group $FG_3$, said $FG_3$ being a functional group selected from the group consisting of alkoxyamino (—ONR'$_2$), hydrazino (—NR'NR'$_2$), hydrazido (—CONR'NR'$_2$), thiol (—SR'), selenyl (—SeR'), phenyl-methanethiol, phenyl-methaneselenol, aryl-methanethiol, aryl-methaneselenol, 2-amino-benzene-thiol, 2-amino-benzene-selenol, 2-amino-aryl-thiol, 2-amino-aryl-selenol, (2-aminophenyl)-methanethiol, (2-aminophenyl)-methaneselenol, (2-aminoaryl)-methanethiol, (2-aminoaryl)-methaneselenol, N-alkyl-(2-aminophenyl)-methanethiol, N-alkyl-(2-aminophenyl)-methaneselenol, N-alkyl-(2-aminoaryl)-methanethiol, N-alkyl-(2-aminoaryl)-methaneselenol, where R' is a hydrogen, alkyl or aryl group,
iii. $(AA)_n$ is a target peptide sequence,
iv. INT is an intein, and
v. $(AA)_p$ is a peptide sequence fused to the C-terminus of the intein;

b. introducing the nucleic acid molecule into an expression system and expressing the nucleic acid molecule in the expression system, thereby producing the polypeptide; and
c. allowing the polypeptide self-processing biosynthetic precursor to undergo cyclization, thereby producing the macrocyclic peptide-containing molecule.

In another embodiment, J is an amino acid of structure:

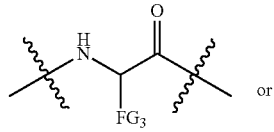

(IX)

or

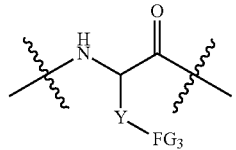

(X)

wherein $FG_3$ is a functional group selected from the group consisting of alkoxyamino (—ONR'$_2$), hydrazino (—NR'NR'$_2$), hydrazido (—CONR'NR'$_2$), thiol (—SR'), selenyl (—SeR'), phenyl-methanethiol, phenyl-methaneselenol, aryl-methanethiol, aryl-methaneselenol, 2-amino-benzene-thiol, 2-amino-benzene-selenol, 2-amino-aryl-thiol, 2-amino-aryl-selenol, (2-aminophenyl)-methanethiol, (2-aminophenyl)-methaneselenol, (2-aminoaryl)-methanethiol, (2-aminoaryl)-methaneselenol, N-alkyl-(2-aminophenyl)-methanethiol, N-alkyl-(2-aminophenyl)-methaneselenol, N-alkyl-(2-aminoaryl)-methanethiol, N-alkyl-(2-aminoaryl)-methaneselenol, where R' is a hydrogen, alkyl or aryl group, and wherein Y is a linker group selected from the group consisting of aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, aryloxy groups.

In another embodiment, Y is a linker group selected from the group consisting of $C_1$-$C_{24}$ alkyl, $C_1$-$C_{24}$ substituted alkyl, $C_1$-$C_{24}$ substituted heteroatom-containing alkyl, $C_1$-$C_{24}$ substituted heteroatom-containing alkyl, $C_2$-$C_{24}$ alkenyl, $C_2$-$C_{24}$ substituted alkenyl, $C_2$-$C_{24}$ substituted heteroatom-containing alkenyl, $C_2$-$C_{24}$ substituted heteroatom-containing alkenyl, $C_5$-$C_{24}$ aryl, $C_5$-$C_{24}$ substituted aryl, $C_5$-$C_{24}$ substituted heteroatom-containing aryl, $C_5$-$C_{24}$ substituted heteroatom-containing aryl, $C_1$-$C_{24}$ alkoxy, $C_5$-$C_{24}$ aryloxy groups.

In another embodiment, the amino acid J is 3-amino-4-mercaptomethyl-phenylalanine.

In another embodiment, the codon encoding for J is an amber stop codon TAG, an ochre stop codon TAA, an opal stop codon TGA, or a four base codon.

In another embodiment, the intein is selected from the group consisting of a naturally occurring intein, an engineered variant of a naturally occurring intein, a fusion of the N-terminal and C-terminal fragments of a naturally occurring split intein and a fusion of the N-terminal and C-terminal fragments of an artificial split intein.

In another embodiment, the intein is selected from the group consisting of GyrA, DnaB, RecA, RIR1, Vma, and DnaE inteins.

In another embodiment, the intein is selected from the group consisting of Mxe GyrA (SEQ ID NO:1), Ssp eDnaB (SEQ ID NO:2), Hsp-NRC1 CDC21 (SEQ ID NO:3), Ceu ClpP (SEQ ID NO:4), Tag Pol-1 (SEQ ID NO:5), Tfu Pol-1 (SEQ ID NO:6), Tko Pol-1 (SEQ ID NO:7), Psp-GBD Pol (SEQ ID NO:8), Tag Pol-2 (SEQ ID NO:9), Thy Pol-1 (SEQ ID NO:10), Tko Pol-2 (SEQ ID NO:11), Tli Pol-1 (SEQ ID NO:12), Tma Pol (SEQ ID NO:13), Tsp-GE8 Pol-1 (SEQ ID NO:14), Tthi Pol (SEQ ID NO:15), Tag Pol-3 (SEQ ID NO:16), Tfu Pol-2 (SEQ ID NO:17), Thy Pol-2 (SEQ ID NO:18), Tli Pol-2 (SEQ ID NO:19), Tsp-GE8 Pol-2 (SEQ ID NO:20), Pab Pol-II (SEQ ID NO:21), Mtu-CDC1551 DnaB (SEQ ID NO:22), Mtu-H37Rv DnaB (SEQ ID NO:23), Rma DnaB (SEQ ID NO:24), Ter DnaE-1 (SEQ ID NO:25), Ssp GyrB (SEQ ID NO:26), Mfl GyrA (SEQ ID NO:27), Mgo GyrA (SEQ ID NO:28), Mkas GyrA (SEQ ID NO:29), Mle-TN GyrA (SEQ ID NO:30), Mma GyrA (SEQ ID NO:31), Ssp DnaX (SEQ ID NO:32), Pab Lon (SEQ ID NO:33), Mja PEP (SEQ ID NO:34), Afu-FRR0163 PRP8 (SEQ ID NO:35), Ani-FGSCA4 PRP8 (SEQ ID NO:36), Cne-A PRP8 (SEQ ID NO:37), Hca PRP8 (SEQ ID NO:38), Pch PRP8 (SEQ ID NO:39), Pex PRP8 (SEQ ID NO:40), Pvu PRP8 (SEQ ID NO:41), Mtu-H37Rv RecA (SEQ ID NO:42), Mtu-So93 RecA (SEQ ID NO:43), Mfl RecA (SEQ ID NO:44), Mle-TN RecA (SEQ ID NO:45), Nsp-PCC7120 RIR1 (SEQ ID NO:120), Ter RIR1-1 (SEQ ID NO:46), Pab RIR1-1 (SEQ ID NO:47), Pfu RIR1-1 (SEQ ID NO:48), Chy RIR1 (SEQ ID NO:49), Mth RIR1 (SEQ ID NO:50), Pab RIR1-3 (SEQ ID NO:51), Pfu RIR1-2 (SEQ ID NO:52), Ter RIR1-2 (SEQ ID NO:53), Ter RIR1-4 (SEQ ID NO:54), CIV RIR1 (SEQ ID NO:55), Ctr VMA (SEQ ID NO:56), Sce VMA (SEQ ID NO:57), Tac-ATCC25905 VMA (SEQ ID NO:58), Ssp DnaB (SEQ ID NO:59), and variants thereof.

In another embodiment, the intein is a fusion product of a split intein selected from the group consisting of Ssp DnaE (SEQ ID NO:60-SEQ ID NO:61), Neq Pol (SEQ ID NO:62-SEQ ID NO:63), Asp DnaE (SEQ ID NO:64-SEQ ID NO:65), Npu-PCC73102 DnaE (SEQ ID NO:66-SEQ ID NO:67), Nsp-PCC7120 DnaE (SEQ ID NO:68-SEQ ID NO:69), Oli DnaE (SEQ ID NO:70-SEQ ID NO:71), Ssp-PCC7002 DnaE (SEQ ID NO:72-SEQ ID NO:73), Tvu DnaE (SEQ ID NO:74-SEQ ID NO:75), and variants thereof.

In another embodiment, the polypeptide $(AA)_m$ comprises an affinity tag, a DNA-binding protein, a protein-binding protein, or a fluorescent protein.

In another embodiment, the affinity tag is selected from the group consisting of polyarginine tag (SEQ ID NO:87), polyhistidine tag (SEQ ID NO:88), Avi-Tag (SEQ ID NO:89), FLAG tag (SEQ ID NO:90), Strep-tag II (SEQ ID NO:91), c-myc tag (SEQ ID NO:92), S tag (SEQ ID NO:93), calmodulin-binding peptide (SEQ ID NO:94), streptavidin-binding peptide (SEQ ID NO:95), chitin-binding domain (SEQ ID NO:110), glutathione S-transferase, and maltose-binding protein (MBP).

In another embodiment, the polypeptide $(AA)_m$ comprises a protein selected from the group consisting of M13 phage protein pVI (SEQ ID NO:76), T7 phage protein 10A (SEQ ID NO:77), T7 phage protein 10B (SEQ ID NO:78), *E. coli* NlpA (SEQ ID NO:79), *E. coli* OmpC (SEQ ID NO:80), *E. coli* FadL (SEQ ID NO:81), *E. coli* Lpp-OmpA (SEQ ID NO:82), *E. coli* PgsA (SEQ ID NO:83), *E. coli* EaeA (SEQ ID NO:84), *S. cerevisiae* Aga2p (SEQ ID NO:85), *S. cerevisiae* Flo1p (SEQ ID NO:121), human NF-κB p50 (SEQ ID NO:86), green fluorescent protein, and variants thereof.

In another embodiment, the polypeptide $(AA)_n$ has a sequence of 3 to 20 amino acids.

In another embodiment, polypeptide $(AA)_p$ comprises an affinity tag.

In another embodiment, the expression system is selected from the group consisting of a prokaryotic cell, a eukaryotic cell, and a cell-free expression system.

In another embodiment, the prokaryotic cell is *Escherichia coli*.

In another embodiment, the eukaryotic cell is a mammalian, insect or plant cell.

In another embodiment, polypeptide $(AA)_n$ or a portion thereof is genetically randomized so that a plurality of macrocyclic peptide-containing molecules is obtained upon cyclization of the polypeptide of formula (VII) or (VIII).

In another embodiment, the polypeptide $(AA)_m$ or a portion thereof is genetically randomized so that a plurality of macrocyclic peptide-containing molecules is obtained upon cyclization of the polypeptide of formula (VII) or (VIII).

A recombinant host cell is also provided comprising:
a. an expression system; and
b. a nucleic acid molecule encoding for a polypeptide of structure:

$$(AA)_m\text{-}Z\text{-}(AA)_n\text{-INT} \quad (I)$$

or $$(AA)_m\text{-}Z\text{-}(AA)_n\text{-INT-}(AA)_p \quad (II)$$

wherein:
i. $(AA)_m$ is a N-terminal amino acid or peptide sequence,
ii. Z is an amino acid carrying a side-chain functional group $FG_1$, said $FG_1$ being a functional group selected from the group consisting of alkynyl (—C≡CR'), azido (—N$_3$), alkoxyamino (—ONR'$_2$), hydrazino (—NR'NR'$_2$), hydrazido (—CONR'NR'$_2$), carbonyl (—CO—R'), alkenyl (—CR'═CR'$_2$), phosphine (—PR'$_2$), thiol (—SR'), selenyl (—SeR'), tetrazole, tetrazine, aziridine, 2H-azirine, norbornadiene, boronaryl (Ar—B(OH)$_2$), and bromoaryl (Ar—Br), iodoaryl (Ar—I) groups, where R' is a hydrogen, alkyl or aryl group and Ar is an aryl group, iii. (AA)$_n$ is a target peptide sequence,
    iv. INT is an intein, and
    v. (AA)$_p$ is a peptide sequence fused to the C-terminus of the intein.

In another embodiment, the expression system expresses the polypeptide when expressed according to the methods provided herein.

In another embodiment, the cell comprises a macrocyclic peptide-containing molecule produced according to the methods provided herein.

A recombinant host cell is also provided comprising:
a. an expression system, and
b. a nucleic acid molecule encoding for a polypeptide of structure:

    (AA)$_m$-J-(AA)$_n$-INT    (VII)

or

    (AA)$_m$-J-(AA)$_n$-INT-(AA)$_p$    (VIII)

wherein:
    i. (AA)$_m$ is a N-terminal amino acid or peptide sequence,
    ii. J is an amino acid carrying a side-chain functional group FG$_3$, said FG$_3$ being a functional group selected from the group consisting of alkoxyamino (—ONR'$_2$), hydrazino (—NR'NR'$_2$), hydrazido (—CONR'NR'$_2$), thiol (—SR'), selenyl (—SeR'), phenyl-methanethiol, phenyl-methaneselenol, aryl-methanethiol, aryl-methaneselenol, 2-amino-benzene-thiol, 2-amino-benzene-selenol, 2-amino-aryl-thiol, 2-amino-aryl-selenol, (2-aminophenyl)-methanethiol, (2-aminophenyl)-methaneselenol, (2-aminoaryl)-methanethiol, (2-aminoaryl)-methaneselenol, N-alkyl-(2-aminophenyl)-methanethiol, N-alkyl-(2-aminophenyl)-methaneselenol, N-alkyl-(2-aminoaryl)-methanethiol, N-alkyl-(2-aminoaryl)-methaneselenol, where R' is a hydrogen, alkyl or aryl group,
    iii. (AA)$_n$ is a target peptide sequence,
    iv. INT is an intein, and
    v. (AA)$_p$ is a peptide sequence fused to the C-terminus of the intein.

In another embodiment, the expression system expresses the polypeptide when expressed according to the methods provided herein.

In another embodiment, the cell comprises a macrocyclic peptide-containing molecule produced according to the methods provided herein.

A compound is also provided of the formula

    (AA)$_m$-J-(AA)$_n$-INT    (VII)

or

    (AA)$_m$-J-(AA)$_n$-INT-(AA)$_p$    (VIII)

wherein:
    i. (AA)$_m$ is a N-terminal amino acid or peptide sequence,
    ii. J is an amino acid of structure:

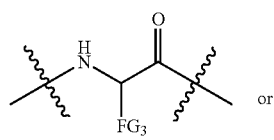
    (IX)

or

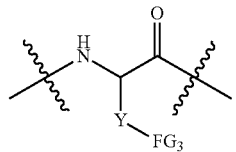
    (X)

iii. FG$_3$ is a functional group selected from the group consisting of alkoxyamino (—ONR'$_2$), hydrazino (—NR'NR'$_2$), hydrazido (—CONR'NR'$_2$), thiol (—SR'), selenyl (—SeR'), phenyl-methanethiol, phenyl-methaneselenol, aryl-methanethiol, aryl-methaneselenol, 2-amino-benzene-thiol, 2-amino-benzene-selenol, 2-amino-aryl-thiol, 2-amino-aryl-selenol, (2-aminophenyl)-methanethiol, (2-aminophenyl)-methaneselenol, (2-aminoaryl)-methanethiol, (2-aminoaryl)-methaneselenol, N-alkyl-(2-aminophenyl)-methanethiol, N-alkyl-(2-aminophenyl)-methaneselenol, N-alkyl-(2-aminoaryl)-methanethiol, N-alkyl-(2-aminoaryl)-methaneselenol, where R' is a hydrogen, alkyl or aryl group,
    iv. Y is a linker group selected from the group consisting of aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, aryloxy groups,
    v. (AA)$_n$ is a target peptide sequence,
    vi. INT is an intein, and
    v. (AA)$_p$ is a peptide sequence fused to the C-terminus of the intein.

In one embodiment, Y is a linker group selected from the group consisting of C$_1$-C$_{24}$ alkyl, C$_1$-C$_{24}$ substituted alkyl, C$_1$-C$_{24}$ substituted heteroatom-containing alkyl, C$_1$-C$_{24}$ substituted heteroatom-containing alkyl, C$_2$-C$_{24}$ alkenyl, C$_2$-C$_{24}$ substituted alkenyl, C$_2$-C$_{24}$ substituted heteroatom-containing alkenyl, C$_2$-C$_{24}$ substituted heteroatom-containing alkenyl, C$_5$-C$_{24}$ aryl, C$_5$-C$_{24}$ substituted aryl, C$_5$-C$_{24}$ substituted heteroatom-containing aryl, C$_5$-C$_{24}$ substituted heteroatom-containing aryl, C$_1$-C$_{24}$ alkoxy, C$_5$-C$_{24}$ aryloxy groups.

In another embodiment, the amino acid J is 3-amino-4-mercaptomethyl-phenylalanine:

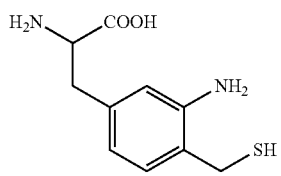
    (XI)

or a salt thereof.

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated or enlarged to facilitate an understanding of the invention.

Figure 1:
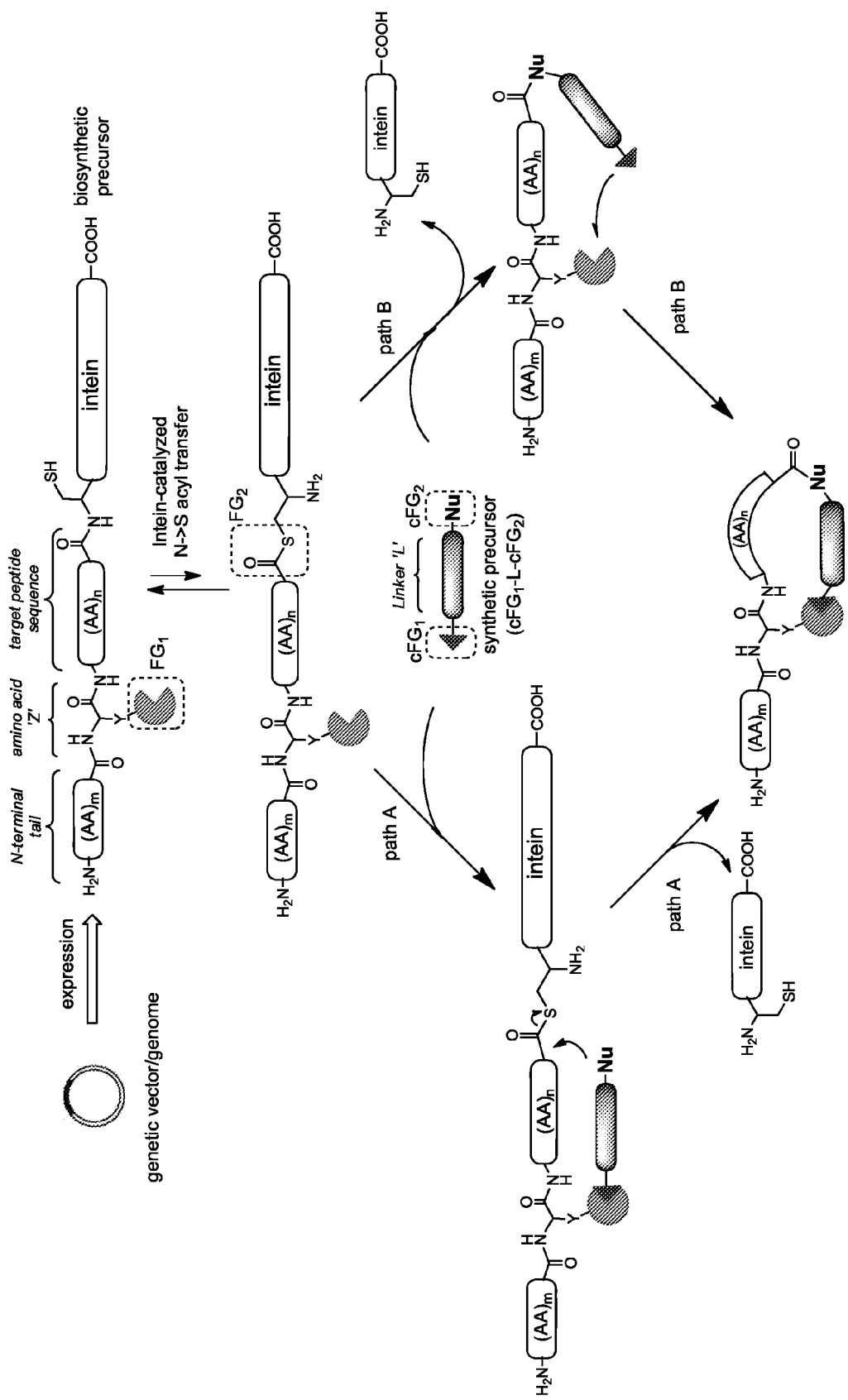

FIG. 1. Schematic representation of a general method for making a macrocyclic peptide-containing molecule within the invention, such method comprising a reaction between a genetically-encoded biosynthetic precursor and a synthetic precursor. The two alternative reaction pathways by which the macrocyclic peptide-containing molecule can be made are also schematically illustrated. Nu=nucleophilic group. AA: amino acid.

Figure 2:
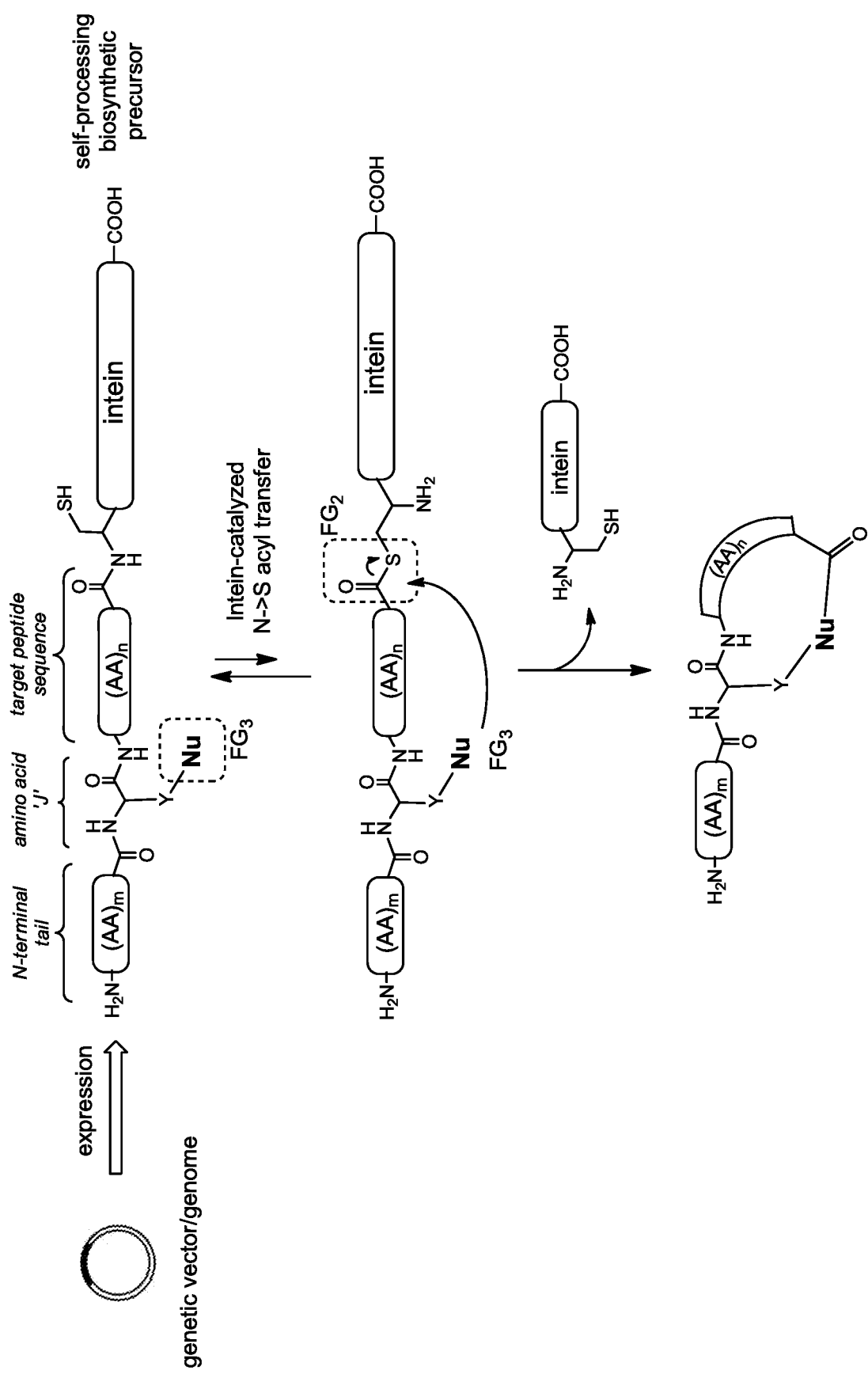

FIG. 2. Schematic representation of a general method for making a macrocyclic peptide-containing molecule within the invention, such method comprising a cyclization reaction of a genetically-encoded self-processing biosynthetic precursor. Nu=nucleophilic group. AA: amino acid.

Figure 3:
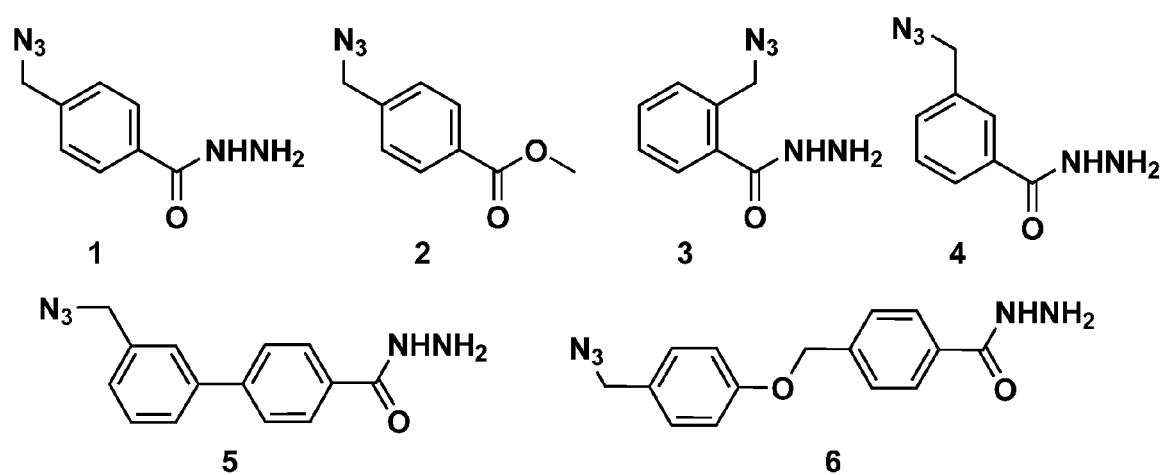

FIG. 3. Structures of bifunctional (azide/hydrazide) synthetic precursors 1, 3-6.

Figure 4:
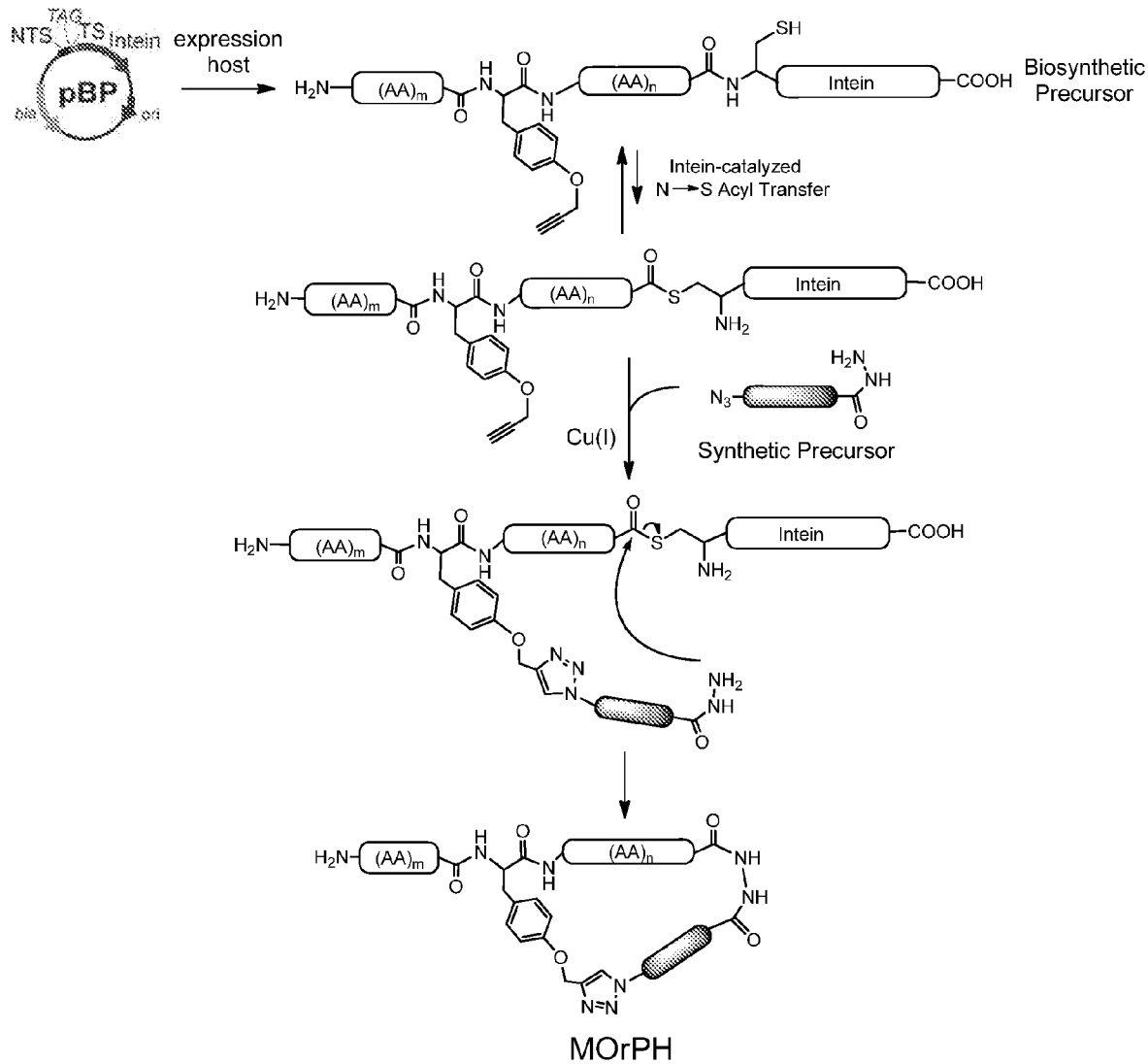

FIG. 4. Schematic representation of another embodiment of the general method of FIG. 1 where the macrocyclic organo-peptide hybrids (MOrPHs) are produced via a tandem Huisgen 1,3-dipolar cycloaddition/hydrazide-induced splicing reaction. In the plasmid vector (pBP): NTS=N-terminal sequence, TAG=amber stop codon, TS=target sequence.

FIGS. 5a-d. Characterization of MOrPHs prepared via Huisgen 1,3-dipolar cycloaddition/hydrazide-induced splicing macrocyclization method. (a) MALDI-TOF spectrum of MG6 after purification (left), after coupling to 1 (middle), and after overnight incubation (right). The peaks corresponding to MG6, MG6-1 adduct, and spliced GyrA intein are indicated along with the observed (o) and calculated (c) masses (m/z [M+H]$^+$). NaAsc=sodium ascorbate. TCEP=tris(2-carboxyethyl)phosphine. (b) Extracted ion chromatogram for m/z corresponding to the macrocycle (shaded area) as obtained from LC-MS analysis of the reaction mixture after 16 hours. The 'GyrA' peak corresponds to unrelated multi-charged ions from spliced GyrA intein. (c) MS/MS spectrum of the macrocycle (precursor ion: m/z 1016.3) and of the acyclic product (precursor ion: m/z 1034.3) with assignment of the fragment ions for the latter. (d) Characterization of the reactions between synthetic precursors 1, 3, 4, 5, and 6 with biosynthetic precursors (MG constructs) containing target sequences of variable length. Upper graph: fraction of macrocyclic product among small MW products as estimated from LC-MS extracted ion chromatograms. Lower graph: percentage of splicing of the BP-SP adducts after overnight incubation. MS/MS spectra for the MOrPHs generated in these reactions are provided in FIGS. 6a-c and 8a-f.

Figure 6A:
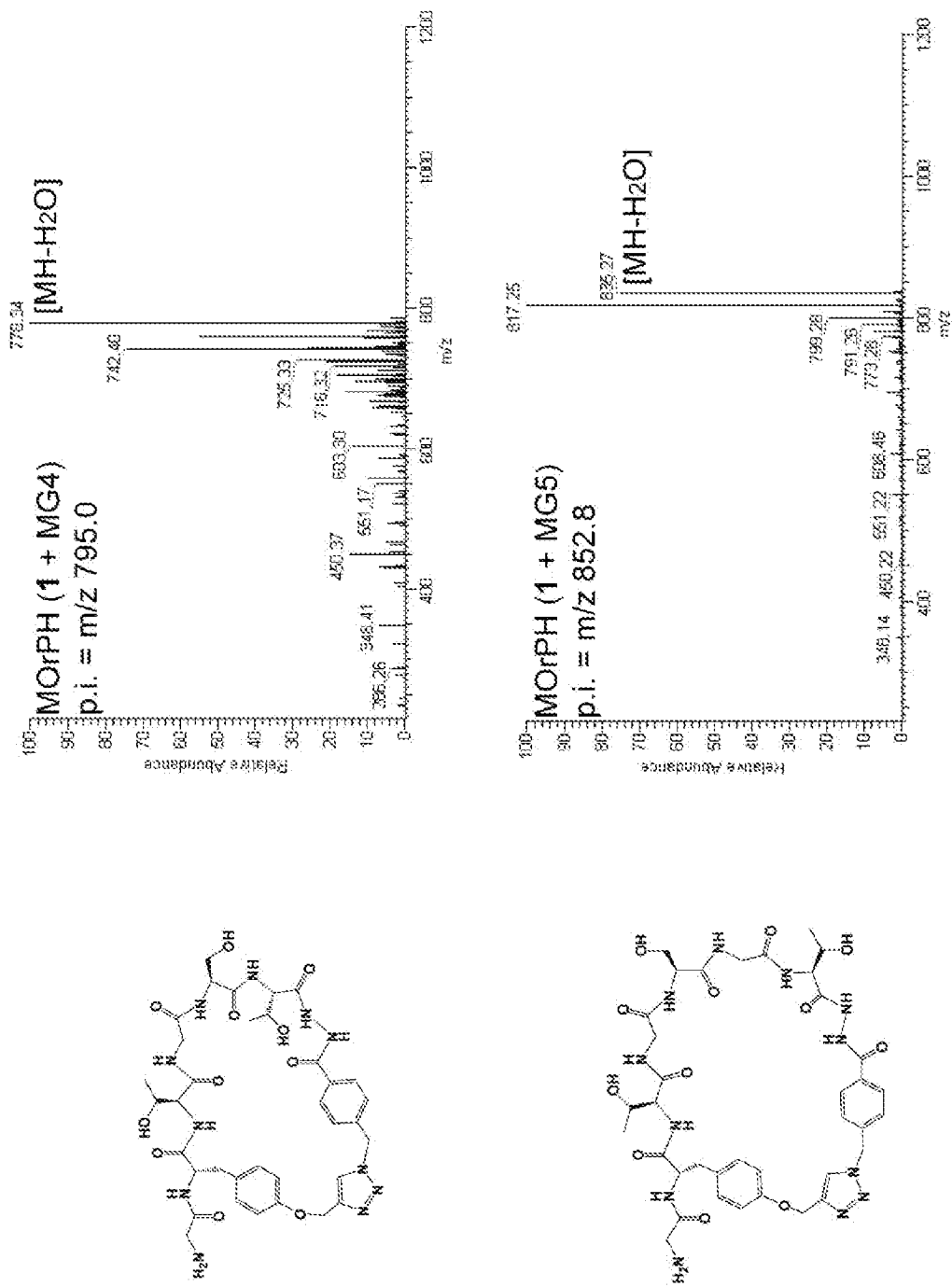
Figure 6B:
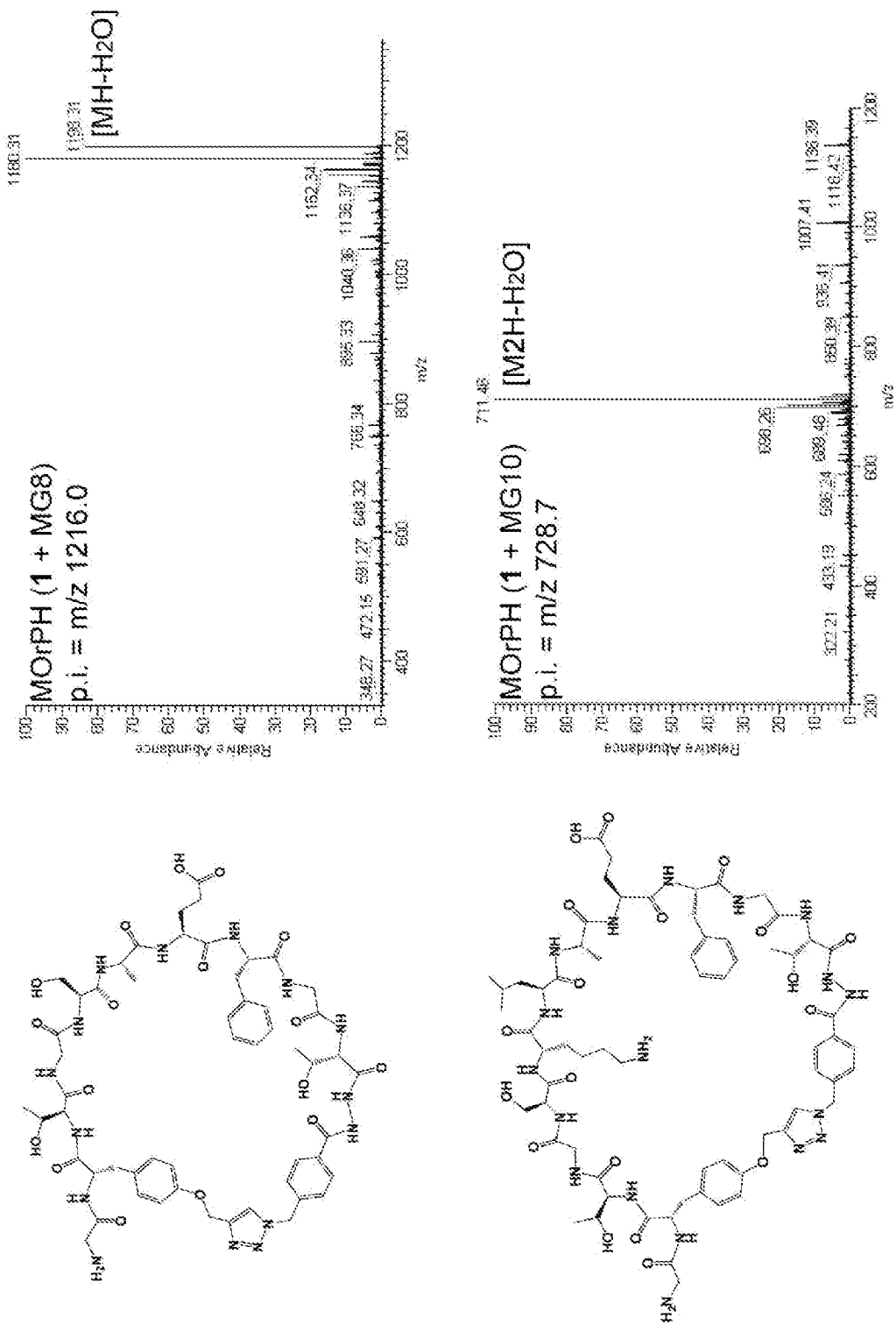

FIGS. 6a-c. MS/MS spectra and chemical structures of the MOrPHs obtained from the reaction of synthetic precursor 1 with biosynthetic precursors MG4, MG5, MG6, MG8, MG10, and MG12. The m/z of the precursor ion (p.i.) is indicated.

Figure 7:
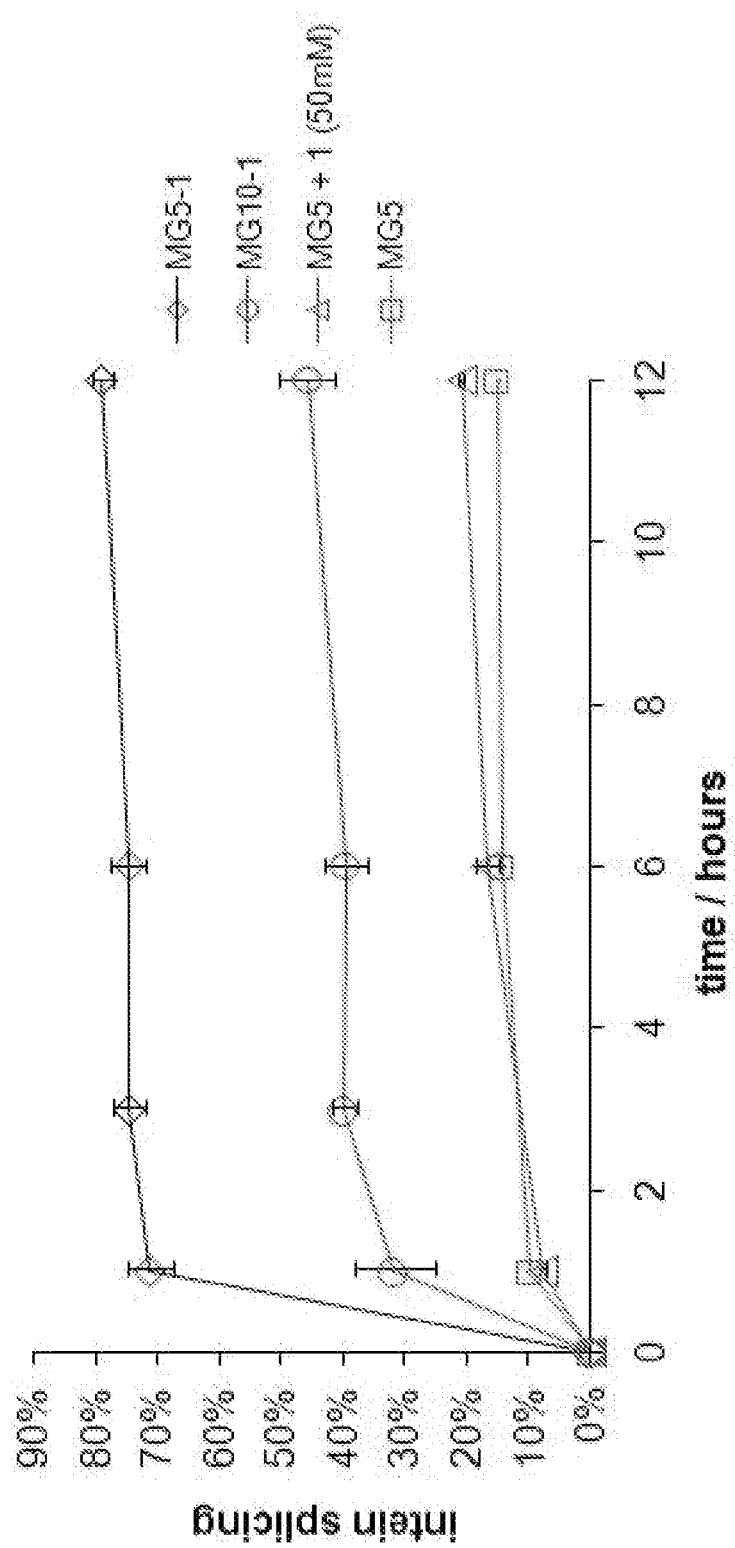
Figure 8A:
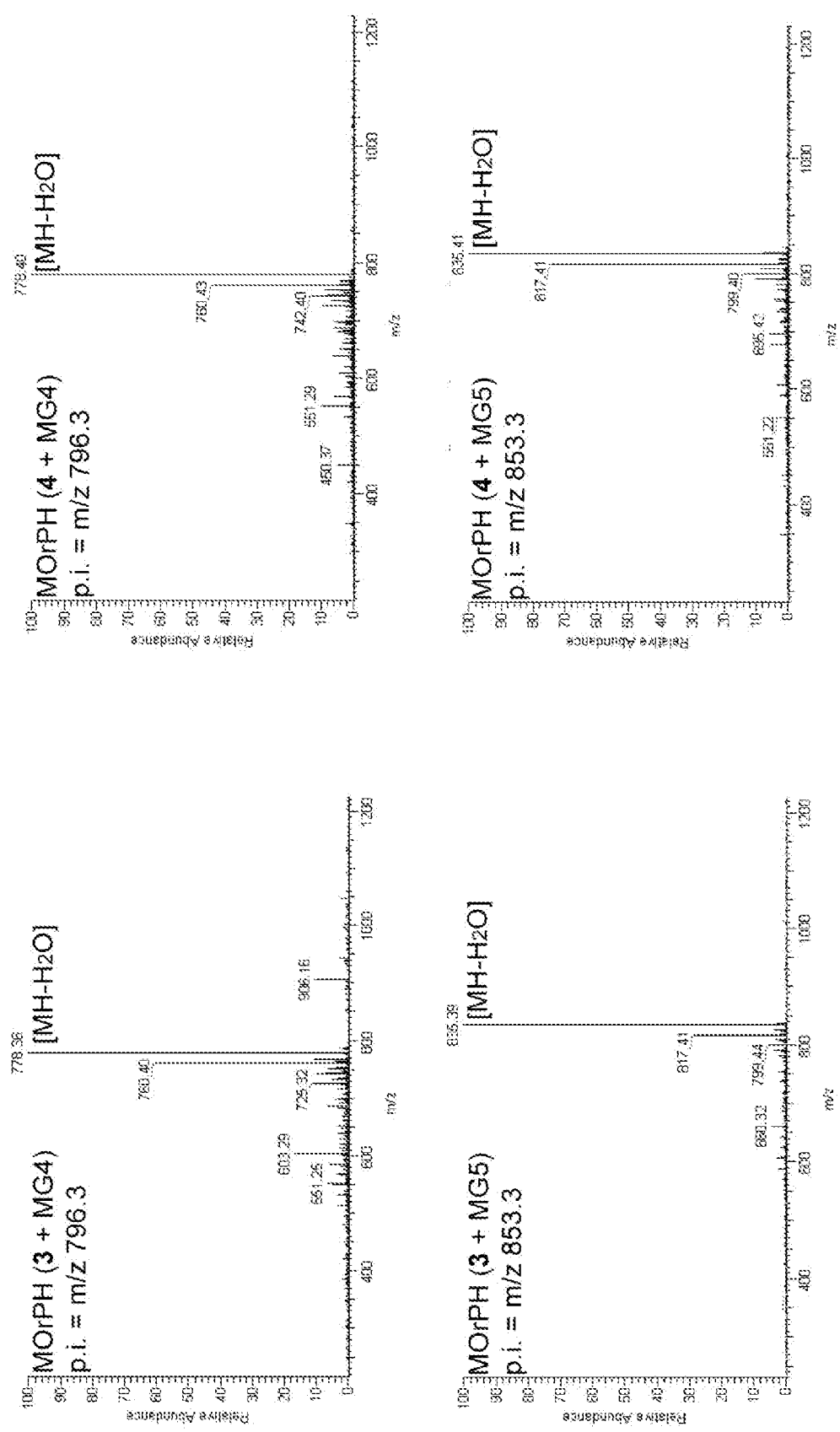
Figure 8B:
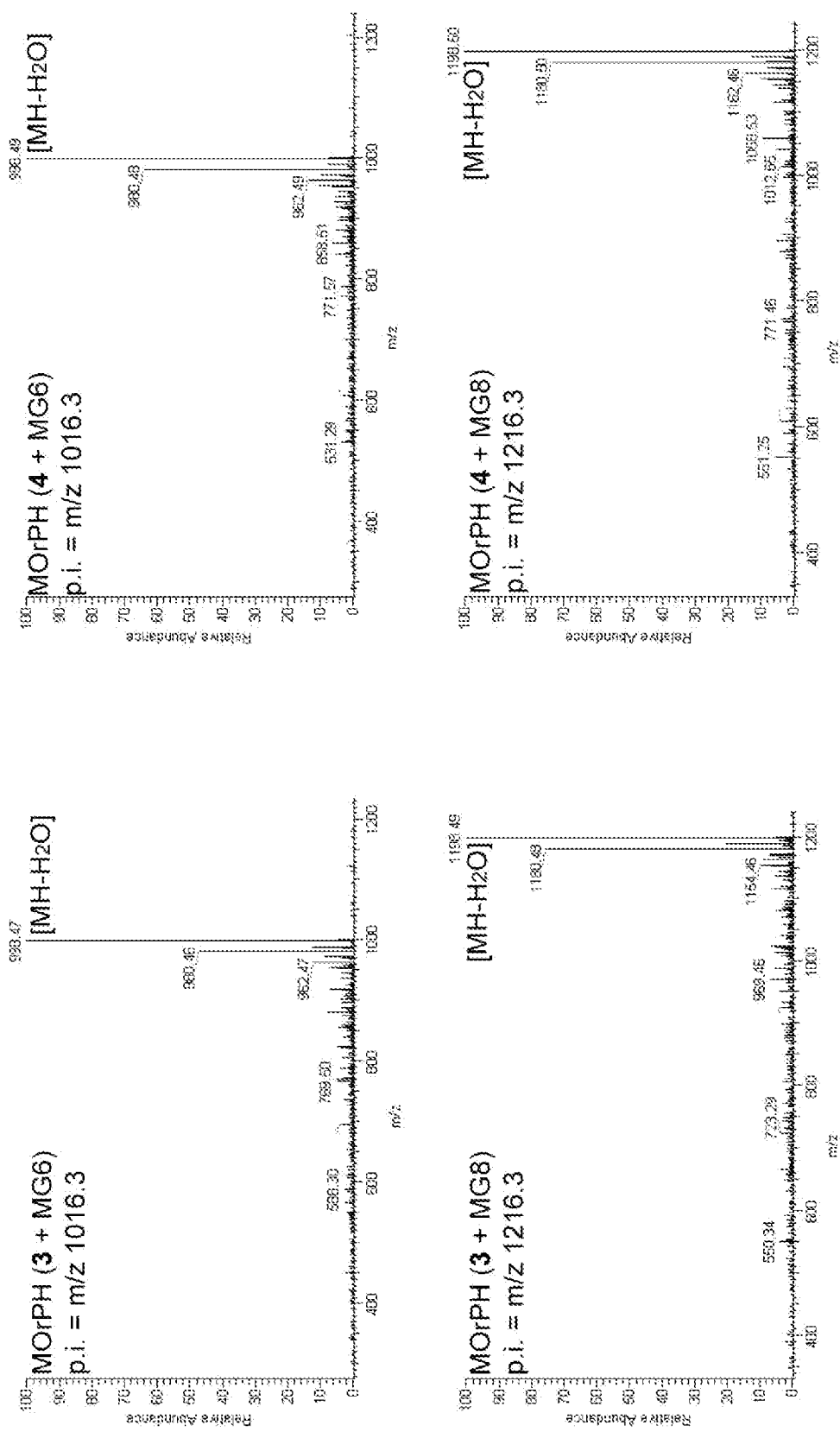
Figure 8C:
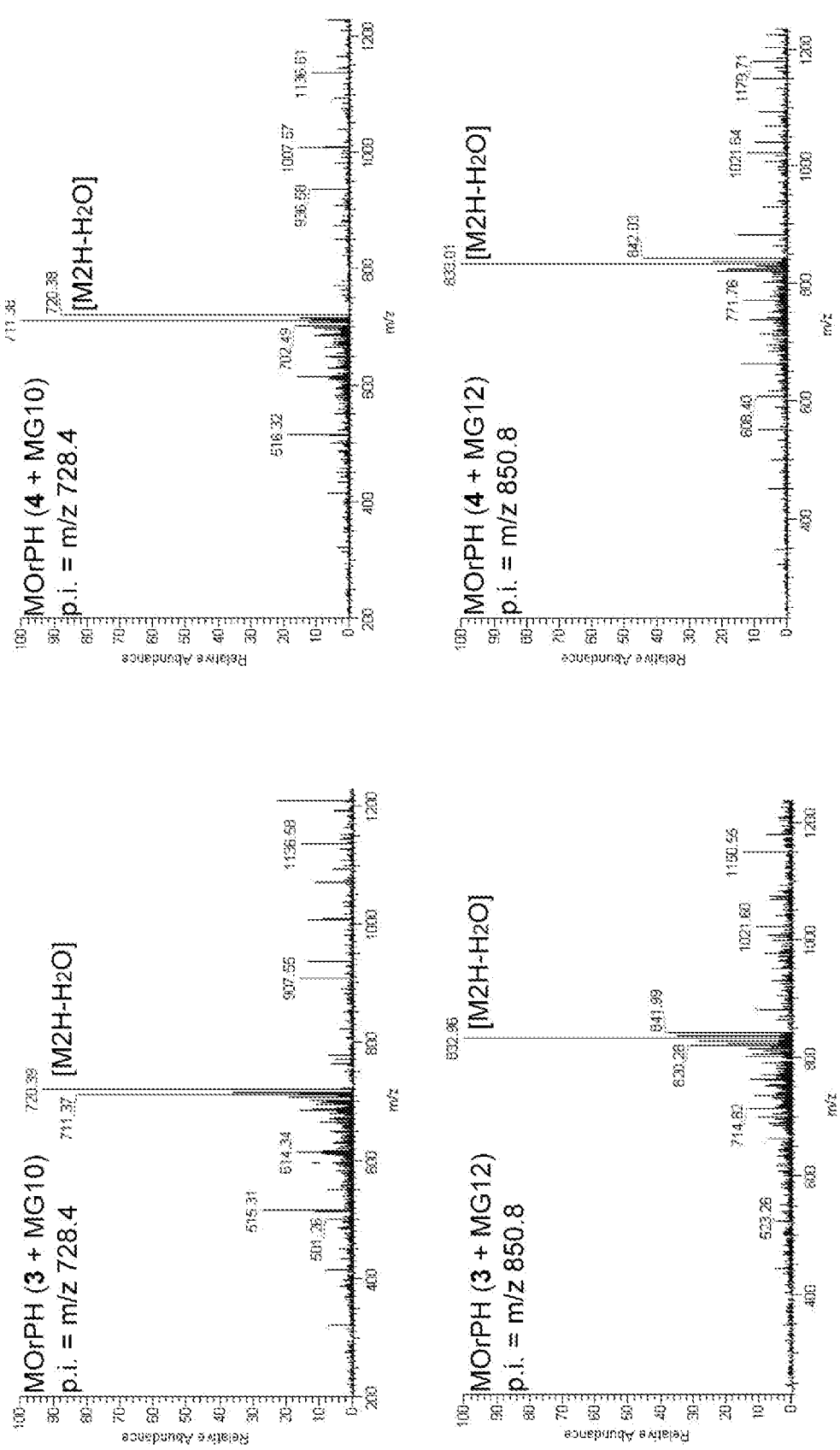
Figure 8D:
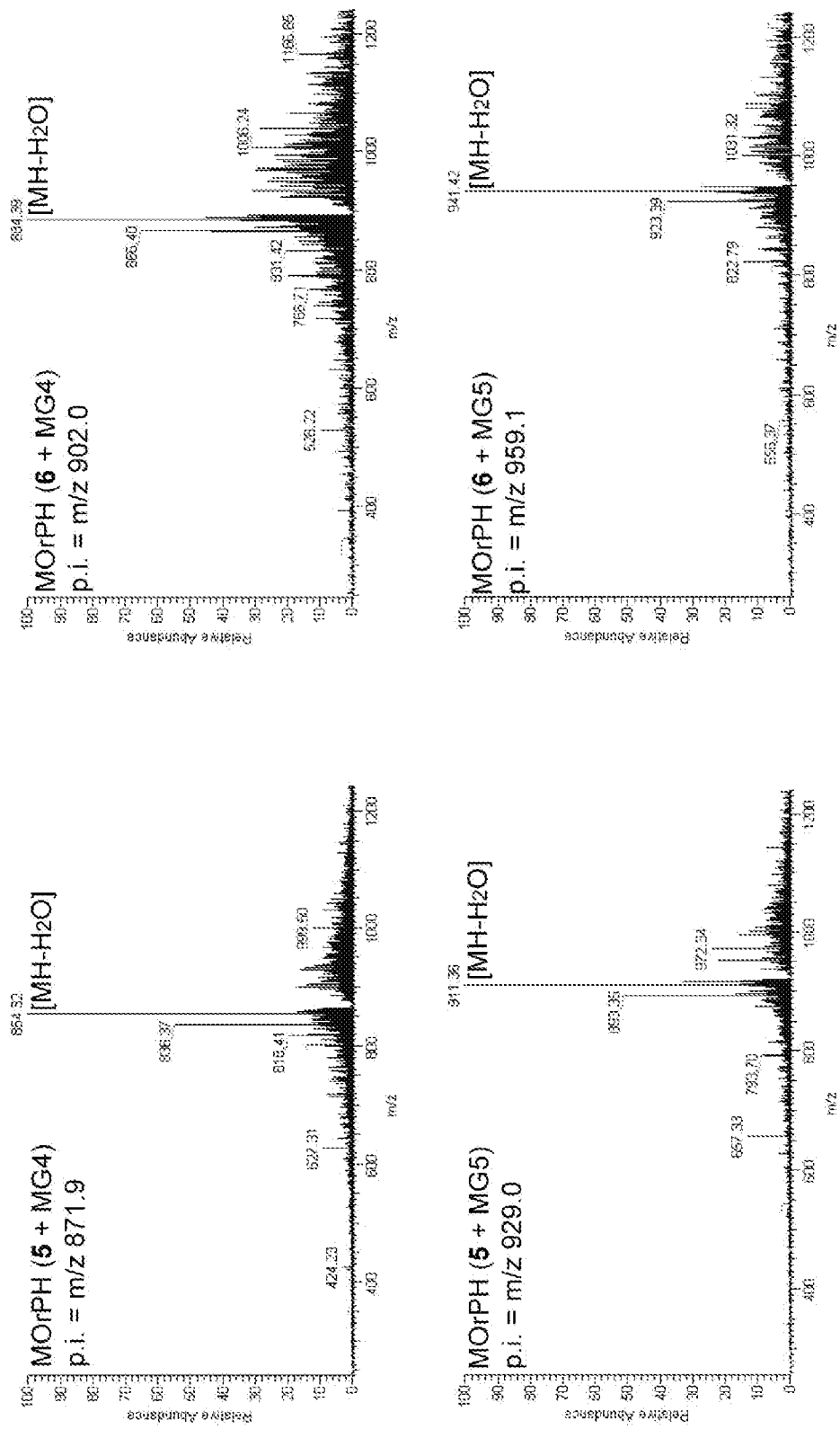
Figure 8E:
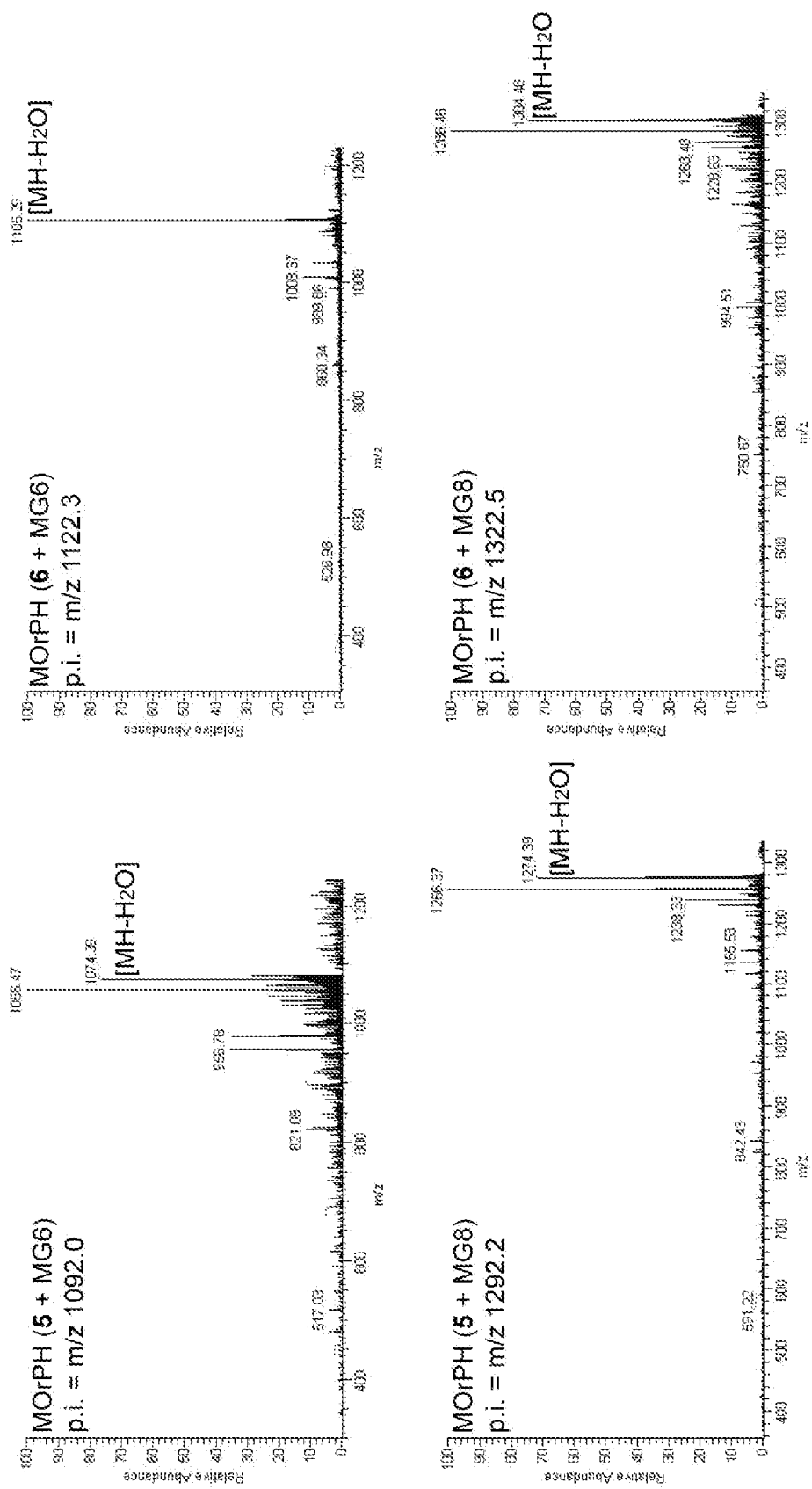
Figure 8F:
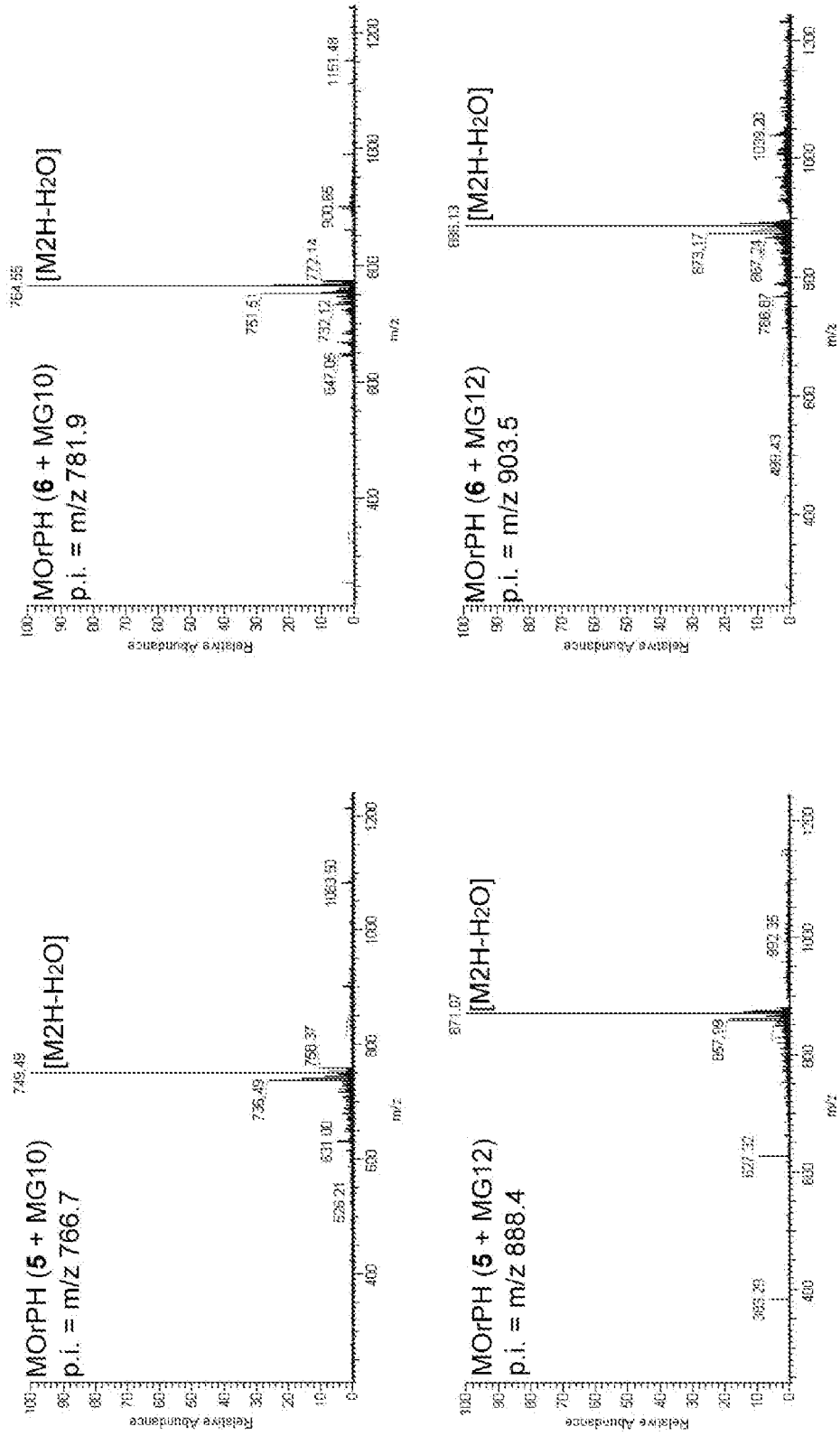

FIG. 7. Time course measurement of GyrA splicing for MG5-1 adduct, MG10-1 adduct, MG5 in the presence of 1 at 50 mM, and MG5 alone as determined by LC-MS analysis at different time points. Mean values and error bars are calculated from experiments carried out in duplicate.

FIGS. 8a-f. MS/MS spectra of the MOrPHs obtained from the reaction of synthetic precursors 3, 4, 5, and 6 with biosynthetic precursors MG4, MG5, MG6, MG8, MG10, and MG12. The m/z of the precursor ion (p.i.) is indicated.

Figure 9:
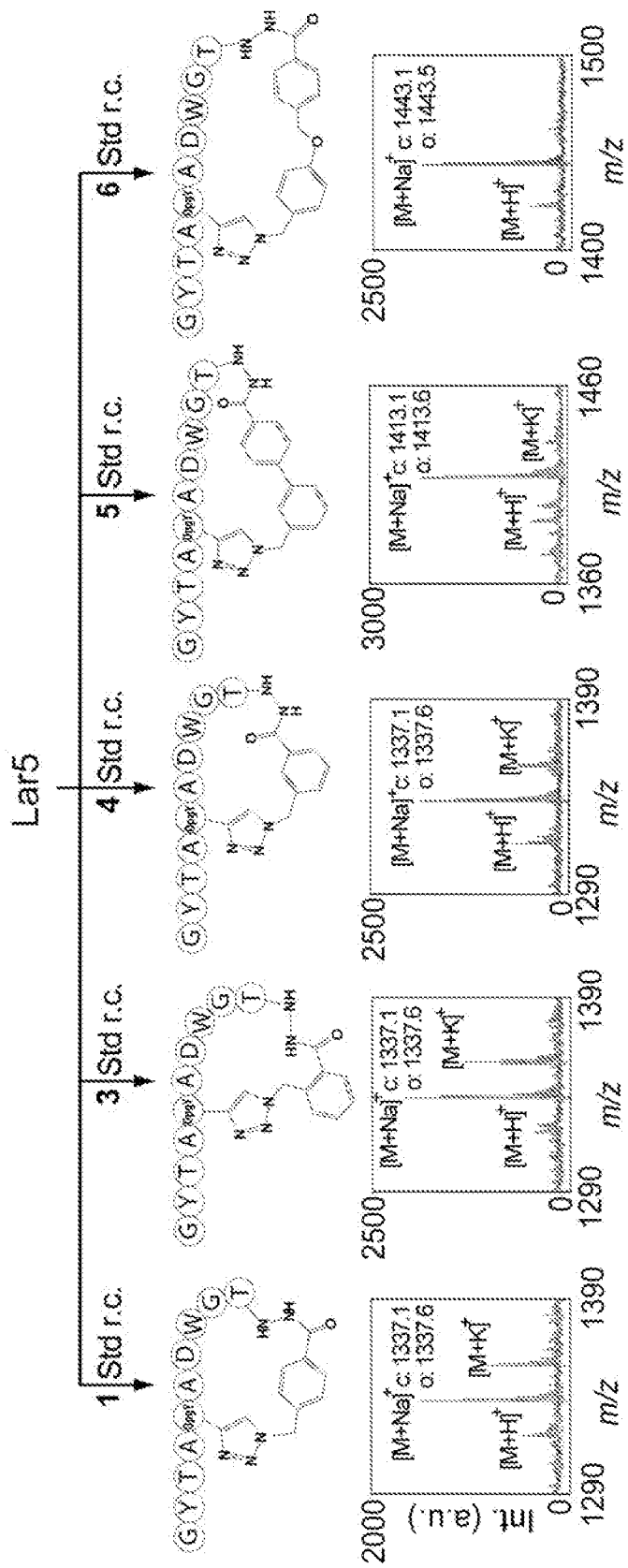

FIG. 9. MALDI-TOF spectra of the lariat MOrPHs prepared by reaction of biosynthetic precursor Lar5 (Table 1) with azide/hydrazide synthetic precursors 1 and 3-6. Calculated (c) and observed (o) m/z values for the sodium adduct are indicated along with the peaks corresponding to the proton and potassium adducts. Std r.c.=standard reaction conditions as described in Example 3.

Figure 10A:
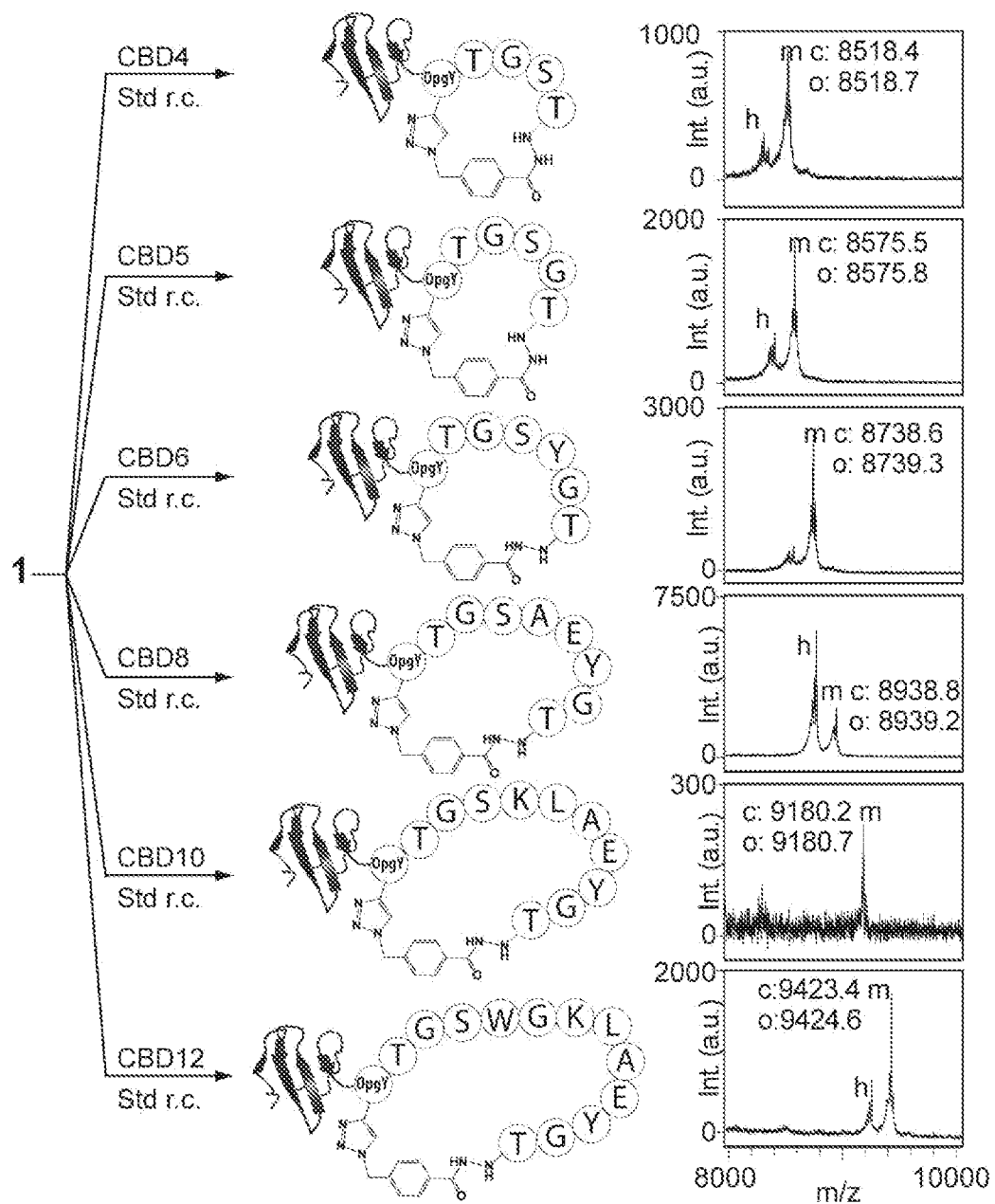
Figure 10B:
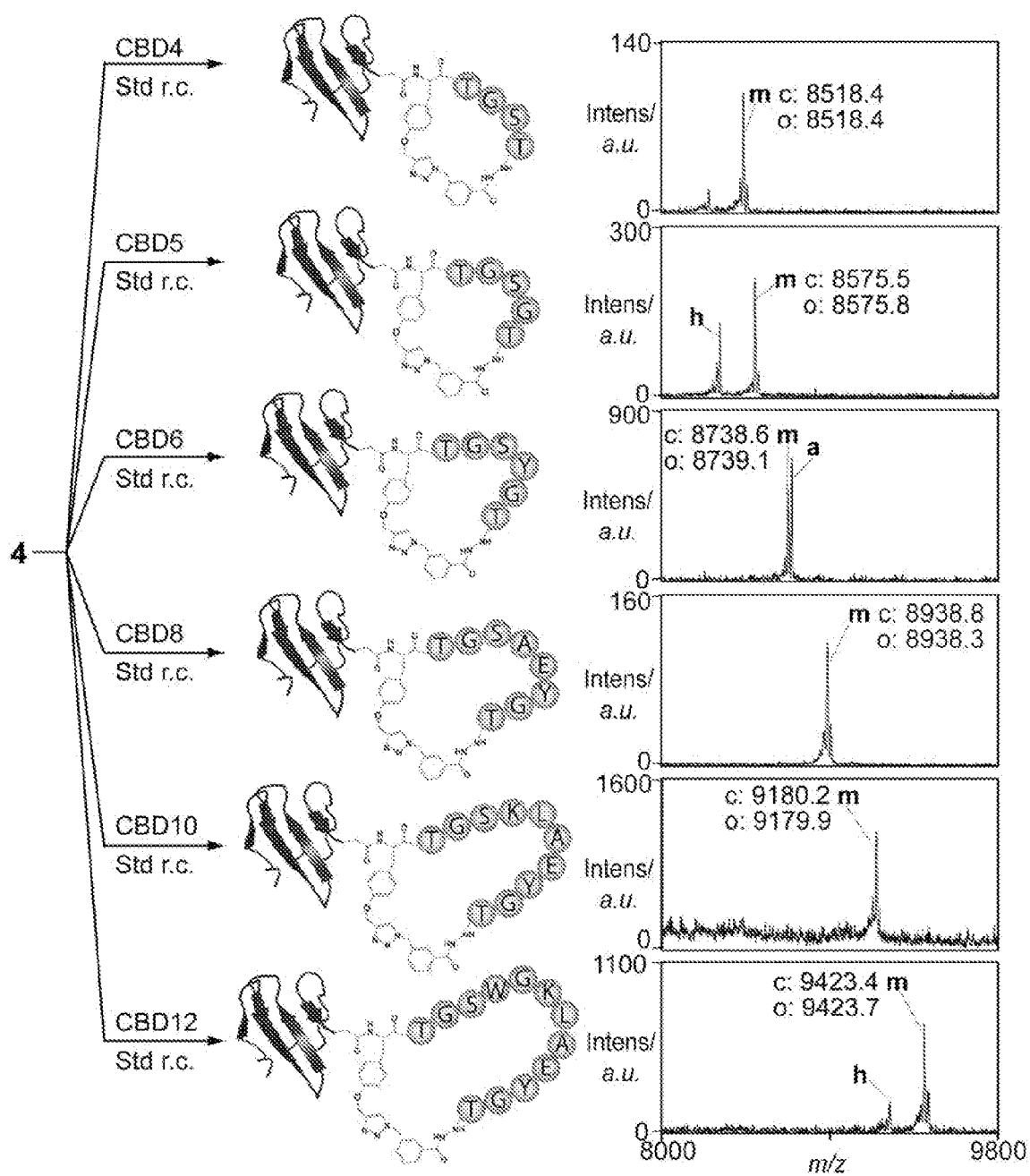
Figure 10C:
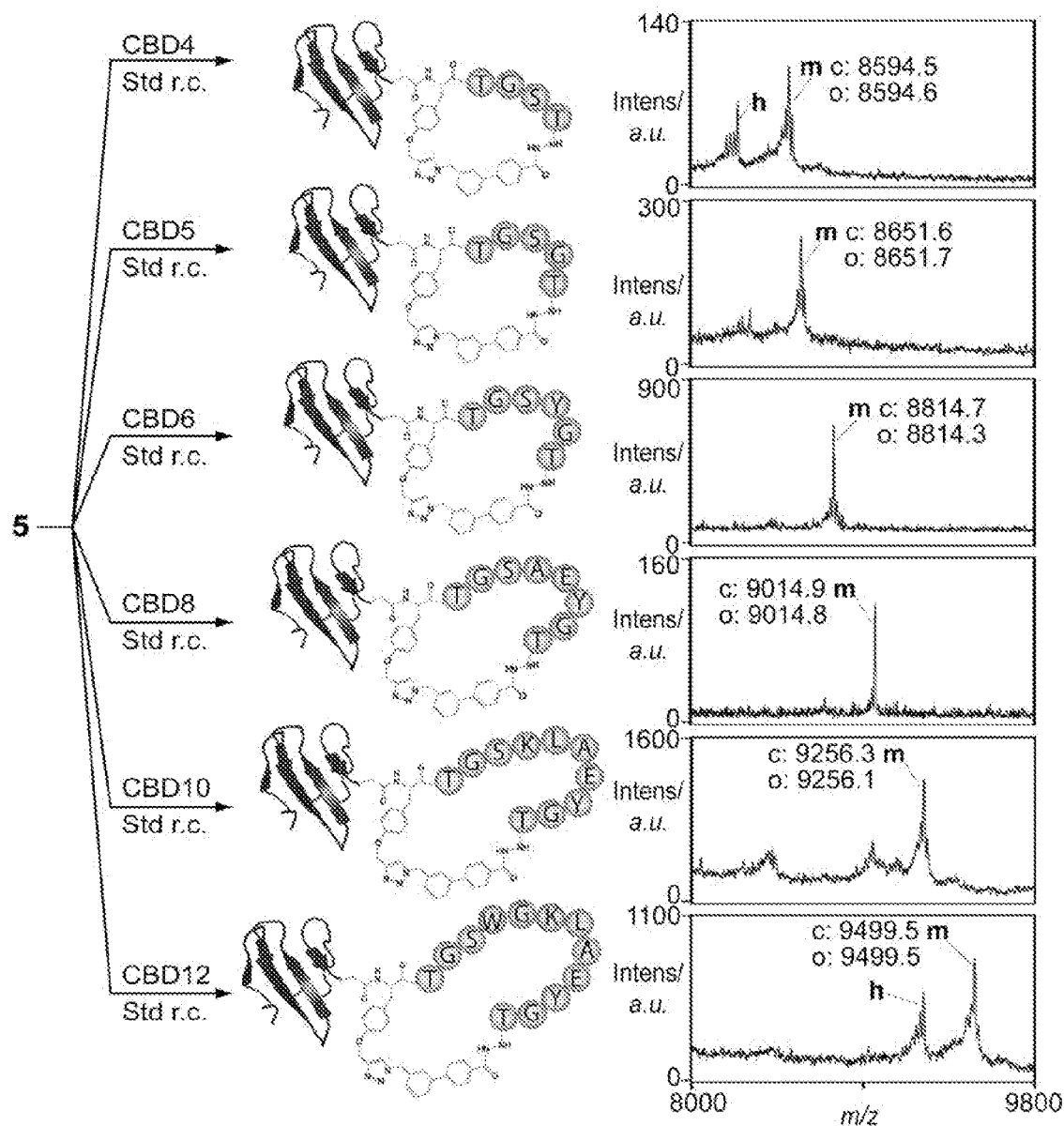

FIGS. 10a-c. MALDI-TOF spectra of the chitin-binding domain (CBD)-fused MOrPHs ('m') obtained with 1, 4, and 5. 'h'=small MW fragment resulting from hydrolysis of unmodified biosynthetic precursor. Std r.c.=standard reaction conditions as described in Example 3.

Figure 11:
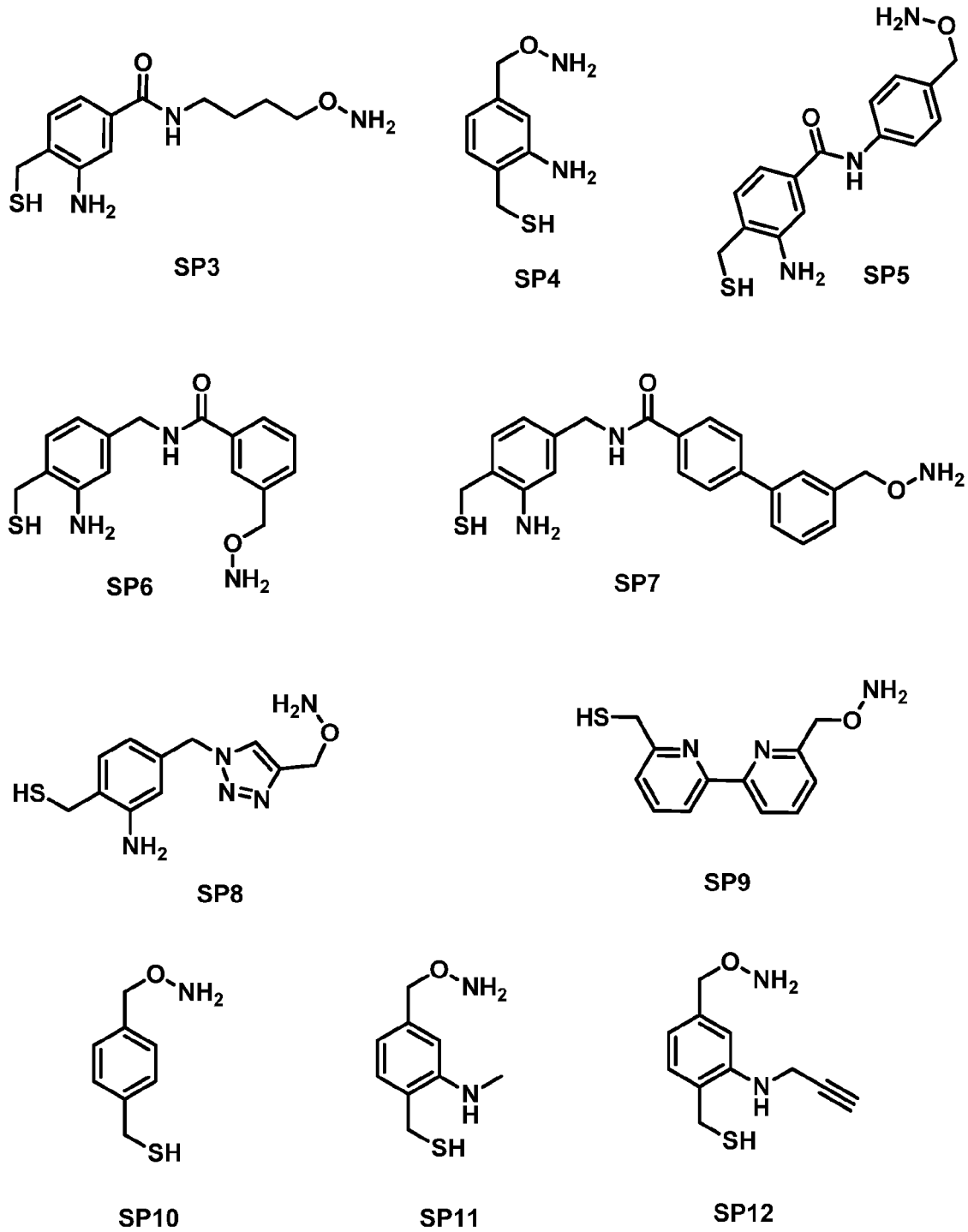

FIG. 11. Chemical structures of bifunctional (oxyamine/amino-thiol, oxyamine/thiol) synthetic precursors.

Figure 12:
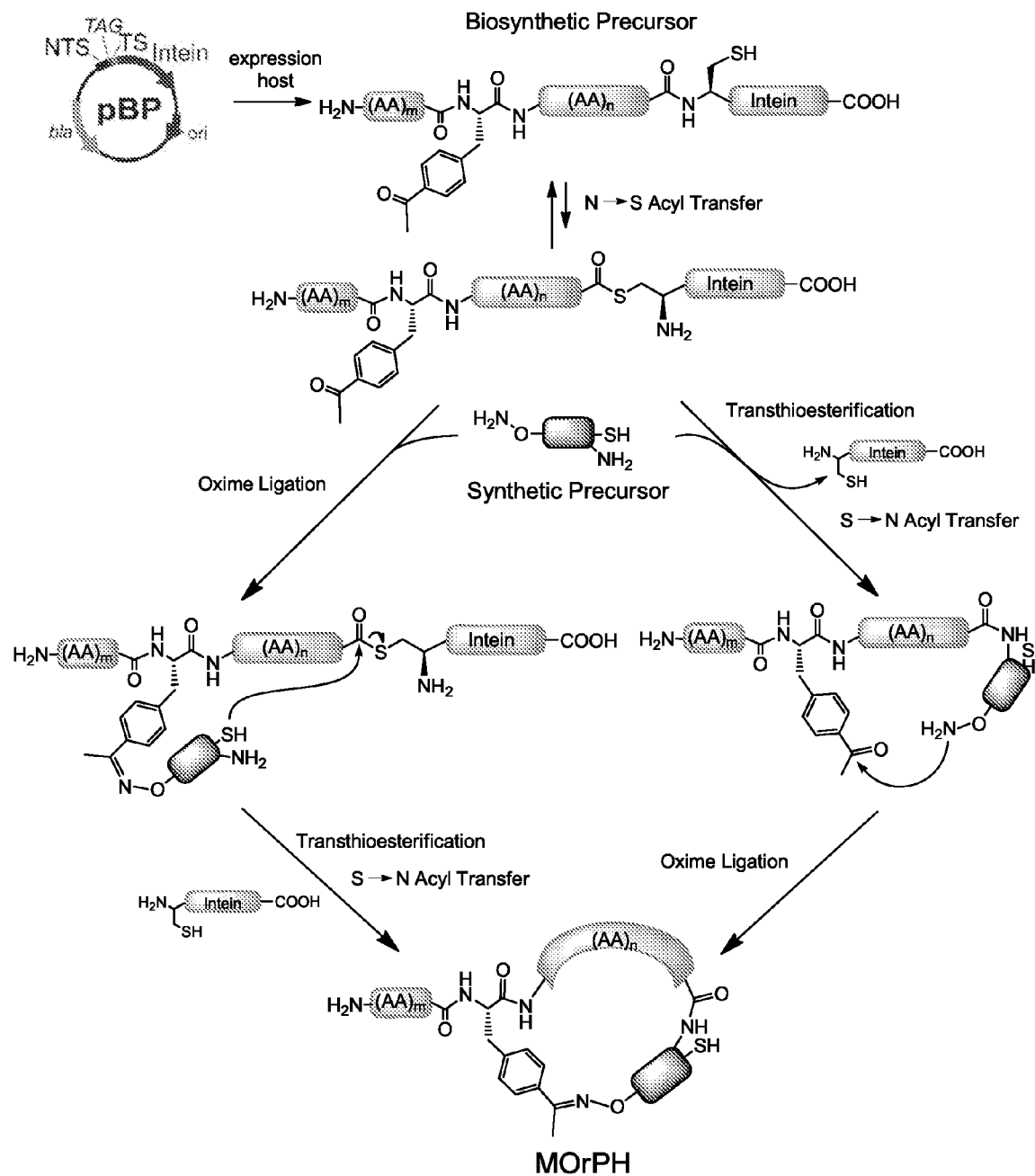

FIG. 12. Schematic representation of another embodiment of the general method of FIG. 1 where the macrocyclic organo-peptide hybrids (MOrPHs) are produced via a tandem oxime/intein-mediated ligation. In the plasmid vector (pBP): NTS=N-terminal sequence, TAG=amber stop codon, TS=target sequence.

Figure 13:
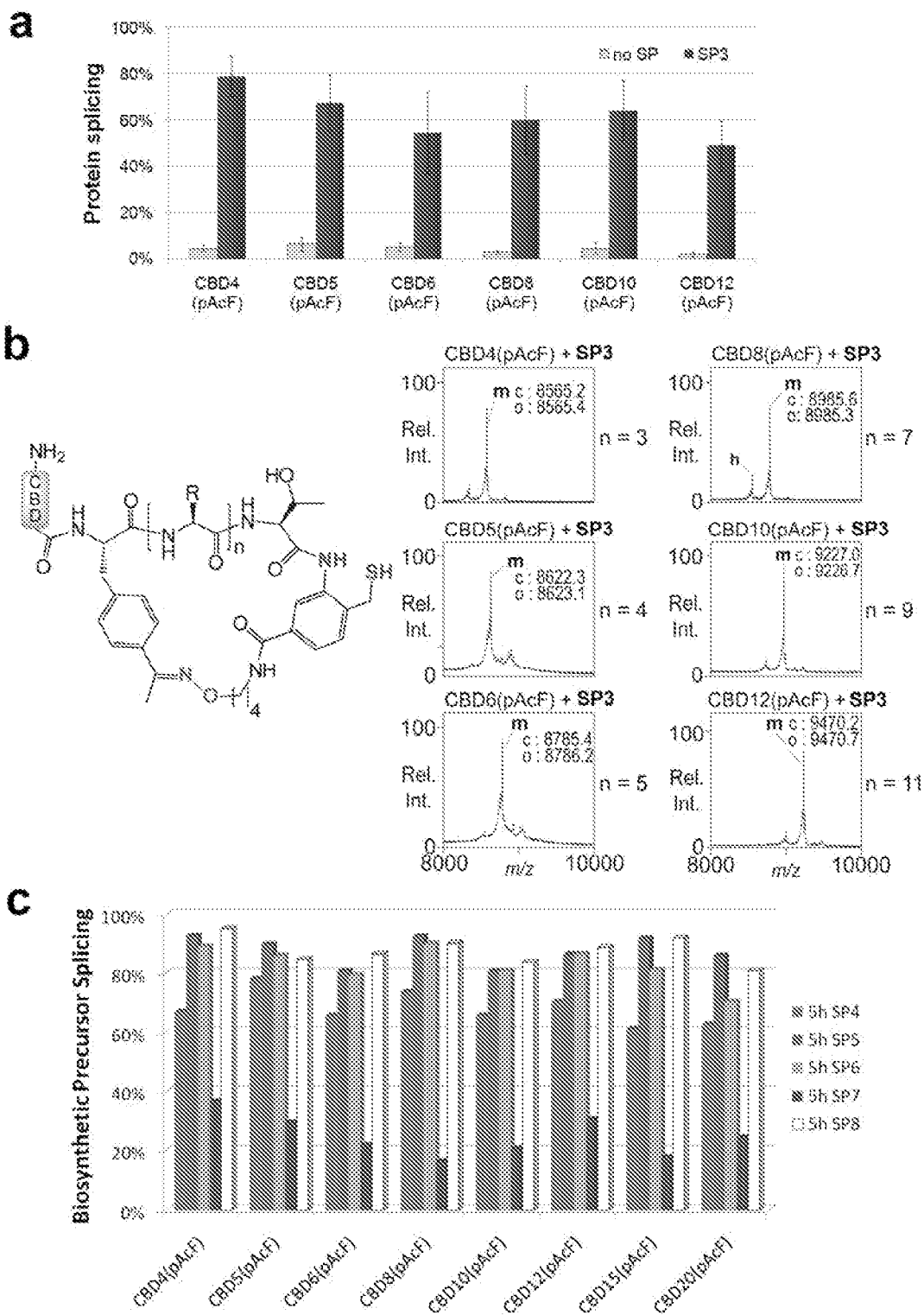

FIGS. 13a-c. (a) Percentage of splicing of pAcF-containing biosynthetic precursors in reactions with no synthetic precursor (SP) and with SP3 (5 hours, room temperature) as determined by SDS-PAGE. Error bars are from triplicate experiments. (b) MALDI-TOF spectra of MOrPHs obtained from reaction of SP3 with biosynthetic precursors CBD4 (pAcF) to CBD12(pAcF). The calculated ('c') and observed ('o') m/z values corresponding to the [M+H]$^+$ adduct of the macrocyclic product ('m') are indicated. (c) Percentage of splicing of CBD-fused pAcF-containing biosynthetic precursors with 4mer to 20mer target sequences in reactions with SP4, SP5, SP6, SP7, SP8 (5 hours, room temperature) as determined by SDS-PAGE.

Figure 14:
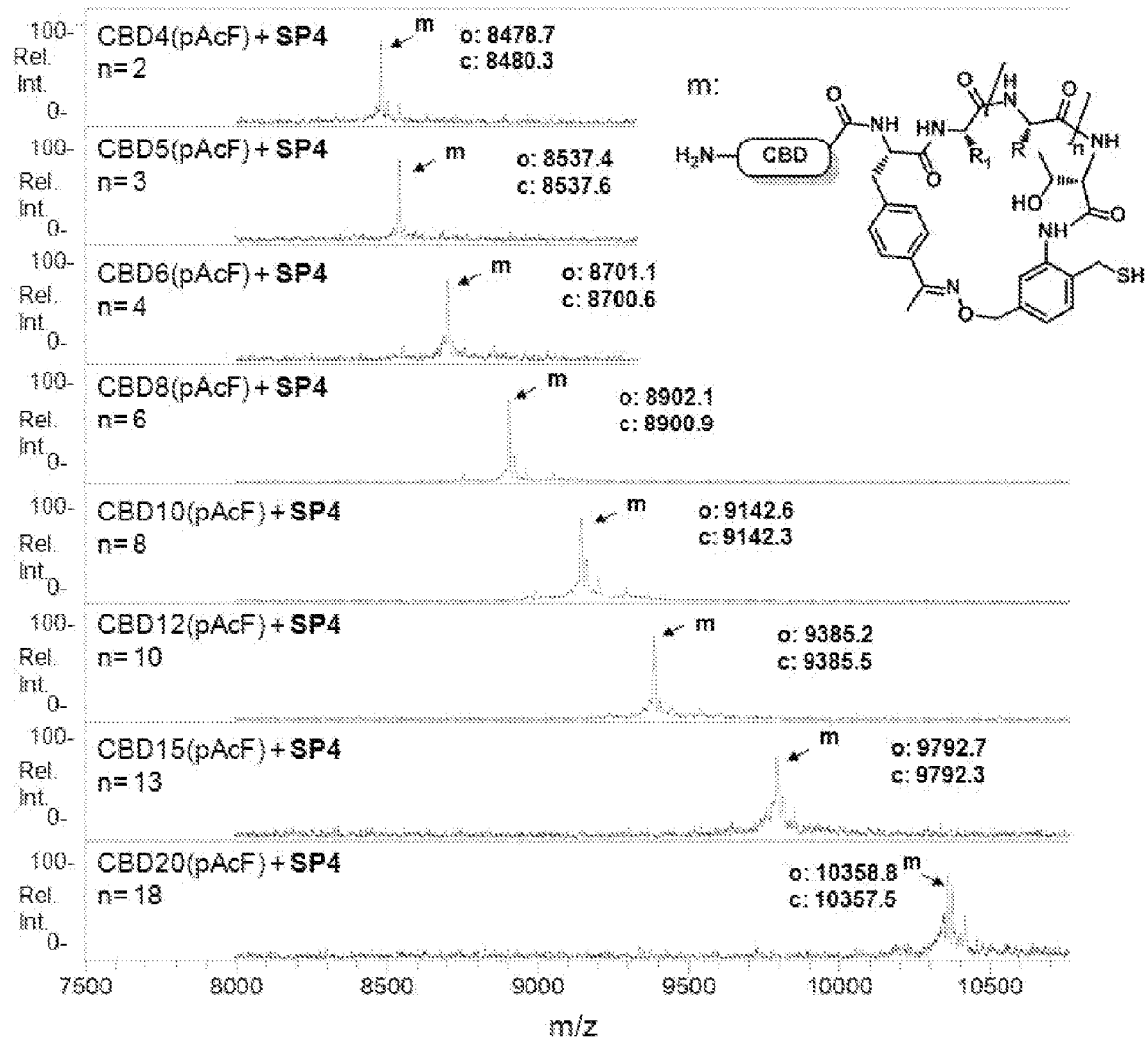

FIG. 14. Representative MALDI-TOF spectra of MOrPHs ('m') obtained from the reaction of SP4 with pAcF-containing biosynthetic precursors with a 4mer to 20mer target sequence. The calculated ('c') and observed ('o') m/z values corresponding to the [M+H]$^+$ adduct of the macrocyclic product ('m') are indicated.

FIGS. 15a-b. Extent of SP3-induced splicing after 5 and 16 hours for 20 variants from the library of pAcF-containing biosynthetic precursors with randomized 5mer (a) and 8mer (b) target sequence.

Figure 16:
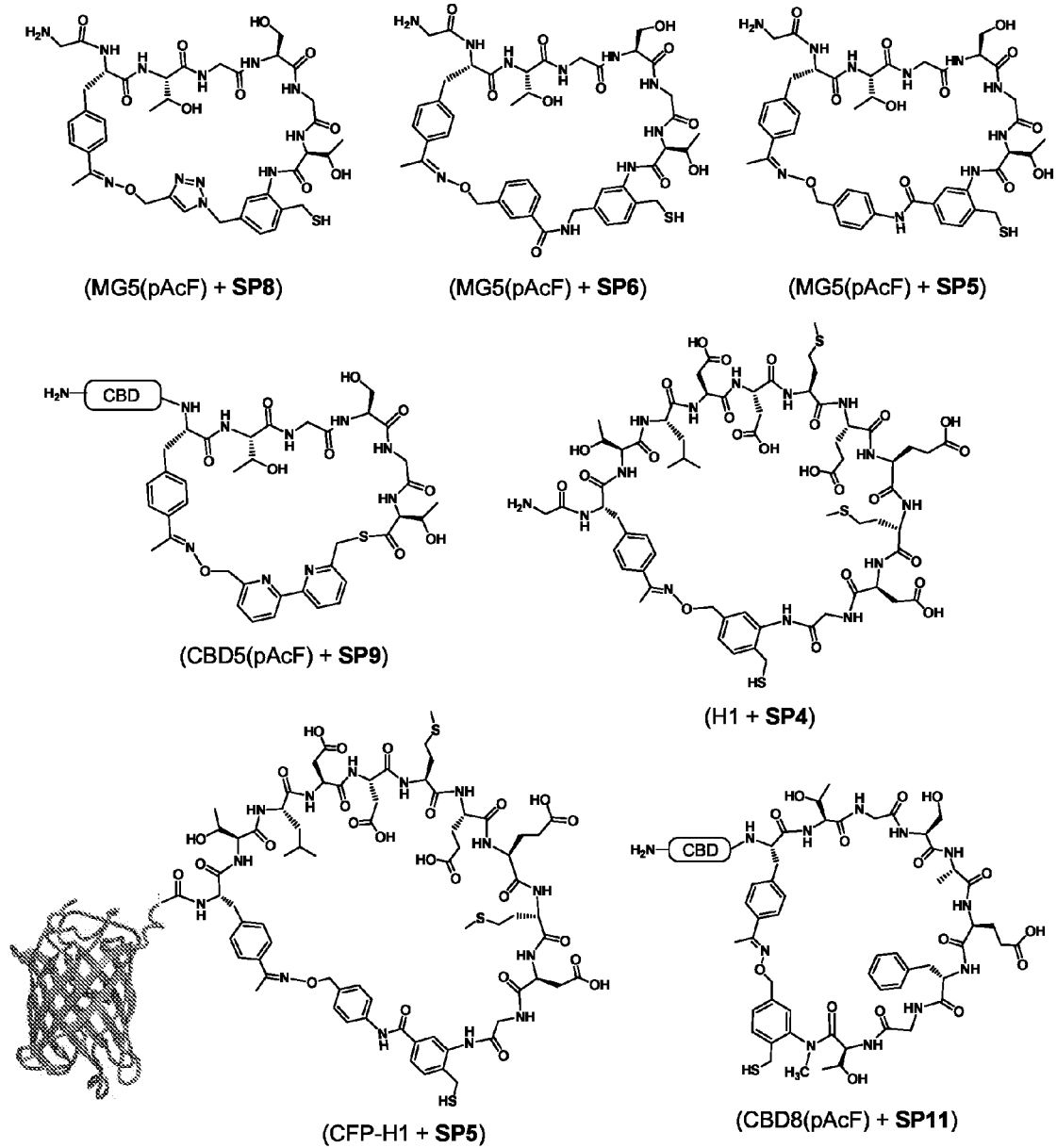

FIG. 16. Structures of representative lariat and protein-fused MOrPHs prepared according to the general strategy of FIG. 1 as described in the Examples. The synthetic precursor and biosynthetic precursors used to prepare these molecules are provided in brackets.

FIGS. 17a-c. Synthesis of fluorine-incorporating MOrPHs. (a) Chemical structure of 2-fluoro-4-acetyl-phenylalanine (2F-pAcF). (b) SDS-PAGE protein gel showing the incorporation of 2F-pAcF into a biosynthetic precursor. (c) MALDI-TOF spectrum of a CBD-fused MOrPH containing the fluorinated amino acid 2F-pAcF. The calculated ('c') and observed ('o') m/z value corresponding to the [M+H]$^+$ adduct of the macrocyclic product ('m') are indicated.

FIGS. 18a-b. (a) HPLC chromatogram and (b) ESI-MS spectrum corresponding to purified MOrPH 7 (see FIG. 5c) obtained from large-scale macrocyclization reaction.

FIGS. 19a-b. Self-processing biosynthetic precursors. (a) SDS-PAGE gel showing the incorporation of the unnatural amino acid AmmF into a test protein (CBD5 construct) using different engineered variants of M. jannaschii tyrosyl-tRNA synthetase. (b) Fraction of protein splicing after 24 hours incubation for AmmF-containing self-processing biosynthetic precursors containing a 4mer to 20mer target sequence.

Figure 20:
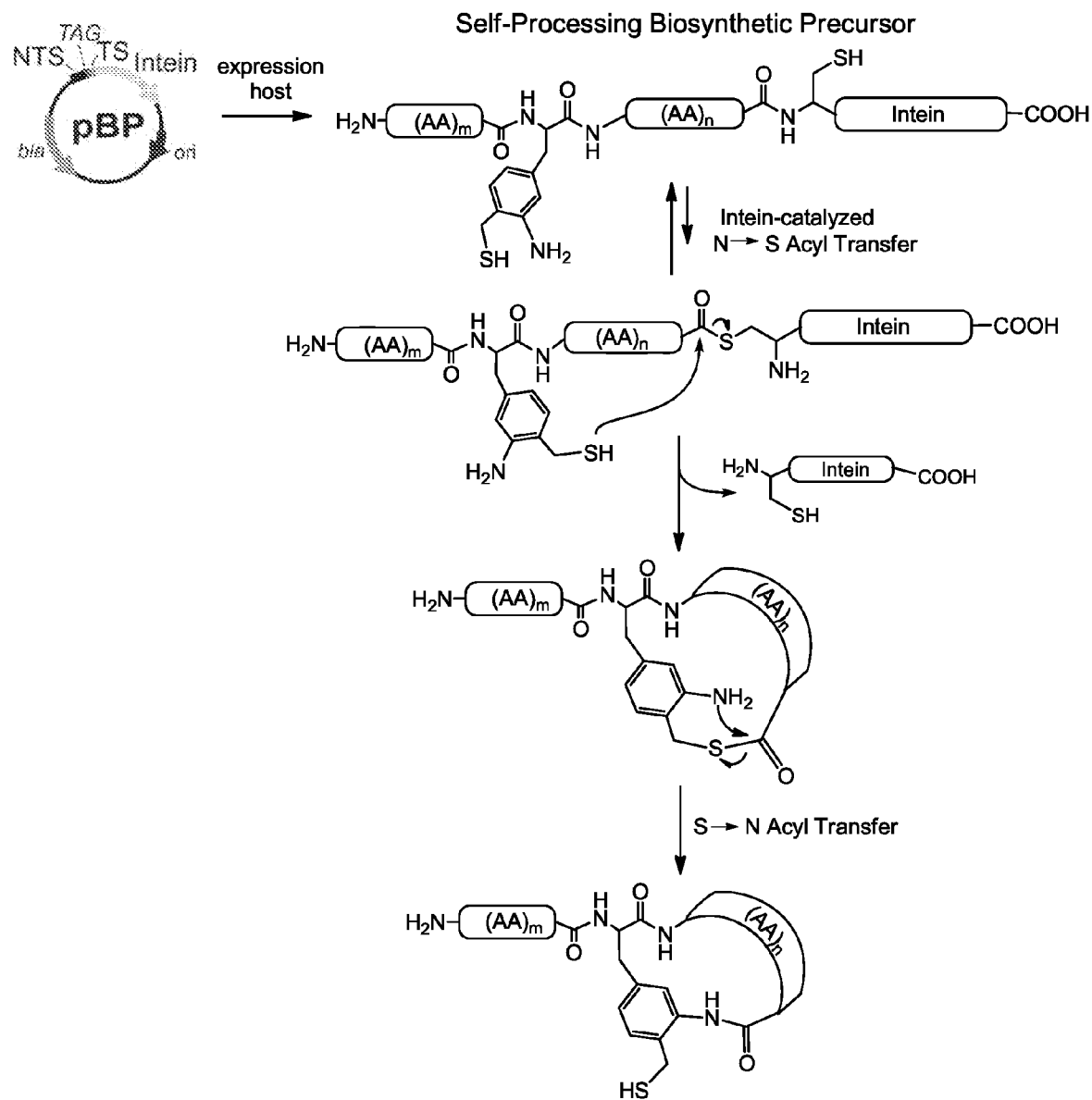

FIG. 20. Schematic representation of one embodiment of the general method of FIG. 2 where the macrocyclic organo-peptide hybrids (MOrPH) is produced via an intramolecular cyclization reaction.

Figure 21:
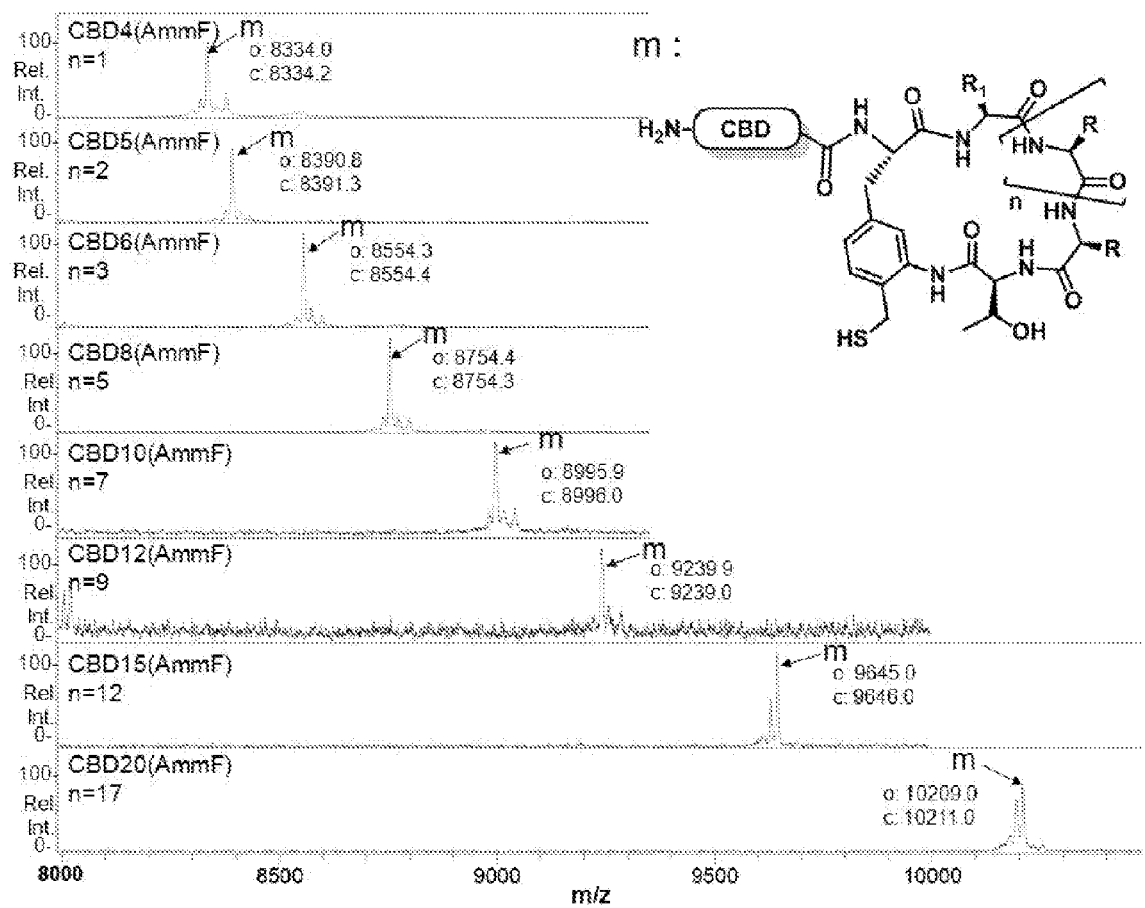

FIG. 21. MALDI-TOF spectra of MOrPHs ('m') obtained via cyclization of AmmF-containing self-processing biosynthetic precursors (4mer to 20mer target sequence) according to the variation of the general method of FIG. 2 illustrated in FIG. 20. The calculated (c) and observed (o) m/z values corresponding to the [M+H]$^+$ adduct of the macrocyclic product ('m') are indicated.

FIGS. 22a-c. In vivo production of MOrPHs. (a) General scheme illustrating the experiment described in Example 14, which involved the synthesis of MOrPHs inside *E. coli* cells via spontaneous cyclization of recombinant self-processing biosynthetic precursors (AmmF/DnaB-containing). (b) Extent of in vivo splicing of AmmF/DnaB-containing self-processing biosynthetic precursors as determined by SDS-PAGE protein gel densitometry (cells harvested after 16 hours at 30° C.). (c) MALDI-TOF spectra of MOrPHs ('m') obtained via cyclization of AmmF/DnaB-containing self-processing biosynthetic precursors. The calculated (c) and observed (o) m/z values corresponding to the [M+H]$^+$ adduct of the acetylated macrocyclic product ('m') are indicated.

FIGS. 23*a-d*. Synthetic schemes.

5. DETAILED DESCRIPTION OF THE INVENTION

For clarity of disclosure, and not by way of limitation, the detailed description of the invention is divided into the subsections set forth below.

5.1 DEFINITIONS

Unless defined otherwise herein, all technical and scientific terms used herein have the same meaning as commonly understood by one of ordinary skill in the art to which the disclosure pertains.

The singular forms "a," "an," and "the" used herein include plural referents unless the content clearly dictates otherwise.

The term "plurality" includes two or more referents unless the content clearly dictates otherwise.

The term "functional group" as used herein refers to a contiguous group of atoms that, together, may undergo a chemical reaction under certain reaction conditions. Examples of functional groups are, among many others, —OH, —NH$_2$, —SH, —(C=O)—, —N$_3$, —C≡CH.

The terms "macrocyclic organo-peptide hydrid(s)" and "MOrPH(s)" as used herein should be considered equivalent to the term "macrocyclic peptide-containing molecule(s)". In general, these terms refer to macrocyclic peptide-containing molecules prepared using the methods of the invention.

The term "aliphatic" is used in the conventional sense to refer to an open-chain or cyclic, linear or branched, saturated or unsaturated hydrocarbon group, including but not limited to alkyl group, alkenyl group and alkynyl groups.

The term "heteroatom-containing aliphatic" as used herein refer to an aliphatic moiety where at least one carbon atom is replaced with a heteroatom, e.g., oxygen, nitrogen, sulphur, selenium, phosphorus, or silicon, and typically oxygen, nitrogen, or sulphur.

The terms "alkyl" and "alkyl group" as used herein refer to a linear, branched, or cyclic saturated hydrocarbon typically containing 1 to 24 carbon atoms, preferably 1 to 12 carbon atoms, such as methyl, ethyl, n-propyl, isopropyl, n-butyl, isobutyl, t-butyl, octyl, decyl and the like.

The term "heteroatom-containing alkyl" as used herein refers to an alkyl moiety where at least one carbon atom is replaced with a heteroatom, e.g., oxygen, nitrogen, sulphur, phosphorus, or silicon, and typically oxygen, nitrogen, or sulphur.

The terms "alkenyl" and "alkenyl group" as used herein refer to a linear, branched, or cyclic hydrocarbon group of 2 to 24 carbon atoms, preferably of 2 to 12 carbon atoms, containing at least one double bond, such as ethenyl, n-propenyl, isopropenyl, n-butenyl, isobutenyl, octenyl, decenyl, and the like.

The term "heteroatom-containing alkenyl" as used herein refer to an alkenyl moiety where at least one carbon atom is replaced with a heteroatom.

The terms "alkynyl" and "alkynyl group" as used herein refer to a linear, branched, or cyclic hydrocarbon group of 2 to 24 carbon atoms, preferably of 2 to 12 carbon atoms, containing at least one triple bond, such as ethynyl, n-propynyl, and the like.

The term "heteroatom-containing alkynyl" as used herein refer to an alkynyl moiety where at least one carbon atom is replaced with a heteroatom.

The terms "aryl" and "aryl group" as used herein refer to an aromatic substituent containing a single aromatic or multiple aromatic rings that are fused together, directly linked, or indirectly linked (such as linked through a methylene or an ethylene moiety). Preferred aryl groups contain 5 to 24 carbon atoms, and particularly preferred aryl groups contain 5 to 14 carbon atoms.

The term "heteroatom-containing aryl" as used herein refer to an aryl moiety where at least one carbon atom is replaced with a heteroatom.

The terms "alkoxy" and "alkoxy group" as used herein refer to an aliphatic group or a heteroatom-containing aliphatic group bound through a single, terminal ether linkage. Preferred aryl alkoxy groups contain 1 to 24 carbon atoms, and particularly preferred alkoxy groups contain 1 to 14 carbon atoms.

The terms "aryloxy" and "aryloxy group" as used herein refer to an aryl group or a heteroatom-containing aryl group bound through a single, terminal ether linkage. Preferred aryloxy groups contain 5 to 24 carbon atoms, and particularly preferred aryloxy groups contain 5 to 14 carbon atoms.

The terms "halo" and "halogen" are used in the conventional sense to refer to a fluoro, chloro, bromo or iodo substituent. By "substituted" it is intended that in the alkyl, alkenyl, alkynyl, aryl, or other moiety, at least one hydrogen atom is replaced with one or more "substituents".

The term "substituents" refers to a contiguous group of atoms. Examples of "substituents" include, without limitation: alkoxy, aryloxy, alkyl, heteroatom-containing alkyl, alkenyl, heteroatom-containing alkenyl, alkynyl, heteroatom-containing alkynyl, aryl, heteroatom-containing aryl, alkoxy, heteroatom-containing alkoxy, aryloxy, heteroatom-containing aryloxy, halo, hydroxyl (—OH), sulfhydryl (—SH), substituted sulfhydryl, carbonyl (—CO—), thiocarbonyl, (—CS—), carboxy (—COOH), amino (—NH$_2$), substituted amino, nitro (—NO$_2$), nitroso (—NO), sulfo (—SO$_2$—OH), cyano (—C≡N), cyanato (—O—C≡N), thiocyanato (—S—C≡N), formyl (—CO—H), thioformyl (—CS—H), phosphono (—P(O)OH$_2$), substituted phosphono, and phospho (—PO$_2$).

The term "contact" as used herein with reference to interactions of chemical units indicates that the chemical units are at a distance that allows short range non-covalent interactions (such as Van der Waals forces, hydrogen bonding, hydrophobic interactions, electrostatic interactions, dipole-dipole interactions) to dominate the interaction of the chemical units. For example, when a protein is 'contacted' with a chemical species, the protein is allowed to interact with the chemical species so that a reaction between the protein and the chemical species can occur.

The term "bioorthogonal" as used herein with reference to a reaction, reagent, or functional group, indicates that such reaction, reagent, or functional group does not exhibit significant or detectable reactivity towards biological molecules such as those present in a bacterial, yeast or mammalian cell.

The biological molecules can be, e.g., proteins, nucleic acids, fatty acids, or cellular metabolites.

In general, the term "mutant" or "variant" as used herein with reference to a molecule such as polynucleotide or polypeptide, indicates that such molecule has been mutated from the molecule as it exists in nature. In particular, the term "mutate" and "mutation" as used herein indicates any modification of a nucleic acid and/or polypeptide which results in an altered nucleic acid or polypeptide. Mutations include any process or mechanism resulting in a mutant protein, enzyme, polynucleotide, or gene. A mutation can occur in a polynucleotide or gene sequence, by point mutations, deletions, or insertions of single or multiple nucleotide residues. A mutation in a polynucleotide includes mutations arising within a protein-encoding region of a gene as well as mutations in regions outside of a protein-encoding sequence, such as, but not limited to, regulatory or promoter sequences. A mutation in a coding polynucleotide such as a gene can be "silent", i.e., not reflected in an amino acid alteration upon expression, leading to a "sequence-conservative" variant of the gene. A mutation in a polypeptide includes but is not limited to mutation in the polypeptide sequence and mutation resulting in a modified amino acid. Non-limiting examples of a modified amino acid include a glycosylated amino acid, a sulfated amino acid, a prenylated (e.g., farnesylated, geranylgeranylated) amino acid, an acetylated amino acid, an acylated amino acid, a PEGylated amino acid, a biotinylated amino acid, a carboxylated amino acid, a phosphorylated amino acid, and the like.

The term "engineer" refers to any manipulation of a molecule that result in a detectable change in the molecule, wherein the manipulation includes but is not limited to inserting a polynucleotide and/or polypeptide heterologous to the cell and mutating a polynucleotide and/or polypeptide native to the cell.

The term "nucleic acid molecule" as used herein refers to any chain of two or more nucleotides bonded in sequence. For example, a nucleic acid molecule can be a DNA or a RNA.

The term "peptide", "polypeptide", and "protein" as used herein refers to any chain of two or more amino acids bonded in sequence, regardless of length or post-translational modification.

The term "peptide-containing molecule" as used herein refers to a molecule that contains two or more amino acids.

The term "non-natural" and "unnatural" as used herein means being directly or indirectly made or caused to be made through human action. Thus, a "non-natural amino acid" is an amino acid that has been produced through human manipulation and does not occur in nature.

The term "cyclic" and "macrocyclic" as used herein means having constituent atoms forming a ring. Thus, a "macrocyclic peptide-containing molecule" is a peptide-containing molecule that contains one or more rings formed by atoms comprised in the molecule.

The terms "cyclization" or "macrocyclization" as used herein refer to a process or reaction whereby a cyclic molecule is formed or is made to be formed.

The term "peptidic backbone" as used herein refers to a sequence of atoms corresponding to the main backbone of a natural protein.

The term "non-peptidic backbone" as used herein refers to a sequence of atoms that does not correspond to a peptidic backbone.

The term "intein" and "intein domain" as used herein refers to a naturally occurring or artificially constructed polypeptide sequence embedded within a precursor protein that can catalyze a splicing reaction during post-translational processing of the protein. The NEB Intein Registry (neb.com/neb/inteins.html) provides a list of known inteins.

The term "split intein" as used herein refers to an intein that has two or more separate components not fused to one another.

The term "splicing" as used herein refers to the process involving the cleavage of the main backbone of an intein-containing polypeptide by virtue of a reaction or process catalyzed by an intein or portions of an intein. "N-terminal splicing" refers to the cleavage of a polypeptide chain fused to the N-terminus of an intein, such reaction typically involving the scission of the thioester (or ester) bond formed via intein-catalyzed N→S (or N→O acyl) transfer, by action of a nucleophilic functional group or a chemical species containing a nucleophilic functional group. "C-terminal splicing" refers to the cleavage of a polypeptide chain fused to the C-terminus of an intein. "Self-splicing" as used herein refers to the process involving the cleavage of an intein from a polypeptide, within which the intein is embedded.

The term "ligation" as used herein refers to a process or reaction that lead to formation of a bond connecting two molecules. The term 'intein-mediated ligation' as used herein refers to a chemical bond-forming reaction that involves a nucleophilic substitution at a thioester or ester linkage formed via intein-catalyzed N→S or N→O acyl transfer, by action of a nucleophilic functional group or a chemical species containing a nucleophilic functional group.

The term "affinity tag" as used herein refers to a polypeptide that is able to bind reversibly or irreversibly to an organic molecule, a metal ion, a protein, or a nucleic acid molecule.

The terms "vector" and "vector construct" as used herein refer to a vehicle by which a DNA or RNA sequence (e.g., a foreign gene) can be introduced into a host cell, so as to transform the host and promote expression (e.g., transcription and translation) of the introduced sequence. A common type of vector is a "plasmid", which generally is a self-contained molecule of double-stranded DNA that can be readily accept additional (foreign) DNA and which can readily introduced into a suitable host cell. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. The terms "express" and "expression" refer to allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

The term "fused" as used herein means being connected through one or more covalent bonds. The term "bound" as used herein means being connected through non-covalent interactions. Examples of non-covalent interactions are van der Waals, hydrogen bond, electrostatic, and hydrophobic interactions. Thus, a "DNA-binding peptide" refers to a peptide capable of connecting to a DNA molecule via non-covalent interactions. The term "tethered" as used herein means being connected through non-covalent interactions or through covalent bonds. Thus, a "polypeptide tethered to a solid support" refers to a polypeptide that is connected to a solid support (e.g., surface, resin bead) either via non-covalent interactions or through covalent bonds.

The term "biosynthetic precursor" as used herein refers to an engineered polypeptide construct suitable for the preparation of macrocyclic peptide-containing molecules upon reaction with a "synthetic precursor" according to some of the methods disclosed herein. The term "synthetic precursor" as used herein refers to a synthetic molecule suitable for the preparation of the macrocyclic peptide-containing molecules upon reaction with a "biosynthetic precursor" according to some of the methods disclosed herein. The term "self-processing biosynthetic precursor" as used herein refers to an artificial polypeptide construct suitable for the preparation of the macrocyclic peptide-containing molecules according to some of the methods disclosed herein. The "self-processing biosynthetic precursor" differs from the "biosynthetic precursor" in that it does not involve a reaction with a "synthetic precursor" to generate the macrocyclic peptide-containing molecules.

5.2 METHODS FOR PRODUCING MACROCYCLIC COMPOUNDS WITH HYBRID PEPTIDIC/NON-PEPTIDIC BACKBONE

Methods and compositions are provided that utilize synthetic molecules and genetically encoded polypeptides to generate macrocyclic peptide-containing molecules with a hybrid peptidic/non-peptidic backbone (also referred to herein as macrocyclic peptide-containing molecules or macrocyclic organo-peptide hybrids or MOrPHs). Also provided are nucleic acid molecules, polypeptides, and methods for generating libraries of macrocyclic peptide-containing molecules with a hybrid peptidic/non-peptidic backbone. These methods can be used, for example, to increase the structural diversity of ligand libraries as well as facilitate the functional screening of these libraries to identify compound(s) with desired activity properties.

The methods provided complement the advantages of biologically-encoded peptide libraries (large library size, rapid deconvolution) with those of synthetic peptide libraries (broader spectrum of functionally and structurally diverse building blocks). These methods greatly accelerate and facilitate the discovery of bioactive compounds as potential drug molecules or the identification of lead structures for the development of new drugs.

In one embodiment, a method is provided for making a macrocyclic peptide-containing molecule with a hybrid peptidic/non-peptidic backbone through the reaction between a genetically encoded polypeptide (referred to herein as a 'biosynthetic precursor') and a bifunctional synthetic molecule (referred to herein as 'synthetic precursor'). The method is based on a dual ligation reaction between a polypeptide comprising an intein and carrying a side-chain functional group $FG_1$ and a chemical species of general formula $cFG_1$-L-$cFG_2$ wherein: $cFG_1$ is a functional group that can react with $FG_1$ thereby forming a covalent bond, $cFG_2$ is a nucleophilic functional group that can react with an intein-catalyzed thioester or ester linkage ($FG_2$) through nucleophilic substitution at said thioester or ester group, and L is a linker organic structure connecting $cFG_1$ and $cFG_2$.

A method is provided for making a macrocyclic peptide-containing molecule, the method comprising the steps of:

a. providing a nucleic acid molecule encoding for a polypeptide of structure:

$$(AA)_m\text{-}Z\text{-}(AA)_n\text{-}INT \tag{I}$$

or

$$(AA)_m\text{-}Z\text{-}(AA)_n\text{-}INT\text{-}(AA)_p \tag{II}$$

wherein:
i. $(AA)_m$ is a N-terminal amino acid or peptide sequence,
ii. Z is an amino acid carrying a side-chain functional group $FG_1$, said $FG_1$ being a functional group selected from the group consisting of alkynyl (—C≡CR'), azido (—$N_3$), alkoxyamino (—ONR'$_2$), hydrazino (—NR'NR'$_2$), hydrazido (—CONR'NR'$_2$), carbonyl (—CO—R'), alkenyl (—CR'═CR'$_2$), phosphine (—PR'$_2$), thiol (—SR'), selenyl (—SeR'), tetrazole, tetrazine, aziridine, 2H-azirine, norbornadiene, boronaryl (Ar—B(OH)$_2$), and bromoaryl (Ar—Br), iodoaryl (Ar—I) groups, where R' is a hydrogen, alkyl or aryl group and Ar is an aryl group,
iii. $(AA)_n$ is a target peptide sequence,
iv. INT is an intein, and
v. $(AA)_p$ is a peptide sequence fused to the C-terminus of the intein;
b. introducing the nucleic acid molecule into an expression system and expressing the nucleic acid molecule, thereby producing the polypeptide; and
c. providing a chemical species of formula

$$cFG_1\text{-}cFG_2 \tag{III}$$

or

$$cFG_1\text{-}L\text{-}cFG_2 \tag{IV}$$

or a salt thereof, wherein:
i. $cFG_1$ is a functional group selected from the group consisting of alkynyl (—C≡CR'), azido (—$N_3$), alkoxyamino (—ONR'$_2$), hydrazino (—NR'NR'$_2$), hydrazido (—CONR'NR'$_2$), carbonyl (—CO—R'), alkenyl (—CR'═CR'$_2$), phosphine (—PR'$_2$), thiol (—SR'), selenyl (—SeR'), tetrazole, tetrazine, aziridine, dihydroazirine, norbornadiene, boronaryl (Ar—B(OH)$_2$), bromoaryl (Ar—Br), and iodoaryl (Ar—I) groups, where R' is a hydrogen, alkyl or aryl group and Ar is an aryl group,
ii. $cFG_2$ is a functional group selected from the group consisting of alkoxyamino (—ONR'$_2$), hydrazino (—NR'NR'$_2$), hydrazido (—CONR'NR'$_2$), thiol (—SR'), selenyl (—SeR'), phenyl-methanethiol, phenyl-methaneselenol, aryl-methanethiol, aryl-methaneselenol, 2-amino-benzene-thiol, 2-amino-benzene-selenol, 2-amino-aryl-thiol, 2-amino-aryl-selenol, (2-aminophenyl)-methanethiol, (2-aminophenyl)-methaneselenol, (2-aminoaryl)-methanethiol, (2-aminoaryl)-methaneselenol, N-alkyl-(2-aminophenyl)-methanethiol, N-alkyl-(2-aminophenyl)-methaneselenol, N-alkyl-(2-aminoaryl)-methanethiol, N-alkyl-(2-aminoaryl)-methaneselenol, where R' is a hydrogen, alkyl or aryl group, and
iii. L is linker group selected from the group consisting of aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, aryloxy groups; and
d. contacting the polypeptide with the chemical species for a time and under conditions to allow a covalent bond-forming reaction between $FG_1$ and $cFG_1$ and a covalent bond-forming reaction between $FG_2$ and $cFG_2$ to occur, thereby producing the macrocyclic peptide-containing molecule.

According to the method, $(AA)_m$ is a N-terminal sequence consisting of one or more amino acids, where AA corresponds to a generic amino acid residue and m corresponds to the number of amino acid residues composing such sequence. $(AA)_m$ is also referred to as 'N-terminal tail'; Z is an amino acid carrying a side-chain functional group $FG_1$. $(AA)_n$ is a peptide sequence of variable length (also referred to as 'target peptide sequence'), where AA corresponds to a generic amino acid residue and n corresponds to the number of amino acid residues composing such peptide sequence; INT is an intein; $(AA)_p$ is an optional peptide sequence fused to the C-terminus of the intein, where AA corresponds to a generic amino acid residue and p corresponds to the number of amino acid residues composing such peptide sequence. Expressing the nucleic acid molecule in the expression system produces a polypeptide of general structure (I) or (II) (also referred to as 'biosynthetic precursor'). When a chemical species is provided of general formula $cFG_1$-$cFG_2$ (III) or $cFG_1$-L-$cFG_2$ (IV) (also referred to as 'synthetic precursor') or a salt of said chemical species wherein: $cFG_1$ is a functional group that can form a covalent bond with the side-chain functional group $FG_1$ of Z under certain reaction conditions, $cFG_2$ is a nucleophilic functional group that can react with a thioester or ester group via nucleophilic substitution, L is a linker organic structure connecting $cFG_1$ and $cFG_2$; contacting the biosynthetic precursor with the synthetic precursor produces a macrocyclic peptide-containing molecule.

One embodiment of the method is schematically presented in FIG. 1. The reactivity of the biosynthetic precursor is conferred by the presence of $FG_1$ carried by the amino acid preceding the peptide target sequence, and by the presence of an electrophilic thioester or ester bond (also referred to herein as $FG_2$) at the junction between the target peptide sequence and the intein, which is formed via reversible, intein-catalyzed N→S or N→O acyl transfer (FIG. 1). A thioester bond is formed when the N-terminal amino acid of the intein is a cysteine, while an ester bond is formed the N-terminal amino acid of the intein is a serine or a threonine. Contacting this polypeptide with a synthetic precursor which carries two functional groups, $cFG_1$ and $cFG_2$, that can react with $FG_1$ and $FG_2$, respectively, thereby forming covalent bonds with such groups, allows for the formation of a macrocyclic peptide-containing molecule featuring a peptidic moiety derived from the biosynthetic precursor and a non-peptidic moiety derived from the synthetic precursor. In the process, the intein is cleaved from the precursor polypeptide by virtue of a nucleophilic substitution at the intein-catalyzed thioester (or ester) linkage via the nucleophilic group $cFG_2$. When m of the N-terminal tail $((AA)_m)$ in the biosynthetic precursor is higher than 1, a macrocyclic peptide-containing molecule featuring a lariat backbone is produced in the reaction. When the N-terminal tail $((AA)_m)$ in the biosynthetic precursor comprise a large polypeptide such as a protein, a protein-fused macrocyclic peptide-containing molecule is produced in the reaction. Depending on (a) the nature of $FG_1$, $cFG_1$, $cFG_2$, (b) the relative rates for the $FG_1$/$cFG_1$ ligation reaction and for the $FG_2$/$cFG_2$ ligation reaction, and (c) the presence of catalysts for the $FG_1$/$cFG_1$ reaction and/or the $FG_2$/$cFG_2$ reaction, the overall reaction between the synthetic precursor and the biosynthetic precursor can proceed through two alternative pathways (path A and B, FIG. 1) leading to the same final product.

A method is also provided for making a macrocyclic peptide-containing molecule with a hybrid peptidic/non-peptidic backbone through cyclization of an intein-containing polypeptide. The method is based on an intramolecular macrocyclization reaction by action of a side-chain nucleophilic functional group $FG_3$ installed within a portion of an intein-containing polypeptide preceding the intein. $FG_3$ is a nucleophilic functional group that can react with a thioester or ester group through nucleophilic substitution at said thioester or ester group.

In one embodiment, the method comprises the steps of:
a. providing a nucleic acid molecule encoding for a polypeptide of structure:

(VII)

or

(VIII)

wherein:
i. $(AA)_m$ is a N-terminal amino acid or peptide sequence,
ii. J is an amino acid carrying a side-chain functional group $FG_3$, said $FG_3$ being a functional group selected from the group consisting of alkoxyamino (—ONR'$_2$), hydrazino (—NR'NR'$_2$), hydrazido (—CONR'NR'$_2$), thiol (—SR'), selenyl (—SeR'), phenyl-methanethiol, phenyl-methaneselenol, aryl-methanethiol, aryl-methaneselenol, 2-amino-benzene-thiol, 2-amino-benzene-selenol, 2-amino-aryl-thiol, 2-amino-aryl-selenol, (2-aminophenyl)-methanethiol, (2-aminophenyl)-methaneselenol, (2-aminoaryl)-methanethiol, (2-aminoaryl)-methaneselenol, N-alkyl-(2-aminophenyl)-methanethiol, N-alkyl-(2-aminophenyl)-methaneselenol, N-alkyl-(2-aminoaryl)-methanethiol, N-alkyl-(2-aminoaryl)-methaneselenol, where R' is a hydrogen, alkyl or aryl group,
iii. $(AA)_n$ is a target peptide sequence,
iv. INT is an intein, and
v. $(AA)_p$ is a peptide sequence fused to the C-terminus of the intein;
b. introducing the nucleic acid molecule into an expression system and expressing the nucleic acid molecule in the expression system, thereby producing the polypeptide; and
c. allowing the polypeptide self-processing biosynthetic precursor to undergo cyclization, thereby producing the macrocyclic peptide-containing molecule.

According to the method, $(AA)_m$ is a N-terminal sequence consisting of one or more amino acids, where AA corresponds to a generic amino acid residue and m corresponds to the number of amino acid residues composing such sequence. $(AA)_m$ is also referred to as 'N-terminal tail'; J is an amino acid carrying a side-chain functional group $FG_3$, where said functional group $FG_3$ is a nucleophilic functional group that can react with a thioester or ester group through nucleophilic substitution at said thioester or ester group. $(AA)_n$ is a peptide sequence of variable length (also referred to as 'target peptide sequence'), where AA corresponds to a generic amino acid residue and n corresponds to the number of amino acid residues composing such peptide sequence; INT is an intein; $(AA)_p$ is an optional peptide sequence fused to the C-terminus of the intein, where AA corresponds to a generic amino acid residue and p corresponds to the number of amino acid residues composing such peptide sequence. When an expression system is provided and the nucleic acid molecule is expressed in the expression system, a polypeptide is produced of general structure (VII) or (VIII) (also referred to herein as 'self-processing biosynthetic precursor'). When the self-processing biosynthetic precursor is allowed to undergo cyclization via intramolecular nucleophilic attack of the functional group $FG_3$ on the thioester or ester bond formed at the junction between the intein and the target peptide sequence, a macrocyclic peptide-containing molecule is thereby produced.

A schematic representation of one embodiment of the method is presented in FIG. 2. The ability of a self-processing biosynthetic precursor to undergo an intramolecular cyclization reaction is provided by the presence of the nucleophilic group $FG_3$ in the portion of the polypeptide preceding the intein and the formation of an electrophilic thioester or ester bond ($FG_2$) formed at the junction between the target peptide sequence and the intein via intein-catalyzed N→S or N→O acyl transfer (FIG. 2). A thioester bond is formed when the N-terminal amino acid of the intein is a cysteine, while an ester bond is formed the N-terminal amino acid of the intein is a serine or a threonine. The intramolecular intein-mediated ligation reaction leads to the formation of a macrocyclic peptide-containing molecule featuring a hybrid peptidic/non-peptidic backbone, where the side-chain of the amino acid J constitutes the non-peptidic portion of such backbone. When m of the N-terminal tail (($AA)_m$) in the self-processing biosynthetic precursor is higher than 1, a macrocyclic peptide-containing molecule featuring a lariat backbone is produced in the reaction. When the N-terminal tail (($AA)_m$) in the self-processing biosynthetic precursor comprise a large polypeptide such as a protein, a protein-fused macrocyclic peptide-containing molecule is produced in the reaction.

A first advantage of the methods disclosed herein is that they provide a highly modular approach for the preparation of macrocyclic peptide-containing molecules, which offers multiple opportunities for a structural and functional diversification of these compounds, namely through variation of the length and composition of the N-terminal tail (($AA)_m$), of the nature of Z (or J), of the length and composition of the target peptide sequence (($AA)_n$), of the structure of the synthetic precursor, and of the type of chemical linkages formed between $FG_1$ and $cFG_1$, between $FG_2$ and $cFG_2$, and between $FG_3$ and $FG_2$. For example, depending on the size of the N-terminal tail (($AA)_m$), cyclic (m=0 or 1), lariat (e.g., m=2-30), or protein-fused (e.g., m>30) macrocyclic peptide-containing molecules can be obtained through these methods.

A second advantage of the methods disclosed herein is that they allow for combining the advantages of combinatorial biological methods with the advantages of combinatorial synthetic methods to generate vast libraries of diverse and conformationally constrained ligands. These ligands can be screened to identify compounds that can modulate, inhibit or promote interactions between biomolecules, such as enzymes, proteins, and nucleic acids.

A third advantage of the methods disclosed herein is to allow for the preparation of macrocyclic peptide-containing molecules fused to a genetically encoded affinity tag, DNA-binding protein/peptide, protein-binding protein/peptide, fluorescent protein, or enzyme, which is possible via the introduction of one or more of these elements within the N-terminal tail of the biosynthetic precursor or the self-processing biosynthetic precursor. These tags/proteins/enzymes can be used to facilitate the purification and/or immobilization of said macrocyclic peptide-containing molecules for functional screening. This feature of the method also allows for the application of display technologies known in the art (e.g., phage display, yeast display, plasmid display, anchored periplasmic display) for the functional screening of these molecules in a high-throughput manner.

A fourth advantage of the methods disclosed herein is that they produce peptide-containing molecules whose conformational flexibility is restrained by virtue of a cyclic structure and which feature a hybrid peptidic/non-peptidic backbone. These features can confer these molecules with advantageous properties (e.g., enhanced binding affinity, increased stability against proteolysis, and/or more favorable membrane-crossing properties) not only compared to linear peptides but also to end-to-tail cyclic peptides.

A fifth advantage of the methods disclosed herein is that the production of the macrocyclic peptide-containing molecules can be carried out under physiological conditions (e.g., in aqueous buffer, neutral pH, physiological temperature).

A sixth advantage of the methods disclosed herein is that the production of the macrocyclic peptide-containing molecules relies on reactions that are bioorthogonal or significantly bioorthogonal, thus allowing for the preparation of these molecules in complex biological media (e.g., inside a cell, in cell lysate) and in the presence of biological molecules (proteins, nucleic acids, cell metabolites) and biological material. One important implication of this is that the production of macrocyclic peptide-containing molecules according to the methods disclosed herein can be coupled to one of the several techniques known in the art for the display and high-throughput screening of biological peptide libraries.

A seventh advantage of the methods disclosed herein is that they can be scaled up to allow for the synthesis and isolation of milligram amounts of a particular macrocyclic peptide-containing molecule. These amounts are typically sufficient for a characterization of the biological activity of a compound (e.g., in an ELISA assay).

Inteins are polypeptides that are found as in-frame insertions in various natural proteins and can undergo a self-catalyzed intramolecular rearrangement leading to self-excision (self-splicing) of the intein and ligation of the flanking polypeptides together. Inteins contain a N-terminal cysteine, serine, or threonine and can catalyze, as part of the mechanism leading to self-splicing, a reversible N(backbone)→S (side-chain) or a N(backbone)→O(side-chain) acyl transfer at the junction between the intein and a polypeptide fused the N-terminus of the intein. The ability of inteins to catalyze such N→S or N→O acyl transfer reactions, thereby forming an electrophilic thioester or ester bond at the N-terminal junction, is exploited within this invention to form a covalent bond between the synthetic precursor and the peptidic backbone of the biosynthetic precursor or between the side chain and the peptidic backbone of the self-processing biosynthetic precursor. While intein-mediated ligation has been used in the past to ligate two linear polypeptides (e.g., in Expressed Protein Ligation) or a small molecule to a protein, its exploitation for generating macrocyclic peptide-containing molecules according to the general methods of FIG. 1 and FIG. 2 is provided herein.

Nucleotide sequences encoding for intein domains that can be used for preparing the biosynthetic precursors and self-processing biosynthetic precursors within the invention can be derived from naturally occurring inteins and engineered variants thereof. A rather comprehensive list of such inteins is provided by the Intein Registry neb.com/neb/inteins.html). Inteins that can be used within the invention include any of the naturally occurring inteins from organisms belonging to the Eucarya, Eubacteria, and Archea. Among these, inteins of the GyrA group (e.g., Mxe GyrA, Mfl GyrA, Mgo GyrA, Mkas GyrA, Mle-TN GyrA, Mma GyrA), DnaB group (e.g., Ssp DnaB, Mtu-CDC1551 DnaB, Mtu-H37Rv DnaB, Rma DnaB), RecA group (e.g., Mtu-H37Rv RecA, Mtu-So93 RecA), RIR1 group (e.g., Mth RIR1, Chy RIR1, Pfu RIR1-2, Ter RIR1-2, Pab RIR1-3), and Vma group (e.g., Sce Vma, Ctr Vma) are preferred and intein Mxe GyrA (SEQ ID NO:1) and the engineered 'mini Ssp DnaB ('eDnaB', SEQ ID NO:2) are particularly preferred.

In particular, natural inteins whose self-splicing mechanism has been confirmed experimentally can be used within the invention. These include Mxe GyrA (SEQ ID NO:1), Ssp eDnaB (SEQ ID NO:2), Hsp-NRC1 CDC21 (SEQ ID NO:3), Ceu ClpP (SEQ ID NO:4), Tag Pol-1 (SEQ ID NO:5), Tfu Pol-1 (SEQ ID NO:6), Tko Pol-1 (SEQ ID NO:7), Psp-GBD Pol (SEQ ID NO:8), Tag Pol-2 (SEQ ID NO:9), Thy Pol-1 (SEQ ID NO:10), Tko Pol-2 (SEQ ID NO:11), Tli Pol-1 (SEQ ID NO:12), Tma Pol (SEQ ID NO:13), Tsp-GE8 Pol-1 (SEQ ID NO:14), Tthi Pol (SEQ ID NO:15), Tag Pol-3 (SEQ ID NO:16), Tfu Pol-2 (SEQ ID NO:17), Thy Pol-2 (SEQ ID NO:18), Tli Pol-2 (SEQ ID NO:19), Tsp-GE8 Pol-2 (SEQ ID NO:20), Pab Pol-II (SEQ ID NO:21), Mtu-CDC1551 DnaB (SEQ ID NO:22), Mtu-H37Rv DnaB (SEQ ID NO:23), Rma DnaB (SEQ ID NO:24), Ter DnaE-1 (SEQ ID NO:25), Ssp GyrB (SEQ ID NO:26), Mfl GyrA (SEQ ID NO:27), Mgo GyrA (SEQ ID NO:28), Mkas GyrA (SEQ ID NO:29), Mle-TN GyrA (SEQ ID NO:30), Mma GyrA (SEQ ID NO:31), Ssp DnaX (SEQ ID NO:32), Pab Lon (SEQ ID NO:33), Mja PEP (SEQ ID NO:34), Afu-FRR0163 PRP8 (SEQ ID NO:35), Ani-FGSCA4 PRP8 (SEQ ID NO:36), Cne-A PRP8 (SEQ ID NO:37), Hca PRP8 (SEQ ID NO:38), Pch PRP8 (SEQ ID NO:39), Pex PRP8 (SEQ ID NO:40), Pvu PRP8 (SEQ ID NO:41), Mtu-H37Rv RecA (SEQ ID NO:42), Mtu-So93 RecA (SEQ ID NO:43), Mfl RecA (SEQ ID NO:44), Mle-TN RecA (SEQ ID NO:45), Nsp-PCC7120 RIR1 (SEQ ID NO:120), Ter RIR1-1 (SEQ ID NO:46), Pab RIR1-1 (SEQ ID NO:47), Pfu RIR1-1 (SEQ ID NO:48), Chy RIR1 (SEQ ID NO:49), Mth RIR1 (SEQ ID NO:50), Pab RIR1-3 (SEQ ID NO:51), Pfu RIR1-2 (SEQ ID NO:52), Ter RIR1-2 (SEQ ID NO:53), Ter RIR1-4 (SEQ ID NO:54), CIV RIR1 (SEQ ID NO:55), Ctr VMA (SEQ ID NO:56), Sce VMA (SEQ ID NO:57), Tac-ATCC25905 VMA (SEQ ID NO:58), Ssp DnaB (SEQ ID NO:59).

Putative ('theoretical') inteins can also be used within the invention, provided they are able to catalyze the required N→S or a N→O acyl transfer reaction. This property can be established experimentally based on the ability of intein-fused polypeptides to splice in the presence of thiophenol or other thiols. These putative inteins include, but are not limited to, Gth DnaB (GenBank accession number 078411), Ppu DnaB (GenBank accession number P51333), Mfl RecA (GenBank accession number not given), Mle DnaB (GenBank accession number CAA17948.1), Mja KlbA (GenBank accession number Q58191), Pfu KlbA (PF_949263 in UMBI), Pfu IF2 (PF_1088001 in UMBI), Pho Lon (GenBank accession number Baa29538.1), Mja r-Gyr (GenBank accession number G64488), Pho RFC (GenBank accession number F71231), Pab RFC-2 (GenBank accession number C75198), Mja RtcB (GenBank accession number Q58095), Pho VMA (NT01PH1971 in Tigr), AP-APSE1 dpol (AAF03988.1 in NCBI), Bde-JEL197 RPB2 (ABC17934 in NCBI), CbP-C-St RNR (BAE47774 in NCBI), CCy Hyp1-Csp-1 (EAZ88681.1 in NCBI), CCy Hyp1-Csp-2 (ACB52109.1 in NCBI), Cne-AD PRP8 (AAX39419 in NCBI), Cth-ATCC27405 TerA (ACG65137.1 in NCBI), Ctr ThrRS (CZ284364 in NCBI), Dhan GLT1 (AAW82371.1 in NCBI), Dra Snf2 (7471820 in NCBI), Hwa MCM-3 (YP_003131067 in NCBI), Hwa PolB-1 (CAJ51833 in NCBI), Mca MupF (NP_852755 in NCBI0, Mja Klba (Q58191 in NCBI), Mja PEP (ZP_00175589 in NCBI), Mja RFC-1 (YP_659332 in NCBI), Mja RFC-3 (ABR56888.1 in NCBI), Mja RNR-1 (ACI21751.1 in NCBI), Mja RNR-2 (H64403 in NCBI), Mja rPol A" (CAJ53490 in NCBI), Mja UDP GD (ZP_01799256.1 in NCBI), MP-Be gp51 (AAR89772 in NCBI), Mtu SufB (NP_855148.1 in NCBI), Npu GyrB (ZP_01622715.1 in NCBI), Pfu RIR1-2 (ABM31270 in NCBI), Pho CDC21-2 (YP_137231 in NCBI), Pho CDC21-2 (CAJ53749.1 in NCBI), Pho LHR (ZP_06213967.1 in NCBI), Pho Pol-II (YP_001403293.1 in NCBI), Pho RadA (YP_288864 in NCBI), PI-PKoI (YP_003246437.1 in NCBI), Pko Pol-1 (ZP_06214852.1 in NCBI), Psy Fha (AAY90835 in NCBI), ShP-Sfv-5 Primase (ABY49883.1 in NCBI), Ssp DnaX (ZP_03271562.1 in NCBI), Ter DnaE-1 (YP_002730690.1 in NCBI), Ter DnaE-2 (YP_002616796 in NCBI), Ter RIR1-4 (ZP_03765843.1 in NCBI), and Tth-HB8-2 DnaE (TIGR contig:4743).

In other variations, intein sequences that can be used within the invention can be derived by fusing together the N-fragment and C-fragment of a naturally occurring split intein. Split inteins include, but are not limited to, Ssp DnaE (SEQ ID NO:60-SEQ ID NO:61), Neq Pol (SEQ ID NO:62-SEQ ID NO:63), Asp DnaE (SEQ ID NO:64-SEQ ID NO:65), Npu-PCC73102 DnaE (SEQ ID NO:66-SEQ ID NO:67), Nsp-PCC7120 DnaE (SEQ ID NO:68-SEQ ID NO:69), Oli DnaE (SEQ ID NO:70-SEQ ID NO:71), Ssp-PCC7002 DnaE (SEQ ID NO:72-SEQ ID NO:73), Tvu DnaE (SEQ ID NO:74-SEQ ID NO:75).

Intein domains suitable in the methods disclosed herein include engineered variants of natural inteins (or fusion of split inteins), which have been modified by mutagenesis in order, for example, to prevent or minimize splicing at the N-terminal or C-terminal end. Examples of these modifications include, but are not limited to, mutation of the conserved asparagine or histidine residue at the C-terminus of the intein (e.g., via substitution to an alanine) with the purpose, for example, of preventing cleavage at the C-terminus and introducing an affinity tag at the C-terminus of the intein in the biosynthetic precursor. Examples of these modifications are provided in Examples 1, 7, and 13.

This affinity tag can be useful, for example, to allow for the purification of the biosynthetic precursor (or self-processing biosynthetic precursor) after expression or to enable the immobilization of the biosynthetic precursor (or self-processing biosynthetic precursor) on a solid support such as resin bead or a surface or to remove the spliced intein after the cyclization reaction. Intein variants useful for the methods of the invention include engineered inteins whose internal endonuclease domain, which is not essential for the splicing mechanism, is removed. For example, a variant of Ssp DnaB ('eDnaB', SEQ ID NO:2) lacking the internal endonuclease domain is used within this invention for the preparation of self-processing biosynthetic precursors (see Example 13). Inteins to be comprised in the biosynthetic precursor (or self-processing biosynthetic precursors) can also be engineered with the purpose, for example, of altering the splicing properties of the intein in order to increase the efficiency of the intein-mediated ligation or in order to make the intein-mediated ligation dependent upon variation of certain parameters such as pH or temperature.

In general, any intein and engineered variant thereof which is capable of catalyzing an N→S or N→O acyl transfer at the junction with a polypeptide when fused to the C-terminus of said polypeptide can be used for the methods of the invention. Such ability can be established according to procedures known in the art such as, for example, by expressing a construct comprising a polypeptide fused to the N-terminus of the intein (or an engineered variant thereof), contacting the expressed protein to a thiol (e.g., thiophenol), and determining the occurrence of splicing via standard analytical methods (HPLC or SDS-PAGE).

In preferred embodiments, the chemical species Z comprised in the biosynthetic precursor of general formula (I) or (II) is a non-natural α-amino acid of general structure

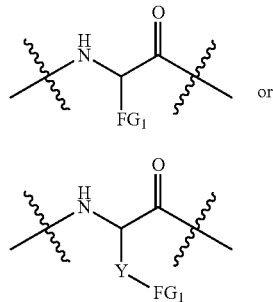

wherein:
FG$_1$ is a functional group selected from the group consisting of alkynyl (—C≡CR'), azido (—N$_3$), alkoxyamino (—ONR'$_2$), hydrazino (—NR'NR'$_2$), hydrazido (—CONR'NR'$_2$), carbonyl (—CO—R'), alkenyl (—CR'=CR'$_2$), phosphine (—PR'$_2$), thiol (—SR'), selenyl (—SeR'), tetrazole, tetrazine, aziridine, 2H-azirine, norbornadiene, boronaryl (Ar—B(OH)$_2$), bromoaryl (Ar—Br), iodoaryl (Ar—I) groups, where R' is a hydrogen, alkyl or aryl group and Ar is an aryl group. Y is an optional linker group selected from the group consisting of aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, aryloxy groups. In particular, Y is a linker group selected from the group consisting of $C_1$-$C_{24}$ alkyl, $C_1$-$C_{24}$ substituted alkyl, $C_1$-$C_{24}$ substituted heteroatom-containing alkyl, $C_1$-$C_{24}$ substituted heteroatom-containing alkyl, $C_2$-$C_{24}$ alkenyl, $C_2$-$C_{24}$ substituted alkenyl, $C_2$-$C_{24}$ substituted heteroatom-containing alkenyl, $C_2$-$C_{24}$ substituted heteroatom-containing alkenyl, $C_5$-$C_{24}$ aryl, $C_5$-$C_{24}$ substituted aryl, $C_5$-$C_{24}$ substituted heteroatom-containing aryl, $C_5$-$C_{24}$ substituted heteroatom-containing aryl, $C_1$-$C_{24}$ alkoxy, $C_5$-$C_{24}$ aryloxy groups.

In other embodiments, the chemical species Z can be an amino acid (e.g., α-, β-, γ-amino acid) or an N-substituted amino acid (e.g., N-substituted α-, β-, γ-amino acid), which carries a side-chain functional group FG$_1$ as defined above connected to the α, β or γ carbon via a linker group Y as defined above.

The chemical species Z can be introduced in the biosynthetic precursor through direct incorporation during expression of the polypeptide or generated post-translationally through enzymatic or chemical modification of the polypeptide, or by a combination of these procedures. In preferred embodiments, the chemical species Z is an unnatural amino acid and said chemical species is introduced into the biosynthetic precursor via site-directed incorporation during expression of the polypeptide (see Examples 1, 7, and 13). Several methods are known in the art for introducing an unnatural amino acid into a polypeptide which can be applied for preparing a biosynthetic precursor suitable for the methods of the invention. These include the use of the amber stop codon suppression method with engineered tRNA/aminoacyl-tRNA synthetase (AARS) pairs such as those derived from *Methanococcus jannaschii* tRNA/AARS (e.g., TyrRS/tRNA$^{Tyr}$) and *Saccharomyces cerevisiae* tRNA/AARS (e.g., AspRS/tRNA$^{Asp}$, GlnRS/tRNA$^{Gln}$, TyrRS/tRNA$^{Tyr}$, and PheRS/tRNA$^{Phe}$) ((Wu, X.; Schultz, P. G. J Am Chem Soc, 2009, 131, 12497; Wang, L.; Xie, J.; Schultz, P. G. Annu Rev Biophys Biomol Struct, 2006, 35, 225; Liu, C. C.; Schultz, P. G. Annu. Rev. Biochem., 2010, 79, 413).

Alternatively, natural or engineered frameshift suppressor tRNAs and their cognate aminoacyl-tRNA synthetases can also be used for the same purpose (Rodriguez, E. A.; Lester, H. A.; Dougherty, D. A. Proc Natl Acad Sci USA, 2006, 103, 8650; Neumann, H.; Wang, K.; Davis, L.; Garcia-Alai, M.; Chin, J. W. Nature, 2010, 464, 441; Neumann, H.; Slusarczyk, A. L.; Chin, J. W. J Am Chem Soc, 2010, 132, 2142; Anderson, J. C.; Wu, N.; Santoro, S. W.; Lakshman, V.; King, D. S.; Schultz, P. G. Proc Natl Acad Sci USA, 2004, 101, 7566). Alternatively, an unnatural amino acid can be incorporated in a polypeptide using chemically (Dedkova, L. M.; Fahmi, N. E.; Golovine, S. Y.; Hecht, S. M. Journal of the American Chemical Society, 2003, 125, 6616) or enzymatically (Bessho, Y.; Hodgson, D. R.; Suga, H. Nat Biotechnol, 2002, 20, 723) aminoacylated tRNA molecules and using a cell-free protein expression system in the presence of the aminoacylated tRNA molecules (Murakami, H.; Ohta, A.; Ashigai, H.; Suga, H. Nat Methods, 2006, 3, 357; Kourouklis, D.; Murakami, H.; Suga, H. Methods, 2005, 36, 239). Any of these methods can be used to introduce an unnatural amino acid carrying a functional group FG$_1$ into an intein-containing polypeptide for the purpose of generating a biosynthetic precursor suitable for the methods of the invention.

Examples of unnatural amino acids suitable for use in the methods of the invention as chemical species Z include, but are not limited to, para-acetyl-phenylalanine, meta-acetyl-phenylalanine, para-butyl-1,3-dione-phenylalanine, O-allyl-tyrosine, O-propargyl-tyrosine, para-azido-phenylalanine, para-borono-phenylalanine, para-bromo-phenylalanine, para-iodo-phenylalanine, 3-iodo-tyrosine, para-benzoyl-phenylalanine, para-benzoyl-phenylalanine, ε-N-allyloxycarbonyl-lysine, ε-N-propargyloxycarbonyl-lysine, ε-N-azidoethyloxycarbonyl-lysine, and ε-N-(o-azido-benzyl)-oxycarbonyl-lysine. Engineered tRNA/aminoacyl-tRNA synthetase pairs suitable for incorporating each of these unnatural amino acids into recombinant proteins are known in the art (see, e.g., Liu, C. C.; Schultz, P. G. Annu. Rev. Biochem., 2010, 79, 413) and these, among others, can be used for generating a biosynthetic precursor useful for the methods of the invention.

In specific embodiments, chemical species Z suitable for use in the methods of the invention are para-acetyl-phenylalanine, 3-fluoro-4-acetyl-phenylalanine, and O-propargyl-tyrosine (see Examples 1, 7, and 11).

In preferred embodiments, the chemical species J comprised in the self-processing biosynthetic precursor of general formula (VII) or (VIII) is a non-natural α-amino acid of general structure

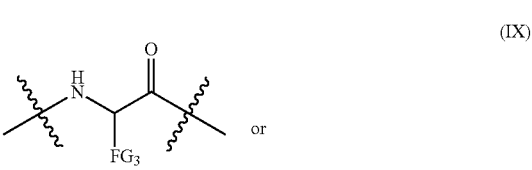

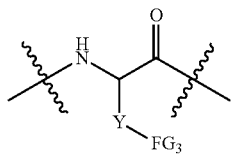

(X)

wherein:

FG₃ precursor is a functional group selected from the group consisting of alkoxyamino (—ONR'₂), hydrazino (—NR'NR'₂), hydrazido (—CONR'NR'₂), thiol (—SR'), selenyl (—SeR'), phenyl-methanethiol, phenyl-methaneselenol, aryl-methanethiol, aryl-methaneselenol, 2-amino-benzene-thiol, 2-amino-benzene-selenol, 2-amino-aryl-thiol, 2-amino-aryl-selenol, (2-aminophenyl)-methanethiol, (2-aminophenyl)-methaneselenol, (2-aminoaryl)-methanethiol, (2-aminoaryl)-methaneselenol, N-alkyl-(2-aminophenyl)-methanethiol, N-alkyl-(2-aminophenyl)-methaneselenol, N-alkyl-(2-aminoaryl)-methanethiol, N-alkyl-(2-aminoaryl)-methaneselenol, where R' is a hydrogen, alkyl or aryl group. Y is an optional linker group selected from the group consisting of aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, aryloxy groups. In particular, Y is a linker group selected from the group consisting of $C_1$-$C_{24}$ alkyl, $C_1$-$C_{24}$ substituted alkyl, $C_1$-$C_{24}$ substituted heteroatom-containing alkyl, $C_1$-$C_{24}$ substituted heteroatom-containing alkyl, $C_2$-$C_{24}$ alkenyl, $C_2$-$C_{24}$ substituted alkenyl, $C_2$-$C_{24}$ substituted heteroatom-containing alkenyl, $C_2$-$C_{24}$ substituted heteroatom-containing alkenyl, $C_5$-$C_{24}$ aryl, $C_5$-$C_{24}$ substituted aryl, $C_5$-$C_{24}$ substituted heteroatom-containing aryl, $C_5$-$C_{24}$ substituted heteroatom-containing aryl, $C_1$-$C_{24}$ alkoxy, $C_5$-$C_{24}$ aryloxy groups.

In other embodiments, the chemical species J can be an amino acid (e.g., α-, β-, γ-amino acid) or an N-substituted amino acid (e.g., N-substituted α-, β-, γ-amino acid), which carries a side-chain functional group FG₃ as defined above connected to the α, β or γ carbon via a group Y as defined above.

The chemical species J can be introduced in the self-processing biosynthetic precursor through direct incorporation during expression of the polypeptide or generated post-translationally through enzymatic or chemical modification of the polypeptide, or by a combination of these procedures.

In preferred embodiments, the chemical species J is an unnatural amino acid and said chemical species is introduced into the self-processing biosynthetic precursor via site-directed incorporation during expression of the polypeptide (see Example 13). Some of the methods known in the art for introducing an unnatural amino acid into a polypeptide have been listed above and these among others can be applied for preparing a self-processing biosynthetic precursor within the invention.

In specific embodiments, a chemical species J suitable for use in the methods of the invention is 3-amino-4-mercaptomethyl-phenylalanine (see Example 13).

The N-terminal tail, $(AA)_m$, in the biosynthetic precursor and self-processing biosynthetic precursor can be a polypeptide comprising 1 to 10,000 amino acid residues. Preferably, $(AA)_m$ consists of a polypeptide comprising 1 to 1,000 amino acid residues and, most preferably, $(AA)_m$ consists of a polypeptide comprising 1 to 600 amino acid residues.

The N-terminal tail, $(AA)_m$, in the biosynthetic precursor and self-processing biosynthetic precursor can comprise an affinity tag, a DNA-binding polypeptide, a protein-binding polypeptide, an enzyme, or a fluorescent protein. Affinity tags that can be comprised within the N-terminal tail of the biosynthetic precursor and self-processing biosynthetic precursor include, among others, a polyarginine tag (e.g., RRRRR) (SEQ ID NO:87), a polyhistidine tag (e.g., HHHHHH) (SEQ ID NO:88), an Avi-Tag (SGLNDIFEAQKIEWHELEL) (SEQ ID NO:89), a FLAG tag (DYKDDDDK) (SEQ ID NO:90), a Strep-tag II (WSHPQFEK) (SEQ ID NO:91), a c-myc tag (EQKLISEEDL) (SEQ ID NO:92), a S tag (KETAAAKFERQHMDS) (SEQ ID NO:93), a calmodulin-binding peptide (KRRWKKNFIAVSAANRFKKI-SSSGAL) (SEQ ID NO:94), a streptavidin-binding peptide (MDEKTTGWRGGHVVEGLAGELEQLRARL-EHHPQGQREP) (SEQ ID NO:95), a chitin-binding domain (SEQ ID NO:110), a glutathione S-transferase (GST), a maltose-binding protein (MBP). Affinity tags that can be comprised within the N-terminal tail of the biosynthetic precursor and self-processing biosynthetic precursor include, among others, streptavidin, thioredoxin, Dsb protein, Nus protein, a fluorescent protein (e.g., green fluorescent protein and variants thereof), M13 phage protein pVI (SEQ ID NO:76), T7 phage protein 10A (SEQ ID NO:77), T7 phage protein 10B (SEQ ID NO:78), *E. coli* NlpA (SEQ ID NO:79), *E. coli* OmpC (SEQ ID NO:80), *E. coli* FadL (SEQ ID NO:81), *E. coli* Lpp-OmpA (SEQ ID NO:82), *E. coli* PgsA (SEQ ID NO:83), *E. coli* EaeA (SEQ ID NO:84), *S. cerevisiae* Aga2p (SEQ ID NO:85), *S. cerevisiae* Flo1p (SEQ ID NO:121), human NF-κB p50 protein (SEQ ID NO:86), luciferase, alkaline phosphatase, and variants thereof. Introduction of these proteins, enzymes, or peptides within the N-terminal tail of the biosynthetic precursor and self-processing biosynthetic precursor via genetic encoding or other methods results in macrocyclic peptide-containing molecules fused to an affinity tag, a DNA-binding polypeptide, a protein-binding polypeptide, an enzyme, or a fluorescent protein. These aspects of the invention are illustrated in Examples 1, 7, 11, and 13.

In specific embodiments, the N-terminal tail, $(AA)_m$, in the biosynthetic precursor and self-processing biosynthetic precursor, comprises a polyhistidine tag (His₆), a chitin-binding domain (SEQ ID NO:110), 13 phage protein pVI (SEQ ID NO:76), T7 phage protein 10A (SEQ ID NO:77), T7 phage protein 10B (SEQ ID NO:78), *E. coli* NlpA signal sequence (SEQ ID NO:79), *S. cerevisiae* protein Aga2p (SEQ ID NO:85), *S. cerevisiae* protein Flo1p (SEQ ID NO:121), human NF-κB p50 protein (SEQ ID NO:86), an Avi-Tag (SEQ ID NO:89), or a fluorescent protein (see Examples 1, 7, 11, and 13).

The target peptide sequence, $(AA)_n$, in the biosynthetic precursor and self-processing biosynthetic precursor can be a polypeptide comprising 2 to 10,000 amino acid residues. Preferably, $(AA)_n$ consists of a polypeptide comprising 3 to 50 amino acid residues and, most preferably, $(AA)_n$ consists of a polypeptide comprising 3 to 20 amino acid residues.

The optional C-terminal peptide sequence, $(AA)_p$, in the biosynthetic precursor and self-processing biosynthetic precursor can be a polypeptide comprising 1 to 10,000 amino acid residues. Preferably, $(AA)_p$ consists of a polypeptide comprising 1 to 1,000 amino acid residues. The initial amino acid of the C-terminal peptide sequence, $(AA)_p$, should not be a cysteine, serine, or threonine. Preferably, when the biosynthetic precursor or self-processing biosynthetic precursor contains a C-terminal peptide sequence $(AA)_p$, the last amino acid residue of the intein, typically an asparagine or histidine, should be removed or mutated to an amino acid residue other than asparagine or histidine (e.g., alanine).

The optional C-terminal peptide sequence, $(AA)_p$, in the biosynthetic precursor and self-processing biosynthetic precursor can comprise an affinity tag, a DNA-binding polypeptide, a protein-binding polypeptide, an enzyme, or a fluorescent protein. Affinity tags that can be comprised within the C-terminal peptide sequence of the biosynthetic precursor and self-processing biosynthetic precursor include, among others, a polyarginine tag (e.g., RRRRR), a polyhistidine tag (e.g., HHHHHH) (SEQ ID NO:88), an Avi-Tag (SGLN-DIFEAQKIEWHELEL) (SEQ ID NO:89), a FLAG tag (DYKDDDDK) (SEQ ID NO:90), a Strep-tag II (SEQ ID NO:91), a c-myc tag (EQKLISEEDL) (SEQ ID NO:92), a S tag (KETAAAKFERQHMDS) (SEQ ID NO:93), a calmodulin-binding peptide (KRRWKKNFIAVSAANRFKKI-SSS-GAL) (SEQ ID NO:94), a streptavidin-binding peptide (MDEKTTGWRGGHVVEGLAGELEQLRARL-EHH-PQGQREP) (SEQ ID NO:95), a chitin-binding domain (SEQ ID NO:110), glutathione S-transferase (GST), a maltose-binding protein (MBP). These aspects of the invention are illustrated in Examples 1, 7, 11, and 13.

In specific embodiments, the C-terminal peptide sequence, $(AA)_p$, in the biosynthetic precursor and self-processing biosynthetic precursor comprises an affinity tag (See Examples 1, 7, 11, and 13).

Nucleic acid molecules for use according to the methods provided herein include those that encode for a polypeptide of general formula (I) or (II) or a polypeptide of general formula (VII) or (VIII). The codon encoding for the amino acid Z in the biosynthetic precursor and for the amino acid J in the self-processing biosynthetic precursor can be one of the 61 sense codons of the standard genetic code, a stop codon (TAG, TAA, TGA), or a four-base codon (e.g., AGGU, CGGG, GGGT, CTCT), with the amber stop codon (TAG) being particularly preferred (see Examples 1, 7, 11, and 13). In specific embodiments, the codon encoding for the amino acid Z in the biosynthetic precursor and for the amino acid J in the self-processing biosynthetic precursor is an amber stop codon (TAG).

Numerous methods for making nucleic acids encoding peptides of a known or random sequence are known to a person skilled in the art. For example, polynucleotides having a predetermined or random sequence can be prepared chemically by solid phase synthesis using commercially available equipments and reagents. Polynucleotides can then be amplified using a polymerase chain reaction, digested via endonucleases, and ligated together according to standard molecular biology protocols known in the art (e.g., Sambrook et al. *Molecular Cloning: A Laboratory Manual* (Third Edition), Cold Spring Harbor Press, 2001). Using these techniques, a person skilled in the art can prepare polynucleotides suitable for the preparation of biosynthetic precursors of general formula (I) or (II), and for the preparation of self-processing biosynthetic precursors of general formula (VII) or (VIII).

The biosynthetic precursors and self-processing biosynthetic precursors can be produced introducing said polynucleotides into an expression vector, introducing the resulting vectors into an expression host, and inducing the expression of the encoded polypeptides in the presence of the amino acid Y in the case of biosynthetic precursors and of the amino acid J in the case of self-processing biosynthetic precursors.

Nucleic acid molecules within the invention can be incorporated into any one of a variety of expression vectors suitable for expressing a polypeptide. Suitable vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated viruses, retroviruses and many others. Any vector that transduces genetic material into a cell, and, if replication is desired, which is replicable and viable in the relevant host can be used. A large number of expression vectors and expression hosts are known in the art, and many of these are commercially available. A person skilled in the art will be able to select suitable expression vectors for a particular application, e.g., the type of expression host (e.g., in vitro systems, prokaryotic cells such as bacterial cells, and eukaryotic cells such as yeast, insect, or mammalian cells) and the expression conditions selected.

Expression hosts that may be used for the preparation of the biosynthetic precursors and self-processing biosynthetic precursors within the invention include any systems that support the transcription, translation, and/or replication of a nucleic acid of the invention. These systems include prokaryotes such as bacteria (e.g., *Escherichia coli*) and eukaryotes such as yeast, insect, and mammalian cells. These systems also include lysates of prokaryotic cells (e.g., bacterial cells) and lysates of eukaryotic cells (e.g., yeast, insect, or mammalian cells). These systems also include in vitro transcription/translation systems, many of which are commercially available. The choice of the expression vector and host system depends on the type of application intended for the methods of the invention and a person skilled in the art will be able to select a suitable expression host based on known features and application of the different expression hosts. For example, when large amounts of the biosynthetic precursors are desired, a bacterial expression host is most suitable. As another example, when it is desired to evaluate the interaction between the macrocyclic peptide-containing molecules generated via the methods disclosed herein with a bacterial, yeast, or a human cell component, a bacterial, yeast, or a human expression host, respectively, can be used.

Methods and systems for amber stop codon suppression known in the art as listed above can be used to incorporate the amino acid Z into the biosynthetic precursor and the amino acid J into the self-processing biosynthetic precursor. In some embodiments, the biosynthetic precursors and the self-processing biosynthetic precursors are prepared by constructing nucleic acid molecules encoding for a N-terminal polypeptide sequence, an amber stop codon (TAG), a polypeptide sequence (corresponding to the target peptide sequence), an intein, and an optional polypeptide sequence. Such nucleic acid molecules are then introduced into an expression vector and the modified expression vectors are introduced into *E. coli* cells, said cells containing a system for amber stop codon suppression, said system consisting of a plasmid-encoded engineered *Methanococcus jannaschi* tRNA$^{Tyr}$/tyrosyl-tRNA synthetase (tRNA$^{Tyr}$/TyrRS) pair. The biosynthetic precursor and self-processing biosynthetic precursor are then produced via inducing the expression of the vectors in culture media supplemented with an amino acid Z (biosynthetic precursor) or J (self-processing biosynthetic precursor). These procedures are described in Examples 1, 7, 11, and 13.

In some embodiments, the synthetic precursor is a chemical species of general formula:

$$cFG_1\text{-}cFG_2 \qquad\qquad (III)$$

or

$$cFG_1\text{-}L\text{-}cFG_2 \qquad\qquad (IV)$$

or a salt of said chemical species wherein:

cFG$_1$ is a functional group selected from the group consisting of alkynyl (—C≡CR'), azido (—N$_3$), alkoxyamino (—ONR'$_2$), hydrazino (—NR'NR'$_2$), hydrazido (—CONR'NR'$_2$), carbonyl (—CO—R'), alkenyl (—CR'=CR'$_2$), phosphine (—PR'$_2$), thiol (—SR'), selenyl (—SeR'), tetrazole, tetrazine, aziridine, dihydroazirine, norbornadiene, boronaryl (Ar—B(OH)$_2$), bromoaryl (Ar—Br), iodoaryl (Ar—I) groups, where R' is a hydrogen, alkyl or aryl group and Ar is an aryl group.

cFG$_2$ precursor is a functional group selected from the group consisting of alkoxyamino (—ONR'$_2$), hydrazino (—NR'NR'$_2$), hydrazido (—CONR'NR'$_2$), thiol (—SR'), selenyl (—SeR'), phenyl-methanethiol, phenyl-methaneselenol, aryl-methanethiol, aryl-methaneselenol, 2-amino-benzene-thiol, 2-amino-benzene-selenol, 2-amino-aryl-thiol, 2-amino-aryl-selenol, (2-aminophenyl)-methanethiol, (2-aminophenyl)-methaneselenol, (2-aminoaryl)-methanethiol, (2-aminoaryl)-methaneselenol, N-alkyl-(2-aminophenyl)-methanethiol, N-alkyl-(2-aminophenyl)-methaneselenol, N-alkyl-(2-aminoaryl)-methanethiol, N-alkyl-(2-aminoaryl)-methaneselenol, where R' is a hydrogen, alkyl or aryl group.

L is an optional linker group selected from the group consisting of aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, aryloxy groups. In particular, L is a linker group selected from the group consisting of C$_1$-C$_{24}$ alkyl, C$_1$-C$_{24}$ substituted alkyl, C$_1$-C$_{24}$ substituted heteroatom-containing alkyl, C$_1$-C$_{24}$ substituted heteroatom-containing alkyl, C$_2$-C$_{24}$ alkenyl, C$_2$-C$_{24}$ substituted alkenyl, C$_2$-C$_{24}$ substituted heteroatom-containing alkenyl, C$_2$-C$_{24}$ substituted heteroatom-containing alkenyl, C$_5$-C$_{24}$ aryl, C$_5$-C$_{24}$ substituted aryl, C$_5$-C$_{24}$ substituted heteroatom-containing aryl, C$_5$-C$_{24}$ substituted heteroatom-containing aryl, C$_1$-C$_{24}$ alkoxy, C$_5$-C$_{24}$ aryloxy groups. The bioorthogonal functional group FG$_1$ in the biosynthetic precursor and cFG$_1$ in the synthetic precursor are chosen so that a chemical bond-forming reaction can occur between these functional groups under certain reaction conditions, with or without the presence of a catalyst or an initiator (e.g., light). The chemical reactivity of functional groups that can be used as FG$_1$ and as cFG$_1$ as defined above is known in the art and descriptions of such reactivity can be found, for example, in Debets, M. F.; van der Doelen, C. W.; Rutjes, F. P.; van Delft, F. L. Chembiochem, 2010, 11, 1168; Jewett, J. C.; Bertozzi, C. R. Chem Soc Rev, 2010, 39, 1272; Lim, R. K.; Lin, Q. Chem Commun (Camb), 2010, 46, 1589; Chattopadhaya, S.; Abu Bakar, F. B.; Yao, S. Q. Curr Med Chem, 2009, 16, 4527; Best, M. D. Biochemistry, 2009, 48, 6571; and van Swieten, P. F.; Leeuwenburgh, M. A.; Kessler, B. M.; Overkleeft, H. S. Org Biomol Chem, 2005, 3, 20. A skilled artisan will be able to select suitable combinations of FG$_1$ and cFG$_1$ for use of the methods of the invention based on these resources, among others, and what is generally known in the art. Examples of how synthetic precursors of general formula (III) or (IV) can be prepared are provided in Examples 2, 8, and 11.

For example, an alkynyl group (—C≡CR') and azido (—N$_3$) can be engaged in a bioorthogonal bond-forming reaction (i.e., Huisgen 1,3-dipolar cycloaddition) via the addition of Cu(I) as catalyst or using a strained alkyne (e.g., cyclooctyne). Carbonyl groups (ketone, aldehyde) can form a stable linkage (oxime or hydrazone linkage) upon reaction with an oxyamino or hydrazino (or hydrazido) group, respectively. A bioorthogonal Staudinger ligation can be carried out between a phosphine (—PR'$_2$) and an azido group. A tetrazole and an alkenyl group (—CR'=CR'$_2$) can be engaged in a bioorthogonal bond-forming reaction ('photoclick' cycloaddition) upon irradiation with 290-350 nm light. A coupling reaction between a boronaryl group (Ar—B(OH)$_2$) and a bromoaryl (Ar—Br) or iodoaryl (Ar—I) groups can be carried out using a Pd-based catalyst. A photoinduced bioorthogonal azirine ligation can be carried between a dihydroazirine (2H-azirine) and an alkenyl group (—CR'=CR'$_2$). All these functional groups and reactions, and functional equivalents thereof, can be used to mediate a ligation reaction between FG$_1$ and cFG$_1$ within the invention.

When a linker group L is included in the synthetic precursor, said L group is chosen so that, preferably, none of the substituents or functional groups comprised within this group can react with FG$_1$, FG$_2$, cFG$_1$, or cFG$_2$, or any of the side-chain functional groups in the twenty natural amino acids. Those of ordinary skill in the art can select suitable linker groups L to connect cFG$_1$ and cFG$_2$ and generate suitable synthetic precursors for use within the invention based on general knowledge in the art. Substituents or functional groups within the group L that may exhibit undesirable reactivity toward FG$_1$, FG$_2$, cFG$_1$, or cFG$_2$ can be protected using a protecting group. A large amount of information is known in the art concerning the use of protecting groups and one of ordinary skill in the art will be capable of selecting appropriate protecting groups for a given application. Such protecting groups can be removed after the cyclization reaction with the purpose of unmasking a functional group useful for labeling or further functionalizing such product.

In a specific embodiment, FG$_1$ is a terminal alkyne (—C≡CH), cFG$_1$ is an azido group (—N$_3$), and cFG$_2$ is a hydrazido group (—CONHNH$_2$). In another specific embodiment, FG$_1$ is a terminal alkyne (—C≡CH), cFG$_1$ is an azido group (—N$_3$), and cFG$_2$ is a 2-amino-benzene-methanethiol group. In another specific embodiment, FG$_1$ is a carbonyl (—CO—), cFG$_1$ is an oxyamine (—ONH$_2$), and cFG$_2$ is an aryl-methanethiol group. In another specific embodiment, FG$_1$ is a carbonyl (—CO—), cFG$_1$ is an oxyamine (—ONH$_2$), and cFG$_2$ is a 2-amino-phenyl-thiol group. In another specific embodiment, FG$_1$ is a carbonyl (—CO—), cFG$_1$ is an oxyamine (—ONH$_2$), and cFG$_2$ is a (2-amino-phenyl)-methanethiol group, where the amino group is either a primary amino group or an alkyl-substituted secondary amino group. These aspects of the invention are illustrated in Examples 2, 3, 4, 8, 9, and 11.

In some embodiments, the reactions between FG$_1$ and cFG$_1$, between FG$_2$ and cFG$_2$, and between FG$_2$ and FG$_3$ can be accelerated or promoted through the use of a chemical catalyst or a metal-based catalyst or through the use of a initiator of the reaction such as, for example, light irradiation. For example, a bond-forming reaction (i.e., Huisgen 1,3-dipolar cycloaddition) between a biosynthetic precursor where FG$_1$ is an alkyne and a synthetic precursor where cFG$_1$ is an azide can be promoted by the addiction of Cu(I) salts to the reaction or via the in situ production of Cu(I) from Cu(II) salts in the reaction mixture. The reaction between a biosynthetic precursor where FG$_1$ is a carbonyl and a synthetic precursor where cFG$_1$ is an oxyamine, hydrazine or hydrazide can be accelerated, for example, by the addiction of aniline. The reaction between FG$_2$ and cFG$_2$ or that between FG$_3$ and cFG$_2$ can be accelerated, for example, by addition of a thiol (e.g., thiophenol, sodium 2-sulfanyl-ethanesulfonate, dithiothreitol) or a selenol to the reaction. One of ordinary skill in the art will be capable of selecting appropriate catalysts or inducers to promote or accelerate the reactions between FG$_1$ and cFG$_1$, between FG$_2$ and cFG$_2$, and between FG$_2$ and FG$_3$ as defined above.

In specific embodiments, the reaction between a biosynthetic precursor where $FG_1$ is an alkyne and a synthetic precursor where $cFG_1$ is an azide is promoted by the addiction of Cu(I) salts to the reaction or via in situ production of Cu(I) from Cu(II) salts in the reaction mixture (see Examples 3, 4, 6).

In some embodiments, the reaction between the biosynthetic precursor and the synthetic precursor leading to the macrocyclic peptide-containing molecule can be performed as follows. Providing a biosynthetic precursor and a synthetic precursor carrying appropriately chosen $FG_1$ and $cFG_1$ groups, the reaction can be carried out in aqueous solvent such as a buffered aqueous solution. The solvent can contain variable amounts of organic solvents to facilitate dissolution of the synthetic precursor in the mixture. The co-solvents include but are not limited to alcohols, acetonitrile, dimethyl sulfoxide, dimethylformamide, acetone. The biosynthetic precursor can be present as free in solution, inside a cell, tethered to a cell, tethered to a bacteriophage, or tethered to a solid support. When in tethered form, the biosynthetic precursor can be tethered to a cell, a bacteriophage, or a solid support via its N-terminal tail (i.e., polypeptide preceding the amino acid Z) or via its C-terminal peptide sequence (i.e., polypeptide following the intein). The synthetic precursor can be present as free in solution or linked to a solid support. The reaction temperature will generally be in the range of 0° C. and 100° C., depending on the nature and stability of the biosynthetic precursor and synthetic precursor, preferably in the range of about 4° C. and 40° C. Depending on the nature of $FG_1$ in the biosynthetic precursor and $cFG_1$ in the synthetic precursor, a catalyst can be added to the reaction mixture to accelerate the bond-forming reaction between these groups. For example, the Huisgen alkyne/azide cycloaddition reaction between a terminal alkyne as $FG_1$ and an azide as $cFG_1$ can be accelerated via the addition of Cu(I), thereby leading to the formation of a triazole linkage. Depending on the nature of $FG_1$ and $cFG_1$, the reaction mixture can be irradiated with light at a defined wavelength to accelerate the bond-forming reaction between these groups. A thiol or a selenol catalyst can be added to the reaction mixture to accelerate the intein-mediated ligation reaction (reaction between $FG_2$ and $cFG_2$). A reducing agent such as tris-(2-carboxyethyl)phosphine)thiol (TCEP) can be added to the reaction mixture to maintain the thiol or selenol groups in the biosynthetic and/or synthetic precursor in reduced form. The cyclization reaction can be monitored via conventional analytical techniques such as HPLC, FPLC, SDS-PAGE, mass spectrometry, etc. or a combination of these techniques. After the cyclization reaction, the macrocyclic peptide-containing molecule product can be analyzed for a specific characteristic (e.g., ability to inhibit an enzyme) directly from the reaction mixture. Alternatively, such product can be purified according to conventional methods for purifying peptides and/or proteins.

In specific embodiments, the reaction between the biosynthetic precursor and the synthetic precursor is carried out within the expression host that produces the biosynthetic precursor, so that the macrocyclic peptide-containing molecule is produced within said expression host. This method comprise the steps of providing a nucleic acid encoding for the biosynthetic precursor, introducing the nucleic acid into the expression host, inducing the expression of the biosynthetic precursor and allowing for sufficient amounts of the biosynthetic precursor to be produced, introducing the synthetic precursor into the expression host, thereby producing the macrocyclic peptide-containing molecule inside the expression host. In specific embodiments, the expression host within which the macrocyclic peptide-containing molecule is produced is a living expression host (e.g., E. coli cells). This aspect of the invention is illustrated in Example 11.

In some embodiments, the macrocyclization reaction leading to the macrocyclic peptide-containing molecule from the self-processing biosynthetic precursor can be performed as follows. Providing a self-processing biosynthetic precursor, the macrocyclization reaction can be carried out in aqueous solvent such as a buffered aqueous solution. The self-processing biosynthetic precursor can be present as free in solution, inside a cell, tethered to a cell, tethered to a bacteriophage, or tethered to a solid support. When in tethered form, the self-processing biosynthetic precursor can be tethered to a cell, bacteriophage, or solid support via its N-terminal tail (i.e., polypeptide preceding the amino acid J) or via its C-terminal peptide (i.e., polypeptide following the intein). The reaction temperature will generally be in the range of 0° C. and 100° C., preferably in the range of about 2° C. and 40° C. A thiol or a selenol catalyst can be added to the reaction mixture to accelerate the macrocylization reaction (reaction between $FG_2$ and $FG_3$). A reducing agent such as tris-(2-carboxyethyl)phosphine)thiol (TCEP) can be added to the reaction mixture to maintain the thiol or selenol groups in the self-processing biosynthetic precursor in reduced form. The cyclization reaction can be monitored via conventional analytical techniques such as HPLC, FPLC, SDS-PAGE, mass spectrometry, etc. or a combination of these techniques. After the cyclization reaction, the macrocyclic peptide-containing molecule product can be analyzed for a specific characteristic (e.g., ability to inhibit an enzyme) directly from the reaction mixture. Alternatively, such product can be purified according to conventional methods for purifying peptides and/or proteins.

In specific embodiments, the macrocyclization reaction of the self-processing biosynthetic precursor is carried out within the expression host that produces said self-processing biosynthetic precursor, so that the macrocyclic peptide-containing molecule is produced within said expression host. This method comprise the steps of providing a nucleic acid encoding for the self-processing biosynthetic precursor, introducing the nucleic acid into the expression host, inducing the expression of the self-processing biosynthetic precursor, allowing for the self-processing biosynthetic precursor to cyclize, thereby producing the macrocyclic peptide-containing molecule inside the expression host. In specific embodiments, the expression host within which the macrocyclic peptide-containing molecule is produced is a living expression host (e.g., E. coli cells). This aspect of the invention is illustrated in Example 15.

A method is also provided for making a library of macrocyclic peptide-containing molecules via the reaction between a synthetic precursor and a plurality of biosynthetic precursors which contain heterogeneous peptide target sequences $(AA)_n$, heterogeneous N-terminal peptide sequences $(AA)_m$, or both. This method comprises the steps of: (a) constructing a plurality of nucleic acid molecules encoding for a plurality of biosynthetic precursors, said biosynthetic precursors having a heterogeneous target peptide sequence $(AA)_n$, a heterogeneous N-terminal peptide sequence $(AA)_m$, or both; (b) introducing each of the plurality of said nucleic acid molecules into an expression vector, and introducing the resulting vectors into an expression host; (c) expressing the plurality of biosynthetic precursors; (d) contacting the plurality of biosynthetic precursors with the synthetic precursor, thereby producing a plurality of macrocyclic peptide-containing molecules. This aspect of the invention is illustrated in Example 10.

In specific embodiments, each member of the plurality of macrocyclic peptide-containing molecules prepared from biosynthetic precursors as described above is tethered to a cell component, to a bacteriophage, to a DNA molecule, or to a solid support via a polypeptide comprised within the N-terminal tail of said peptide-containing molecules.

In another embodiment, parallel libraries of macrocyclic peptide-containing molecules are prepared by contacting a plurality of biosynthetic precursors to a plurality of synthetic precursors featuring different core structures and degree and nature of chemical functionalities appended to these core structures.

A method is also provided for making a library of macrocyclic peptide-containing molecules via macrocylization of a plurality of self-processing biosynthetic precursors which contain heterogeneous peptide target sequences $(AA)_n$, heterogeneous N-terminal peptide sequence $(AA)_m$, or both. This method comprises the steps of: (a) constructing a plurality of nucleic acid molecules encoding for a plurality of self-processing biosynthetic precursors, said self-processing biosynthetic precursors having a heterogeneous target peptide sequence $(AA)_n$, a heterogeneous N-terminal peptide sequence $(AA)_m$, or both; (b) introducing each of the plurality of said nucleic acid molecules into an expression vector, and introducing the resulting vectors into an expression host; (c) expressing the plurality of self-processing biosynthetic precursors; (d) allowing for the macrocylization to occur, thereby producing a plurality of macrocyclic peptide-containing molecules.

In specific embodiments, each of the plurality of macrocyclic peptide-containing molecules prepared from self-processing biosynthetic precursors as described above is tethered to a cell component, to a bacteriophage, to a DNA molecule, or to a solid support via a polypeptide comprised within the N-terminal tail of said peptide-containing molecules. Several methods of making polynucleotides encoding for heterogeneous peptide sequences are known in the art. These include, among many others, methods for site-directed mutagenesis (Botstein, D.; Shortle, D. Science (New York, N.Y., 1985, 229, 1193; Smith, M. Annual review of genetics, 1985, 19, 423; Dale, S. J.; Felix, I. R. Methods in molecular biology (Clifton, N. J., 1996, 57, 55; Ling, M. M.; Robinson, B. H. Analytical biochemistry, 1997, 254, 157), oligonucleotide-directed mutagenesis (Zoller, M. J. Current opinion in biotechnology, 1992, 3, 348; Zoller, M. J.; Smith, M. Methods Enzymol, 1983, 100, 468; Zoller, M. J.; Smith, M. Methods Enzymol, 1987, 154, 329), mutagenesis by total gene synthesis and cassette mutagenesis (Nambiar, K. P.; Stackhouse, J.; Stauffer, D. M.; Kennedy, W. P.; Eldredge, J. K.; Benner, S. A. Science (New York, N.Y., 1984, 223, 1299; Grundstrom, T.; Zenke, W. M.; Wintzerith, M.; Matthes, H. W.; Staub, A.; Chambon, P. Nucleic acids research, 1985, 13, 3305; Wells, J. A.; Vasser, M.; Powers, D. B. Gene, 1985, 34, 315), and the like. Additional methods are described in the following U.S. patents, PCT publications, and EPO publications: U.S. Pat. No. 5,605,793 "Methods for In vitro Recombination", U.S. Pat. No. 5,830,721 "DNA Mutagenesis by Random Fragmentation and Reassembly", WO 95/22625 "Mutagenesis by Random Fragmentation and Reassembly", WO 96/33207 "End Complementary Polymerase Chain Reaction", EP 752008 "DNA Mutagenesis by Random Fragmentation and Reassembly", WO 98/27230 "Methods and Compositions for Polypeptide Engineering", WO 00/00632, "Methods for Generating Highly Diverse Libraries", WO 98/42832 "Recombination of Polynucleotide Sequences Using Random or Defined Primers", WO 99/29902 "Method for Creating Polynucleotide and Polypeptide Sequences". Any of these methods or modifications thereof can be utilized for generating nucleotide molecules that encode for biosynthetic precursors with heterogeneous peptide target sequences $(AA)_n$, heterogeneous N-terminal peptide sequence $(AA)_m$, or both for use in the invention.

5.3 COMPOSITIONS FOR USE IN PRODUCING MACROCYCLIC COMPOUNDS WITH HYBRID PEPTIDIC/NON-PEPTIDIC BACKBONE

In one embodiment, a compound is proviced of the formula

(VII)

or

(VIII)

wherein:
i. $(AA)_m$ is a N-terminal amino acid or peptide sequence,
ii. J is an amino acid of structure:

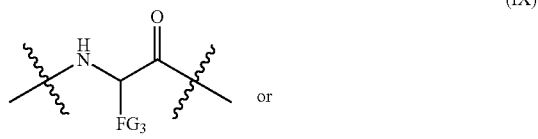

(IX)

or

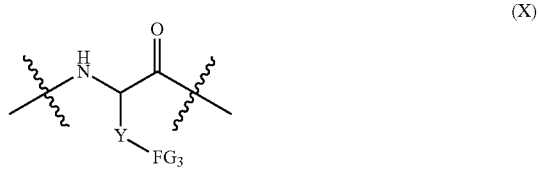

(X)

iii. $FG_3$ is a functional group selected from the group consisting of alkoxyamino (—$ONR'_2$), hydrazino (—$NR'NR'_2$), hydrazido (—$CONR'NR'_2$), thiol (—SR'), selenyl (—SeR'), phenyl-methanethiol, phenyl-methaneselenol, aryl-methanethiol, aryl-methaneselenol, 2-amino-benzene-thiol, 2-amino-benzene-selenol, 2-amino-aryl-thiol, 2-amino-aryl-selenol, (2-aminophenyl)-methanethiol, (2-aminophenyl)-methaneselenol, (2-aminoaryl)-methanethiol, (2-aminoaryl)-methaneselenol, N-alkyl-(2-aminophenyl)-methanethiol, N-alkyl-(2-aminophenyl)-methaneselenol, N-alkyl-(2-aminoaryl)-methanethiol, N-alkyl-(2-aminoaryl)-methaneselenol, where R' is a hydrogen, alkyl or aryl group,
iv. Y is a linker group selected from the group consisting of aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, aryloxy groups,
v. $(AA)_n$ is a target peptide sequence,
vi. INT is an intein, and
v. $(AA)_p$ is a peptide sequence fused to the C-terminus of the intein.

In one embodiment, Y is a linker group selected from the group consisting of $C_1$-$C_{24}$ alkyl, $C_1$-$C_{24}$ substituted alkyl, $C_1$-$C_{24}$ substituted heteroatom-containing alkyl, $C_1$-$C_{24}$ substituted heteroatom-containing alkyl, $C_2$-$C_{24}$ alkenyl, $C_2$-$C_{24}$ substituted alkenyl, $C_2$-$C_{24}$ substituted heteroatom-containing alkenyl, $C_2$-$C_{24}$ substituted heteroatom-containing alkenyl, $C_5$-$C_{24}$ aryl, $C_5$-$C_{24}$ substituted aryl, $C_5$-$C_{24}$ substituted heteroatom-containing aryl, $C_5$-$C_{24}$ substituted heteroatom-containing aryl, $C_1$-$C_{24}$ alkoxy, $C_5$-$C_{24}$ aryloxy groups.

In another embodiment, the amino acid J is 3-amino-4-mercaptomethyl-phenylalanine:

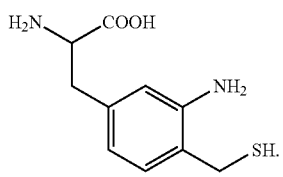

(XI)

or a salt thereof.

In certain embodiments, compound disclosed herein can be conjugated to a moiety such as a targeting agent, a drug molecule, an isotopically labeled compound, a fluorescent dye, a carrier or a solid support.

In other embodiments, derivatives of the compounds such as salts, esters, N-protected, S-protected derivatives are provided. Such derivatives can be routinely produced by one of ordinary skill in the art.

The compounds provided herein may contain one or more chiral centers. Accordingly, the compounds are intended to include racemic mixtures, diastereomers, enantiomers, and mixture enriched in one or more stereoisomer. When a group of substituents is disclosed herein, all the individual members of that group and all subgroups, including any isomers, enantiomers, and diastereomers are intended to be included in the disclosure. Additionally, all isotopic forms of the compounds disclosed herein are intended to be included in the disclosure. For example, it is understood that any one or more hydrogens in a molecule disclosed herein can be replaced with deuterium or tritium.

A skilled artisan will appreciate that starting materials, biological materials, reagents, synthetic methods, purification methods, analytical methods, assay methods, and biological methods other than those specifically exemplified can be employed in the practice of the invention. All art-known functional equivalents of any such materials and methods are intended to be included in the invention.

Unless otherwise indicated, the disclosure is not limited to specific molecular structures, substituents, synthetic methods, reaction conditions, or the like, as such may vary. It is to be understood that the embodiments are not limited to particular compositions or biological systems, which can, of course, vary.

The terms and expression that are employed herein are used as terms of description and not of limitation, and there is no intention that in the use of such terms and expressions of excluding any equivalents of the features shown and described and portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to those skilled in the art, and that such modifications and variations are considered to be within the scope of the invention as defined by the appended claims.

6. EXAMPLES

The following examples are offered by way of illustration and not by way of limitation.

6.1 Example 1

Construction and Preparation of Biosynthetic Precursors for MOrPH Synthesis Via Huisgen 1,3-Dipolar Cycloaddition/Hydrazide-Induced Splicing This example demonstrates the construction, production, and isolation of biosynthetic precursors suitable for the preparation of macrocyclic peptide-containing molecules according to a variation of the general method depicted in FIG. 1.

A series of biosynthetic precursors (Table 1) were prepared by constructing plasmids encoding for polypeptide constructs of the type $H_2N$-$(AA)_m$-OpgY-$(AA)_n$-GyrA-LEHH-HHHH (SEQ ID NO: 122), where a target sequence $(AA)_n$ of variable length (i.e., n from 4 to 12) and composition is framed between the unnatural amino acid O-propargyltyrosine (OpgY), which carries a functional group $FG_1$ in the form of a terminal alkyne, and the intein GyrA from *Mycobacterium xenopi* (Mxe GyrA). In the various constructs, the N-terminal tail was designed to correspond to a dipeptide (e.g., Met-Gly, Met-Lys), a pentapeptide (e.g., Met-Gly-Tyr-Thr-Ala) (SEQ ID NO: 123), or a protein (e.g., chitin-binding domain). The C-terminal asparagine of intein GyrA was mutated to an alanine (N198A) to prevent C-terminal splicing and allow for the introduction of a polyhistidine affinity tag at the C-terminus of the polypeptide constructs. To produce the biosynthetic precursors, the various constructs were expressed in *E. coli* cells co-expressing an engineered OpgY-specific *M. janaschii* tyrosyl-tRNA synthetase (MjTyrRS)/$tRNA_{CUA}$ ($MjtRNA_{CUA}$) pair[43] encoded by a second vector pEVOL. The latter allows for the site-selective incorporation of OpgY at the N-terminal end of the target peptide sequence via amber stop codon suppression. The unnatural amino acid O-propargyl-tyrosine was synthesized starting from N-Boc tyrosine via alkylation with propargyl bromide followed by Boc deprotection and ester hydrolysis. OpgY was added to the bacterial culture medium during expression of the biosynthetic precursors. After expression, the different polypeptide constructs were purified using Ni-affinity chromatography and their identity confirmed by MALDI-TOF. Typical expression yields for the OpgY-containing biosynthetic precursors were 30-40 mg $L^{-1}$ culture.

TABLE 1

Opg-Y containing biosynthetic precursors.

| Name | $(AA)_m$ | Z | $(AA)_n$ | Intein | $(AA)_p$ |
|---|---|---|---|---|---|
| MG4 | MG | OpgY | TGST (SEQ ID NO: 96) | Mxe GyrA (N198A) | LE(H)$_6$ SEQ ID NO: 122 |
| MG5 | MG | OpgY | TGSGT (SEQ ID NO: 97) | Mxe GyrA (N198A) | LE(H)$_6$ SEQ ID NO: 122 |

TABLE 1-continued

Opg-Y containing biosynthetic precursors.

| Name | (AA)$_m$ | Z | (AA)$_n$ | Intein | (AA)$_p$ |
|---|---|---|---|---|---|
| MG6 | MG | OpgY | TGSYGT (SEQ ID NO: 98) | Mxe GyrA (N198A) | LE(H)$_6$ SEQ ID NO: 122 |
| MG7 | MG | OpgY | TGSEYGT (SEQ ID NO: 99) | Mxe GyrA (N198A) | LE(H)$_6$ SEQ ID NO: 122 |
| MG8 | MG | OpgY | TGSAEYGT (SEQ ID NO: 100) | Mxe GyrA (N198A) | LE(H)$_6$ SEQ ID NO: 122 |
| MG10 | MG | OpgY | TGSKLAEYGT (SEQ ID NO: 101) | Mxe GyrA (N198A) | LE(H)$_6$ SEQ ID NO: 122 |
| MG12 | MG | OpgY | TGSWGKLAEYGT (SEQ ID NO: 102) | Mxe GyrA (N198A) | LE(H)$_6$ SEQ ID NO: 122 |
| Sfi-aMR | | OpgY | TKSIPPI (SEQ ID NO: 103) | Mxe GyrA (N198A) | LE(H)$_6$ SEQ ID NO: 122 |
| Sfi-bMK | | OpgY | RSTKSIPPI (SEQ ID NO: 104) | Mxe GyrA (N198A) | LE(H)$_6$ SEQ ID NO: 122 |
| Lar5 | MGYTA | OpgY | ADWGT (SEQ ID NO: 105) | Mxe GyrA (N198A) | LE(H)$_6$ SEQ ID NO: 122 |
| Lar5b | MKYI | OpgY | VRPIAT (SEQ ID NO: 106) | Mxe GyrA (N198A) | LE(H)$_6$ SEQ ID NO: 122 |
| CBD4 | Chitin-binding domain (CBD) | OpgY | TGST (SEQ ID NO: 96) | Mxe GyrA (N198A) | LE(H)$_6$ SEQ ID NO: 122 |
| CBD5 | Chitin-binding domain (CBD) | OpgY | TGSGT (SEQ ID NO: 97) | Mxe GyrA (N198A) | LE(H)$_6$ SEQ ID NO: 122 |
| CBD6 | Chitin-binding domain (CBD) | OpgY | TGSYGT (SEQ ID NO: 98) | Mxe GyrA (N198A) | LE(H)$_6$ SEQ ID NO: 122 |
| CBD8 | Chitin-binding domain (CBD) | OpgY | TGSAEYGT (SEQ ID NO: 100) | Mxe GyrA (N198A) | LE(H)$_6$ SEQ ID NO: 122 |
| CBD10 | Chitin-binding domain (CBD) | OpgY | TGSKLAEYGT (SEQ ID NO: 101) | Mxe GyrA (N198A) | LE(H)$_6$ SEQ ID NO: 122 |
| CBD12 | Chitin-binding domain (CBD) | OpgY | TGSWGKLAEYGT (SEQ ID NO: 102) | Mxe GyrA (N198A) | LE(H)$_6$ SEQ ID NO: 122 |

TABLE 1-continued

Opg-Y containing biosynthetic precursors.

| Name | $(AA)_m$ | Z | $(AA)_n$ | Intein | $(AA)_p$ |
|---|---|---|---|---|---|
| CBD5W | Chitin-binding domain (CBD) | OpgY | TGSGW (SEQ ID NO: 107) | Mxe GyrA (N198A) | LE(H)$_6$ SEQ ID NO: 122 |
| CBD8W | Chitin-binding domain (CBD) | OpgY | TGSAEYGW (SEQ ID NO: 108) | Mxe GyrA (N198A) | LE(H)$_6$ SEQ ID NO: 122 |
| CBD8K | Chitin-binding domain (CBD) | OpgY | TGSAEYGK (SEQ ID NO: 109) | Mxe GyrA (N198A) | LE(H)$_6$ SEQ ID NO: 122 |

The Chitin-binding domain (also indicated as 'CBD') corresponds to:

(SEQ ID NO: 110)
MKIEEGKLTNPGVSAWQVNTAYTAGQLVTYNGKTYKCLQPHTSLAGWEPS

NVPALWQLQNNGNNGLELRHG.

Experimental Details for Example 1. Cloning and plasmid construction. The plasmid vector pET22b(+) (Novagen) was used as cloning vector to prepare the pBP plasmids for the expression of the biosynthetic precursors. Oligonucleotides were purchased from Integrated DNA Technologies. The gene encoding for GyrA intein from *Mycobacterium xenopi*[44] and the gene encoding for the Chitin Binding Domain (CBD) of chitinase A1 from *Bacillus circulans*[45] were extracted from pTWIN-1 plasmid (New England Biolabs). After amplification by PCR, the GyrA gene (0.6 Kbp) was used as template for a second PCR reaction to fuse the sequence MG (amber stop) TSGYST (SEQ ID NO: 124) to the N-terminal cysteine of GyrA. The resulting product (0.62 Kbp) was digested with Nde I and Xho I and cloned into pET22b(+) to provide plasmid pBP_MG6 for the expression of biosynthetic precursor MG6 fused at the C-terminus to a poly-histidine tag. Genes encoding for MG4, MG5, and MG8 were prepared by PCR using pMG6 plasmid as template, and cloned into pMG6 to provide pBP_MG4, pBP_MG5, and pBP_MG8. Genes encoding for MG10 and MG12 were prepared by PCR using pMG8 plasmid as template and cloned into pMG6 to provide pBP_MG10 and pBP_MG12. Vectors for the expression of biosynthetic precursors Lar5, Lar5b, Sfi-a, Sfi-b were prepared in a similar manner. The CBD-fusion constructs were prepared by amplifying by PCR the CBD gene from *Mycobacterium* sp. using pTWIN-1 vector and by cloning the purified PCR product (0.21 Kbp) into pBP_MG4, pBP_MG5, pBP_MG6, pBP_MG8, pBP_MG10, and pBP_MG12 with Nde I and BamH I restriction enzymes to provide expression vectors pBP_CBD4, pBP_CBD5, pBP_CBD6, pBP_CBD8, pBP_CBD10, and pBP_CBD12, respectively. Using a similar procedure, vectors for the expression of the biosynthetic precursors CBD5W, CBD8W and CBD8K were prepared. In all the pBP vectors, the genes encoding for the biosynthetic precursor are under the control of an IPTG-inducible T7 promoter. The sequences of the plasmid constructs were confirmed by DNA sequencing.

Biosynthetic Precursor Expression and Purification. To express the OpgY-containing biosynthetic precursors, each of the pBP vectors was co-transformed with vector pEVOL_OpgY into BL21(DE3) *E. coli* cells. The plasmid pEVOL_OpgY encodes for an engineered *Methanococcus jannaschii* tRNA$_{CUA}$ (MjtRNA$^{CUA}$) and aminoacyl-tRNA synthetase (MjTyrRS) suitable for amber stop codon (TAG) suppression with O-propargyl tyrosine (OpgY) as described.[46] Overnight cultures were grown in LB media (ampicillin 50 mg L$^{-1}$, chloramphenicol 34 mg L$^{-1}$) and used to inoculate a 0.4 L M9 media (ampicillin 50 mg L$^{-1}$; chloramphenicol 34 mg L$^{-1}$). At OD$_{600}$=0.6, protein expression was induced by adding 0.05% L-arabinose, 0.25 mM IPTG, and 1 mM OpgY. Cultures were harvested after 16 hours (27° C.). Frozen cell pellets were resuspended in 50 mM Tris, 300 mM NaCl, 20 mM imidazole buffer (pH 7.4) and the cells lysed through sonication. After centrifugation, the cell lysate was loaded onto a Ni-NTA affinity column and the protein eluted with 50 mM Tris, 150 mM NaCl, 300 mM imidazole (pH 7.4). After pooling and concentration of the protein-containing fractions, the buffer was exchanged with potassium phosphate 50 mM, NaCl 150 mM buffer (pH 7.5) and aliquots of the protein solutions stored at −80° C. Protein concentration was determined using the extinction coefficient at 280 nm ($\epsilon_{280}$) calculated based on the protein primary sequence. The identity of the isolated proteins was confirmed by MALDI-TOF.

Synthesis of O-propargyltyrosine (OpgY) (see Scheme 1, FIG. 23a). (L)-N-tert-butoxycarbonyl-tyrosine 7 (6.0 g, 21.0 mmol) and potassium carbonate (9.0 g, 63.0 mmol) were added to a reaction flask containing anhydrous DMF (30 mL). Propargyl bromide (6.3 ml, 63.0 mmol) was added and the reaction mixture stirred at room temperature for 20 hours. The product was extracted from water (150 ml) with 2×100 ml diethyl ether, and the combined organic layers dried over magnesium sulfate. The solvent was removed under reduced pressure, yielding 8 as crude product (yellow oil, 6.8 g, 91%). Compound 8 (6.8 g, 19.04 mmol) was added to a mixture of acetyl chloride (21 mL) in methanol (180 mL) at 0° C. The reaction mixture was stirred for 4 hours while warming to room temperature. Volatiles were removed under reduced pressure yielding 9 as a crude product (yellow solid, 4.9 g, quant.). Compound 9 (4.9 g, 19.04 mmol) was added to a mixture of 2 N NaOH (42 mL) and methanol (30 mL) and the mixture stirred at room temperature. Upon complete hydrolysis as determined by TLC (2 hours), the pH was adjusted to 7.0 with concentrated HCl and the mixture was stirred overnight at 4° C. The precipitate was filtered, washed with cold water, and dried under reduced pressure overnight, yielding 10 in 98% purity as a white powder (3.3 g, 80%). $^1$H NMR (400 MHz, D$_2$O) δ 2.78 (s, 2H), 2.94 (dd, J=6.8, 22.4 Hz, 1H), 3.08 (dd, J=9.6, 20 Hz, 1H), 3.81 (dd, J=2.0, 12.8 Hz, 1H), 6.92 (d, J=8.8 Hz, 2H), 7.13 (d, J=8.4 Hz, 2H); $^{13}$C NMR (100 MHz, D$_2$O) δ 35.4, 56.0, 76.6, 78.7, 115.6, 128.5, 130.6, 156.1, 173.9. MS (ESI) calcd for C$_{12}$H$_{13}$NO$_3$ [M+H]$^+$: m/z 220.1. found: 220.3.

6.2 Example 2

Synthesis of Synthetic Precursors for MOrPH Synthesis Via Huisgen 1,3-Dipolar Cycloaddition/Hydrazide-Induced Splicing This example demonstrates the preparation of various bifunctional (azide/hydrazide) synthetic precursors suitable for the preparation of macrocyclic peptide-containing molecules according to a variation of the general method depicted in FIG. 1.

A first synthetic precursor, 1, was designed to contain an alkyl azide as cFG$_1$ and a hydrazido group (—CONHNH$_2$) as cFG2 connected through a phenyl ring (as L group). This compound was synthesized by the route in Scheme 2 (FIG. 23a). To further demonstrate the possibility of diversifying MOrPH structure by varying the nature of the synthetic precursor, synthetic precursors 3, 4, 5, and 6 (Schemes 2-5, FIGS. 23a-b) were also synthesized which are based on phenyl, biphenyl, and diphenyl scaffolds. Bi- and di-aryl structures are, among others, recurring motifs ('privileged structures') in small molecules with biological activity, including those found to inhibit protein-protein interactions. In addition to having a different core structure, these compounds also feature a varying distance between the azide and the hydrazide functional groups, increases in the order: 3 (5.5 Å), 4 (6 Å), 1 (7 Å), 5 (9-11 Å), 6 (12-15 Å) as calculated based on energy-minimized conformations of these molecules (MM2 force field).

Experimental details for Example 2. Synthesis of synthetic precursor 1 (4-(azidomethyl)benzohydrazide) (see Scheme 2, FIG. 23a). 4-(bromomethyl)benzoate (1.0 g, 4.36 mmol) and NaN$_3$ (0.851 g, 13.1 mmol) were heated to 70° C. in DMF (15 ml). The reaction was quenched with water (25 ml) and the product extracted with ethyl acetate (3×20 ml). The organic fraction was washed with brine (30 ml), dried over Na$_2$SO$_4$, and concentrated in vacuo to yield a yellow oil (0.830 g, quant.). 4-(azidomethyl)benzoate 2 (0.830 g, 4.36 mmol) was heated to reflux in EtOH (14 ml, 80° C.) in the presence of hydrazine monohydrate (3.20 ml of a 20.63 M solution), and the reaction was stirred for 5 hours. The reaction was concentrated in vacuo. Water (30 ml) was added, the product extracted with ethyl acetate (5×30 ml), dried over Na$_2$SO$_4$, and concentrated in vacuo to yield a white solid. The product was isolated by crystallization using 2:1 ethanol:ethyl acetate (0.496 g, 60%). $^1$H NMR (400 MHz, (CD$_3$)$_2$SO) δ 4.48 (s, 2H), 7.41 (d, J=8.0 Hz, 2H), 7.81 (d, J=8.0 Hz, 2H), 9.77 (br s, 1H); $^{13}$C NMR (100 MHz, (CD$_3$)$_2$SO) δ 53.6, 127.8, 128.7, 133.5, 139.1, 166.0; MS (ESI) calcd for C$_8$H$_9$N$_5$O [M+H]$^+$: m/z 192.2. found: 192.1.

Synthesis of synthetic precursor 3 (2-(azidomethyl)benzohydrazide) (see Scheme 3, FIG. 23a). 2-methylbenzoate 12 (1.00 g, 6.65 mmol), N-bromosuccinimide (1.30 g, 7.32 mmol), and benzoyl peroxide (0.032 g, 0.133 mmol) were dissolved in CCl$_4$ (10 ml) and heated to 80° C. After 5 hours, the reaction was placed in an ice-water bath, diluted with dichloromethane (50 ml), filtered, and the organic layer washed with saturated NH$_4$Cl (30 ml). The solution was dried over Na$_2$SO$_4$ and concentrated in vacuo to afford 2-(bromomethyl)benzoate 13 as a yellow oil (crude product: 1.6 g). 2-(bromomethyl)benzoate 13 (1.00 g crude, 4.36 mmol) and NaN$_3$ (0.570 g, 8.72 mmol) were dissolved in DMF (10 ml) and heated to 70° C. overnight. The reaction was quenched with water (30 ml) and the product extracted with ethyl acetate (3×30 ml). The organic layers were washed with brine (40 ml), dried over Na$_2$SO$_4$, and concentrated in vacuo to yield a yellow oil (0.665 g, 80%). 2-(azidomethyl)benzoate 14 (0.980 g, 5.13 mmol) was dissolved in ethanol (8 ml) followed by the addition of hydrazine monohydrate (3.7 ml of a 20.6 M solution). The reaction mixture was heated at reflux and stirred for 12 hours. The solution was concentrated in vacuo to remove excess ethanol. Water (30 ml) was added, the product extracted with ethyl acetate (5×20 ml), dried over Na$_2$SO$_4$, and concentrated in vacuo to yield 3 as a white solid. The product was purified by crystallization in 2:1 ethanol: ethyl acetate (0.734 g, 75%). $^1$H NMR (400 MHz, (CD$_3$)$_2$SO) δ 4.45 (br s, 2H), 4.56 (s, 2H), 7.36-7.49 (m, 4H), 9.60 (s, br, 1H). $^{13}$C NMR (100 MHz, (CD$_3$)$_2$SO) δ 51.7, 128.3, 128.6, 130.4, 130.6, 134.5, 135.3, 167.9; MS (ESI) calculated for C$_8$H$_9$N$_5$O [M+H]$^+$: m/z 192.2. found [M+H]$^+$: 192.0

Synthesis of synthetic precursor 4 (3-(azidomethyl)benzohydrazide) (Scheme 4, FIG. 23a). 3-(bromomethyl)benzoate 15 (0.500 g, 2.18 mmol) and NaN$_3$ (0.426 g, 6.55 mmol) were heated to 70° C. in DMF (7 ml) overnight. The reaction was quenched with water (15 ml) and the product extracted with ethyl acetate (3×15 ml). The organic layers were washed with brine (20 ml), dried over Na$_2$SO$_4$, and concentrated in vacuo to yield a yellow oil (0.416 g, quant.). The product was used in the next reaction without further purification. 3-(azidomethyl)benzoate 16 (0.416 g, 2.18 mmol) was heated to reflux in ethanol (9 ml, 70° C.) in the presence of hydrazine monohydrate (1.60 ml of 20.63 M solution), and the reaction was stirred for 5 hours. The reaction was then concentrated in vacuo to remove excess ethanol. Water (20 ml) was added, the product extracted with ethyl acetate (5×20 ml), dried over Na$_2$SO$_4$, and concentrated in vacuo to yield 4 as a white solid. The product was isolated by crystallization using 2:1 ethanol: ethyl acetate (0.290 g, 70%). $^1$H NMR (400 MHz, (CD$_3$)$_2$SO) δ 4.49 (s, 2H), 7.49-7.43 (m, 2H), 7.76 (d, J=6.8 Hz, 1H), 7.81 (s, 1H), 9.80 (br s, 1H); $^{13}$C NMR (100 MHz, (CD$_3$)$_2$SO) δ 53.8, 126.9, 127.6, 129.2, 131.4, 134.2, 136.4, 165.9; MS (ESI) calculated for C$_8$H$_9$N$_5$O [M+H]$^+$: m/z 192.2. found [M+H]$^+$: 192.1.

Synthesis of synthetic precursor 5 (Methyl 3'-(azido-methyl)biphenyl-4-carbohydrazide) (Scheme 5, FIG. 23a). Compound 17 (0.400 g, 1.66 mmol) was placed in ethanol (10 ml) and stirred in an ice-water bath while sodium borohydride (0.063 g, 1.66 mmol) was added. The reaction was brought to room temperature and stirred for 2 hours. The reaction was quenched with water (2 ml), diluted with a saturated NH$_4$Cl solution, and extracted with ethyl acetate. The solution was concentrated in vacuo to yield 18 as a pale orange solid (0.390 g, 99% yield). The product was used in the next step without further purification. Methyl 3'-(hydroxymethyl)bi-phenyl-4-carboxylate 18 (0.210 g, 0.867 mmol) was dissolved in dichloromethane (4 ml) and placed under argon in an ice-water bath. To this solution was added dropwise 0.870 ml of 1.0 M phosphorous tribromide in dichloromethane. The reaction was stirred at room temperature for 2.5 hours and then quenched with 1:1 saturated NaHCO$_3$:water followed by extraction with diethyl ether. The organic layer was dried over Na$_2$SO$_4$ and concentrated in vacuo to yield 19 as a white solid (0.277 g, quant. yield). The product was used for the next reaction without further purification. Methyl 3'-(bromomethyl)biphenyl-4-carboxylate 19 (0.278 g, 0.876 mmol) and sodium azide (0.113 g, 1.73 mmol) were heated to 70° C. in DMF (4 ml) overnight with vigorous stiffing. After 12 hours, the reaction was quenched with water (10 ml) and the product extracted with ethyl acetate (3×10 ml). The organic layers were washed with brine (15 ml), dried over Na$_2$SO$_4$, and concentrated in vacuo to yield 20 as a yellow oil. The product was purified by column chromatography (6:1 Hexane:ethyl acetate) to afford 3'-(azidomethyl)biphenyl-4-carboxylate as a pale orange solid (0.225 g, 92%). $^1$H NMR (400 MHz, CDCl$_3$) δ 3.94 (s, 3H), 4.42 (s, 2H), 7.34 (d, J=7.6 Hz, 1H), 7.48 (t, J=7.6 Hz, 1H), 7.55-7.60 (m, 2H), 7.66 (d, J=8.4 Hz, 2H), 8.11 (d, J=8.4 Hz, 2H). 3'-(azidomethyl)-biphenyl-4-carboxylate 20 (0.150 g, 0.561 mmol) was heated to reflux in EtOH (4 ml, 80° C.) in the presence of hydrazine monohydrate (0.96 ml of a 20.63 M solution), and the solution was left to stir overnight (12 hours). The reaction was then concentrated in vacuo to remove excess ethanol. Water (10 ml) was added, and the product extracted with ethyl acetate (5×10 ml), dried over Na$_2$SO$_4$, and concentrated in vacuo to yield 5 as a pale yellow solid. The product was isolated by crystallization in 2:1 ethanol:ethyl acetate (0.127 g, 85%). $^1$H NMR (400 MHz, (CD$_3$)$_2$SO) δ 4.51 (s, 2H), 7.39 (d, J=7.2, 1H), 7.50 (t, J=7.6, 1H), 7.68-7.75 (m, 4H), 7.91 (d, J=8.0 Hz, 2H) $^{13}$C NMR (100 MHz, (CD$_3$)$_2$SO) δ 54.0, 127.0, 127.4, 128.1, 128.5, 130.0, 132.8, 136.9, 140.0, 142.6, 165.9; MS (ESI) calculated for C$_{14}$H$_{13}$N$_5$O [M+H]$^+$: m/z 268.3. found [M+H]$^+$: 268.2

Synthesis of synthetic precursor 6 (4-((4-(azidomethyl)phenoxy)-methyl)-benzohydrazide) (see Scheme 6, FIG. 23b). 4-(hydroxylmethyl)phenol 21 (1.00 g, 8.06 mmol) was dissolved in dry DMF, then cooled in an ice-water bath. Imidazole (0.658 g, 9.67 mmol) and tert-butyldimethylsilyl chloride (1.46 g, 9.67 mmol) were added and the reaction warmed to room temperature. After 1.5 hours, the reaction was diluted with ether (50 ml) and washed with saturated NH$_4$Cl (50 ml) and brine (25 ml). The organic layer was dried over Na$_2$SO$_4$ and concentrated in vacuo to yield 22 as a yellow oil (1.82 g, 95%). $^1$H NMR (400 MHz, CDCl$_3$) δ 0.079 (s, 6H), 0.907 (s, 9H), 4.65 (s, 2H), 6.78 (d, J=8.8 Hz, 2H), 7.17 (d, J=8.8 Hz, 2H). To a solution of 22 (0.416 g, 1.75 mmol) in dry DMF (8 ml) was added 4-(bromomethyl)benzoate (0.400 g, 1.75 mmol) and potassium carbonate (0.265 g, 1.92 mmol) and the reaction mixture stirred vigorously at room temperature. After 30 hours, the mixture was diluted in water (40 ml) and extracted with diethyl ether (2×40 ml). The organic layer was dried with Na$_2$SO$_4$ and concentrated in vacuo to yield methyl 4-((4-((tert-butyldimethylsilyloxy)-methyl)phenoxy)-methyl)-benzoate as a yellow oil (0.674 g, quant). A solution of methyl 4-((4-((tert-butyldimethylsilyloxy)methyl)phenoxy)methyl)benzoate (0.674 g, 1.75 mmol) in dry THF was added with tetrabutylammonium fluoride (2.26 ml, 1.0 M solution in THF) under argon. The reaction mixture was stirred at room temperature overnight and then diluted with saturated NH$_4$Cl solution and extracted with ethyl acetate (2×40 ml). The organic fraction was dried with Na$_2$SO$_4$ and concentrated in vacuo to yield a pale yellow solid. The product was purified by column chromatography to yield 23 as a white solid (0.453 g, 95% over two steps). $^1$H NMR (400 MHz, (CD$_3$)$_2$SO) δ 3.83 (s, 3H), 4.38 (d, J=5.6 Hz, 2H), 5.03 (t, J=5.6 Hz, 1H), 5.24 (s, 2H), 6.94 (d, J=8.8 Hz, 2H), 7.20 (d, J=8.8 Hz, 2H), 7.55 (d, J=8.4 Hz, 2H), 7.95 (d, J=8.4 Hz, 2H). Methyl 4-((4-((hydroxyl-methyl)phenoxy)methyl)benzoate 23 (0.37 g, 1.35 mmol) was dissolved in dichloromethane (7 ml) under argon. To this solution was added 1.35 ml phosphorous tribromide (1.0 M in dichloromethane) dropwise in an ice-water bath. The reaction was stirred at room temperature for 2.5 hours. The reaction solution was then diluted in 1:1 sat. NaHCO$_3$:H$_2$O and extracted with dichloromethane. The organic fraction was washed with brine, dried over Na$_2$SO$_4$, and concentrated in vacuo to yield 24 as a pale yellow solid (0.450 g, 99%). Methyl 4-((4-((bromomethyl)-phenoxy)methyl)benzoate 24 (0.450 g, 1.33 mmol) and sodium azide (0.174 g, 2.67 mmol) were heated to 60° C. in DMF (5 ml) overnight with vigorous stirring. After 12 hours, the reaction was quenched with water (20 ml) and the product extracted with ethyl acetate (3×15 ml). The organic fraction was washed with brine (30 ml), dried over Na$_2$SO$_4$, and concentrated in vacuo to yield a white solid. The solid was purified by column chromatography (6:1 hexane:ethyl acetate) to afford 25 (0.337 g, 85%). $^1$H NMR (400 MHz, (CD$_3$)$_2$SO) δ 3.83 (s, 3H), 4.33 (s, 2H), 5.20 (s, 2H), 7.02 (d, J=8.4 Hz, 2H), 7.29 (d, J=8.8 Hz, 2H), 7.57 (d, J=8.0 Hz, 2H), 7.92 (d, J=8.0 Hz, 2H). Methyl 4-((4-((azidomethyl)-phenoxy)methyl)benzoate 25 (0.337 g, 1.13 mmol) was heated to reflux in ethanol (7 ml, 60° C.) in the presence of hydrazine monohydrate (0.96 ml of a 20.63 M solution), and the solution was left to stir overnight (12 hours). The reaction was then concentrated in vacuo to remove excess ethanol. Water (15 ml) was added, the product extracted with ethyl acetate (5×15 ml), dried over Na$_2$SO$_4$, and concentrated in vacuo to yield 6 as a pale yellow solid. The product was purified by crystallization using 2:1 ethanol:ethyl acetate (0.238 g, 70%). $^1$H NMR (400 MHz, (CD$_3$)$_2$SO) δ 4.31 (s, 2H), 5.14 (s, 2H), 7.01 (d, J=8.4 Hz, 2H), 7.27 (d, J=8.8 Hz, 2H), 7.48 (d, J=8.0 Hz, 2H), 7.78 (d, J=8.0 Hz, 2H); $^{13}$C NMR (100 MHz, (CD$_3$)$_2$SO) δ 53.6, 69.2, 115.4, 127.6, 127.8, 128.3, 130.5, 133.2, 140.5, 158.6, 166.1; MS (ESI) calculated for C$_{15}$H$_{15}$N$_5$O$_2$ [M+H]$^+$: m/z 298.3. found [M+H]$^+$: 298.2

6.3 Example 3

Synthesis of Macrocyclic Peptide-Containing Molecules Via Huisgen 1,3-Dipolar Cycloaddition/Hydrazide-Induced Splicing This example demonstrates how the general synthetic strategy schematically illustrated in FIG. 1 can be applied for the preparation of macrocyclic organo-peptidic hybrids. In particular, this example illustrates an embodiment of the general method of FIG. 1 where the macrocylization is carried out via a tandem Huisgen 1,3-dipolar cycloaddition/hydrazide-induced splicing reaction (FIG. 4). This example also demonstrates how macrocyclic organo-peptidic hybrids comprising peptidic moieties of varying composition and size can be prepared using this method.

An initial macrocylization reaction was carried out using synthetic precursor 1 (FIG. 3) and biosynthetic precursor MG6 (Table 1). To a buffer solution (KPi, pH 7.5) containing compound 1 and MG6, Cu(I) was added (via in situ reduction of CuSO$_4$ with sodium ascorbate) to enable a chemoselective and bioorthogonal coupling reaction to occur between the azide in the synthetic precursor and the alkyne in the biosynthetic precursor via a Cu(I)-catalyzed Huisgen 1,3-dipolar cycloaddition. After 20 minutes, the copper catalyst and excess 1 were removed by fast buffer exchange (2 min) Formation of the branched MG6-1 adduct occurred quantitatively and was followed by complete splicing of the GyrA intein after 16 hours as indicated by MALDI-TOF analysis (FIG. 5a). This was accompanied by the accumulation of the desired MOrPH product (7, m/z 1016.3) as revealed by LC-MS (FIG. 5b). In addition to the major macrocyclic product, the formation of a small amount (~20%) of the acyclic peptide H$_2$N-G(OpgY-1)TGSYGT-COOH (8, m/z: 1034.3) was also observed, indicating that hydrolysis of the MG6-1 adduct competes to a minor extent with the macrocylization process. The cyclic backbone of the predominant MOrPH product (7) was further evidenced by MS/MS analysis (FIG. 5c) which shows the occurrence of few fragments as a result of multiple ring-opening pathways leading to acylium ions of the same m/z as observed in cyclic peptides. In comparison, the minor acyclic product (8) exhibited a fragmentation pattern typical of a linear peptide (FIG. 5c).

Control experiments were carried out to confirm the mechanism and specificity of the reaction. Omitting the copper catalyst from the reaction with 1 resulted in no macrocycle formation and much reduced splicing of the intein-fusion protein (~15%, 16 hours). The reaction was then carried out using an analogue of 1 (compound 2) which carries a methyl ester in place of the hydrazide. After coupling 2 to MG6, only minimal background splicing of the MG6-2 adduct (~20%, 16 hours) was observed, which confirmed the direct involvement of the hydrazide in 1 in the macrocyclization. Finally, the regioselectivity of the Cu(I)-catalyzed azide-alkyne cycloaddition was investigated by coupling 1 (and the other synthetic precursors described later) to N-Boc-O-propargyl-tyrosine methyl ester under identical conditions used for MOrPH synthesis (50 mM KPi, pH 7.5). This reaction afforded the disubstituted 1,4-triazole product as single regioisomer as determined by $^1$H-NMR and NOE experiments, confirming the excellent regioselectivity of this reaction.[47,48] Altogether, these studies demonstrated that the assembly of the hybrid macrocycle occurred with the expected regiochemistry and according to the envisioned route, that is, via intramolecular attack of the nucleophilic hydrazide on the thioester linkage after formation of the biosynthetic precursor-synthetic precursor adduct.

We then investigated the utility of this strategy to produce structurally diverse MOrPHs by varying the target peptide sequence in the genetically encoded biosynthetic precursors. To this end, biosynthetic precursors comprising shorter (MG4, MG5) and longer (MG8, MG10, MG12) target sequences than MG6 (Table 1) were reacted with 1. The desired MOrPH product formed as the almost exclusive product (95-100%) from all the reactions except that involving MG4, which yielded a 1:1 ratio of macrocyclic and acyclic product as estimated from the corresponding LC-MS extracted ion chromatograms (FIG. 5d, top panel). Tandem mass spectrometry further confirmed the cyclic structure of all the produced MOrPHs (FIGS. 6a-c). Importantly, these results indicated that the method allowed for the efficient assembly of MOrPHs of variable ring size (FIGS. 6a-c). In these reactions, splicing of the biosynthetic precursor-synthetic precursor adduct was determined to be 90-100% in the context of MG4, MG5, and 50-75% with MG8, MG10, and MG12 after overnight incubation at room temperature (FIG. 5d, bottom panel). As observed with MG6, the Cu(I)-catalyzed alkyne/azide cycloaddition coupling proceeded quantitatively with the various biosynthetic precursors as judged from complete disappearance of the peak corresponding to the unmodified protein in MALDI-TOF spectra acquired immediately after the coupling reaction. Based on this, the percentage of MOrPH produced (FIG. 5d), and the extent of protein splicing (FIG. 5d), the overall yield for MOrPH formation in the reaction of 1 with the MG constructs was estimated to range from ~50% (MG4, MG8, MG10, MG12) to more than 80% for MG5 and MG6.

To investigate the kinetics of MOrPH formation, splicing of MG5-1 and MG10-1 adducts, which produce MOrPH almost exclusively, was monitored over time. These studies revealed that adduct splicing (and thus MOrPH formation) occurs in large part within the first two hours from the coupling reaction (FIG. 7). In contrast, high concentration of unbound 1 (50 mM) caused a negligible amount of protein splicing (over background hydrolysis) even over extended periods of time (12 hours). Overall, these results denoted the large rate acceleration in the hydrazide-induced intein splicing reaction for the intramolecular vs. intermolecular mechanism. An important consequence of this rate difference is that hydrazide-dependent splicing occurs exclusively after tethering of the synthetic precursor to the protein, providing an excellent control over the route of MOrPH formation.

To further demonstrate the applicability of the method across target peptide sequences of varying length and composition, biosynthetic precursors Sfi-a and Sfi-b (Table 1) were made react with synthetic precursor 1 according to standard reaction conditions (see Experimental Details). Also in this case, the desired MOrPH products were obtained from these reactions as determined by LC-MS (1+Sfi-a: obs. [M+H]$^+$ m/z: 1416.54 (calc. 1416.48); (1+Sfi-b: obs. [M+H]$^+$ m/z: 1631.61 (calc. 1631.73).

Experimental details for Example 3.

Reaction conditions for MOrPH synthesis via Huisgen 1,3-dipolar cycloaddition/hydrazine-induced splicing. Reactions between the synthetic precursors (SPs) and the biosynthetic precursors (BPs) were carried out at 40 μL scale by adding to a solution of BP (100 μM) in potassium phosphate buffer (50 mM, NaCl 150 mM, pH 7.5) sodium ascorbate (5 mM), the synthetic precursor (50 mM), and CuSO$_4$ (1 mM). After 15 min, TCEP and EDTA were added to a final concentration of 10 mM and 30 mM, respectively. After 5 min, the solution was diluted three-fold with potassium phosphate buffer and the unbound synthetic precursor, Cu ions, and sodium ascorbate were removed by fast desalting chromatography. The recovered protein solution (50 μL) was added with TCEP (3 mM) and incubated at room temperature until further analysis.

Analysis of the macrocyclization reactions. LC-MS analyses were carried out using an Accela U-HPLC system (Thermo Scientific, Runcorn, UK) coupled to a LTQ Velos ESI-IT mass spectrometer (Thermo Scientific, Runcorn, UK). For LC analysis, protein samples were diluted to 10 μM in 90% acetonitrile in water. Chromatographic separations were performed using a 100×4.6 mm Vydac TP 3 μm C$_4$ column (Grace) with the column maintained at 25° C., a binary mobile phase system consisting of A: water+0.1% formic acid and B: acetonitrile+0.1% formic acid, a linear gradient from 5 to 95% of B (12 min), and a flow rate of 0.5 mL/min. The extent of splicing of the BP-SP adducts after overnight incubation at room temperature was estimated based on the corresponding LC-MS chromatograms using ProMass deconvolution software for mass determination of the high molecular weight analytes (BP-SP adduct, spliced GyrA) and peak assignment. The good correlation between the percentage of protein splicing determined by LC-MS and determined by densitometry analysis (NIH Image software) of SDS-PAGE gels was established in control experiments using CBD-fusion proteins exposed to thiophenol for varying lengths of time in order to induce 20 to 90% splicing of the full-length protein (correlation coefficient ($R^2$)=0.8). Analysis of the small molecular weight products was carried out generating extracted ion extract chromatograms based on the m/z (M+H) of the macrocyclic product (m) and the acyclic product (a). The chromatograms were integrated and the area-under-the-curve (AUC) was used to estimate the relative abundance of the two species. For the time-course experiments, reactions between 1 and MG5 and between 1 and MG10 were carried out in duplicate at a 200 μL scale. Aliquots of the protein samples were removed at intervals of time, flash-frozen in dry ice, and subsequently analyzed by LC-MS as described above. MALDI-TOF analyses were carried out on a Bruker Autoflex III MALDI-TOF spectrometer.

Prior to analysis, protein samples were diluted in 50% acetonitrile in $H_2O$ (0.1% TFA) and this solution mixed with a matrix solution (10 mg/mL in 50% acetonitrile in $H_2O$ with 0.1% TFA) of α-cyano-4-hydroxycinnamic acid (CHCA) for mass determination of analytes smaller than 10 kDa and of sinapinic acid (SA) for mass determination of proteins and protein-adducts larger than 10 kDa. A linear positive (LP) mode was used for the analysis of protein with molecular weight higher than 10 kDa while smaller proteins were analyzed in reflectron positive (RP) mode.

6.4 Example 4

Synthesis of Diverse MOrPHs from Different Azide/Hydrazide Synthetic Precursors This example demonstrates how the general synthetic strategy of FIG. 1, within the variation of this method as depicted in FIG. 4, can be applied for the preparation of structurally diverse macrocyclic organo-peptidic hybrids using different bifunctional synthetic precursors.

To further demonstrate the possibility of diversifying MOrPH structure by varying the nature of the synthetic precursor, a set of azide/hydrazide synthetic precursors (compounds 3, 4, 5, 6, FIG. 3) incorporating diverse core structures (phenyl, biphenyl, diphenyl) were synthesized (See Example 2). Macrocyclization reactions involving 3, 4, 5, or 6 with biosynthetic precursors containing target sequences of varying length (MG4 to MG 12, Table 1) were performed as described for 1 (see Example 3). Formation of the desired MOrPH product was observed for all the 24 combinations tested as determined by LC-MS (FIG. 5*d*) and MS/MS analysis (FIGS. 8*a-f*), demonstrating the functionality of the method across widely different synthetic precursor structures and its versatility to afford diverse MOrPHs by varying the synthetic and peptidic portion of these structures. Analysis of the ratio of macrocycle vs. acyclic product produced in these reactions (FIG. 5*d*) indicated that the macrocyclization reaction occurred with highest efficiency (>85%) with the 5mer target sequence (MG5) and all the synthetic precursors and with the 6mer, 8mer, 10mer, and 12mer target sequences (i.e., MG6, MG8, MG10, MG12) and 1, 5, and 6. Albeit less efficiently than the latter, synthetic precursors with closely-spaced azide and hydrazide (<6 Å as in 3 and 4) were still able to drive MOrPH assembly in the context of target sequences longer than six amino acid residues. With respect to the extent of biosynthetic precursor-synthetic precursor adduct splicing, the trend observed in the reactions with 1 was reproduced in the reactions with the other four synthetic precursors as well (FIG. 5*d*).

6.5 Example 5

Synthesis of Lariat MOrPHs Via Huisgen 1,3-Dipolar Cycloaddition/Hydrazide-Induced Splicing This example demonstrates how the general synthetic strategy of FIG. 1, within the variation of this method as depicted in FIG. 4, can be applied for the preparation of diverse lariat-type macrocyclic organo-peptidic hybrids by extending the N-terminal tail in the biosynthetic precursor.

Various bioactive peptides and depsipeptides found in nature display a lariat backbone, where an N- or C-terminal tail is connected to a cyclized portion of the peptide sequence. To demonstrate the utility of the method disclosed herein to prepare MOrPHs in lariat configuration, the five azide/hydrazide synthetic precursors 1, 3-6 were made react with the biosynthetic precursor Lar5 (Table 1), which contains a pentamer N-terminal tail (MGYTA) and a pentamer target sequence (ADWGT) (SEQ ID NO:105), using the standard reactions conditions described in Example 3. Macrocyclization proceeded efficiently in all cases as indicated by the extent of splicing of the biosynthetic precursor (50-60%) as determined by SDS-PAGE, and the observation of the desired lariat MOrPH as the sole product by MALDI-TOF (FIG. 9). Similar results were obtained with the biosynthetic precursor Lar5b, which contains a different pentamer N-terminal tail (MKYI) and a different pentamer target sequence (VRPIAT) (SEQ ID NO:106). As for the MG constructs, the amino acid sequences in Lar5 and Lar5b were randomly chosen and designed to incorporate a representation of the various naturally occurring amino acids. Reaction of Lar5b with 1 yielded the desired lariat-type MOrPH (obs. $[M+H]^+$ m/z: 1565.88; calculated: 1565.67).

6.6 Example 6

Synthesis of Protein-Fused MOrPHs Via Huisgen 1,3-Dipolar Cycloaddition/Hydrazide-Induced Splicing This example demonstrates how the general synthetic strategy of FIG. 1, within the variation of this method as depicted in FIG. 4, can be applied for the preparation of diverse protein-fused macrocyclic organo-peptidic hybrids by employing biosynthetic precursors comprising an affinity tag protein (i.e., chitin-binding domain or CBD) within the N-terminal tail.

To demonstrate this aspect of the invention, nine biosynthetic precursors comprising 4mer to 12mer target sequences of randomly chosen composition (Table 1) and the chitin-binding domain (CBD) of chitinase A1 from *Bacillus circulans* within the N-terminal portion of the polypeptide were constructed and isolated (see Example 1). The CBD-containing biosynthetic precursors were made react with synthetic precursors 1 and 3-6 according to the standard reaction conditions provided in Example 3. The desired CBD-fused MOrPHs were obtained as the sole or the predominant product from most of these macrocyclization reactions, as illustrated by the representative MALDI-TOF data in FIGS. 10*a-c*. Other data are provided in Table 2. Coupling of the synthetic precursor to the CBD constructs via Cu(I)-catalyzed azide/alkyne cycloaddition proceeded with 70-100% efficiency in most cases. Compounds 1, 5, 6 exhibited highest efficiency for MOrPH synthesis as judged by the occurrence of no or little acyclic by-product. Altogether, these studies showed that the present methodology can be readily extended to afford structurally diverse MOrPHs linked to the C-terminus of a protein.

TABLE 2

MALDI-TOF data for CBD-fused MOrPH products. BP = biosynthetic precursor; SP = synthetic precursor.

| BP | SP | Observed m/z $[M + H]^+$ | Calculated m/z $[M + H]^+$ |
|---|---|---|---|
| CBD4 | 3 | 8519.2 | 8518.4 |
| CBD5 | 3 | 8575.8 | 8575.8 |
| CBD6 | 3 | 8738.3 | 8738.6 |
| CBD8 | 3 | 8938.3 | 8938.8 |
| CBD10 | 3 | 9181.3 | 9180.2 |
| CBD12 | 3 | 9423.3 | 9423.4 |

TABLE 2-continued

MALDI-TOF data for CBD-fused MOrPH products. BP = biosynthetic precursor; SP = synthetic precursor.

| BP | SP | Observed m/z [M + H]+ | Calculated m/z [M + H]+ |
|---|---|---|---|
| CBD5 | 6 | 8682.0 | 8681.6 |
| CBD6 | 6 | 8845.4 | 8844.7 |
| CBD8 | 6 | 9044.4 | 9044.9 |
| CBD10 | 6 | 9286.4 | 9286.3 |
| CBD12 | 6 | 9529.8 | 9539.5 |
| CBD5W | 1 | 8659.5 | 8658.5 |
| CBD8W | 1 | 9022.8 | 9021.9 |
| CBD8K | 1 | 8964.8 | 8965.8 |
| CBD5W | 4 | 8659.5 | 8658.5 |
| CBD8W | 4 | 9022.8 | 9021.9 |
| CBD8K | 4 | 8964.8 | 8965.8 |

6.7 Example 7

Construction and Isolation of Biosynthetic Precursors for MOrPH Synthesis Via Oxime/Intein-Mediated Ligation This example demonstrates the construction, production, and isolation of biosynthetic precursors suitable for the preparation of macrocyclic peptide-containing molecules according to a variation of the general method depicted in FIG. 1.

A series of biosynthetic precursors (Table 3) were prepared by constructing plasmids encoding for polypeptide constructs of the type $H_2N\text{-}(AA)_m\text{-}pAcF\text{-}(AA)_n\text{-}GyrA\text{-}LEHHH\text{-}HHH$, where a target sequence $(AA)_n$ of variable length (i.e. n from 4 to 20) and composition is framed between the unnatural amino acid para-acetyl-phenylalanine (pAcF), which carries a functional group $FG_1$ in the form of a ketone, and the intein Mxe GyrA. In the various constructs, the N-terminal tail was designed to correspond to either a dipeptide (e.g., Met-Gly, Met-Lys) or to a protein (e.g., chitin-binding domain, cyan fluorescent protein). The C-terminal asparagine of intein GyrA was mutated to an alanine (N198A) to prevent C-terminal splicing and allow for the introduction of a polyhistidine affinity tag at the C-terminus of the polypeptide constructs. To produce the biosynthetic precursors, the various constructs were expressed in *E. coli* cells co-expressing an engineered pAcF-specific *M. janaschii* tyrosyl-tRNA synthetase (MjTyrRS)/tRNA$_{CUA}$ (MjtRNA$_{CUA}$) pair[49] encoded by a second vector pEVOL. The latter allows for the site-selective incorporation of pAcF at the N-terminal end of the target peptide sequence via amber stop codon suppression. The unnatural amino acid pAcF was synthesized according to the route in Scheme 7 (FIG. 23b). Briefly, 4-methyl-acetophenone was subjected to benzylic bromination with NBS and AIBN, followed by alkylation with acetoamido malonate diethyl ester and potassium tertbutoxide, followed by hydrolysis/decarboxylation in HCl/dioxane to yield pAcF. pAcF was added to the bacterial culture medium during expression of the biosynthetic precursors. After expression, the different polypeptide constructs were purified using Ni-affinity chromatography and their identity confirmed by MALDI-TOF. Typical expression yields for the pAcF-containing biosynthetic precursors were 25-45 mg L$^{-1}$ culture.

TABLE 3 pAcF-containing biosynthetic precursors.

| Name | (AA)$_m$ | Z | (AA)$_n$ | Intein | (AA)$_p$ |
|---|---|---|---|---|---|
| MG5(pAcF) | MG | pAcF | TGSGT (SEQ ID NO: 97) | Mxe GyrA (N198A) | LE(H)$_6$ |
| MG6(pAcF) | MG | pAcF | TGSYGT (SEQ ID NO: 98) | Mxe GyrA (N198A) | LE(H)$_6$ |
| MG8(pAcF) | MG | pAcF | TGSAEYGT (SEQ ID NO: 100) | Mxe GyrA (N198A) | LE(H)$_6$ |
| Sfi-a(pAcF) | MR | pAcF | TKSIPPI (SEQ ID NO: 103) | Mxe GyrA (N198A) | LE(H)$_6$ |
| Sfi-b(pAcF) | MK | pAcF | RSTKSIPPI (SEQ ID NO: 104) | Mxe GyrA (N198A) | LE(H)$_6$ |
| H1 | MG | pAcF | TLDDMEEMDG (SEQ ID NO: 111) | Mxe GyrA (N198A) | LE(H)$_6$ |
| H2 | MG | pAcF | GMITLDDMEEMDGLSDF (SEQ ID NO: 112) | Mxe GyrA (N198A) | LE(H)$_6$ |
| AviG6T | Avi-Tag | pAcF | TGSYGT (SEQ ID NO: 98) | Mxe GyrA (N198A) | LE(H)$_6$ |
| CBD4(pAcF) | Chitin-binding domain (CBD) | pAcF | TGST (SEQ ID NO: 96) | Mxe GyrA (N198A) | LE(H)$_6$ |
| CBD5(pAcF) | Chitin-binding domain (CBD) | pAcF | TGSGT (SEQ ID NO: 97) | Mxe GyrA (N198A) | LE(H)$_6$ |
| CBD6(pAcF) | Chitin-binding domain (CBD) | pAcF | TGSYGT (SEQ ID NO: 98) | Mxe GyrA (N198A) | LE(H)$_6$ |
| CBD8(pAcF) | Chitin-binding domain (CBD) | pAcF | TGSAEYGT (SEQ ID NO: 100) | Mxe GyrA (N198A) | LE(H)$_6$ |
| CBD10(pAcF) | Chitin-binding domain (CBD) | pAcF | TGSKLAEYGT (SEQ ID NO: 101) | Mxe GyrA (N198A) | LE(H)$_6$ |

TABLE 3-continued pAcF-containing biosynthetic precursors.

| Name | (AA)$_m$ | Z | (AA)$_n$ | Intein | (AA)$_p$ |
|---|---|---|---|---|---|
| CBD12(pAcF) | Chitin-binding domain (CBD) | pAcF | TGSWGKLAEYGT (SEQ ID NO: 102) | Mxe GyrA (N198A) | LE(H)$_6$ |
| CBD15(pAcF) | Chitin-binding domain (CBD) | pAcF | TGSHNRWGKLAEYGT (SEQ ID NO: 113) | Mxe GyrA (N198A) | LE(H)$_6$ |
| CBD20(pAcF) | Chitin-binding domain (CBD) | pAcF | TGSYTGDQHNRWGKLA EYGT (SEQ ID NO: 114) | Mxe GyrA (N198A) | LE(H)$_6$ |
| CFP-H1 | Cyan Fluorescent Protein (CFP) | pAcF | TLDDMEEMDG (SEQ ID NO: 111) | Mxe GyrA (N198A) | LE(H)$_6$ |
| CFP-H2 | Cyan Fluorescent Protein (CFP) | pAcF | GMITLDDMEEMDGLSD F (SEQ ID NO: 112) | Mxe GyrA (N198A) | LE(H)$_6$ |
| CBD5Y(pAcF) | Chitin-binding domain (CBD) | pAcF | TGSGY (SEQ ID NO: 115) | Mxe GyrA (N198A) | LE(H)$_6$ |
| CBD5F(pAcF) | Chitin-binding domain (CBD) | pAcF | TGSGF (SEQ ID NO: 116) | Mxe GyrA (N198A) | LE(H)$_6$ |

AviTag corresponds to: MSGLNDIFEAQKIEWHELEL-RHG (SEQ ID NO:137).

The cyan fluorescent protein (CFP) corresponds to:

(SEQ ID NO: 117)
MVSKGEELFTGVVPILVELDGDVNGHKFSVSGEGEGDATYGKLTLKFICT

TGKLPVPWPTLVTTLTWGVQCFSRYPDHMKQHDFFKSAMPEGYVQERTIF

FKDDGNYKTRAEVKFEGDTLVNRIELKGIDFKEDGNILGHKLEYNYISHN

VYITADKQKNGIKANFKIRHNIEDGSVQLADHYQQNTPIGDGPVLLPDNH

YLSTQSALSKDPNEKRDHMVLLEFVTAAGITLGMDELYK.

Experimental Details for Example 7

Cloning and plasmid construction. The pBP plasmids for the expression of the pAcF-containing biosynthetic precursors were prepared by PCR amplification, followed by endonuclease digestion and cloning of the digested engineered constructs into pET22b(+) vector using procedures similar to those as described in Example 1. The sequences of the plasmid constructs were confirmed by DNA sequencing.

Biosynthetic Precursor Expression and Purification. The pAcF-containing biosynthetic precursors were expressed and purified as described for the OpgY-containing biosynthetic precursors (see Example 1), with the following modifications: (a) the expression host BL21(DE3) E. coli cells were co-transformed with the pBP vector (biosynthetic precursor-encoding vector) and vector pEVOL_pAcF which encodes for an amber stop codon suppression system specific for pAcF; (b) pAcF (2 mM) was added to the culture medium prior to IPTG induction of the expression of the biosynthetic precursor. Protein concentration was determined using the extinction coefficient at 280 nm ($\epsilon_{280}$) calculated based on the protein primary sequence. The identity of the isolated proteins was confirmed by MALDI-TOF.

Synthesis of para-acetylphenylalanine (pAcF) (see Scheme 7, FIG. 23b). 4-methyl acetophenone (10 mL, 74.5 mmol) was dissolved in 80 mL anhydrous acetonitrile in a dry flask under argon. N-bromosuccinimide (NBS) (14.6 g, 82 mmol), freshly re-crystallized from water, was added to the solution followed by addition of azo-bis-isobutyronitrile (AIBN) (1.23 g, 7.49 mmol). The reaction mixture was heated at reflux for 1.5 hour and then cooled to room temperature. Volatiles were removed in vacuo and the resulting oil was re-dissolved in 500 mL dichloromethane and washed once with 1 M HCl, twice with a saturated solution of NaHCO$_3$, and once with a saturated solution of NaCl. The organic layer was dried over MgSO$_4$ and filtered. Volatiles were removed to yield 4-bromomethyl acetophenone as a yellow oil (16.9 g). This compound (4.3 g, 20.2 mmol) was dissolved in 200 mL anhydrous ethanol in a dry flask under argon. The solution was added with diethylacetamidomalonate (4.82 g, 27.2 mmol) followed by 1 M potassium tert-butoxide in tert-butanol (24.25 mL, 24.2 mmol). The reaction mixture was stirred at reflux for 24 hours and then cooled to room temperature. The reaction was concentrated in vacuo to about 20 mL and then diluted with 50 mL cold diethylether. The off white precipitate was collected by filtration and the procedure was repeated on the filtrate solution. The combined solids were dried in vacuo to yield diethyl 2-acetamido-2-(4-acetyl-benzyl)malonate as a white solid (6.24 g, 88.3%). This compound (1.8 g, 5.2 mmol) was dissolved in 8 N HCl in dioxane and the reaction mixture was heated to reflux for 8 hour and then cooled to room temperature. Volatiles were removed in vacuo yielding p-acetylphenylalanine (7) as a light brown solid (1.25 g, quant.) $^1$H NMR (CD$_3$OD, 400 MHz): $\delta$ 2.60 (s, 3H), 3.27 (m, 1H), 3.4 (m, 1H), 4.33 (dd, J=7.2 Hz, 1H), 7.45 (d, J=8 Hz, 2H), 7.99 (d, J=8 Hz, 2H). $^{13}$C NMR (100 MHz, CD$_3$OD): $\delta$ 26.7, 37.2, 54.7, 130.1, 130.9, 137.8, 141.4, 170.9, 200.0. MS (ESI) calcd for C$_{11}$H$_{13}$NO$_3$ [M+H]$^+$: m/z 208.1. found: 208.1

6.8 Example 8

Preparation of Oxyamine/Amino-Thiol Synthetic Precursors for MOrPH Synthesis Via Oxime/Intein-Mediated Ligation This example demonstrates the preparation of various bifunctional (oxyamine/amino-thiol) synthetic precursors suitable for the preparation of macrocyclic peptide-containing molecules according to a variation of the general method illustrated in FIG. 1.

A first synthetic precursor, SP3, was designed to carry an oxyamine as $cFG_1$ and a (2-aminophenyl)-methanethiol as cFG2 connected through a —$CONH(CH_2)_4$— linker (L group) (FIG. 11). To further demonstrate the possibility of diversifying MOrPH structure by varying the nature of the synthetic precursor, synthetic precursors SP4, SP5, SP6, SP7, and SP8 (FIG. 11) were also synthesized which carry various linker moieties such as a single methylene (SP4) or a phenyl (SP5, SP6), triazole (SP8), or biphenyl (SP7) scaffold. In addition to incorporating different core structures, these compounds also feature a different spacing distance between the oxyamine and the amino/thiol functional groups and different conformational flexibility (e.g., SP3 vs. SP5 or SP5 vs. SP6).

Experimental details for Example 8. Synthesis of synthetic precursor SP3 (see Scheme 8, FIG. 23b). 4-bromomethyl-3-nitrobenzoic acid 19a (2 g, 7.69 mmol) was dissolved in tetrahydrofuran (40 mL) and the solution added with trityl mercaptan (2.34 g, 8.46 mmol) and diisopropyl ethylamine (2.8 mL, 16.14 mmol) at room temperature. The reaction mixture was stirred for 36 hours and then was quenched with a saturated solution of ammonium chloride (4 mL) followed by extraction with ethyl acetate. The organic layer was washed with brine and the solvent evaporated under reduced pressure. The residue was purified by flash chromatography using 7.5% methanol in dichloromethane to yield 20a (2.5 g, 70% yield). $^1$H NMR (CDCl$_3$, 400 MHz): δ 3.80 (s, 2H), 6.80-6.90 (m, 1H), 7.15-7.50 (m, 15H), 7.95-8.05 (m, 1H), 8.55 (s, 1H); $^{13}$C NMR (100 MHz, CDCl$_3$): δ 33.8, 68.1, 126.1, 126.5, 127.0, 128.1, 129.0, 129.6, 129.7, 130.0, 132.93, 133.5, 133.6, 139.1, 139.3, 144.0, 148.5, 163.7. MS (ESI) calcd. for $C_{27}H_{21}NO_4S$ [M+H]$^+$: m/z 456.1. found: 456.4. 3-nitro-4-((tritylthio)methyl)benzoic acid 20a (1.86 g, 3.428 mmol) was dissolved in methanol (40 mL) and the solution added with SnCl$_2$.2H$_2$O (3.85 g, 17.14 mmol). The reaction mixture was heated to 65° C. and stirred for 2 hours. The solvent was evaporated and the residue added with saturated sodium bicarbonate solution to reach pH 6 followed by extraction with ethyl acetate. The organic layer was washed with brine and evaporated under reduced pressure. The residue purified by flash chromatography using 35% ethyl acetate in hexanes to yield 21a (0.746 g, 51% yield). $^1$H NMR (CDCl$_3$, 400 MHz): δ 3.34 (s, 2H), 7.11-7.13 (m, 1H), 7.28-7.45 (m, 12H), 7.55-7.59 (m, 5H). MS (ESI) calcd. for $C_{27}H_{23}NO_2S$ [M+H]$^+$: m/z 426.5. found: 426.6. 3-amino-4-((tritylthio)methyl)benzoic acid (21a) (0.372 g, 0.875 mmol) was dissolved in CH$_2$Cl$_2$ and the solution added with t-butyl-4-aminobutoxycarbamate 11a (0.196 g, 0.962 mmol), HBTU (0.497 g, 1.31 mmol), and DIPEA (0.38 mL, 2.187 mmol) under argon. The reaction mixture was stirred at room temperature. After 3 hours, the reaction mixture was diluted with water and extracted with dichloromethane (3×30 mL). The combined organic layers were concentrated under reduced pressure and the residue was purified by flash column chromatography in 35% ethyl acetate in hexanes to give tert-butyl-4-(3-amino-4-((tritylthio)methyl)benzamido)butoxycarbamate (22a, 0.45 g, 84% yield). $^1$H NMR (CDCl$_3$, 400 MHz): δ 1.44 (s, 9H), 1.65-1.75 (m, 4H), 3.40-3.48 (q, J=6.5, 12.5 Hz, 2H), 3.64 (s, 2H), 3.85 (t, J=5.8 Hz, 2H), 6.34 (t, J=5.9 Hz, 1H), 6.95-7.04 (m, 3H), 7.20-7.26 (m, 5H), 7.28-7.33 (m, 5H), 7.47-5.72 (m, 5H); $^{13}$C NMR (75 MHz, CDCl$_3$): δ 25.2, 26.1, 28.3, 33.3, 39.5, 67.2, 81.7, 114.7, 116.6, 123.5, 125.9-131.4 (m), 135.2, 144.4, 145.4, 156.8, 167.7. MS (ESI) calcd. for $C_{36}H_{41}N_3O_4S$ [M+H]$^+$: m/z 612.8. found: 612.6. 22a (47 mg, 0.076 mmol), triisopropylsilane (31 μL, 0.152 mmol) and water (0.1 mL) were dissolved in 50% TFA in dicholoromethane (3 mL) at 0° C. under argon. The reaction mixture was stirred for an hour in ice and completion of the deprotection was monitored by thin layer chromatography. Volatiles were then removed by evaporation and the residue washed with hexanes (3×20 mL) to yield SP3. NMR (D6-DMSO, 500 MHz): δ=1.57-1.66 (m, 4H), 3.26 (dt, J=6.45 Hz, 6.15 Hz, 2H), 3.81 (s, 2H), 3.89 (t, J=6.1 Hz, 2H), 6.79 (dd, J=7.75 Hz, 1.14 Hz, 1H), 7.06 (d, J=7.85, 1H), 7.13 (d, J=1.45, 1H), 8.25 (t, J=5.9 Hz, 1H). $^{13}$C NMR (125 MHz, D6-DMSO): δ=25.18, 25.91, 30.43, 74.43, 114.39, 114.62, 122.70, 131.42, 135.47, 146.75, 167.18. MS (ESI) calcd. for $C_{12}H_{19}N_3O_2S$ $C_{11}H_{13}NO_3$ [M+H]$^+$: 270.1. found: 270.2.

Figure 23C:
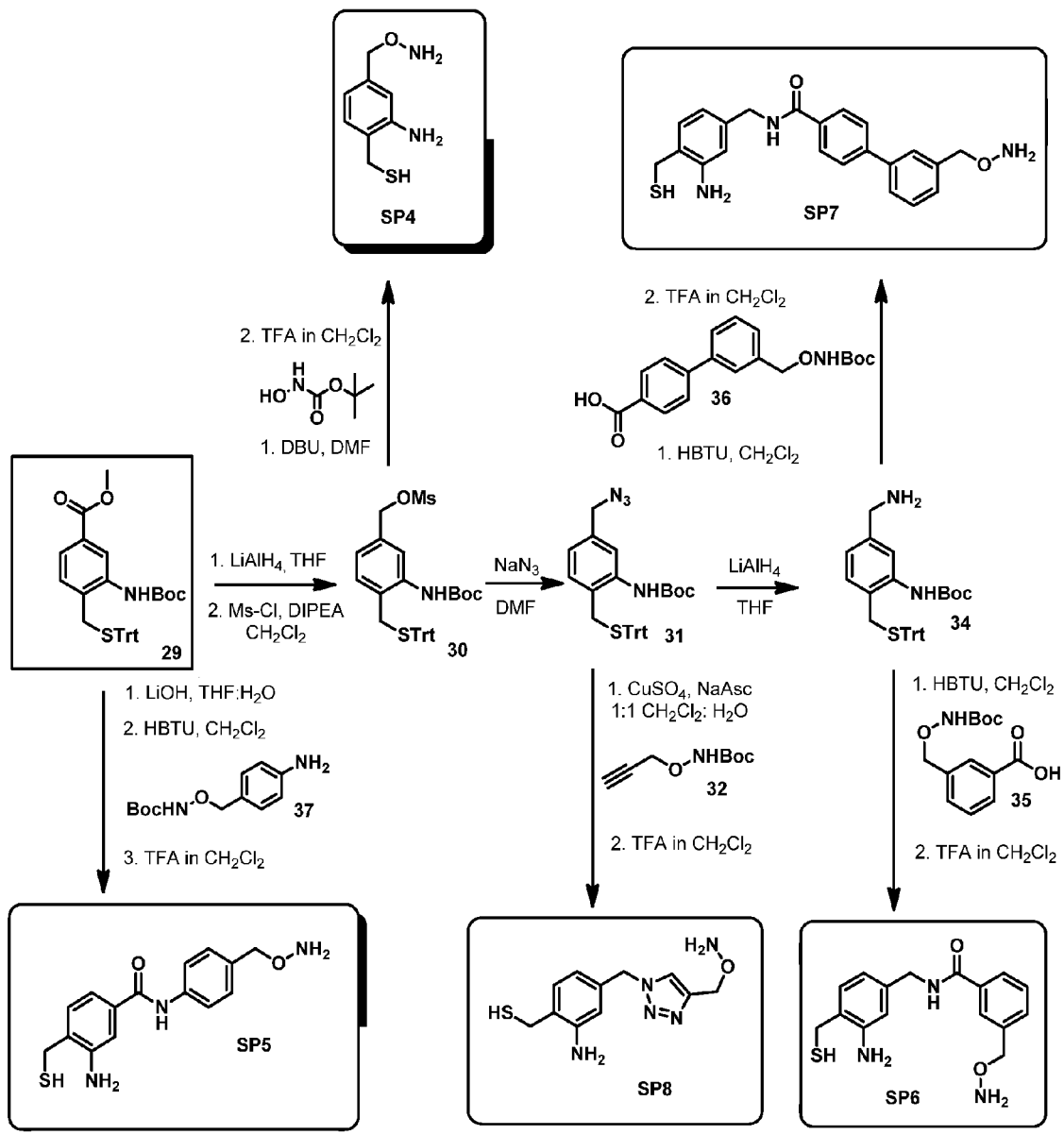

Synthesis of synthetic precursor SP4, SP5, SP6, SP7, and SP8. These compounds were synthesized according to the synthetic routes in Scheme 9 (FIG. 23c). Synthesis of SP4. Methyl 3-((tert-butoxycarbonyl)amino)-4-((tritylthio)methyl)benzoate (29) was reduced to the benzylic alcohol with lithium aluminum hydride in anhydrous THF then the resulting (5-(hydroxymethyl)-2-((tritylthio)methyl)phenyl)carbamate (9.3 g, 18.19 mmol) was dissolved in 100 mL anhydrous dichloromethane and the solution was cooled to 0° C. Methanesulfonylchloride (1.8 mL, 23.66 mmol, 1.3 eq) was added and the reaction mixture and stirred at 0° C. for 15 minutes. DIPEA (4.2 mL, 23.66 mmol, 1.3 eq) was added and the reaction stirred under argon at 0° C. for 2 hours. Following completion, the reaction mixture was dilute to 300 mL of dichloromethane, washed twice with Saturated Sodium Bicarbonate solution then once with Saturated Sodium Chloride. The organic layer was dried over magnesium sulfate and volatiles were removed to afford yellow solid (30) (9.42 g, 88% yield). The material was carried forward without further purification. $^1$H NMR (500 MHz, CDCl$_3$) δ 7.88 (s, 1H), 7.49 (d, J=7.3 Hz, 5H), 7.34 (t, J=7.7 Hz, 5H), 7.26 (d, J=14.6 Hz, 5H), 7.16 (d, J=7.8 Hz, 1H), 7.04 (d, J=9.5 Hz, 1H), 6.75 (s, 1H), 5.18 (s, 2H), 3.17 (s, 2H), 2.90 (s, 3H), 1.54 (s, 9H). $^{13}$C NMR (126 MHz, CDCl3) δ 152.85, 144.14, 137.33, 133.72, 131.28, 129.32, 128.23, 126.97, 126.26, 123.83, 121.95, 80.79, 71.27, 67.32, 38.45, 33.92, 28.40. Mesylate (30) (1.06 g, 1.8 mmol) was dissolved in 18 ml anhydrous Acetonitrile. The resulting solution was cooled to 0° C. To this solution was added tert Butyl N-Hydroxycarbamate (0.32 g, 2.4 mmol, 1.3 eq). The reaction mixture was stirred at 0° C. for 15 min. then 1,8-diazabicyclounedec-7-ene (DBU) (0.37 ml, 2.4 mmol, 1.3 eq) was slowly added. The reaction stirred at 0° C. for 1 hour and was then warmed to ambient temperature and stirred under argon overnight. Following completion volatiles were removed under reduced pressure and the resulting crude mixture was dissolved in dichloromethane and washed with Saturated K$_2$CO$_3$ solution then with Saturated Sodium Chloride Solution. The organic layer was dried over magnesium sulfate the concentrated afford a yellow oil. The crude material was purified via flash chromatography (silica gel, Hex:EtOAc) to afford an off-yellow oil (1.005 g, 89% yield). MS-ESI [M+Na]$^+$ for $C_{37}H_{42}N_2O_5S$ calculated 649.79. found 649.33; $^1$HNMR (400 MHz, CDCl$_3$) δ 7.81 (s, 1H), 7.49 (d, J=7.6 Hz, 6H), 7.32 (q, J=7.6 Hz, 6H), 7.24 (t, J=7.2 Hz, 3H), 7.13 (d, J=7.6 Hz, 2H), 7.02 (dd, J=8 Hz, 1.6 Hz, 1H), 6.74 (s, 1H), 4.79 (s, 2H), 3.17 (s, 1H), 1.54 (s, 9H), 1.46 (s, 4H); $^{13}$CNMR (126 MHz, CDCl$_3$) δ 156.58, 152.91, 144.23, 136.89, 136.29, 130.84, 129.33, 128.16, 126.86, 125.41, 124.17, 122.32, 81.61, 80.46, 77.9, 67.19, 33.95, 28.37, 27.56. The SP4 precursor was dissolved in 9 mL anhydrous dichloromethane. The resulting solution was cooled to 0° C. To this solution was added Triisopropylsilane (TIPS) (0.45 mL, 2.2 mmol) followed by the slow addition of 2 mL Trifloroacetic acid (TFA). The reaction stirred under argon at 0° C. for 30 minutes, then warmed to ambient temperature and concentrated under reduced pressure to afford an off-white solid. This solid washed with ice-cold hexanes to afford SP4 as an off-white solid (0.366 g, Quantitative yield). MS-ESI [M+H]+ for disulfide $C_{16}H_{22}N_4O_2S_2$ calculated 367.51. found 367.53

Synthesis of SP5. Methyl Ester (29) was hydrolyzed with LiOH (aq) in THF to the corresponding carboxylic acid. $^1$HNMR (400 MHz, D4-MeOH) δ 7.99 (s, 1H), 7.67 (dd, J=7.97, 1.62 Hz, 1H), 7.43 (q, J=3.13 Hz, 6H), 7.31 (t, J=7.46 Hz, 6H), 7.23 (t, J=7.31 Hz, 3H), 7.09 (d, J=8.07 Hz, 2H), 3.33 (s, 2H), 1.49 (s, 9H) The carboxylic acid (1.03 g, 2 mmol) and amine (37) (0.6195 g, 2.6 mmol, 1.3 eq) were dissolved in 4 mL anhydrous dichloromethane. To this solution was added of 2-(1H-benzotriazol-1-yl)-1,1,3,3 tetramethyluronium hexafluorophosphate (HBTU) (1.1379 g 3 mmol, 1.5 eq) then diisopropylethylamine (DIPEA) (2.6 mL, 2.5 eq). The reaction was heated to 30° C. and allowed to stir under argon for 48 hours. Following completion the reaction mixture was dilute in 100 mL DCM, and washed once with 20 mL $H_2O$, once with 20 mL saturated Sodium Bicarbonate solution then dried over magnesium sulfate. Volatiles were removed to yield crude product as red-yellow oil. This material was purified via flash chromatography (silica gel, Hex: EtOAc) to afford a yellow oil (0.536 g, 26% yield). $^1$HNMR (400 MHz, CDCl$_3$) δ 8.23 (s, 1H), 8.08 (s, 1H), 7.63 (d, J=8.4 Hz, 1H), 7.56 (dd, J=7.6, 1.2 Hz, 1H), 7.49 (d, J=7.6 Hz, 6H), 7.35 (t, J=7.6 Hz, 6H), 7.28-7.21 (m, 6H), 7.11 (s, 1H), 6.82 (s, 1H), 4.82 (s, 2H), 3.21 (s, 1H), 1.56 (s, 9H), 1.49 (s, 9H). $^{13}$CNMR (126 MHz, CDCl$_3$) δ 165.21, 156.61, 153.00, 143.97, 138.23, 136.65, 134.95, 131.38, 131.06, 129.72, 129.19, 128.11, 126.87, 123.26, 120.22, 81.44, 80.91, 77.77, 67.27, 33.80, 28.26, 28.09. The precursor was de protected under acidic conditions as described above to yield SP5 (Quantitative). MS-ESI [M+H]+ for disulfide $C_{30}H_{32}N_6O_4S_2$ calculated 605.75. found 605.57

Synthesis of SP6. Azide (31) (2.3 g) was dissolved in 30 mL anhydrous Tetrahydrofuran (THF). The reaction flask was cooled to 0° C. then 1M Lithium Aluminum Hydride (LAH) in THF solution (5.16 mL, 5.16 mmol) was slowly added. The reaction stirred at 0° C. under argon for 2 hr and once the reaction was complete it was quenched with the slow addition of 3 mL cold $H_2O$ and 1 mL 4N NaOH$_{(aq)}$ then stirred for 10 min at room temperature. Volatiles were removed under reduced pressure and the resulting material was dilute in a mixture of 100 mL ethyl acetate with 15 mL saturated Sodium Bicarbonate Solution. The resulting heterogeneous solution was filtered through a Celite pad and the filtrate was concentrated under reduced pressure to afford a beige solid. This crude product was purified via flash chromatography (Hex:EtOAc) to afford a off white solid (34) (2 g, 95% yield).). $^1$HNMR (400 MHz, CDCl$_3$) δ 7.74 (s, 1H), 7.49 (d, J=7.70 Hz, 6H), 7.34 (t, J=7.71 Hz, 6H), 7.26-7.25 (m, 4H), 7.10 (d, J=8.70 Hz, 1H), 6.39 (d, J=7.63 Hz, 1H), 6.73 (s, 1H), 3.80 (s, 2H), 3.16 (s, 2H), 1.54 (s, 9H); $^{13}$CNMR (126 MHz, CDCl$_3$) δ 153.08, 144.31, 143.97, 136.88, 130.89, 129.36, 128.17, 126.17, 122.40, 120.49, 80.42, 67.13, 46.32, 33.95, 28.43. Amine (34) (0.263 g, 0.98 mmol) was dissolved in 8 mL dichloromethane. To this solution was added (35) (0.4867 g, 0.98 mmol, 1 eq). To this mixture was added 2-(1H-benzotriazol-1-yl)-1,1,3,3 tetramethyluronium hexafluorophosphate (HBTU) (0.5576 g, 1.47 mmol, 1.5 eq) followed by the slow addition of N,N-diisopropylethylamine (DIPEA) (0.43 mL, 2.45 mmol, 2.5 eq). The reaction stirred at ambient temperature under argon for 3 hours. Following completion the reaction was dilute in dichloromethane and washed once with water and once with Saturated Sodium Chloride Solution. The organic layer was dried over magnesium sulfate and concentrated under reduced pressure to afford yellow oil that was purified via flash chromatography (silica gel, Hex:EtOAc) to afford a yellow oil (0.4 g, 55% yield). $^1$HNMR (400 MHz, CDCl$_3$) δ 7.80 (d, J=7.4 Hz, 2H), 7.64 (d, J=7.8 Hz, 1H), 7.5 (s, 1H), 7.48 (d, J=7.5 Hz, 6H) 7.41 (t, J=7.65 Hz, 1H), 7.33 (t, J=7.5, 6H) 7.25 (d, J=5.7 Hz, 3H) 7.23 (s, 1H) 7.19 (br s, 1H) 7.11 (d, J=7.8 Hz, 1H) 7.01 (d, J=7.8 Hz, 1H) 6.73 (s, 1H), 4.87 (s, 2H), 4.57 (d, J=5.5, 2H), 3.16 (s, 2H), 1.53 (s, 9H), 1.44 (s, 9H); $^{13}$CNMR (126 MHz, CDCl$_3$) δ 166.95, 156.73, 153.05, 144.23, 138.52, 136.99, 136.40, 134.71, 131.85, 131.21, 129.33, 128.73, 128.17, 127.32, 127.13, 126.88, 123.53, 121.48, 81.87, 80.59, 77.85, 67.19, 43.99, 33.88, 28.39, 28.15. The precursor was de protected under acidic conditions as described above to yield SP6 (Quantitative) MS-ESI [H+H]+ for disulfide $C_{32}H_{36}N_6O_4S_2$ calculated 633.80. found 633.60.

Synthesis of SP7. Carboxylic Acid (36) was synthesized in 4 steps from commercially available Methyl 4-(3-formylphenyl)benzoate. First the aldehyde was selectively reduced with Sodium Borohydride followed by bromination of the resulting benzylic alcohol by PBr$_3$. The resulting bromide was then substituted with tert-butyl-N-hydroxycarbamate. The methyl ester was then hydrolyzed with LiOH (aq) in THF to the corresponding carboxylic acid (36). Amine (34) (0.268 g, 0.54 mmol) and carboxylic acid (36) (0.186 g, 0.54 mmol, 1 eq) were dissolved in 18 mL dichloromethane. To this mixture was added 2-(1H-benzotriazol-1-yl)-1,1,3,3 tetramethyluronium hexafluorophosphate (HBTU) (0.303 g, 0.8 mmol, 1.5 eq) followed by the slow addition of N,N-diisopropylethylamine (DIPEA) (0.24 mL, 1.4 mmol, 2.5 eq). The reaction stirred at ambient temperature under argon for 24 hours. Following completion the reaction was dilute in dichloromethane and washed once with water and once with Saturated Sodium Chloride Solution. The organic layer was dried over magnesium sulfate and concentrated under reduced pressure to afford yellow oil that was purified via flash chromatography (silica gel, Hex:EtOAc) to afford a yellow oil (0.045 g, 10% yield). $^1$H NMR (400 MHz, CDCl3) δ 7.84 (d, J=8 Hz, 2H), 7.80 (s, 1H), 7.62 (d, J=8.4 Hz, 2H), 7.56 (d, J=7.2 Hz, 1H), 7.49 (d, J=8 Hz, 6H), 7.45-7.39 (m, 3H), 7.34 (t, J=7.6 Hz, 6H), 7.26-7.23 (m, 3H), 7.12 (d, J=7.6 Hz, 1H), 7.03 (d, J=7.2 Hz, 1H), 6.75 (s, 1H), 6.54 (br s, 1H), 4.91 (s, 2H), 4.59 (d, J=5.2 Hz, 2H), 3.17 (s, 2H), 1.54 (s, 9H), 1.47 (s, 9H). The precursor was de protected under acidic conditions as described above to yield SP7 (Quantitative) MS-ESI [M+H]+ for disulfide $C_{44}H_{44}N_6O_4S_2$ calculated 786.0. found 785.55

Synthesis of SP8.

Sodium azide (0.56 g) was added to as solution of mesylate (30) (2.5 g) in 30 mL anhydrous DMF. The reaction stirred under argon at ambient temperature for 12 hours. Following completion the reaction mixture was dilute in 150 mL dichloromethane and washed once with saturated sodium bicarbonate solution then once with saturated sodium chloride solution. The organic layer was dried over magnesium sulfate and concentrated under reduced pressure afford a yellow-oil. This crude material was passed through a plug of silica in 1:1 Hex:EtOAc to afford a yellow oil (31) (2.3 g, Quantitative yield). MS-ESI [M+Na]+ for $C_{32}H_{32}N_4O_2S$ calculated 559.68. found 559.22; $^1$HNMR (400 MHz, CDCl$_3$) δ 7.80 (s, 1H), 7.50 (t, J=4.38 Hz, 6H), 7.34 (t, J=7.64 Hz, 6H), 7.25 (t, J=7.28, 3H), 7.14 (d, J=7.80 Hz, 1H), 6.94 (dd, J=7.98, 1.70 Hz, 1H), 6.76 (s, 1H), 4.28 (s, 2H), 3.17 (s, 2H), 1.55 (s, 9H); $^{13}$CNMR (126 MHz, CDCl$_3$) δ 152.91, 144.21, 137.22, 135.83, 131.17, 129.34, 128.20, 126.92, 123.17, 121.35, 80.64, 67.24, 54.49, 33.93, 28.40. Azide (31) (0.1 g, 0.186 mmol) and Alkyne (32) (0.127 g, 0.745 mmol, 4 eq) were dissolved in 6 mL 1:1 THF:H$_2$O. CuSO$_4$ (0.045 g, 0.28 mmol, 1.5 eq) and Sodium Ascorbate (0.147 g, 0.745 mmol, 4 eq)

were added and the reaction mixture was stirred at room temperature for 30 min. Following completion, the reaction mixture was dilute in Dichloromethane and washed twice with concentrated Ammonium Hydroxide, once with Saturated Sodium Bicarbonate solution, once with Saturated Sodium Chloride solution, then dried over Magnesium Sulfate. Volatiles were removed under reduced pressure and the resulting material was purified by flash column chromatography (silica gel, Hex:EtOAc) to yield SP8 precursor (0.094 g, 72% yield). MS-ESI [M+Na]$^+$ for $C_{40}H_{45}N_5O_5S$ calculated 730.87. found 730.26; $^1$HNMR (400 MHz, CDCl$_3$) δ 7.77 (br s, 1H), 7.54 (s, 1H), 7.47 (d, J=4 Hz, 6H), 7.38 (s, 1H), 7.33 (t, J=8 Hz, 6H), 7.26-7.23 (m, 3H), 7.11 (d, J=8 Hz, 1H), 6.68-6.83 (m, 1H), 6.76 (s, 1H), 5.47 (s, 2H), 4.96 (s, 2H), 3.15 (s, 2H), 1.53 (s, 9H), 1.45 (s, 1H) The precursor was de protected under acidic conditions as described above to yield SP8 (Quantitative) MS-ESI [M+H]$^+$ for disulfide $C_{22}H_{28}N_{10}O_2S_2$ calculated 529.66. found 529.18

6.9 Example 9

Synthesis of Macrocyclic Peptide-Containing Molecules Via Catalyst-Free Oxime/Intein-Mediated Ligation This example demonstrates a variation of the general synthetic strategy schematically illustrated in FIG. 1 for the preparation of macrocyclic organo-peptide hybrids. In this case, the macrocylization reaction is carried out via a catalyst-free, tandem oxime/intein-mediated ligation between a recombinant pAcF-containing biosynthetic precursor and a bifunctional oxyamine/amino-thiol synthetic precursor (FIG. 12). This example also demonstrates how macrocyclic organo-peptidic hybrids comprising peptidic moieties of varying composition and size can be prepared using this method.

Initial studies were carried out with SP3 and CBD-fusion pAcF-containing biosynthetic precursors comprising a 4 to 12 amino acid-long target sequence ((CBD4(pAcF) to CBD12(pAcF), Table 3). Each protein construct (100 μM) was mixed with SP3 (15 mM) in phosphate buffer at pH 7.5. Tris(2-carboxyethyl)phosphine (TCEP, 20 mM) was added to the reactions to maintain the thiol groups in the reactants in reduced form. Splicing of the protein constructs over time was quantified by SDS-PAGE followed by densitometric analysis of the gel bands corresponding to the full-length protein (31 kDa) and the splicing fragments, GyrA (22 kDa) and the CBD-linked products (8 kDa). These experiments revealed that a considerable amount of biosynthetic precursor splicing (50-80%) occurred after 5 hours (FIG. 13A) and quantitative splicing (90-100%) occurred after overnight incubation. In the absence of SP3, only minimal background hydrolysis of the protein was observed (FIG. 13A). MALDI-TOF analysis of the small molecular weight products showed the formation of the desired CBD-fused MOrPH as the only product obtained from these reactions (FIG. 13B). Also notable was that SP3-induced macrocyclization occurred with almost equally high efficiency across all the different target sequence lengths, including the short 4mer sequence (TGST) (SEQ ID NO:96) and the considerably longer 12mer target sequence (TGSWGKLAEYGT) (SEQ ID NO:102).

Similar experiments were then carried out using synthetic precursors SP4, SP5, SP6, SP7, and SP8 (FIG. 11) and including also two biosynthetic precursors with a 15mer and 20mer target sequence (CBD15(pAcF), CBD20(pAcF), Table 3). As observed with SP3, these reactions led to the formation of the desired CBD-fused MOrPH as the only (or largely predominant) product as determined by MALDI-TOF (e.g., FIG. 14). For all compounds except SP7, splicing of the biosynthetic precursor amounted to 60-95% within 5 hours (FIG. 13c) and was quantitative after overnight incubation at room temperature. Altogether, these data illustrate the efficiency of the presented macrocyclization method and its versatility toward giving access to macrocyclic organo-peptide hybrids with very different ring size and highly diverse structure as given by the varying target sequence length and nature of the synthetic precursor. This To shed light on the reaction path(s) involved in MOrPH formation via this method and discern the relative contribution of path 'A' and path 'B' to the reaction (FIG. 12), the extent of protein splicing induced by SP3 was monitored over time in parallel reactions with CBD5(pAcF) and CBD5 (OpgY). In the latter, pAcF is replaced with OpgY which lacks the side chain ketone required for oxime ligation, allowing measurement of the rate at which the protein is spliced solely by action of the amino-thiol moiety in the synthetic precursor (i.e., path 'B'). These studies revealed that the amount of spliced protein in the reaction with CBD(OpgY) was about 70% of that observed with CBD(pAcF) across the different time points. This indicated that both reaction pathways participate in the MOrPH-forming process, with path 'B' being the predominant one. Furthermore, whereas the biosynthetic precursor alone undergoes slow hydrolysis (~15% splicing after 16 hours, FIG. 13a), the observation of no hydrolyzed product ('h') in nearly all the reactions with SP3 and the other precursors (FIG. 13b and FIG. 14) indicate that macrocyclization largely outcompetes the undesired hydrolysis process, even in the context of the extended 12- and 15-amino acid target sequences. Finally, to establish whether the (2-aminophenyl)-methanethiol moiety of SP3 was capable of undergoing the desired S→N acyl transfer after transthioesterification, the reaction mixtures were treated with iodoacetamide (20 mM) for 2 hours followed by MALDI-TOF analysis. Such treatment led to complete disappearance of the [M+H]$^+$ species corresponding to the unmodified MOrPHs and to the appearance of a species with an m/z of +58, which is consistent with the addition of an acetamido moiety to these molecules. These tests evidenced the accessibility of the benzylic thiol in the MOrPH-embedded 3 to electrophilic attack by the alkylating agent, supporting the occurrence of the amide-forming intramolecular rearrangement.

Experimental details for Example 9. Macrocyclization reactions. Reactions were carried out at 20 μL scale by adding synthetic precursor SP3, SP4, SP5, SP6, SP7, or SP8 (final concentration: 15 mM) to a solution of protein precursor (100 μM) in potassium phosphate buffer (50 mM, NaCl 150 mM, pH 7.5) in the presence of TCEP (final concentration: 20 mM). For SDS-PAGE analyses, 5 μl of the reaction mixture were removed at the indicated time point(s), diluted in DTT-free 4× loading buffer, and analysed on 18% polyacrylamide gels. The extent of protein splicing was measured and quantified by densitometry analysis using the NIH Image Software. The percentage of SP-induced protein splicing was calculated based on the difference between the amount of spliced protein at time zero and at the time of the analysis. MALDI-TOF analyses of the small molecular weight products (8-10 kDa) of the reactions were carry out on a Bruker Autoflex III MALDI-TOF spectrometer. Prior to analysis, protein samples were diluted in 50% acetonitrile in H$_2$O (0.1% TFA) and this solution mixed with a sinapinic acid solution (10 mg/mL in 50% acetonitrile in H$_2$O with 0.1%

TFA). The samples were analyzed using reflectron positive (RP) mode and calibration using small molecular weight (2-15 kDa) protein standards.

6.10 Example 10

Preparation of Libraries of MOrPHs with Randomized Target Sequences Via Oxime/Intein-Mediated Ligation Method This example illustrates how libraries of structurally diverse MOrPHs can be generated via the general strategy of FIG. 1 (in particular, via the variation of this method depicted in FIG. 12) by performing the macrocyclization reaction with a library of biosynthetic precursors with genetically randomized target sequences.

Vectors for the expression of two biosynthetic precursor libraries with randomized 5mer and 8mer target sequences were constructed via multiple site-saturation mutagenesis. These constructs corresponded to CBD-(pAcF)-X$_4$T-GyrA and CBD-(pAcF)-X$_7$T-GyrA, respectively, where X corresponds to a fully randomized position encoded by the degenerate codon NNK (20 amino acids, 32 codons). After transformation of the vector library into E. coli cells, about 5,000 recombinants from each biosynthetic precursor library were pooled together and expressed in E. coli. SDS-PAGE analysis revealed that 86% (5mer) and 78% (8mer) of the resulting protein libraries occurred as full-length, indicating only a small amount of premature splicing (due to hydrolysis) during expression. For both protein libraries (100 μM in phosphate buffer), addition of SP3 (15 mM) induced more than 35% and 60% splicing of the full-length constructs after 5 hours and 16 hours, respectively. To confirm the occurrence of macrocylization, 18 randomly chosen recombinants from each DNA library were transformed into E. coli cells and the expressed protein product was purified individually. Each of these proteins was then made react with SP3 and the products characterized. Remarkably, all the recombinants from the 5mer BP library and all but one of the 18 recombinants from the 8mer BP library yielded the desired hybrid macrocycle. For only 2/18 of the 5mer BPs and 1/18 of the 8mer BPs a small amount of acyclic product (15-25%) was observed. Not surprisingly, the different protein precursors displayed differential reactivity toward SP3-induced MOrPH formation (FIGS. 15a-b). Nevertheless, all the constructs reacted with SP3 and the majority of the 5mer and 8mer BP variants (63% and 58%, respectively) underwent more than 50% splicing after overnight incubation at room temperature (FIGS. 15a-b). These experiments show the capability of the method to give access to diverse libraries of MOrPH ligands using genetically randomized target sequences.

6.11 Example 11

Additional Cyclic and Protein-Fused MOrPHs

This example further demonstrates the scope and versatility of the general synthetic strategy of FIG. 1 toward obtaining MOrPHs in cyclic configuration (i.e., comprising a short N-terminal tail) and MOrPHs fused to the C-terminus of an affinity tag (i.e., AviTag, chitin-binding domain) or a protein such as a fluorescent protein (i.e., cyan fluorescent protein or CFP). Furthermore, this example demonstrates the viability of this general method in the context of additional synthetic precursor structures such as ones carrying an oxyamine (cFG$_1$)/thiol (cFG$_2$) functional group pair (SP9 and SP10, FIG. 11) and an oxyamine (cFG$_1$)/(2-aminophenyl)-methanethiol (cFG$_2$) functional group pair with substitutions at the 2-amino group (SP11 and SP12, FIG. 11). Finally, this example demonstrates the possibility to introduce additional variation in the MOrPH structure via modification of the FG$_1$-bearing unnatural amino acid in the biosynthetic precursor (amino acid 'Z' in general scheme of FIG. 1).

Macrocyclization reactions between different amino-thiol synthetic precursors (SP3, SP4, SP5, SP6, SP8; FIG. 11) and a series of pAcF-containing biosynthetic precursors carrying a short N-terminal tail (m=2, FIG. 1) and diversified target sequences (H1, H2, Sfi-a, Sfi-b, MG5(pAcF), MG6(pAcF) in Table 3) were carried out according to the mild and catalyst-free reaction conditions described in Example 9. In each case, the reaction led to the formation of the desired MOrPH as determined by LC-MS (Table 4). The occurrence of a cyclic backbone in these molecules was further confirmed by MS/MS as indicated by their characteristic fragmentation pattern. As observed with the CBD constructs (Example 9), significant levels of biosynthetic precursor splicing (75%-100%) were observed upon addition of the oxyamino/amino-thiol based synthetic precursors to these proteins, resulting in high to quantitative yields for the macrocyclization reaction. Similar results were obtained with a biosynthetic precursor comprising an AviTag within the N-terminal tail (AviTagG6T), Table 3). Reactions with SP4, SP5, SP6, SP8 led to the expected macrocyclic products as determined by MALDI-TOF (Table 4). Structures for representative macrocyclic products obtained in these experiments are provided in FIG. 16.

To demonstrate the possibility to generate MOrPHs fused to a fluorescent protein using the methods disclosed herein, two biosynthetic precursor constructs (CFP-H1 and CFP-H2, Table 3) comprising a cyan fluorescent protein within their N-terminal tail ((AA)$_m$) and target sequences of varying length (10mer and 17mer, respectively) were expressed and purified. The purified proteins were then mixed with either SP4 or SP5 (15 mM) in phosphate buffer (pH 7.5) in the presence of TCEP (20 mM). These reactions led to the formation of the expected CFP-fused MOrPHs (one of which is schematically represented in FIG. 16) as determined by MALDI-TOF (Table 4).

Additional synthetic precursors that can operate according to the general method of FIG. 1 were synthesized and tested for macrocyclization efficiency. The two bifunctional oxyamino/thiol synthetic precursors SP9 and SP10 (FIG. 11) were made react with CBD5(pAcF) and CBD8(pAcF), respectively, resulting in the desired macrocyclic products as determined by MALDI-TOF (Table 4). Oxyamine/(2-aminophenyl)-methanethiol based synthetic precursors carrying substitutions at the amino group (SP11 and SP12, FIG. 11) were also able to induce MOrPH formation as determined through the analysis of test reactions with biosynthetic precursors CBD6(pAcF) and CBD8(pAcF) (Table 4). Structures for exemplary macrocyclic products obtained in these experiments are provided in FIG. 16.

TABLE 4

MALDI-TOF data for various MOrPH products obtained using oxime/intein-mediated ligation. BP = biosynthetic precursor; SP = synthetic precursor.

| BP | SP | Observed m/z [M + H]$^+$ | Calculated m/z [M + H]$^+$ |
|---|---|---|---|
| MG5(pAcF) | SP4 | 816.4 | 816.4 |
| MG5(pAcF) | SP5 | 935.5 | 935.5 |
| MG5(pAcF) | SP6 | 949.4 | 949.2 |

TABLE 4-continued

MALDI-TOF data for various MOrPH products obtained using oxime/intein-mediated ligation. BP = biosynthetic precursor; SP = synthetic precursor.

| BP | SP | Observed m/z [M + H]+ | Calculated m/z [M + H]+ |
|---|---|---|---|
| MG5(pAcF) | SP8 | 897.5 | 897.4 |
| MG6(pAcF) | SP4 | 979.3 | 980.0 |
| MG6(pAcF) | SP5 | 1098.4 | 1099.1 |
| MG6(pAcF) | SP6 | 1112.3 | 1113.2 |
| MG6(pAcF) | SP8 | 1060.3 | 1061.1 |
| H1 | SP4 | 1549.5 | 1549.7 |
| H1 | SP5 | 1695.9[a] | 1694.7[a] |
| H2 | SP4 | 2313.8 | 2313.7 |
| H2 | SP5 | 2460.5[a] | 2459.7[a] |
| Sfi-a(pAcF) | SP3 | 1465.3 | 1464.5 |
| Sfi-b(pAcF) | SP3 | 1679.6 | 1679.7 |
| Sfi-a(pAcF) | SP4 | 1380.3 | 1379.7 |
| Sfi-b(pAcF) | SP4 | 1594.8 | 1594.9 |
| AviTagG6T | SP4 | 3527.4 | 3526.1 |
| AviTagG6T | SP5 | 3646.5 | 3645.1 |
| AviTagG6T | SP6 | 3660.6 | 3659.2 |
| AviTagG6T | SP8 | 3608.4 | 3607.1 |
| CFP-H1 | SP4 | 28927 | 28913 |
| CFP-H2 | SP5 | 29781 | 29783 |
| CBD5(pAcF) | SP9 | 8601.9 | 8601.6 |
| CBD8(pAcF) | SP10 | 8887.8 | 8886.8 |
| CBD6(pAcF) | SP11 | 8716.6 | 8715.7 |
| CBD8(pAcF) | SP11 | 8918.0 | 8915.9 |
| CBD6(pAcF) | SP12 | 8741.6 | 8739.7 |
| CBD8(pAcF) | SP12 | 8942.0 | 8939.9 |

[a]m/z value of [M + K]+ ion.

Aminoacyl-tRNA synthetases engineered to recognize a given unnatural amino acid with orthogonal reactivity with respect to the naturally occurring amino acids often exhibit broad substrate specificity toward additional unnatural amino acids.[50] To demonstrate the possibility of diversifying MOrPH structure via modification of the unnatural amino acid in the biosynthetic precursor, 2-fluoro-4-acetyl-phenylalanine (2F-pAcF, FIG. 17a) was synthesized according to the route in Scheme 7 (FIG. 23b) starting from 3'-fluoro-4'-methyl-acetophenone. Expression of the vector encoding for the construct CBD-(amber stop)-TGSGT-GyrA in E. coli in the presence of 2F-pAcF and the pAcF-specific MjTyrRS/tRNA$_{CUA}$ amber suppression system described in Example 7 allowed for the successful production of a 2F-pAcF-containing biosynthetic precursor, corresponding to CBD-(2F-pAcF)-TGSGT-GyrA-His$_6$ (CBD5(2F-pAcF), FIG. 17b). After purification via Ni-affinity chromatography, this protein construct was allowed to react with SP4, resulting in the formation of a CBD-fused MOrPH incorporating a fluorine atom at the level of the unnatural amino acid (FIG. 17c). These experiments demonstrate how alternative amino acids can be introduced as 'Z' in the biosynthetic precursor (FIG. 1) for diversification of MOrPH structure. As described within this invention, the only requirement is that such an amino acid carries a suitable side-chain functional group as 'FG$_1$' according to the method of FIG. 1 (e.g., keto group in 2F-pAcF).

Finally, MOrPH-forming reactions were carried out according to the variation of the general method of FIG. 1 described in Example 9 (oxime/intein-mediated ligation method) using pAcF-containing biosynthetic precursors (i.e., CBD5(pAcF), CBD5Y(pAcF), CBD5F(pAcF), Table 3) within permeabilized E. coli cells where these proteins were expressed prior to the reaction. Suspensions of biosynthetic precursor-expressing E. coli cells (1 mL, OD$_{600}$~3) were permeabilized by one round of flash freezing/thawing followed by treatment with lysozyme (to partially digest the cell wall), and then added with SP4 at 20 mM. After incubation at room temperature for 12 hours, the cells were lysed by sonication and the cell lysate was passed through a CBD-affinity resin (chitin beads). After washing with phosphate buffer, the chitin beads were eluted with 50% acetonitrile in water and the eluted solution analyzed by MALDI-TOF. MS analysis revealed the presence of the expected CBD-fused MOrPHs (CBD5(pAcF) cells+SP4: obs. m/z [M+H]+: 8539.5, calc. 8537.3; CBD5Y(pAcF) cells+SP4: obs. m/z [M+H]+: 8599.3, calc. 8601.1 CBD5F(pAcF) cells+SP4: obs. m/z [M+H]+: 8584.7; calc. 8583.2). These experiments demonstrate how MOrPHs can be generated according to the methods of the invention within a cell expressing the biosynthetic precursor. In addition, they demonstrate the possibility to isolate the MOrPH product after the macrocyclization reaction from a complex mixture (i.e., cell lysate) via an affinity tag comprised within the N-terminal tail ((AA)$_m$) of the biosynthetic precursor and thus of the resulting hybrid macrocycle.

Experimental details for Example 11. Synthesis of synthetic precursor SP10. Compound SP10 was obtained according to Scheme 10 (FIG. 23d) applying identical reaction conditions as described for equivalent steps in Scheme 9 (FIG. 23c).

Synthesis of synthetic precursor SP9 (see Scheme 11, FIG. 23d). 6-bromopicolinaldehyde (37) was reduced with sodium borohydride to corresponding alcohol (38). To prepare symmetrical diol (39) Zinc (0.344 g, 5.31 mmol, 1 eq) was added to a solution of NiCl$_2$.6H$_2$O (1.264 g, 5.31 mmol, 1 eq) and PPh$_3$ (5.56 g, 21.25 mmol, 4 eq) in 50 mL anhydrous DMF. The mixture was activated by stirring at 50° C. for 2 hr changing color from dark blue to dark red. After catalyst activation, (38) (1.00 g, 5.31 mmol, 1 eq) was added to the reaction mixture. The mixture was stirred at 50° C. for 3 hr then cooled to ambient temperature before being poured into a separatory funnel containing 100 mL of 5:5:1:1 Concentrated Ammonium Hydroxide:H$_2$O:Saturated Potassium Carbonate Solution:Saturated EDTA Solution. The resulting mixture was extracted with 3:1 CHCl$_3$:Isopropanol and the organic layer was washed once with Saturated Sodium Chloride solution before being dried over Magnesium Sulfate. Volatiles were removed to yield an off white solid which was re dissolved in Dichloromethane and precipitated by bubbling HCl gas through the solution. The precipitate was collected as the dihydrochloride salt of the desired compound via filtration (39) (0.355 g, 23% yield) $^1$HNMR (400 MHz, D4-MeOH) δ 8.22 (d, J=7.6, 2H), 7.90 (t, J=7.6, 2H), 7.52 (d, J=7.6 Hz, 2H), 4.76 (s, 4H). The diol 39 (0.2 g, 0.925 mmol) was dissolved in 9 mL anhydrous THF and the solution was cooled to 0° C. 1.0M PBr$_3$ in CH$_2$Cl$_2$ solution (2.78 mmol, 3 eq) was added to the solution. The reaction was stirred at ambient temperature under argon for 12 hr. Water was added to quench the reaction and volatiles were removed under reduced pressure. The resulting material was dissolved in Dichloromethane and washed twice with 2.0M NaOH (aq) then once with Saturated Sodium Chloride Solution. The organic layer was dried over Magnesium Sulfate and volatiles were removed to yield (40) (0.143 g 45% yield) $^1$HNMR (400 MHz, CDCl$_3$) δ 8.37 (d, J=8 Hz, 2H), 7.81 (t, J=8 Hz, 2H), 7.46 (d, J=7.6 Hz, 2H), 4.62 (s, 4H). In a dry argon filled round bottom flask triphenylmethylmercaptan (0.02 g, 0.073 mmol) was dissolved in 2 mL anhydrous DMF followed by the addition of 0.013 mL of N,N-Diisopropylethylamine (DIPEA). The mixture was stirred for 5 min then 6,6'-bis(bromomethyl)-2,2'-bipyridine (40) (0.025 g, 0.073 mmol) was added. The mixture was stirred under argon for 8 hr. Following completion the reaction was dilute in dichloromethane and washed once with Saturated Bicarbonate and once with Saturated Sodium Chloride solution, dried over Magnesium Sulfate and volatiles were removed to yield a crude mixture. The Mixture was re dissolved in 2.5 mL anhydrous Acetonitrile and tert Butyl N-hydroxycarbalate (40 mg) was added followed by 0.025 mL of DBU. The reaction mixture was heated to 50° C. for 5 hr then cooled to ambient temperature. Volatiles were removed and the crude mixture was purified on silica gel (Hex:EtOAc) to yield (41) (0.005 g 12% yield).). $^1$HNMR (400 MHz, CDCl$_3$) δ 8.38 (d, J=8 Hz, 1H), 8.23 (d, J=8 Hz, 1H), 7.82 (t, J=7.6 Hz, 1H), 7.65-7.61 (m, 2H), 7.51-7.49 (d, J=8 Hz, 6H), 7.43 (d, J=7.6 Hz, 1H), 7.31-7.25 (m, 6H), 7.21-7.19 (m, 3H), 7.00 (d, J=7.6 Hz, 1H), 5.06 (s, 2H), 3.59 (s, 2H), 1.48 (s, 9H). Precursor (41) (0.1 g, 0.169 mmol) was dissolved in 6 mL anhydrous dichloromethane and the solution was cooled to 0° C. To that solution was added Triisopropylsilane (TIPS) (0.07 mL, 0.34 mmol, 2 eq) followed by 3 mL trifluoroacetic acid (TFA). The reaction mixture was stirred at 0° C. for 15 min then warmed to ambient temperature. Volatiles were removed under reduced pressure and the material was washed exhaustively with cold hexanes to yield SP9 (0.07 g, 87% yield) $^1$HNMR (400 MHz, D$_4$-MeOH) δ 8.43-8.31 (m, 2H), 8.29 (t, J=8 Hz, 1H), 8.16 (t, J=8 Hz, 1H), 7.83 (d, J=8 Hz, 1H), 7.69 (d, J=8 Hz, 1H), 5.3 (s, 2H), 4.12 (s, 2H).

6.12 Example 12

Synthesis and Isolation of MOrPHs in Pure Form

This example demonstrates how the general synthetic strategy of FIG. 1, within the variation of this method as depicted in FIG. 4, can be applied to produce milligram amounts of pure MOrPH product.

To demonstrate this aspect of the invention, a scaled-up reaction was carried out using synthetic precursor 1 (FIG. 3) and ~50 mg purified OpgY-containing biosynthetic precursor MG6 (Table 1) according to the reaction conditions provided in Example 3. After the Cu(I)-catalyzed cycloaddition reaction (FG$_1$/cFG$_1$ coupling), the branched protein-synthetic precursor adduct (FIG. 4) was separated from the copper salts and excess 1 by size-exclusion filtration. The isolated adduct was then allowed to cyclize for 12 hours. The small molecular weight products were isolated from the reaction mixture by solid-phase extraction, yielding ~2 mg of a mixture of 7 and 8 in about 80:20 ratio and 90% purity. The MOrPH product (7) was then successfully isolated in >95% purity by further purification using C$_{18}$-reverse phase HPLC (FIGS. 18a-b).

6.13 Example 13

Synthesis of a Novel Amino Acid for Preparation of Self-Processing Biosynthetic Precursors Based on our studies (Examples 1-11), we envisioned that nucleophilic groups capable of directing an intein-mediated ligation (hydrazide, methanethiol, (2-aminophenyl)-methanethiol group, and functional equivalents) could be directly installed upstream of the target sequence, thereby furnishing a method to obtain MOrPHs via an intramolecular side-chain-to-tail cyclization as schematically illustrated in FIG. 2. To illustrate this point, we designed an unnatural amino acid (3-amino-4-mercaptomethyl-phenylalanine or AmmF) incorporating a side-chain (2-aminophenyl)-methanethiol group, which was meant to serve as FG$_3$ functional group in the general method of FIG. 2. Our experiments showed that this moiety can efficiently orchestrate an intein-mediated ligation via transthioesterification at the intein N-terminus followed by intramolecular S→N acyl transfer to form a stable amide bond (Example 9). The novel amino acid 3-amino-4-mercaptomethyl-phenylalanine (AmmF) was synthesized according to the route in Scheme 12, FIG. 23d).

To identify an aminoacyl-tRNA synthetase suitable for the preparation of AmmF-containing self-processing biosynthetic precursors, we tested a set of MjTyrRS variants for their ability to recognize AmmF and enable its incorporation into a protein in response to the amber stop codon via a cognate MjtRNA$_{CUA}$. These included MjTyrRS variants evolved for amber stop codon suppression with p-azidophenylalanine (pAzF), napthylalanine (NapA), para-acetylphenylalanine (pAcF) and O-propargyltyrosine (OpgY). These studies revealed that the pAzF-specific MjTyrRS variant was also able to recognize AmmF, enabling the efficient incorporation of this unnatural amino acid into a test protein containing an amber stop, as illustrated by the SDS-PAGE gel in FIG. 19a. Using this orthogonal aminoacyl-tRNA synthetase, it is thus possible to prepare AmmF-containing self-processing biosynthetic precursors.

This example illustrates how unnatural amino acids of the type 'J' in FIG. 2 can be prepared and how methods can be found for the incorporation of these unnatural amino acids into a protein for the purpose of preparing self-processing biosynthetic precursors.

Experimental details for Example 13. Synthesis of 3-amino-4-mercaptomethyl-phenylalanine (AmmF) (see Scheme 12, FIG. 23d)). To a dry, argon-filled round-bottom flask was added methyl 3-((tert-butoxycarbonyl)amino)-4-methylbenzoate (6.63 g, 25 mmol). This material was diluted in 100 mL carbon tetrachloride and the flask was heated to 70° C. to aid solubility. To the warmed solution was added N-bromo-succidimide (4.89 g, 27.5 mmol, 1.1 eq). The reaction vessel was equipped with a reflux condenser and irradiated with UV light for 3 hours. Following completion then reaction was cooled to room temperature then filtered. The filtrate was dilute in 100 mL dichloromethane, washed with Saturated Potassium Carbonate solution, saturated Sodium Chloride solution then dried over Magnesium sulfate. Volatiles were removed to afford 6.7 g (78%) orange-white solid. $^1$H NMR (500 MHz, CDCl$_3$) δ 8.47 (s, 1H), 7.73 (dd, J=8.0, 1.7 Hz, 1H), 7.36 (d, J=8.0 Hz, 1H), 6.75 (s, 1H), 4.50 (s, 2H), 3.91 (s, 3H), 1.55 (s, 9H). $^{13}$C NMR (126 MHz, CDCl$_3$) δ 28.2, 29.9, 52.3, 81.3, 123.8, 125.1, 130.0, 131.5, 131.7, 136.9, 152.6, 166.2

To a dry argon filled flask containing methyl 4-(bromomethyl)-3-((tert-butoxycarbonyl)amino)benzoate was (6.7 g, 19.59 mmol) triphenyl-methyl mercaptan (6.49 g, 23.5 mmol, 1.2 eq) and Potassium Carbonate (3.2479 g, 23.5 mmol, 1.2 eq). The mixture was dissolved in 100 ml anhydrous dimethylformamide (DMF). The reaction stirred under argon at room temperature for 15 h. The reaction mixture was then concentrated to 10 mL and then taken up in dichloromethane. The solution was washed once with ice-cold H$_2$O, once with Saturated Sodium Bicarbonate Solution, and finally once with Saturated Sodium Chloride solution. The organic layer was dried over magnesium sulfate, and volatiles were removed to afford a golden-yellow solid (10.24 g, 97% crude yield). Material was carried forward without further purification. $^1$H NMR (500 MHz, CDCl$_3$) δ 8.41 (s, 1H), 7.65 (d, J=7.9 Hz, 1H), 7.48 (d, J=8.0 Hz, 5H), 7.34 (t, J=7.8 Hz, 6H), 7.25 (t, J=7.3 Hz, 5H), 7.18 (d, J=8.0 Hz, 1H), 6.72 (s, 1H), 3.88 (s, 3H), 3.21 (s, 2H), 1.56 (d, J=12.5 Hz, 9H). $^{13}$C NMR (126 MHz, CDCl$_3$) δ 166.69, 152.84, 144.09, 136.93, 130.75, 129.34, 128.23, 126.98, 124.89, 123.09, 80.77, 67.42, 52.14, 34.08, 28.38.

To a dry, argon-filled round-bottom flask was added methyl 3-((tert-butoxycarbonyl)amino)-4-((tritylthio)methyl)benzoate (20.32 g, 48 mmol). This was dilute in 400 mL anhydrous Tetrahydrofuran then the solution was cooled to 0° C. To this solution was slowly added 1M Lithium Aluminium Hydride (LAH) in THF solution (52.8 mL, 52.8 mmol, 1.1 eq). The reaction stirred at 0° C. under argon for 3 hours. Another 5 mL (5 mmol, 0.1 eq) of 1M LAH was added after 3 hours to push reaction to completion. Reaction quenched with the slow addition of 3 mL cold $H_2O$ and 1 mL 4 N NaOH then stirred for 10 min at room temperature. The resulting mixture was concentrated under reduced pressure to 20 mL and taken up in a mixture of 300 mL ethyl acetate and 30 mL sodium bicarbonate, agitated to suspend insoluble solids then filtered through a Celite pad. The filtrate was washed once with Saturated Sodium Bicarbonate solution then once with Saturated Sodium Chloride. The organic layer was dried with magnesium sulfate and volatiles were removed to afford yellow solid which was purified via flash column chromatography (silica gel, Hex:EtOAc) to afford a yellow oil (18 g, 95% yield). $^1$H NMR (500 MHz, $CDCl_3$) δ 7.78 (s, 1H), 7.49 (d, J=7.3 Hz, 5H), 7.34 (t, J=7.7 Hz, 5H), 7.26 (t, J=3.0 Hz, 5H), 7.13 (d, J=7.8 Hz, 1H), 7.01 (d, J=7.8 Hz, 1H), 6.73 (s, 1H), 4.63 (s, 2H), 3.17 (s, 2H), 1.54 (s, 9H). $^{13}$C NMR (126 MHz, $CDCl_3$) δ 153.06, 144.28, 141.49, 136.85, 130.96, 129.35, 128.18, 126.88, 124.50, 122.23, 120.36, 80.49, 67.17, 65.09, 33.91, 28.41.

To a dry, argon-filled round-bottom flask was added tert-butyl (5-(hydroxymethyl)-2-((tritylthio)methyl)phenyl)carbamate (9.3 g, 18.19 mmol). This was dissolved in 100 mL anhydrous dichloromethane and the solution was cooled to 0° C. To this solution was added Methane Sulfonylchloride (1.8 mL, 23.66 mmol, 1.3 eq) and the reaction mixture allowed to stir at 0° C. for 15 min. To this solution was added N,N-diisopropylethylamine (4.2 mL, 23.66 mmol, 1.3 eq). The reaction stirred under argon at 0° C. for 2 hours. Following completion, the reaction mixture was dilute to 300 mL of dichloromethane, washed twice with Saturated Sodium Bicarbonate solution then once with Saturated Sodium Chloride. The organic layer was dried over magnesium sulfate and volatiles were removed to afford yellow solid (9.42 g, 88% yield). The material was carried forward without further purification. $^1$H NMR (500 MHz, $CDCl_3$) δ 7.88 (s, 1H), 7.49 (d, J=7.3 Hz, 5H), 7.34 (t, J=7.7 Hz, 5H), 7.26 (d, J=14.6 Hz, 5H), 7.16 (d, J=7.8 Hz, 1H), 7.04 (d, J=9.5 Hz, 1H), 6.75 (s, 1H), 5.18 (s, 2H), 3.17 (s, 2H), 2.90 (s, 3H), 1.54 (s, 9H). $^{13}$C NMR (126 MHz, CDCl3) δ 152.85, 144.14, 137.33, 133.72, 131.28, 129.32, 128.23, 126.97, 126.26, 123.83, 121.95, 80.79, 71.27, 67.32, 38.45, 33.92, 28.40.

To a dry argon-filled round-bottom flask was added 3-((tert-butoxycarbonyl)amino)-4-((tritylthio)methyl)benzyl methanesulfonate (9.42 g). To this was added Diethylacetamidomalonate (4.52 g, 20.8 mmol, 1.3 eq) and the contents were dissolved in 50 mL anhydrous DMF. To a second dry argon-filled round-bottom flask was added 60% sodium hydride in mineral oil dispersion (0.84 g, 20.8 mmol, 1.3 eq) which was washed with 20 mL anhydrous pentane to remove the mineral oil. The resulting sodium hydride was suspended in 50 mL anhydrous DMF then the solution was cooled to 0° C. The first solution was then transferred to the solution of sodium hydride via cannula and the reaction mixture stirred under argon for 15 hours at 0° C. Following completion the reaction was concentrated to 10 mL, re dissolved in 350 mL dichloromethane, and washed twice with cold Saturated Sodium Bicarbonate solution then once with Saturated Sodium Chloride solution. The organic layer was dried over magnesium sulfate and volatiles were removed to afford a crude yellow solid which was then purified via flash chromatography (silica gel, Hex:EtOAc) to afford a white solid (5.4 g, 60% yield) [$^1$H NMR (500 MHz, $CDCl_3$) δ 7.64 (m, 6H), 7.44 (t, 5H), 7.29 (d, 5H), 7.02 (d, J=7.8 Hz, 1H), 6.66 (s, 1H), 6.63 (d, J=7.7 Hz, 1H), 6.56 (s, 1H), 4.28 (m, 4H), 3.57 (s, 2H), 3.11 (s, 2H), 2.04 (s, 3H), 1.53 (s, 9H), 1.35 (t, 6H). $^{13}$C NMR (126 MHz, $CDCl_3$) δ 169.24, 167.41, 152.76, 144.23, 136.74, 135.59, 130.53, 129.32, 128.16, 126.85, 125.25, 123.91, 123.37, 80.20, 67.15, 62.66, 37.57, 33.89, 28.36, 22.95, 13.95.

To a dry argon-filled round-bottom flask was added diethyl 2-acetamido-2-(3-((tert-butoxycarbonyl)amino)-4-((tritylthio)methyl)benzyl)malonate (5.4 g, 7.6 mmol). This material was dissolved in 70 mL dichloromethane. To this solution was added Triisopropylsilane (TIPS) (3.88 mL, 19 mmol, 2.5 eq). The reaction mixture was cooled to 0° C. then 18 mL Trifluoroacetic acid (TFA) was slowly added. The reaction stirred under argon at 0° C. for 30 minutes and was then warmed to room temperature. Volatiles were then removed under reduced pressure. To this resulting oil was added 30 mL 8 M HCl in dioxane. The reaction mixture stirred under argon at reflux for 9 hours. Following completion the reaction mixture was dried under reduced pressure to afford a brown solid, which was washed with cold hexanes to yielding 2.27 g of the dihydrochloride salt of desired product. (100% yield) MS-ESI $[M+H]^+$ for $C_{10}H_{14}N_2O_2S$ calculated 227.3. found 227.12

6.14 Example 14

Synthesis of MOrPHs Via Cyclization of Self-Processing Biosynthetic Precursors

This example demonstrates how macrocyclic peptide-containing molecules can be prepared according to the general method of FIG. 2, and in particular through a variation of this method schematically described in FIG. 20. This example also illustrates how MOrPHs featuring variable ring size and in lariat—as well as protein-fused configuration can be obtained using these methods of the invention by varying the composition of the target sequence and of the N-terminal tail in the self-processing biosynthetic precursor.

Using the AmmF-recognizing MjtRNA/MjTyrRS pair identified in Example 13 and the vectors described in Example 1 and 7, a series of AmmF-containing self-processing biosynthetic precursors with variable target sequence (4mer to 20mer) and variable N-terminal tail were produced in *E. coli* via expression of these vectors in AmmF-supplemented media (Table 5). After purification via Ni-affinity chromatography, these proteins were incubated at 37° C. at a concentration of 100 μM in phosphate buffer (50 mM KPi, 150 mM NaCl, pH 7.5). TCEP (3 mM) was added to maintain the thiols in reduced form. After 24 hours, these samples were analyzed by SDS-PAGE protein gel densitometry to establish the extent of splicing and by LC-MS or MALDI-TOF to analyze the product of the reactions. These studies revealed that all the constructs underwent intramolecular cyclization, leading to the expected CBD-fused or lariat MOrPHs according to the nature of the N-terminal sequence. For the CBD-containing constructs, the degree of protein splicing was found to vary from 5 to 35% according to the length of the target sequence (FIG. 19*b*). With all the constructs, the desired CBD-fused macrocycle was the only or largely predominant product produced as determined by MALDI-TOF (FIG. 21). Similar results were obtained for the AmmF-containing self-processing biosynthetic precursors with a short N-terminal sequence such as MG8(AmmF), Sfi-a(AmmF), and Sfi-b(AmmF) (Table 5). These constructs were found to undergo cyclization leading to the expected macrocyclic product as determined by LC-MS (MG8(AmmF)=obs. m/z [M+H]$^+$: 1033.0, calc.: 1033.1; Sfi-a(AmmF)=obs. m/z [M+H]$^+$: 1221.2, calc.: 1221.5; Sfi-b(AmmF)=obs. m/z [M+H]$^+$: 1436.0, calc.: 1436.4) and MS/MS (cyclic backbone).

(SEQ ID NO:119) target sequence were prepared utilizing an engineered variant of Synechocystis species (Ssp.) DnaB intein (referred to as 'engineered DnaB' or 'eDnaB'), where the centrally located endonuclease domain (275 aa) is removed to leave a mini 154-amino acid intein. The C-terminal asparagine was then mutated to alanine (N154A) to pre-

TABLE 5

AmmF-containing self-processing biosynthetic precursors.

| Name | (AA)$_m$ | J | (AA)$_n$ | Intein | (AA)$_p$ |
|---|---|---|---|---|---|
| MG8(AmmF) | MG | AmmF | TGSAEYGT (SEQ ID NO: 100) | GyrA (N198A) | LE(H)$_6$ |
| Sfi-a(AmmF) | MR | AmmF | TKSIPPI (SEQ ID NO: 103) | GyrA (N198A) | LE(H)$_6$ |
| Sfi-b(AmmF) | MK | AmmF | RSTKSIPPI (SEQ ID NO: 104) | GyrA (N198A) | LE(H)$_6$ |
| CBD4(AmmF) | Chitin-binding domain (CBD) | AmmF | TGST (SEQ ID NO: 96) | GyrA (N198A) | LE(H)$_6$ |
| CBD5(AmmF) | Chitin-binding domain (CBD) | AmmF | TGSGT (SEQ ID NO: 97) | GyrA (N198A) | LE(H)$_6$ |
| CBD6(AmmF) | Chitin-binding domain (CBD) | AmmF | TGSYGT (SEQ ID NO: 98) | GyrA (N198A) | LE(H)$_6$ |
| CBD8(AmmF) | Chitin-binding domain (CBD) | AmmF | TGSAEYGT (SEQ ID NO: 100) | GyrA (N198A) | LE(H)$_6$ |
| CBD10(AmmF) | Chitin-binding domain (CBD) | AmmF | TGSKLAEYGT (SEQ ID NO: 101) | GyrA (N198A) | LE(H)$_6$ |
| CBD12(AmmF) | Chitin-binding domain (CBD) | AmmF | TGSWGKLAEYGT (SEQ ID NO: 102) | GyrA (N198A) | LE(H)$_6$ |
| CBD15(AmmF) | Chitin-binding domain (CBD) | AmmF | TGSHNRWGKLAEYGT (SEQ ID NO: 113) | GyrA (N198A) | LE(H)$_6$ |
| CBD20(AmmF) | Chitin-binding domain (CBD) | AmmF | TGSYTGDQHNRWGKLAEYGT (SEQ ID NO: 114) | GyrA (N198A) | LE(H)$_6$ |

6.15 Example 15

Synthesis of MOrPHs Via Cyclization of Self-Processing Biosynthetic Precursors in Living Cells This example demonstrates how MOrPHs can be produced in living expression hosts (in vivo) via spontaneous cyclization of a self-processing biosynthetic precursor with the cell expressing the protein. This example also demonstrates how alternative intein proteins, and engineered variant thereof, can be used within the methods of the invention according.

The results described in Example 14 showed how MOrPHs can be produced in vitro according to the general method of FIG. 2, and in particular via the variation of this method described in FIG. 20. For these GyrA-based constructs, little macrocyclization occurs in vivo (i.e., within the expression host cell) which is useful when synthesis of MOrPHs from isolated, purified proteins using this method is desired. Production of the MOrPH directly within the expression host cell is desirable for a number of other applications such as, for example, for coupling MOrPH library production to a display system or to a genetic reporter system. To this end, we evaluated alternative inteins for their ability to mediate a faster cyclization reaction according to this general strategy. Two plasmids encoding for CBD-fused constructs containing a 5mer (TGSYGS) (SEQ ID NO:118) and 8mer (TGSAEYGS) vent splicing at the C-terminus and allow for the introduction of a polyhistidine tag at the C-terminal end of the construct ((AA)$_p$ in FIG. 2).

These plasmids were then expressed in E. coli BL21(DE3) cells in the presence of the unnatural amino acid AmmF and the appropriate amber stop codon suppression system (AmmF-recognizing MjtRNA/MjTyrtRS in Example 13) to yield the corresponding DnaB-based self-processing biosynthetic precursors (Table 6). Occurrence and quantitation of in vivo splicing was carried out via SDS-PAGE protein gel densitometric analysis of samples obtained by lysing the cells and isolating the Ni-binding protein fraction from the cell lysate. Since the Ni-affinity polyhistidine tag is at the C-terminus of the construct, this fraction contains both the full-length (unspliced) protein construct and the spliced DnaB. The flow-through sample from the N-affinity chromatography step was then passed through chitin beads, which trap the spliced CBD-containing products (i.e., CBD-fused MOrPH and linear hydrolysis by-product if present). The eluates from the chitin-beads were then analyzed by MALDI-TOF. A general scheme of this process (in vivo production of MOrPH) and the results of these experiments are summarized in FIGS. 22a-c. Both constructs were found to be about 90% spliced after overnight expression (16 hours, 30° C.) (FIG. 22b). Importantly, MALDI-TOF analysis revealed the occurrence and formation of only the desired CBD-fused MOrPH for both constructs (no linear hydrolysis by-product) as shown in FIG. 22c.

This example demonstrates how macrocyclic peptide-containing molecules can be generated, using the methods disclosed herein, within the cell expressing the self-processing biosynthetic precursor as schematically described in FIG. 22a. It is also shown how the in vivo produced MOrPH product can be readily isolated from a complex mixture (i.e., cell lysate) by taking advantage of one of the features of the method, namely the possibility of introducing an affinity tag within the N-terminal tail of the macrocycle.

TABLE 6

AmmF-containing self-processing biosynthetic precursors.

| Name | $(AA)_m$ | J | $(AA)_n$ | Intein | $(AA)_p$ |
|---|---|---|---|---|---|
| CBD6S(AmmF) | Chitin-binding domain (CBD) | AmmF | TGSYGS (SEQ ID NO: 118) | eDnaB (N154A) | LE(H)$_6$ |
| CBD8S(AmmF) | Chitin-binding domain (CBD) | AmmF | TGSAEYGS (SEQ ID NO: 119) | eDnaB (N154A) | LE(H)$_6$ |

Experimental Details for Example 14 and 15

Expression and isolation of the self-processing biosynthetic precursors. Plasmids encoding for the various constructs described in Tables 5 and 6 were co-transformed into chemically competent E. coli BL21(DE3) cells together with a pEVOL vector encoding for the pAzF-specific engineered MjtRNA$_{CUA}$/MjTyrRS pair. Cells were grown and induced as described in Example 1. At the time of the induction with IPTG, cultures were added with AmmF (2 mM). Cells were harvested by centrifugation and lysed by sonication. The GyrA-containing proteins were isolated by Ni-affinity chromatography as described in Example 1. An identical protocol was utilized to isolate the DnaB-containing constructs via Ni-affinity chromatography. Chitin-affinity chromatography involved passing the lysate over chitin beads, followed by washing with KPi Buffer, and elution with 75% acetonitrile in water. SDS-PAGE and MALDI-TOF analyses were carried out as described in the previous Examples.

The compounds provided herein may contain one or more chiral centers. Accordingly, the compounds are intended to include racemic mixtures, diastereomers, enantiomers, and mixture enriched in one or more stereoisomer. When a group of substituents is disclosed herein, all the individual members of that group and all subgroups, including any isomers, enantiomers, and diastereomers are intended to be included in the disclosure. Additionally, all isotopic forms of the compounds disclosed herein are intended to be included in the disclosure. For example, it is understood that any one or more hydrogens in a molecule disclosed herein can be replaced with deuterium or tritium.

A skilled artisan will appreciate that starting materials, biological materials, reagents, synthetic methods, purification methods, analytical methods, assay methods, and biological methods other than those specifically exemplified can be employed in the practice of the invention. All art-known functional equivalents of any such materials and methods are intended to be included in the invention.

Unless otherwise indicated, the disclosure is not limited to specific molecular structures, substituents, synthetic methods, reaction conditions, or the like, as such may vary. It is to be understood that the embodiments are not limited to particular compositions or biological systems, which can, of course, vary.

The terms and expression that are employed herein are used as terms of description and not of limitation, and there is no intention that in the use of such terms and expressions of excluding any equivalents of the features shown and described and portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to those skilled in the art, and that such modifications and variations are considered to be within the scope of the invention as defined by the appended claims.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A method for making a macrocyclic peptide comprising a target peptide molecule, the method comprising the steps of:

a) providing a nucleic acid molecule encoding for a polypeptide of structure:

$$(AA)_m\text{-}Z\text{-}(AA)_n\text{-}INT \quad (I)$$

or $$(AA)_m\text{-}Z\text{-}(AA)_n\text{-}INT\text{-}(AA)_p \quad (II)$$

wherein:

i) $(AA)_m$ is a N-terminal amino acid or peptide sequence, wherein AA is an amino acid residue and m is the number of amino acid residues in the N-terminal amino acid or peptide sequence, ii) Z is an amino acid carrying a side-chain functional group $FG_1$, said $FG_1$ being a functional group selected from the group consisting of alkynyl (—C≡CR'), azido (—N$_3$), alkoxyamino (—ONR'$_2$), hydrazino (—NR'NR'$_2$), hydrazido (—CONR'NR'$_2$), carbonyl (—CO—R'), alkenyl (—CR'═CR'$_2$), phosphine (—PR'$_2$), thiol (—SR'), selenyl (—SeR'), tetrazole, tetrazine, aziridine, 2H-azirine, norbornadiene, boronaryl (Ar—B(OH)$_2$), and bromoaryl (Ar—Br), iodoaryl (Ar—I) groups, where R' is a hydrogen, alkyl or aryl group and Ar is an aryl group, iii) $(AA)_n$ is a target peptide sequence, wherein AA is an amino acid residue and n is the number of amino acid residues in the target peptide sequence, iv) INT is an intein, and v) $(AA)_p$ is a peptide sequence fused to the C-terminus of the intein, wherein AA is an amino acid residue and p is the number of amino acid residues in the peptide sequence fused to the C-terminus of the intein;

b) introducing the nucleic acid molecule into an expression system and expressing the nucleic acid molecule, thereby producing the polypeptide; and c) providing a chemical species of formula $$cFG_1\text{-}cFG_2 \quad (III)$$

or $$cFG_1\text{-}L\text{-}cFG_2 \quad (IV)$$

or a salt thereof, wherein:

i) $cFG_1$ is a functional group selected from the group consisting of alkynyl (—C≡CR'), azido (—N$_3$), alkoxyamino (—ONR'$_2$), hydrazino (—NR'NR'$_2$), hydrazido (—CONR'NR'$_2$), carbonyl (—CO—R'), alkenyl (—CR'═CR'$_2$), phosphine (—PR'$_2$), thiol (—SR'), selenyl (—SeR'), tetrazole, tetrazine, aziridine, dihydroazirine, norbornadiene, boronaryl (Ar—B(OH)$_2$), bromoaryl (Ar—Br), and iodoaryl (Ar—I) groups, where R' is a hydrogen, alkyl or aryl group and Ar is an aryl group, ii) $cFG_2$ is a functional group selected from the group consisting of alkoxyamino (—ONR'$_2$), hydrazino (—NR'NR'$_2$), hydrazido (—CONR'NR'$_2$), thiol (—SR'), selenyl (—SeR'), phenyl-methanethiol, phenyl-methaneselenol, aryl-methanethiol, aryl-methaneselenol, 2-amino-benzene-thiol, 2-amino-benzene-selenol, 2-amino-aryl-thiol, 2-amino-arylselenol, (2-aminophenyl)-methanethiol, (2-aminophenyl)-methaneselenol, (2-aminoaryl)-methanethiol, (2-aminoaryl)-methaneselenol, N-alkyl-(2-aminophenyl)-methanethiol, N-alkyl-(2-aminophenyl)-methaneselenol, N-alkyl-(2-aminoaryl)-methanethiol, N-alkyl-(2-aminoaryl)-methaneselenol, where R' is a hydrogen, alkyl or aryl group, and iii) L is linker group selected from the group consisting of $C_1$-$C_{24}$ alkyl, $C_1$-$C_{24}$ substituted alkyl, $C_1$-$C_{24}$ substituted heteroatom-containing alkyl, $C_1$-$C_{24}$ substituted heteroatom-containing alkyl, $C_2$-$C_{24}$ alkenyl, $C_2$-$C_{24}$ substituted alkenyl, $C_2$-$C_{24}$ substituted heteroatom-containing alkenyl, $C_2$-$C_{24}$ substituted heteroatom-containing alkenyl, $C_5$-$C_{24}$ aryl, $C_5$-$C_{24}$ substituted aryl, $C_5$-$C_{24}$ substituted heteroatom-containing aryl, $C_1$-$C_{24}$ alkoxy, and $C_5$-$C_{24}$ aryloxy groups; and d) contacting the polypeptide with the chemical species for a time and under conditions to allow a covalent bond-forming reaction between $FG_1$ and $cFG_1$ and a covalent bond-forming reaction between $FG_2$ and $cFG_2$ to occur, wherein $FG_2$ is an intein-catalyzed thioester or ester linkage ($FG_2$), thereby:

forming covalent bonds between $FG_1$ and $cFG_1$ and between $FG_2$ and $cFG_2$, cleaving the intein from the polypeptide, and producing the macrocyclic peptide comprising the target peptide molecule.

2. The method of claim 1 wherein Z is an amino acid of structure:

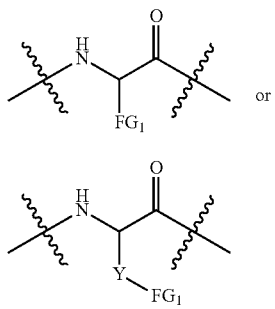

wherein $FG_1$ is a functional group selected from the group consisting of alkynyl (—C≡CR'), azido (—$N_3$), alkoxyamino (—ONR'$_2$), hydrazino (—NR'NR'$_2$), hydrazido (—CONR'NR'$_2$), carbonyl (—CO—R'), alkenyl (—CR'=CR'$_2$), phosphine (—PR'$_2$), thiol (—SR'), selenyl (—SeR'), tetrazole, tetrazine, aziridine, 2H-aziridine, norbornadiene, boronaryl (Ar—B(OH)$_2$), bromoaryl (Ar—Br), iodoaryl (Ar—I) groups, where R' is a hydrogen, alkyl or aryl group and Ar is an aryl group, and wherein Y is a linker group selected from the group consisting of $C_1$-$C_{24}$ alkyl, $C_1$-$C_{24}$ substituted alkyl, $C_1$-$C_{24}$ substituted heteroatom-containing alkyl, $C_1$-$C_{24}$ substituted heteroatom-containing alkyl, $C_2$-$C_{24}$ alkenyl, $C_2$-$C_{24}$ substituted alkenyl, $C_2$-$C_{24}$ substituted heteroatom-containing alkenyl, $C_2$-$C_{24}$ substituted heteroatom-containing alkenyl, $C_5$-$C_{24}$ aryl, $C_5$-$C_{24}$ substituted aryl, $C_5$-$C_{24}$ substituted heteroatom-containing aryl, $C_1$-$C_{24}$ alkoxy, and $C_5$-$C_{24}$ aryloxy groups.

3. The method of claim 1 wherein the amino acid Z is selected from the group consisting of para-acetyl-phenylalanine, O-propargyl-tyrosine, 3-fluoro-4-acetyl-phenylalanine, meta-acetyl-phenylalanine, para-butyl-1,3-dione-phenylalanine, O-allyl-tyrosine, para-azido-phenylalanine, para-borono-phenylalanine, para-bromo-phenylalanine, para-iodo-phenylalanine, 3-iodo-tyrosine, para-benzoyl-phenylalanine, para-benzoyl-phenylalanine, ε-N-allyloxycarbonyl-lysine, ε-N-propargyloxycarbonyl-lysine, ε-N-azidoethyloxycarbonyl-lysine, and ε-N-(o-azido-benzyl)-oxycarbonyl-lysine.

4. The method of claim 1 wherein the codon encoding for Z is an amber stop codon TAG, an ochre stop codon TAA, an opal stop codon TGA, or a four base codon.

5. The method of claim 1 wherein the intein is selected from the group consisting of a naturally occurring intein, an engineered variant of a naturally occurring intein, a fusion of the N-terminal and C-terminal fragments of a naturally occurring split intein and a fusion of the N-terminal and C-terminal fragments of an artificial split intein.

6. The method of claim 5 wherein the intein is selected from the group consisting of Mxe GyrA (SEQ ID NO:1), Ssp eDnaB (SEQ ID NO:2), Hsp-NRC1 CDC21 (SEQ ID NO:3), Ceu ClpP (SEQ ID NO:4), Tag Pol-1 (SEQ ID NO:5), Tfu Pol-1 (SEQ ID NO:6), Tko Pol-1 (SEQ ID NO:7), Psp-GBD Pol (SEQ ID NO:8), Tag Pol-2 (SEQ ID NO:9), Thy Pol-1 (SEQ ID NO:10), Tko Pol-2 (SEQ ID NO:11), Tli Pol-1 (SEQ ID NO:12), Tma Pol (SEQ ID NO:13), Tsp-GE8 Pol-1 (SEQ ID NO:14), Tthi Pol (SEQ ID NO:15), Tag Pol-3 (SEQ ID NO:16), Tfu Pol-2 (SEQ ID NO:17), Thy Pol-2 (SEQ ID NO:18), Tli Pol-2 (SEQ ID NO:19), Tsp-GE8 Pol-2 (SEQ ID NO:20), Pab Pol-II (SEQ ID NO:21), Mtu-CDC1551 DnaB (SEQ ID NO:22), Mtu-H37Rv DnaB (SEQ ID NO:23), Rma DnaB (SEQ ID NO:24), Ter DnaE-1 (SEQ ID NO:25), Ssp GyrB (SEQ ID NO:26), Mfl GyrA (SEQ ID NO:27), Mgo GyrA (SEQ ID NO:28), Mkas GyrA (SEQ ID NO:29), Mle-TN GyrA (SEQ ID NO:30), Mma GyrA (SEQ ID NO:31), Ssp DnaX (SEQ ID NO:32), Pab Lon (SEQ ID NO:33), Mja PEP (SEQ ID NO:34), Afu-FRR0163 PRP8 (SEQ ID NO:35), Ani-FGSCA4 PRP8 (SEQ ID NO:36), Cne-A PRP8 (SEQ ID NO:37), Hca PRP8 (SEQ ID NO:38), Pch PRP8 (SEQ ID NO:39), Pex PRP8 (SEQ ID NO:40), Pvu PRP8 (SEQ ID NO:41), Mtu-H37Rv RecA (SEQ ID NO:42), Mtu-So93 RecA (SEQ ID NO:43), Mfl RecA (SEQ ID NO:44), Mle-TN RecA (SEQ ID NO:45), Nsp-PCC7120 RIR1 (SEQ ID NO:120), Ter RIR1-1 (SEQ ID NO:46), Pab RIR1-1 (SEQ ID NO:47), Pfu RIR1-1 (SEQ ID NO:48), Chy RIR1 (SEQ ID NO:49), Mth RIR1 (SEQ ID NO:50), Pab RIR1-3 (SEQ ID NO:51), Pfu RIR1-2 (SEQ ID NO:52), Ter RIR1-2 (SEQ ID NO:53), Ter RIR1-4 (SEQ ID NO:54), CIV RIR1 (SEQ ID NO:55), Ctr VMA (SEQ ID NO:56), Sce VMA (SEQ ID NO:57), Tac-ATCC25905 VMA (SEQ ID NO:58), Ssp DnaB (SEQ ID NO:59), split intein Ssp DnaE (SEQ ID NO:60-SEQ ID NO:61), split intein Neq Pol (SEQ ID NO:62-SEQ ID NO:63), split intein Asp DnaE (SEQ ID NO:64-SEQ ID NO:65), split intein Npu-PCC73102 DnaE (SEQ ID NO:66-SEQ ID NO:67), split intein Nsp-PCC7120 DnaE (SEQ ID NO:68-SEQ ID NO:69), split intein Oli DnaE (SEQ ID NO:70-SEQ ID NO:71), split intein Ssp-PCC7002 DnaE (SEQ ID NO:72-SEQ ID NO:73), split intein Tvu DnaE (SEQ ID NO:74-SEQ ID NO:75), and a functional variant thereof.

7. The method of claim 1 wherein the polypeptide $(AA)_m$ comprises an affinity tag, a DNA-binding protein, a protein-binding protein, or a fluorescent protein.

8. The method of claim 7 wherein the affinity tag is selected from the group consisting of polyarginine tag, polyhistidine tag, Avi-Tag (SEQ ID NO:89), FLAG tag (SEQ ID NO:90), Strep-tag II (SEQ ID NO:91), c-myc tag (SEQ ID NO:92), S tag (SEQ ID NO:93), calmodulin-binding peptide (SEQ ID NO:94), streptavidin-binding peptide (SEQ ID NO:95), chitin-binding domain (SEQ ID NO:110), glutathione S-transferase, and maltose-binding protein (MBP).

9. The method of claim 1 wherein the polypeptide $(AA)_m$ comprises a protein selected from the group consisting of M13 phage protein pVI (SEQ ID NO:76), T7 phage protein 10A (SEQ ID NO:77), T7 phage protein 10B (SEQ ID NO:78), *E. coli* NlpA signal peptide sequence (SEQ ID NO:79), *E. coli* OmpC (SEQ ID NO:80), *E. coli* FadL (SEQ ID NO:81), *E. coli* Lpp-OmpA (SEQ ID NO:82), *E. coli* PgsA (SEQ ID NO:83), *E. coli* EaeA (SEQ ID NO:84), *S. cerevisiae* protein Aga2p (SEQ ID NO:85), *S. cerevisiae* protein Flo1p (SEQ ID NO:121), human NF-κB p50 protein (SEQ ID NO:86), green fluorescent protein, and a functional variant thereof.

10. The method of claim 1 wherein:
   $FG_1$ is a terminal alkyne (—C≡CH), $cFG_1$ is an azido group (—$N_3$), and $cFG_2$ is a hydrazido group (—CONHNH$_2$), or
   $FG_1$ is a carbonyl (—CO—), $cFG_1$ is an oxyamine (—ONH$_2$), and $cFG_2$ is selected from the group consisting of aryl-methanethiol group, (2-amino-aryl)-methanethiol group, and N-substituted (2-amino-aryl)-methanethiol group.

11. The method of claim 1 wherein the expression system is selected from the group consisting of a prokaryotic cell, a an eukaryotic cell, and a cell-free expression system.

12. The method of claim 11 wherein the prokaryotic cell is *Escherichia coli* and the eukaryotic cell is yeast.

13. The method of claim 1 wherein:
a) the polypeptide $(AA)_n$, or a portion thereof, is genetically randomized, and/or
b) the polypeptide $(AA)_m$, or a portion thereof is genetically randomized so that a plurality of macrocyclic peptide-containing molecules is obtained upon reaction with a chemical species of formula (III) or (IV).

14. A method for making a macrocyclic peptide comprising a target peptide molecule, the method comprising the steps of:
a) providing a nucleic acid molecule encoding for a polypeptide of structure:

$(AA)_m\text{-J-}(AA)_n\text{-INT}$  (VII)

or $(AA)_m\text{-J-}(AA)_n\text{-INT-}(AA)_p$  (VIII)

wherein:
i) $(AA)_m$ is a N-terminal amino acid or peptide sequence,
ii) J is an amino acid carrying a side-chain functional group $FG_3$, said $FG_3$ being a functional group selected from the group consisting of alkoxyamino (—ONR'$_2$), hydrazino (—NR'NR'$_2$), hydrazido (—CONR'NR'$_2$), thiol (—SR'), selenyl (—SeR'), phenyl-methanethiol, phenyl-methaneselenol, aryl-methanethiol, aryl-methaneselenol, 2-amino-benzene-thiol, 2-amino-benzene-selenol, 2-amino-aryl-thiol, 2-amino-aryl-selenol, (2-aminophenyl)-methanethiol, (2-aminophenyl)-methaneselenol, (2-aminoaryl)-methanethiol, (2-aminoaryl)-methaneselenol, N-alkyl-(2-aminophenyl)-methanethiol, N-alkyl-(2-aminophenyl)-methaneselenol, N-alkyl-(2-aminoaryl)-methanethiol, N-alkyl-(2-aminoaryl)-methaneselenol, where R' is a hydrogen, alkyl or aryl group,
iii) $(AA)_n$ is a target peptide sequence,
iv) INT is an intein, and
v) $(AA)_p$ is a peptide sequence fused to the C-terminus of the intein;

b) introducing the nucleic acid molecule into an expression system and expressing the nucleic acid molecule in the expression system, thereby producing the polypeptide; and
c) allowing the polypeptide self-processing biosynthetic precursor to undergo cyclization between $FG_3$ and a thioester or an ester linkage produced by the intein, thereby producing the macrocyclic peptide comprising the target peptide molecule.

15. The method of claim 14 wherein J is an amino acid of structure:

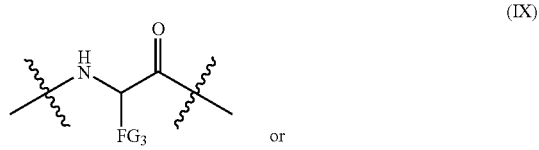

or

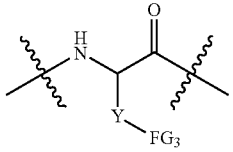

wherein $FG_3$ is a functional group selected from the group consisting of alkoxyamino (—ONR'$_2$), hydrazino (—NR'NR'$_2$), hydrazido (—CONR'NR'$_2$), thiol (—SR'), selenyl (—SeR'), phenyl-methanethiol, phenyl-methaneselenol, aryl-methanethiol, aryl-methaneselenol, 2-amino-benzene-thiol, 2-amino-benzene-selenol, 2-amino-aryl-thiol, 2-amino-aryl-selenol, (2-aminophenyl)-methanethiol, (2-aminophenyl)-methaneselenol, (2-aminoaryl)-methanethiol, (2-aminoaryl)-methaneselenol, N-alkyl-(2-aminophenyl)-methanethiol, N-alkyl-(2-aminophenyl)-methaneselenol, N-alkyl-(2-aminoaryl)-methanethiol, N-alkyl-(2-aminoaryl)-methaneselenol, where R' is a hydrogen, alkyl or aryl group, and
wherein Y is a linker group selected from the group consisting of $C_1$-$C_{24}$ alkyl, $C_1$-$C_{24}$ substituted alkyl, $C_1$-$C_{24}$ substituted heteroatom-containing alkyl, $C_1$-$C_{24}$ substituted heteroatom-containing alkyl, $C_2$-$C_{24}$ alkenyl, $C_2$-$C_{24}$ substituted alkenyl, $C_2$-$C_{24}$ substituted heteroatom-containing alkenyl, $C_2$-$C_{24}$ substituted heteroatom-containing alkenyl, $C_5$-$C_{24}$ aryl, $C_5$-$C_{24}$ substituted aryl, $C_5$-$C_{24}$ substituted heteroatom-containing aryl, $C_1$-$C_{24}$ alkoxy, and $C_5$-$C_{24}$ aryloxy groups.

16. The method of claim 14 wherein the amino acid J is 3-amino-4-mercaptomethyl-phenylalanine:

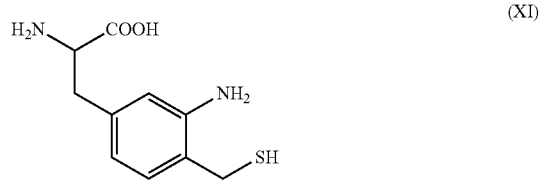 [SMILES: Nc1cc(CC(N)C(=O)O)ccc1CS]

or a salt thereof.

17. The method of claim 14 wherein the codon encoding for J is an amber stop codon TAG, an ochre stop codon TAA, an opal stop codon TGA, or a four base codon.

18. The method of claim 14 wherein the intein is selected from the group consisting of a naturally occurring intein, an engineered variant of a naturally occurring intein, a fusion of the N-terminal and C-terminal fragments of a naturally occurring split intein and a fusion of the N-terminal and C-terminal fragments of an artificial split intein.

19. The method of claim 18 wherein the intein is selected from the group consisting of Mxe GyrA (SEQ ID NO:1), Ssp eDnaB (SEQ ID NO:2), Hsp-NRC1 CDC21 (SEQ ID NO:3), Ceu ClpP (SEQ ID NO:4), Tag Pol-1 (SEQ ID NO:5), Tfu Pol-1 (SEQ ID NO:6), Tko Pol-1 (SEQ ID NO:7), Psp-GBD Pol (SEQ ID NO:8), Tag Pol-2 (SEQ ID NO:9), Thy Pol-1 (SEQ ID NO:10), Tko Pol-2 (SEQ ID NO:11), Tli Pol-1 (SEQ ID NO:12), Tma Pol (SEQ ID NO:13), Tsp-GE8 Pol-1 (SEQ ID NO:14), Tthi Pol (SEQ ID NO:15), Tag Pol-3 (SEQ ID NO:16), Tfu Pol-2 (SEQ ID NO:17), Thy Pol-2 (SEQ ID NO:18), Tli Pol-2 (SEQ ID NO:19), Tsp-GE8 Pol-2 (SEQ ID NO:20), Pab Pol-II (SEQ ID NO:21), Mtu-CDC1551 DnaB (SEQ ID NO:22), Mtu-H37Rv DnaB (SEQ ID NO:23), Rma DnaB (SEQ ID NO:24), Ter DnaE-1 (SEQ ID NO:25), Ssp GyrB (SEQ ID NO:26), Mfl GyrA (SEQ ID NO:27), Mgo GyrA (SEQ ID NO:28), Mkas GyrA (SEQ ID NO:29), Mle-TN GyrA (SEQ ID NO:30), Mma GyrA (SEQ ID NO:31), Ssp DnaX (SEQ ID NO:32), Pab Lon (SEQ ID NO:33), Mja PEP (SEQ ID NO:34), Afu-FRR0163 PRP8 (SEQ ID NO:35), Ani-FGSCA4 PRP8 (SEQ ID NO:36), Cne-A PRP8 (SEQ ID NO:37), Hca PRP8 (SEQ ID NO:38), Pch PRP8 (SEQ ID NO:39), Pex PRP8 (SEQ ID NO:40), Pvu PRP8 (SEQ ID NO:41), Mtu-H37Rv RecA (SEQ ID NO:42), Mtu-So93 RecA (SEQ ID NO:43), Mfl RecA (SEQ ID NO:44), Mle-TN RecA (SEQ ID NO:45), Nsp-PCC7120 RIR1 (SEQ ID NO:120), Ter RIR1-1 (SEQ ID NO:46), Pab RIR1-1 (SEQ ID NO:47), Pfu RIR1-1 (SEQ ID NO:48), Chy RIR1 (SEQ ID NO:49), Mth RIR1 (SEQ ID NO:50), Pab RIR1-3 (SEQ ID NO:51), Pfu RIR1-2 (SEQ ID NO:52), Ter RIR1-2 (SEQ ID NO:53), Ter RIR1-4 (SEQ ID NO:54), CIV RIR1 (SEQ ID NO:55), Ctr VMA (SEQ ID NO:56), Sce VMA (SEQ ID NO:57), Tac-ATCC25905 VMA (SEQ ID NO:58), Ssp DnaB (SEQ ID NO:59), split intein Ssp DnaE (SEQ ID NO:60-SEQ ID NO:61), split intein Neq Pol (SEQ ID NO:62-SEQ ID NO:63), split intein Asp DnaE (SEQ ID NO:64-SEQ ID NO:65), split intein Npu-PCC73102 DnaE (SEQ ID NO:66-SEQ ID NO:67), split intein Nsp-PCC7120 DnaE (SEQ ID NO:68-SEQ ID NO:69), split intein Oli DnaE (SEQ ID NO:70-SEQ ID NO:71), split intein Ssp-PCC7002 DnaE (SEQ ID NO:72-SEQ ID NO:73), split intein Tvu DnaE (SEQ ID NO:74-SEQ ID NO:75), and a functional variant thereof.

20. The method of claim 14 wherein the polypeptide $(AA)_m$ comprises an affinity tag, a DNA-binding protein, a protein-binding protein, or a fluorescent protein.

21. The method of claim 20 wherein the affinity tag is selected from the group consisting of polyarginine tag (SEQ ID NO:87), polyhistidine tag (SEQ ID NO:88), Avi-Tag (SEQ ID NO:89), FLAG tag (SEQ ID NO:90), Strep-tag II (SEQ ID NO:91), c-myc tag (SEQ ID NO:92), S tag (SEQ ID NO:93), calmodulin-binding peptide (SEQ ID NO:94), streptavidin-binding peptide (SEQ ID NO:95), chitin-binding domain (SEQ ID NO:110), glutathione S-transferase, and maltose-binding protein (MBP).

22. The method of claim 14 wherein the polypeptide $(AA)_m$ comprises a protein selected from the group consisting of M13 phage protein pVI (SEQ ID NO:76), T7 phage protein 10A (SEQ ID NO:77), T7 phage protein 10B (SEQ ID NO:78), *E. coli* N1 pA (SEQ ID NO:79), *E. coli* OmpC (SEQ ID NO:80), *E. coli* FadL (SEQ ID NO:81), *E. coli* Lpp-OmpA (SEQ ID NO:82), *E. coli* PgsA (SEQ ID NO:83), *E. coli* EaeA (SEQ ID NO:84), *S. cerevisiae* Aga2p (SEQ ID NO:85), *S. cerevisiae* Flo1p (SEQ ID NO:121), human NF-κB p50 (SEQ ID NO:86), green fluorescent protein, and a functional variant thereof.

23. The method of claim 14 wherein the expression system is selected from the group consisting of a prokaryotic cell, a an eukaryotic cell, and a cell-free expression system.

24. The method of claim 23 wherein the prokaryotic cell is *Escherichia coli* and the eukaryotic cell is yeast.

25. The method of claim 14 wherein:
   a) the polypeptide $(AA)_n$, or a portion thereof, is genetically randomized, and/or
   b) the polypeptide $(AA)_m$ or a portion thereof is genetically randomized so that a plurality of macrocyclic peptide comprising the target peptide molecule is obtained upon cyclization of the polypeptide of formula (VII) or (VIII).

* * * * *

UNITED STATES PATENT AND TRADEMARK OFFICE
CERTIFICATE OF CORRECTION

| | | |
|---|---|---|
| PATENT NO. | : 8,986,953 B2 | Page 1 of 1 |
| APPLICATION NO. | : 13/980083 | |
| DATED | : March 24, 2015 | |
| INVENTOR(S) | : Rudi Fasan et al. | |

It is certified that error appears in the above-identified patent and that said Letters Patent is hereby corrected as shown below:

In the specification

At Column 1, Line 15, please add the following:

"STATEMENT REGARDING FEDERALLY SPONSORED RESEARCH OR DEVELOPMENT

This invention was made with government support under CHE 1112342 awarded by the National Science Foundation. The government has certain rights in the invention."

Signed and Sealed this
Third Day of May, 2016

Michelle K. Lee
*Director of the United States Patent and Trademark Office*